US011655477B2

(12) United States Patent
Loria et al.

(10) Patent No.: US 11,655,477 B2
(45) Date of Patent: May 23, 2023

(54) **METHODS FOR THAXTOMIN PRODUCTION AND ENGINEERED NON-NATIVE *STREPTOMYCES* WITH INCREASED THAXTOMIN PRODUCTION**

(71) Applicant: University of Florida Research Foundation, Inc., Gainesville, FL (US)

(72) Inventors: Rosemary Loria, Gainesville, FL (US); Yucheng Zhang, Gainesville, FL (US); Yousong Ding, Gainesville, FL (US); Guangde Jiang, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/616,059

(22) PCT Filed: May 23, 2018

(86) PCT No.: PCT/US2018/034071
§ 371 (c)(1),
(2) Date: Nov. 22, 2019

(87) PCT Pub. No.: WO2018/217855
PCT Pub. Date: Nov. 29, 2018

(65) Prior Publication Data
US 2020/0140905 A1    May 7, 2020

Related U.S. Application Data

(60) Provisional application No. 62/509,792, filed on May 23, 2017, provisional application No. 62/646,626, filed on Mar. 22, 2018.

(51) Int. Cl.
*C12N 15/76* (2006.01)
*C12N 1/20* (2006.01)
*C12P 17/16* (2006.01)
*A01N 63/28* (2020.01)

(52) U.S. Cl.
CPC ............ *C12N 15/76* (2013.01); *A01N 63/28* (2020.01); *C12N 1/20* (2013.01); *C12P 17/165* (2013.01); *C12N 2510/02* (2013.01)

(58) Field of Classification Search
None
See application file for complete search history.

(56) References Cited

U.S. PATENT DOCUMENTS

2010/0167930 A1    7/2010  Koivunen et al.
2013/0217573 A1    8/2013  Koivunen et al.

FOREIGN PATENT DOCUMENTS

WO    2008124675 A2    10/2008
WO    2010121079 A2    10/2010
WO    2014149171 A1     9/2014
WO    2016044527 A1     3/2016

OTHER PUBLICATIONS

Kers et al.,"A large, mobile pathogenicity island confers plant pathogenicity on Streptomyces species", Molecular Microbiology 55(4) : 1025-1033 (Year: 2005).*
International Search Report and Written Opinion for PCT/US2018/034071 dated Aug. 8, 2018.
Zhang, et al. "Promiscuous Pathogenicity Islands and Phylogeny of Pathogenic *Streptomyces* spp.," MPMI, Aug. 9, 2016, vol. 29, No. 8, pp. 640-650.
Zaburannyi, et al. "Insights into naturally minimised *Streptomyces albus* J1074 genome," BMC Genomics, Feb. 5, 2014, vol. 15, No. 97, pp. 1-11.
Bignell, et al. "Phytotoxins produced by plant pathogenic *Streptomyces* species," Journal of Applied Microbiology, Nov. 7, 2013, vol. 116, No. 2, pp. 223-234.
Bukhalid, et al. "Cloning and Expression of a Gene from *Streptomyces scabies* Encoding a Putative Pathogenicity Factor," Journal of Bacteriology, Dec. 31, 1997, vol. 179, No. 24, pp. 7776-7783.
Zhang, et al. "Emergence of Novel Pathogenic *Streptomyces* Species by Site-Specific Accretion and cis-Mobilization of Pathogenicity Islands," MPMI, Jan. 30, 2017, vol. 30, No. 1, pp. 72-82.
LombóF, Velasco A, Castro A, De la Calle F, Brana AF, Sanchez-Puelles JM, Mendez C, Salas J A. 2006. Deciphering the biosynthesis pathway of the antitumor thiocoraline from a marine actinomycete and its expression in two Streptomyces species. ChemBioChem 7:366-376.
Loria, R., Bignell, D. R. D., Moll, S., Huguet-Tapia, J. C., Joshi, M. V., Johnson, E. G., Seipke, R. F., and Gibson, D. M. 2008. Thaxtomin biosynthesis: the path to plant pathogenicity in the genus Streptomyces. Antonie Van Leeuwenhoek. 94:3-10.
Loria, R., Kers, J., and Joshi, M. 2006. Evolution of Plant Pathogenicity in Streptomyces. Annu. Rev. Phytopathol. 14:469-487.
MacNeil, D. J., Gewain, K. M., Ruby, C. L., Dezeny, G., Gibbons, P. H., and MacNeil, T. 1992. Analysis of Streptomyces avermitilis genes required for avermectin biosynthesis utilizing a novel integration vector. Gene. 111:61-38.
Makitrynskyy R, Rebets Y, Ostash B, Zaburannyi N, Rabyk M, Walker S, Fedorenko V. 2010. Genetic factors that nfluence moenomycin production in streptomycetes. J Ind Microbiol Biotechnol 37:559-566.

(Continued)

*Primary Examiner* — Anand U Desai
(74) *Attorney, Agent, or Firm* — Thomas Horstemeyer, LLP

(57) ABSTRACT

The present disclosure includes genetically engineered, non-pathogenic *Streptomyces* bacterium with exogenous, non-native Thaxtomin A (ThxA) biosynthetic gene clusters conferring the genetically engineered, non-pathogenic *Streptomyces* bacterium with the ability to produce thaxtomin A. Also included are methods of providing thaxtomin producing capability in non-native *Streptomyces* bacterial strains, methods of producing thaxtomin compounds with the genetically engineered *Streptomyces* bacteria of the present disclosure, and methods of producing thaxtomin compounds and nitro-tryptophan analogs, and fluorinated thaxtomin compounds, analogs, and intermediates with the genetically engineered *Streptomyces* bacteria of the present disclosure.

19 Claims, 27 Drawing Sheets

Specification includes a Sequence Listing.

(56) References Cited

OTHER PUBLICATIONS

Mathee, K., et al., 2008. Dynamics of Pseudomonas aeruginosa genome evolution. Proc. Natl. Acad. Sci. U.S.A. 105:3100-3105.
Molesworth PP, Gardiner MG, Jones RC, Smith JA, Tegg RS, Wilson C. 2010. Synthesis and phytotoxicity of structural analogues of thaxtomin natural products Aust J Chem 63:813-820.
Sánchez, C., Butovich, I. A., Braña, A. F., Rohr, J., Méndez, C., and Salas, J. A. 2002. The biosynthetic gene cluster for the antitumor rebeccamycin: characterization and generation of indolocarbazole derivatives. Chem. Biol. 9:519-531.
Scheible WR, Fry B, Kochevenko A. 2003. An arabidopsis mutant resistant to thaxtomin A, a cellulose synthesis nhibitorfrom Streptomyces species. Plant Cell 15:1781-1794.
Simon, R., Priefer, U., and Puhler, A. 1983. A Broad Host Range Mobilization System for In Vivo Genetic Engineering Transposon Mutagenesis in Gram Negative Bacteria. Nat. Biotechnol. 1:784 791.
Stegmann, E., Rausch, C., Stockert, S., Burkert, D., and Wohlleben, W. 2006. The small MbtH-like protein encoded by an internal gene of the balhimycin biosynthetic gene cluster is not required for glycopeptide production. FEMS Microbiol. Lett. 262:85-92.
Strauss MJ. 1979. The nitroaromatic group in drug design: pharmacology and toxicology (for nonpharmacologists). Ind Eng Chem Prod Res Dev 18:158-166.
Streibig JC, Rudemo M, Jensen JE. 1993. Dose-response curves and statistical models. In herbicide bioassays Streibig, J. C., Kudsk, P., Eds.; CRC Press: Boca Raton, FL, 29-55.
Van Wezel GP, McKenzie NL, Nodwell JR. 2009. Applying the genetics of secondary metabolism in model actinomycetes to the discovery of new antibiotics. Methods Enzymol 458:117-141.
Xu Z, Zhang F, Zhang L, Jia Y. 2011. Total synthesis of (-)-indolactam V. Org. Biomol Chem 9:2512-2517.
Wach MJ, Krasno SB, Loria R, Gibson DM. 2007. Effect of carbohydrates on the production of thaxtomin A by Streptomyces acidiscabiei. Arch Microbiol 188:81-88.
Nendt-Pienkowski E, Huang Y, Zhang J, Li B, Jiang H, Kwon H, Hutchinson CR, Shen B. 2005. Cloning, sequencing, analysis, and heterologous expression of the fredericamycin biosynthetic gene cluster from Streptomyces griseus. J Am Chem Soc 127:16442-16452.
Winter JM, Moffill MC, Zazopoulos E, McAlpine JB, Dorrestein PC, Moore BS. 2007. Molecular basis for chloronium-mediated meroterpene cyclization: cloning, sequencing, and heterologous expression of the napyradiomycin biosynthetic gene cluster. J Biol Chem. 282:16362-16368.
Zhang H, Ning X, Hang H, Ru X, Li H, Li Y, Wang L, Zhang X, Yu S, Qiao Y, Wang X, Wang, p. 2013. Total synthesis of thaxtomin A and its stereoisomers and findings of their biological activities. Org Lett 15:5670-5673.
Zhang H, Wang Q, Ning X, Hang H, Ma J, Yang X, Lu X, Zhang J, Li Y, Niu C, Song H, Wang X, and Wang p. 2015. Synthesis and biological evaluations of a series of thaxtomin analogues J Agric Food Chem 63:3734 3741.
Zhang Y, Jiang G, Ding Y, Loria R. 2018. Genetic background affects pathogenicity island function and pathogen emergence in Streptomyces Mol Plant Pathol doi: 10.1111/mpp.12656.
Zuo R, Zhang Y, Huguet-Tapia JC, Mehta M, Dedic E, Bruner SD, Loria R, Ding Y. 2016. An artificial self-sufficient cytochrome P450 directly nitrates fluorinated tryptophan analogs with a different regio-selectivity. Biotechnol J 11:624-332.
Zuo R, Zhang Y, Jiang C, Hackett JC, Loria R, Bruner SD, Ding Y. 2017 Engineered P450 biocatalysts show improved activity and regio-promiscuity in aromatic nitration Sci Rep 7:842.
Barry SM, Kers JA, Johnson EG, Song L, Aston PR, Patel B, Krasnoff SB, Crane BR, Gibson DM, Loria R, Challis GL. 2012. Cytochrome P450-catalyzed l-tryptophan nitration in thaxtomin phytotoxin biosynthesis. Nat Chern Biol 8:814-316.
Bentley, S D., et al. 2002. Complete genome sequence of the model actinomycete Streptomyces coelicolor A3(2) Nature. 417:141-147.

Bibb MJ. 2005. Regulation of secondary metabolism in streptomycetes. CurrOpin Microbiol. 8:208-215.
Bibb M, Hesketh A. 2009. Analyzing the regulation of antibiotic production in streptomycetes. Methods Enzymol 458:93-116.
Bierman, M., Logan, R., O'Brien, K., Seno, E T., Rao, R N., and Schoner, B. E. 1992. Plasmid cloning vectors for the conjugal transfer of DNA from Escherichia coli to Streptomyces spp. Gene. 116:43-49.
Bignell, D. R D., Francis, I M., Fyans, J K , and Loria, R. 2014a. Thaxtomin A Production and Virulence Are Controlled by Several bld Gene Global Regulators in Streptomyces scabies. Mol Plant Microbe Interact. 27:875-885.
Bischoff, V., Cookson, S. J., Wu, S., and Scheible, W.-R. 2009. Thaxtomin A affects CESA-complex density, expression of cell wall genes, cell wall composition, and causes ectopic lignification in Arabidopsis thaliana seedlings. J. Exp. Bot. 60:955-965.
Bourgault JP, Maddirala AR, Andreana PR 2014 A one-pot multicomponent coupling/cyclization for natural product herbicide (±)-thaxtomin A. Org Biomol Chern 12:8125-8127.
Burrus, V , Pavlovic, G., Decaris, B., and Guedon, G. 2002. Conjugative transposons: the tip of the iceberg. Mol Microbiol. 46:601-610.
Butler AR, Bate N, Cundliffe E. 1999. Impact of thioesterase activity on tylosin biosynthesis in Streptomyces fradiae. Them Biol 6:287-292.
Cantrell CL, Dayan FE, Duke SO. 2012. Natural products as sources for new pesticides. J Nat Prod 75:1231-1242.
Chapleau, M., Guertin, J. F., Lerat, S., Burrus, V., and Beaulieu, C. 2016. Identification of genetic and environmental factors stimulating excision from Streptomyces scabiei chromosome of the toxicogenic region responsible for pathogenicity. Mol. Plant Pathol. 17:501-509.
Chater KF, Wilde LC. 1976. Restriction of a bacteriophage of Streptomyces albus G involving endonuclease SaiI. J Bacteriol 128:644-650.
Chen Y, Wendt-Pienkowski E, Shen B. 2008. Identification and utility of FdmR1 as a Streptomyces antibiotic regulatory protein activator for fredericamycin production in Streptomyces griseus ATCC 49344 and heterologous hosts. J Bacteriol 190:5587-5596.
Copping LG, Duke SO. 2007. Natural products that have been used commercially as crop protection agents. Pest Manage Sci 63:524 554.
Dayan FE, Owens DK, Duke SO. 2012. Rationale for a natural products approach to herbicide discovery. Pest Manage Sci 68, 519-528.
Duke SO, Cantrell CL, Meepagala KM, Wedge DE, Tabanca N, Schrader KK. 2010. Natural toxins for use in pest management. Toxins 2:1943-1962.
Feng Z, Wang L, Rajski SR, Xu Z, Coeffet-LeGal MF, Shen B. 2009. Engineered production of iso-migrastatin in Teterologous Streptomyces hosts. Bioorg Med Chern 17:2147-2153.
Francis, I. M., Jourdan, S., Fanara, S., Loria, R., and Rigali, S. 2015. The cellobiose sensor CebR is the gatekeeper of Streptomyces scabies pathogenicity. MBio 6:e02018.
Fry, B. A., and Loria, R. 2002. Thaxtomin A: evidence for a plant cell wall target. Physiol Mol Plant Path. 60:1-8.
Gibson DG, Young L, Chuang Y, Venter JC, Hutchison Iii Ca, Smith HO. 2009. Enzymatic assembly of DNA molecules up to several hundred kilobases. Nat Methods 6:343-345.
Goyer C, Charest PM, Toussaint V, Beaulieu C. 2000. Ultrastructural effects of thaxtomin A produced by Streptomyces scabiei on mature potato tuber tissues Can J Bot 78:374 380.
Gullón S, Olano C, Abdelfattah MS, Brana AF, Rohr J, Mendez C, Salas JA. 2006. Isolation, characterization, and heterologous expression of the biosynthesis gene cluster for the antitumor anthracycline steffimycin. Appl Environ Microbiol 72:4172-4183.
Gust, B., Challis, G. L., Fowler, K., Kieser, T., and Chater, K. F. 2003. PCR-targeted Streptomyces gene replacement dentifies a protein domain needed for biosynthesis of the sesquiterpene soil odor geosmin. Proc. Natl. Acad. Sci. U.S. A 100:1541-1546.
Healy F, Krasnoff SB, Wach M, Gibson DM, Loria R. 2002. Involvement of a cytochrome P450 monooxygenase in thaxtomin A biosynthesis by Streptomyces acidiscabiei. J Bacteriol 184:2019-2029.

(56) References Cited

OTHER PUBLICATIONS

Herbst, D. A., Boll, B., Zocher, G., Stehle, T., and Heide, L. 2013. Structural basis of the interaction of MbtH-like proteins, putative regulators of nonribosomal peptide biosynthesis, with adenylating enzymes. J. Biol. Chern. 288:1991-2003.

Hüter OF. 2011. Use of natural products in the crop protection industry. Phytochem Rev 10:185-194.

Johnson, E. G., Joshi, M. V., Gibson, D. M., and Loria, R. 2007. Cello-oligosaccharides released from host plants nduce pathogenicity in scab-causing Streptomyces species. Physiol Mol Plant Path. 71:18-25.

Joshi, M. V., Bignell, D. R. D., Johnson, E. G., Sparks, J. P., Gibson, D. M., and Loria, R. 2007. The AraC/XylS Yegulator TxtR modulates thaxtomin biosynthesis and virulence in Streptomyces scabiei. Mol. Microbiol. 66:633-642.

Ju KS, Parales RE. 2010. Nitroaromatic compounds, from synthesis to biodegradation. Microbiol Mol Biol Rev 74:250-272.

Kallifidas D, Brady SF. 2012. Reassembly of functionally intact environmental DNA-derived biosynthetic gene clusters. Methods Enzymol 517:225-239.

Kers JA, Wach MJ, Krasnoff SB, Widom J, Cameron KD, Bukhalid RA, Gibson DM, Crane BR, and Loria R. 2004. Nitration of a peptide phytotoxin by bacterial nitric oxide synthase Nature 429:79-82.

Kieser, T., Bibb, M. J., Buttner, M. J., Chater, K. F., and Hopwood, D. A. 2000. Practical Streptomyces Genetics. Norwich, United Kindom.

Kim SY, Zhao p. Igarashi M, Sawa R, Tomita T, Nishiyama M, Kuzuyama T. 2009. Cloning and heterologous expression of the cyclooctatin biosynthetic gene cluster afford a diterpene cyclase and two P450 hydroxylases. Chem Biol 16:736-743.

Kim JH, Feng Z, Bauer JD, Kallifidas D, Calle PY, Brady SF. 2010. Cloning large natural product gene clusters from the environment: piecing environmental DNA gene clusters back together with TAR. Biopolymers 93:833-844.

King RR, Lawrence CH. 1995. 4-Nitrotryptophans associated with the in vitro production of thaxtomin A by Streptomyces scabiei. Phytochemistry 40:41-43.

King, RR, Lawrence CH, Calhoun LA. 1992. Chemistry of phytotoxins associated with Streptomyces scabiei, the causal organism of potato common scab. J Agric Food Chem 40:834 837.

King, R. R., and Calhoun, L. A. 2009. The thaxtomin phytotoxins: Sources, synthesis, biosynthesis, biotransformation and biological activity Phytochemistry. 70:833-841.

King RR, Calhoun LA. 2009. Synthesis and NMR characteristics of N-acetyl-4-nitro, N-acetyl-5-nitro, N-acetyl-6-nitro and N-acetyl-7-nitrotryptophan methyl esters. Magn Reson Chem 47:273-276.

King RR, Lawrence CH, Clark MC, Calhoun LA. 1989. Isolation and characterization of phytotoxins associated with Streptomyces scabiei. J Chern Soc Chem Commun 0:849-850.

King RR, and Lawrence CH. 1994. Isolation and characterization of thaxtomin-type phytotoxins associated with Streptomyces iponweae. J Agric Food Chem 42:1791-1794.

King RR. 1997. Synthesis of thaxtomin C. Can J Chem 75:1172-1173.

King RR., and Lawrence CH. 1996. Characterization of new thaxtomin A analogues generated in vitro by Streptomyces scabiei. J Agric Food Chem 44:1108-1110.

King, R. R., Lawrence, C. H., and Gray, J. A. 2001. Herbicidal properties of the thaxtomin group of phytotoxins. J. Agric Food Chem. 49:2298-2301.

Kondoh SK, Nagasawa HK. 2009. Significance of nitroimidazole compounds and hypoxia-inducible factor-1 for imaging tumor hypoxia. Cancer Sci 100:1366-1373.

Kouprina, N., Noskov, V. N., and Larionov, V. 2006. Selective isolation of large chromosomal regions by transformation-associated recombination cloning for structural and functional analysis of mammalian genomes. Methods MoL Biol. 349:85-101.

Krasnoff SB, Lobkovsky EB, Wach MJ, Loria R, Gibson DMJ. 2005. Chemistry and phytotoxicity of thaxtomin A alkyl ethers. J Agric Food Chem. 53:9446-9451.

Lawrence CH, Clark MC, King RR. 1990. Induction of common scab symptoms in aseptically cultured potato tubers by the vivotoxin, thaxtomin Phytopathology 80:606-608.

Leiner RH, Fry BA. 1996. Probable involvement of thaxtomin A in pathogenicity of Streptomyces scabiei on seedlings. Phytopathology 86:709-713.

Ilardi EA, Vitaku E, Njardarson JT. 2014. Data-mining for sulfur and fluorine: An evaluation of pharmaceuticals to Yeveal opportunities for drug design and discovery. J Med Chem 57:2832-2842.

* cited by examiner

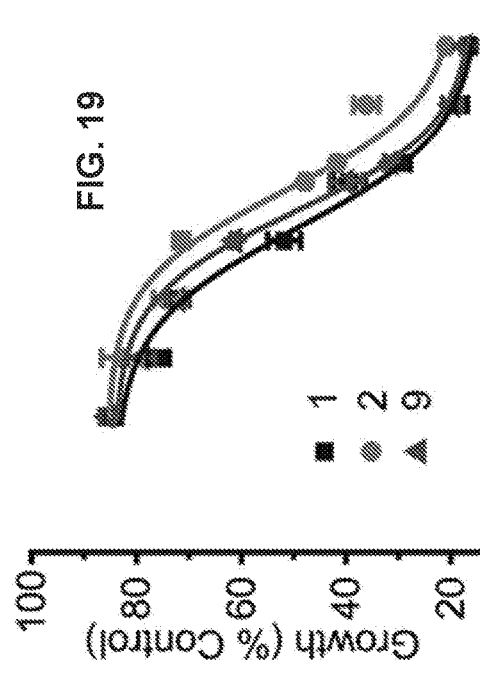
FIG. 19
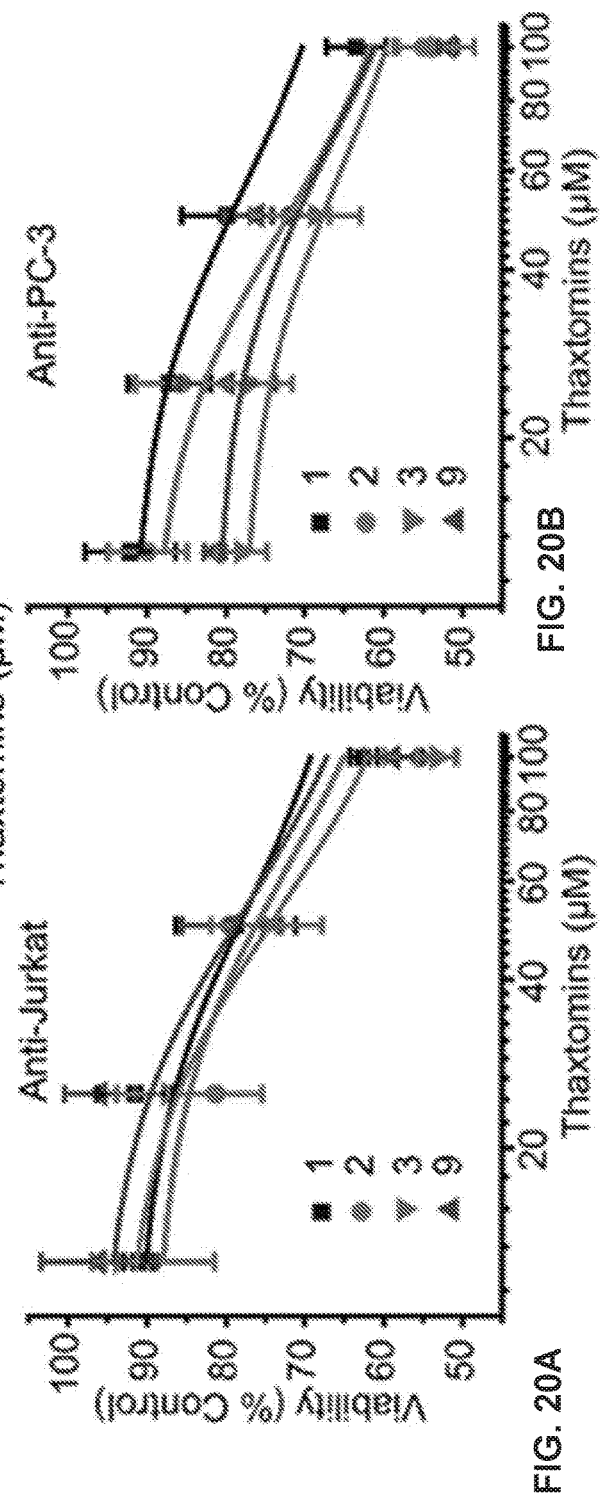
FIG. 20B
FIG. 20A

SEQUENCE LISTING

```
<160> NUMBER OF SEQ ID NOS: 64

<210> SEQ ID NO 1
<211> LENGTH: 4377
<212> TYPE: DNA
<213> ORGANISM: Streptomyces scabies

<400> SEQUENCE: 1
gtgtcgcacc tgaccggtga agatctcccg gagggagcgc tcgccacgac gtggccgagt       60
ctcctcgaag cgcgggtggc cgacacacct gacgccatcg cgctcgtcgc cggggacacg      120
gcgctcacgt acgcgcagtt caatgcccgt gcgaaccggc tcgcccggtg gctgaagtac      180
ctcggcgccg ggccggagcg gtcggtcggg ctggtgctgg gcaggtccgc ggacttcttc      240
ctgtgcgcga cggccgtgct caagtgcggg gccgcgtacc tgccgctgga tccgaactac      300
cccgtggagc gactgtcctt catggcccgg gacgcagcac ccgtggtgct ggtgacgacg      360
tcggacgtcc ggggcgacct tctgggccag ctgcccaccg gcagcctcgt ggtactggac      420
gacgaggcca ccgaggacgt actgcgccgt ctgccggacc acgacatgga ggacggggaa      480
cgtttggagc cactgcgccc cgcgagtccc gcctacatca tctacacctc cggctccacg      540
gggatcccca agggagtcgt cgtcacccac caaggcgtcg cgagcctgat cgcgacccag      600
cgtcgtcgcc tcgccgtcac cggcgcctca cgcgtgctcg ccttctcgtc cccgagtttc      660
gacgccagtt tctgggagat gtcgatggcg ctgctggccg gggccgcgct cgtggtcggc      720
aggccggggc ggctgctgcc cgacgccgaa ctggccgcgt tgatcgcgga ccacggagtc      780
actcatgtca ctctcccgcc ctcggtcgcg ggtgcgctgg ccccgacat gctgcctccg      840 agcgtgacgc tggtcgtcgc gggcgaagcg tgcccggcgg ctctcgtgca gcgctggcgc      900
ccgcaccgga cgatggtgaa cgcctacggc ccgacggagt ccaccgtctg cgccaccatg      960
agcgatccgc tggccgacga cgtggcgccg ccggtcggcc gggcggtgga cggcacccgg     1020
atccatgtcc tcgacgaccg cctcgcaccg gttgtgccgg gagcggtcgg cgagatctac     1080
atcgcggggc acagcctggc acgcgggtac ctcgagcggc cgggtctgac cgcgcagcgg     1140
```

```
ttcgtggcgg accccttcgg cccggccggc agccgtatgt accgcagcgg tgacctcggc    1200
cgctggaccc gttcaggaga cctggagttc gtcggcaggg cggacgacca ggtcaaggta    1260
cgcggcttcc gtatcgagcc gggcgagatc gaatccgtca tcgccgggtg ccgcggggtc    1320
cggcaggccg ccgtcgtcct gcgtgaggac cggcccggag agccatacct cgccgcctac    1380
gtcatacccg agaacgcggc cgccgacgag gcggccggcg aggaaccgga cggtcaactc    1440
gatgcctggc gacggctcta cgacgatctg tacggccgag ccgacaccgc cgacttcggc    1500
gaggacttct ccggctgggt gagcagttat ggcgggcggc cgatcgaggg gatgcgcgaa    1560
tggcgtgagc agaccgtgcg gcagatccgc gaactggctc cgccgcgt actggagatc     1620 ggctgcggtt ccggtctgct gctctcgcag ctggcgggtg actgcgaaag ctactggggc    1680
accgacatct ccggggccct gatcgagcgg ctgcgcgggc aggtcgccga gcgccccggc    1740
ctcgcggacc gggtcgtcct gcatcagctc tccgcccatg agctggggag tctgcccagc    1800
ggcggcttcg acaccgtcgt gctcaactcc gtgatccagt actttccctc aggcgattac    1860
ctgttcgacc tactcgcga ggtgtcccgg ctcctggtac ccggggcgc ggtgttcctc      1920 ggcgacgtcc gtaaccttcg tctgctgcgc accttccacg ccgggggct gctggcggcg    1980 gccacgcaca ccgacactcc gcagacggtc tgcgcggcga tcgaccgggc catggcgcag    2040
gagaaggaac tgctcgtgga cccggagttc ttcacgacgg ccgtcggcgc gctgcccggc    2100
atgacgctgg agtcgtgcac gctcaaacgg ggcgggtacg acaacgaact cagccgctat    2160
cgctacgagg tggtgctgcg caagcatgcc gggcctgccg atgacaccgg gcccacggac    2220 gacgcgggc cggtcgtgcg actgcggtgg gacggcgaga tggcgagcct ggccgacgtc     2280
gccgatcggc tgcgtcgtgg gaaaccggag cggttgtgcg tcaccgggat ccccaacggc    2340
cgggtggccg gcgagcatgc cgcgacactc gcgctgttcg accggcgccc cctgcacgag    2400
gtgctgtccc tggggcaggc tccggcgggc gtggcaccgg aggacctgcg ccggctgggc    2460
gcggaactgg gctaccgggt cgactgcacc tggtcgtccg aggacgacgc cctgatcgac    2520
gcttccttca cacgcgccgg agcgctcgtg ccgcgtcccg cccccgac cgacgcggag      2580 ccggacggtt tctccccggc ccggttcacc aacaggccgg cgttcgcccg cccgactcc    2640 cagacgatgg cctctcttcc cgggcaggtc gcggcgaagc tgccggcctt catggtcccg    2700
gaggtcttcg tcccgctcga caggctgccg gtcacggtga acgaaagct cgaccgcggc     2760 gccctgcccc ggccgcggcg cgccgcccat gcctcgggac gtccgcccag gaccgcccgc    2820
gaggaggtac tggcggcgat cttcgccgac gtactcgcga cagccgacgt cacagccgac    2880
agcgacttct tcgccgtcgg cggcaactcc ctgctggcca cccgactcgc gccgaggtc     2940 cggcggcgcc tgaacaccga gatgccgctg tcgtggctgt tcgagtcgcc caccgtcggc    3000
gcgctcgccg cccgcttcga cgcggggac gaggccaggc cgctgcccgt gccgagcgag    3060
tacgcctccg gcagcacggc gccgttgtcg gcccagcaga tgcagatgtg gcacgagtac    3120
cgccgaagcc tgtgtcgcga catgttcaac gtgccgctgt cgcagcggct gaccggtgcc    3180
gtcgacgccg aggcactgcg cgccgccctc gccgatgtcg tcacccggca cgttccgctg    3240
cgcacgctcg tccaggacga cggcagcggt ccgtgtgcgc tgatcacgga agccaccgcg    3300
gacgacatcc catggacgga gaccaggacc acgcccgagc ggctgtccga ggatctcgcg    3360
cacgccgccc ccgccacttt cgacctcgag accgagatcc cgctgcgggc cgtactgttc    3420
acgctcggcc cggacgagtc cgtactgctg ctggtcatgc atcacatcgc cgccgacggc    3480
```

```
tggtccttcg gccccctgct ggaggacctg gtccgcgcct accgcgcccg gaccgagggg    3540
cgcgcaccac agtgggagcc gctgtccttc ggctacctcg actacgtcgc ctggcagcgc    3600
cggctgctcg gcgccacgga cgacccgagc gacgtcgcgc tgcgccaggc ggagtactgg    3660
aggaagacgc tgcacggtgc cgacgacagg ccggtcctgg agaccgacag cccggcgccg    3720
gcccagcagg actttgccgg caggtccctc gatcttccgc tcgaagtcgg cggccaccgg    3780
gtgctgacag ccgcggcccg tgagcacggt gtcaccgtct tcatgatcct gcacgccgcg    3840
ctcgtcgcac tgctcgcccg caggggagca ggaggggacg tcaccgtcgt gaccgcggtg    3900
gccggccgga ccgacaccca gttcgaaccg ctggtgggcc tcttcgccaa caccttggcg    3960
ctgcgcaccg acacgtcggg caaccccacc ttccgcgaac tgctggaccg ggtccgcgtg    4020
accgatctcg gtgcctatgc ccaccaggac ctgctcttcg agcgcctggc cgacgtgcca    4080 ccgcccagg tgtcactcgt cctgcgcacg gtcgcagctc cgccggccga cctgccgggc    4140
ctcaccatca gtcccggccc acggccggcg agcgaatccg cccgctatcc ggtgctgtgg    4200
accgtggagc atctggcctc cgccgcggac ggcgggacgc tgcgcagcca catccagtac    4260
cagagcgggc tgctgcgcga cgacacggtc gtccggctcg cccagcagta cgaagtcgtg    4320
ctgtccctgt tgttgaagga tcccgatctc cgcgtccagg acctcccact gcagtga       4377
```

<210> SEQ ID NO 2
<211> LENGTH: 1458
<212> TYPE: PRT
<213> ORGANISM: Streptomyces scabies

<400> SEQUENCE: 2

```
Val Ser His Leu Thr Gly Glu Asp Leu Pro Glu Gly Ala Leu Ala Thr
1               5                   10                  15

Thr Trp Pro Ser Leu Leu Glu Ala Arg Val Ala Asp Thr Pro Asp Ala
            20                  25                  30

Ile Ala Leu Val Ala Gly Asp Thr Ala Leu Thr Tyr Ala Gln Phe Asn
        35                  40                  45

Ala Arg Ala Asn Arg Leu Ala Arg Trp Leu Lys Tyr Leu Gly Ala Gly
    50                  55                  60

Pro Glu Arg Ser Val Gly Leu Val Leu Gly Arg Ser Ala Asp Phe Phe
65                  70                  75                  80

Leu Cys Ala Thr Ala Val Leu Lys Cys Gly Ala Ala Tyr Leu Pro Leu
                85                  90                  95

Asp Pro Asn Tyr Pro Val Glu Arg Leu Ser Phe Met Ala Arg Asp Ala
            100                 105                 110

Ala Pro Val Val Leu Val Thr Thr Ser Asp Val Arg Gly Asp Leu Leu
        115                 120                 125

Gly Gln Leu Pro Thr Gly Ser Leu Val Val Leu Asp Asp Glu Ala Thr
    130                 135                 140

Glu Asp Val Leu Arg Arg Leu Pro Asp His Asp Met Glu Asp Gly Glu
145                 150                 155                 160

Arg Leu Glu Pro Leu Arg Pro Ala Ser Pro Ala Tyr Ile Ile Tyr Thr
                165                 170                 175

Ser Gly Ser Thr Gly Ile Pro Lys Gly Val Val Thr His Gln Gly
            180                 185                 190

Val Ala Ser Leu Ile Ala Thr Gln Arg Arg Leu Ala Val Thr Gly
        195                 200                 205

Ala Ser Arg Val Leu Ala Phe Ser Ser Pro Ser Phe Asp Ala Ser Phe
    210                 215                 220
```

-continued

```
Trp Glu Met Ser Met Ala Leu Leu Ala Gly Ala Ala Leu Val Val Gly
225                 230                 235                 240

Arg Pro Gly Arg Leu Leu Pro Asp Ala Glu Leu Ala Ala Leu Ile Ala
            245                 250                 255

Asp His Gly Val Thr His Val Thr Leu Pro Pro Ser Val Ala Gly Ala
            260                 265                 270

Leu Gly Pro Asp Met Leu Pro Pro Ser Val Thr Leu Val Val Ala Gly
            275                 280                 285

Glu Ala Cys Pro Ala Ala Leu Val Gln Arg Trp Arg Pro His Arg Thr
290                 295                 300

Met Val Asn Ala Tyr Gly Pro Thr Glu Ser Thr Val Cys Ala Thr Met
305                 310                 315                 320

Ser Asp Pro Leu Ala Asp Val Ala Pro Pro Val Gly Arg Ala Val
                325                 330                 335

Asp Gly Thr Arg Ile His Val Leu Asp Asp Arg Leu Ala Pro Val Val
            340                 345                 350

Pro Gly Ala Val Gly Glu Ile Tyr Ile Ala Gly His Ser Leu Ala Arg
            355                 360                 365

Gly Tyr Leu Glu Arg Pro Gly Leu Thr Ala Gln Arg Phe Val Ala Asp
370                 375                 380

Pro Phe Gly Pro Ala Gly Ser Arg Met Tyr Arg Ser Gly Asp Leu Gly
385                 390                 395                 400

Arg Trp Thr Arg Ser Gly Asp Leu Glu Phe Val Gly Arg Ala Asp Asp
                405                 410                 415

Gln Val Lys Val Arg Gly Phe Arg Ile Glu Pro Gly Glu Ile Glu Ser
            420                 425                 430

Val Ile Ala Gly Cys Arg Gly Val Arg Gln Ala Ala Val Val Leu Arg
            435                 440                 445

Glu Asp Arg Pro Gly Glu Pro Tyr Leu Ala Ala Tyr Val Ile Pro Glu
450                 455                 460

Asn Ala Ala Ala Asp Glu Ala Gly Glu Glu Pro Asp Gly Gln Leu
465                 470                 475                 480

Asp Ala Trp Arg Arg Leu Tyr Asp Asp Leu Tyr Gly Arg Ala Asp Thr
                485                 490                 495

Ala Asp Phe Gly Glu Asp Phe Ser Gly Trp Val Ser Ser Tyr Gly Gly
            500                 505                 510

Arg Pro Ile Glu Gly Met Arg Glu Trp Arg Glu Gln Thr Val Arg Gln
            515                 520                 525

Ile Arg Glu Leu Ala Pro Arg Val Leu Glu Ile Gly Cys Gly Ser
530                 535                 540

Gly Leu Leu Leu Ser Gln Leu Ala Gly Asp Cys Glu Ser Tyr Trp Gly
545                 550                 555                 560

Thr Asp Ile Ser Gly Ala Leu Ile Glu Arg Leu Arg Gly Gln Val Ala
                565                 570                 575

Glu Arg Pro Gly Leu Ala Asp Arg Val Val Leu His Gln Leu Ser Ala
            580                 585                 590

His Glu Leu Gly Ser Leu Pro Ser Gly Phe Asp Thr Val Val Leu
            595                 600                 605

Asn Ser Val Ile Gln Tyr Phe Pro Ser Gly Asp Tyr Leu Phe Asp Leu
            610                 615                 620

Leu Arg Glu Val Ser Arg Leu Leu Val Pro Gly Gly Ala Val Phe Leu
625                 630                 635                 640
```

-continued

```
Gly Asp Val Arg Asn Leu Arg Leu Leu Arg Thr Phe His Ala Gly Gly
            645                 650                 655

Leu Leu Ala Ala Ala Thr His Thr Asp Thr Pro Gln Thr Val Cys Ala
        660                 665                 670

Ala Ile Asp Arg Ala Met Ala Gln Glu Lys Glu Leu Leu Val Asp Pro
    675                 680                 685

Glu Phe Phe Thr Thr Ala Val Gly Ala Leu Pro Gly Met Thr Leu Glu
690                 695                 700

Ser Cys Thr Leu Lys Arg Gly Gly Tyr Asp Asn Glu Leu Ser Arg Tyr
705                 710                 715                 720

Arg Tyr Glu Val Val Leu Arg Lys His Ala Gly Pro Ala Asp Asp Thr
                725                 730                 735

Gly Pro Thr Asp Asp Ala Gly Pro Val Val Arg Leu Arg Trp Asp Gly
            740                 745                 750

Glu Met Ala Ser Leu Ala Asp Val Ala Asp Arg Leu Arg Arg Gly Lys
        755                 760                 765

Pro Glu Arg Leu Cys Val Thr Gly Ile Pro Asn Gly Arg Val Ala Gly
    770                 775                 780

Glu His Ala Ala Thr Leu Ala Leu Phe Asp Arg Arg Pro Leu His Glu
785                 790                 795                 800

Val Leu Ser Leu Gly Gln Ala Pro Ala Gly Val Ala Pro Glu Asp Leu
                805                 810                 815

Arg Arg Leu Gly Ala Glu Leu Gly Tyr Arg Val Asp Cys Thr Trp Ser
            820                 825                 830

Ser Glu Asp Asp Ala Leu Ile Asp Ala Ser Phe Thr Arg Ala Gly Ala
        835                 840                 845

Leu Val Pro Arg Pro Ala Pro Arg Thr Asp Ala Glu Pro Asp Gly Phe
    850                 855                 860

Ser Pro Ala Arg Phe Thr Asn Arg Pro Ala Phe Ala Arg Pro Asp Ser
865                 870                 875                 880

Gln Thr Met Ala Ser Leu Pro Gly Gln Val Ala Ala Lys Leu Pro Ala
                885                 890                 895

Phe Met Val Pro Glu Val Phe Val Pro Leu Asp Arg Leu Pro Val Thr
            900                 905                 910

Val Asn Gly Lys Leu Asp Arg Gly Ala Leu Pro Arg Pro Arg Arg Ala
        915                 920                 925

Ala His Ala Ser Gly Arg Pro Pro Arg Thr Ala Arg Glu Glu Val Leu
    930                 935                 940

Ala Ala Ile Phe Ala Asp Val Leu Ala Thr Ala Asp Val Thr Ala Asp
945                 950                 955                 960

Ser Asp Phe Phe Ala Val Gly Gly Asn Ser Leu Leu Ala Thr Arg Leu
                965                 970                 975

Ala Ala Glu Val Arg Arg Arg Leu Asn Thr Glu Met Pro Leu Ser Trp
            980                 985                 990

Leu Phe Glu Ser Pro Thr Val Gly Ala Leu Ala Ala Arg Phe Asp Ala
        995                 1000                1005

Gly Asp Glu Ala Arg Pro Leu Pro Val Pro Ser Glu Tyr Ala Ser
    1010                1015                1020

Gly Ser Thr Ala Pro Leu Ser Ala Gln Gln Met Gln Met Trp His
    1025                1030                1035

Glu Tyr Arg Arg Ser Leu Cys Arg Asp Met Phe Asn Val Pro Leu
    1040                1045                1050

Ser Gln Arg Leu Thr Gly Ala Val Asp Ala Glu Ala Leu Arg Ala
```

-continued

```
                1055                1060                1065
Ala Leu Ala Asp Val Val Thr Arg His Val Pro Leu Arg Thr Leu
            1070                1075                1080
Val Gln Asp Asp Gly Ser Gly Pro Cys Ala Val Ile Thr Glu Ala
            1085                1090                1095
Thr Ala Asp Asp Ile Pro Trp Thr Glu Thr Arg Thr Thr Pro Glu
            1100                1105                1110
Arg Leu Ser Glu Asp Leu Ala His Ala Ala Arg Arg His Phe Asp
            1115                1120                1125
Leu Glu Thr Glu Ile Pro Leu Arg Ala Val Leu Phe Thr Leu Gly
            1130                1135                1140
Pro Asp Glu Ser Val Leu Leu Leu Val Met His His Ile Ala Ala
            1145                1150                1155
Asp Gly Trp Ser Phe Gly Pro Leu Leu Glu Asp Leu Val Arg Ala
            1160                1165                1170
Tyr Arg Ala Arg Thr Glu Gly Arg Ala Pro Gln Trp Glu Pro Leu
            1175                1180                1185
Ser Phe Gly Tyr Leu Asp Tyr Val Ala Trp Gln Arg Arg Leu Leu
            1190                1195                1200
Gly Ala Thr Asp Asp Pro Ser Asp Val Ala Leu Arg Gln Ala Glu
            1205                1210                1215
Tyr Trp Arg Lys Thr Leu His Gly Ala Asp Asp Arg Pro Val Leu
            1220                1225                1230
Glu Thr Asp Ser Pro Ala Pro Ala Gln Gln Asp Phe Ala Gly Arg
            1235                1240                1245
Ser Leu Asp Leu Pro Leu Glu Val Gly Gly His Arg Val Leu Thr
            1250                1255                1260
Ala Ala Ala Arg Glu His Gly Val Thr Val Phe Met Ile Leu His
            1265                1270                1275
Ala Ala Leu Val Ala Leu Leu Ala Arg Arg Gly Ala Gly Gly Asp
            1280                1285                1290
Val Thr Val Val Thr Ala Val Ala Gly Arg Thr Asp Thr Gln Phe
            1295                1300                1305
Glu Pro Leu Val Gly Leu Phe Ala Asn Thr Leu Ala Leu Arg Thr
            1310                1315                1320
Asp Thr Ser Gly Asn Pro Thr Phe Arg Glu Leu Leu Asp Arg Val
            1325                1330                1335
Arg Val Thr Asp Leu Gly Ala Tyr Ala His Gln Asp Leu Leu Phe
            1340                1345                1350
Glu Arg Leu Ala Asp Val Pro Pro Gln Val Ser Leu Val Leu
            1355                1360                1365
Arg Thr Val Ala Ala Pro Pro Ala Asp Leu Pro Gly Leu Thr Ile
            1370                1375                1380
Ser Pro Gly Pro Arg Pro Ala Ser Glu Ser Ala Arg Tyr Pro Val
            1385                1390                1395
Leu Trp Thr Val Glu His Leu Ala Ser Ala Ala Asp Gly Gly Thr
            1400                1405                1410
Leu Arg Ser His Ile Gln Tyr Gln Ser Gly Leu Leu Arg Asp Asp
            1415                1420                1425
Thr Val Val Arg Leu Ala Gln Gln Tyr Glu Val Val Leu Ser Leu
            1430                1435                1440
Leu Leu Lys Asp Pro Asp Leu Arg Val Gln Asp Leu Pro Leu Gln
            1445                1450                1455
```

<210> SEQ ID NO 3
<211> LENGTH: 4467
<212> TYPE: DNA
<213> ORGANISM: Streptomyces scabies

<400> SEQUENCE: 3

```
atgtccatgc tgccgccggg gcgaagccgc accacggcct cgcccgccgg ggcccaggcc      60
ggccccgagt tcaccccggg cctatgggga cggctcttcg aagcccgtgt cgacgccgcc     120
cccgaatcca ccgcgatcaa ctccgcgagc gagcggctga gttacgccga actgaaccgg     180
cgggccaacc gcctcgccag gttgctcatc gcacgtggcg ccggcccgga gagcctggtc     240
ggtctcgccc tgccgcgctc gaccgacttc gtggtggccg tggcggccgt actgaaatcg     300
ggcgccggct acttcccgat ggatccggac tatcctccgc agcggctggc gttcatgctc     360
gccgacgccg ctcccatgct ggtgctgacc aggagtgaca tcgagcccga gctgccggcc     420
gaggcggcct cccgcacggt ggtgctggac gacccggccg tcgtacggac cctggccgac     480
tgctccgcgg cggatgtggc ggacgacgaa cgcggcgccc cgctccggac ccggcatccg     540
gcctatgtca tctacacctc gggttccacc ggtactccca aaggagtggt cctcacccac     600
cacggcatcg ccagcctggt gggcagccat gcgcgggacc tggggatcgg gccgtccagc     660
cggttgctgc tcttttcctc gccgagtttc gacggcgcct tctgggacgt gtcgatggcc     720
ttgctcactg gcgccacgct ggtggtcgca ccgcgtgaac ggctcctgcc cggaccggag     780
ttcagtgcgc tcgccgccga ggagggcatc acccacttca ccctgccggc ctccacgctc     840
gccgccctgc cggacggcgc tctgcccgcc ggggccaccg tcgtcaatgt gggcgaggcc     900
tgcaacagcg agctggtgcg ccgctggtcg ccgggccggc tgctggtgaa cgcgtacgga     960
ccgaccgaat cgaccgtctc cgcgaccatg agcggaccgt tggccggggc aggcatcccg    1020
cccatcggcc gtccgctctc ggacacccgc atccacgtcc tcgacgagcg gctccggccg    1080
gtaccgccgg gagcggtcgg agagatccac atcgccggag cggggctggc ccgcgggtac    1140
ctggggcggc ccgcgctgac cgccgagcgg ttcgtggccg acccccttcgg acgccgggc    1200
gagcggatgt accggaccgg cgaccgggtg agggtgcgtg acgacgggca actggagttc    1260
gtgggccggg tcgacgacca ggcgaagata cggggtttcc gagtggagcc ggcgaggtc    1320
gaagccgtgc tgcgcgacca tcccgaggtc gcgcaggccg cggtggtggt ccgggaggac    1380
actccgggag accagaggct cgtcgcctat gtcgtgccgg accacccggc cgtgcggcag    1440
gccgacgaca ccacctcgga gcacgtcgag gaatggcaac ggctctacga cgaggtctac    1500
agcgcagtgg gagcgctccc cctggggag gacttcagcg gctggaacag cacctacgac    1560
ggcgagccca ttcccgtgcc tcagatgcaa gcctggcggg acgccacggt cgacagcatc    1620
cgtgccctgc gaccgcgccg ggtactggag atcgcgtgg gcaccgggct gctgctgtcc    1680
cgcctcgccg gtgactgcga ggcgtactgg gccaccgact tctccgccga ggtgatcgag    1740
acactcggca agaaggtgga cgtcgacccg gtgctgcggg agaaggtcca cctgctgcac    1800
ggtcccgcac acgacctccc cggcctcccc gaggggtact tcgacaccgt tgtcctcaac    1860
tcggtgatcc agtactttcc gtcggccgac tacctggtga gcgtcctgcg cgaggcggca    1920
cgcctgctgg cgccgggcgg ccgggtgttc gtcggcgaca tccggcacct gcgtctgctg    1980
cgcccgctgc gcagcgccgt ccggctgcgc tccgccaccc ggcgggaagc ctctgcctcc    2040
gccgtccgcg cggcggtcga gcaggacctg gtggatgaga aggagttgct cctcgacccc    2100
```

```
gcgttcttcg ccgcggtacc ccggtggatc ccgcagctcc gcggggtacg cacagcggtg    2160
cagcgcggca cgcaccacaa cgaactgacc cgctaccggt acgacgcggt gctcatcaag    2220
gagccggtgg aaaccggtac cgctgcgccg gacgcgcaga cactgacctg gggcacggat    2280
gtcagcggac tgcaggagtt gtccggcctg ctggcccgca cccgcacgtc gctgctgctg    2340
cgcggcgtgc cgaacagccg gatcctcggt gaggcatcgg ccgcgacggc gctgaccacg    2400
gcccggtcgc tcgacgagcc gttgcggttg ctgcaagaac cggcggcagg gatcgacccc    2460
gaggaactgc acgccctggg cggggggcgcc ggctgcgagg tccacctcac gtggtcggcg    2520 caggaccccca cgcgactgga cgcctgtttc acacccgtgg gcggtgaacc gggcgccgtc    2580
ccgctggcgg agtccgccga cagcggcagg acgtcgcccg gtgaccacgc caaccagccg    2640
accacgcacc ggaccggcaa cgccctgatg ggcaagctcc ccggctatct ggccgccagg    2700
ctccccgcgt acctgcggcc cagcgccgtg gtacgcatcg cgtcgctccc cctcaccgtc    2760
aacggcaagc tcgaccgcac ggcgctgccc cgtcccgccc tgttcccgcg ggctgacggg    2820
caggcgcccc gcactccgcg cgaggagatc ctcgccaatc tcttcgccga tgtgctcggc    2880
ctgcccgggg tgccgaggga cgccgacttc ttcgccctgg gcggcaactc gctactggcc    2940
acgcgcctcg tcggccgtat cgcgaaacac ctcgaagtcg atgttccgat cgcctggatc    3000
ttcgagacac cgaccgtcga gggcctggcc gggcgtaccg ctccggcgag caggctccgc    3060
ccgctgttgc tctgccgcga cgagaaccac gcggcggtgc cgctctcgca cagccagtac    3120
ggcatgtggt tcatcaacca actcggcgga cccgcgagcc ggatctacaa cgtgccgtac    3180
tgcctgcgga tcacgggccg ggtggacacc ggggcgctgc ggaccgcact cgatgacgtc    3240
gtggctcgtc acgaacccct gcgtaccgtc ttccccgatg acggtgacgg ccccgccaa    3300 cgggtcctcg ccccccgagga cgccgcgtg gtccttcatg agaccgacgc cgccgaagac    3360
cgtctggccg gccacctggc gcgggccgcg gcggaaccct tcgagctcag gacggacctt    3420
cccctgcgcg cacgcctgtt ccggcacgga caggaccggt acacgctcct gctcctgatg    3480
caccacatca ccgtggacgc ctggtcgctg gccccctga cggcggacct ggcgcacgcc    3540
taccgggcgc ggctggggca gcgggccccg cagtggcagc cgctgccggt tcactatcgc    3600
gactacgccg tatggcacaa cgagcaagca gccgaggcgc aggaccgcgg cagcggcttc    3660
gggcgccagc tcgccttctg ggagcggacg ctgcgcggtc ttccggtcga dacgcggctg    3720
ccggccgacc ggagccgtcc ggccagacct acctatcgtg gcggcaccgt ccacacccac    3780
gtcgaagcct ccctccatca ggaactgctc aactgcgcgc gggagacggg cgcgacgctc    3840
ttcatggtgc tgcacgccgc gctcgcggca ctgctgaccc ggctgggcgg cggcaccgac    3900
atcgtcgtcg gcaccgctgc cgcggcgcgc acggaccccg cgctggacga cctcgtcggg    3960
ctgttcgcca acagtgtcgt ccttcgcgtc gacacctcgg gcgacccgac gttccgcacc    4020
ctgctcgctc ggaccgggc cgtggacctc gacgccttca cccaccagga ggtcccgttc    4080
gaccaggtgg tggatcgcgt caacccggca cgccacccgg cacgtcaccc gctctaccag    4140
acggccctcg tcctgcacgc accgcccggc gacggccatc gggccgactc cgtcaccctc    4200 accccccgaac cgccccgaa caccggaacg gcccgcttcg atctgatgtt caactgggac    4260
gagagccggg acagcgccgg cctcgcccag ggcctcaccg gccgtaccga gtacagctcg    4320
gacctcttct cccaggagac agtcgaactg ctcctggagc ggtatctcct gctgctgtcc    4380
gccgcggtcc gcgaccggga cgcacgcctt cacaccctgg acatcctcac cgagccggaa    4440
cggcgggcct tctcaccacg gccgtag                                       4467
```

-continued

```
<210> SEQ ID NO 4
<211> LENGTH: 1488
<212> TYPE: PRT
<213> ORGANISM: Streptomyces scabies

<400> SEQUENCE: 4
```

| | | | | | | | | | | | | | | |
|---|---|---|---|---|---|---|---|---|---|---|---|---|---|---|
| Met | Ser | Met | Leu | Pro | Pro | Gly | Arg | Ser | Arg | Thr | Thr | Ala | Ser | Pro | Ala |
| 1 | | | | 5 | | | | | 10 | | | | | 15 | |
| Gly | Ala | Gln | Ala | Gly | Pro | Glu | Phe | Thr | Pro | Gly | Leu | Trp | Gly | Arg | Leu |
| | | | 20 | | | | | 25 | | | | | 30 | | |
| Phe | Glu | Ala | Arg | Val | Asp | Ala | Ala | Pro | Glu | Ser | Thr | Ala | Ile | Asn | Ser |
| | | 35 | | | | | 40 | | | | | 45 | | | |
| Ala | Ser | Glu | Arg | Leu | Ser | Tyr | Ala | Glu | Leu | Asn | Arg | Arg | Ala | Asn | Arg |
| | 50 | | | | | 55 | | | | | 60 | | | | |
| Leu | Ala | Arg | Leu | Leu | Ile | Ala | Arg | Gly | Ala | Gly | Pro | Glu | Ser | Leu | Val |
| 65 | | | | | 70 | | | | | 75 | | | | | 80 |
| Gly | Leu | Ala | Leu | Pro | Arg | Ser | Thr | Asp | Phe | Val | Val | Ala | Val | Ala | Ala |
| | | | | 85 | | | | | 90 | | | | | 95 | |
| Val | Leu | Lys | Ser | Gly | Ala | Gly | Tyr | Phe | Pro | Met | Asp | Pro | Asp | Tyr | Pro |
| | | | 100 | | | | | 105 | | | | | 110 | | |
| Pro | Gln | Arg | Leu | Ala | Phe | Met | Leu | Ala | Asp | Ala | Ala | Pro | Met | Leu | Val |
| | | 115 | | | | | 120 | | | | | 125 | | | |
| Leu | Thr | Arg | Ser | Asp | Ile | Glu | Pro | Glu | Leu | Pro | Ala | Glu | Ala | Ala | Ser |
| | 130 | | | | | 135 | | | | | 140 | | | | |
| Arg | Thr | Val | Val | Leu | Asp | Asp | Pro | Ala | Val | Arg | Thr | Leu | Ala | Asp |
| 145 | | | | | 150 | | | | | 155 | | | | | 160 |
| Cys | Ser | Ala | Ala | Asp | Val | Ala | Asp | Glu | Arg | Gly | Ala | Pro | Leu | Arg |
| | | | | 165 | | | | | 170 | | | | | 175 | |
| Thr | Arg | His | Pro | Ala | Tyr | Val | Ile | Tyr | Thr | Ser | Gly | Ser | Thr | Gly | Thr |
| | | | 180 | | | | | 185 | | | | | 190 | | |
| Pro | Lys | Gly | Val | Val | Leu | Thr | His | His | Gly | Ile | Ala | Ser | Leu | Val | Gly |
| | | 195 | | | | | 200 | | | | | 205 | | | |
| Ser | His | Ala | Arg | Asp | Leu | Gly | Ile | Gly | Pro | Ser | Ser | Arg | Leu | Leu | Leu |
| | 210 | | | | | 215 | | | | | 220 | | | | |
| Phe | Ser | Ser | Pro | Ser | Phe | Asp | Gly | Ala | Phe | Trp | Asp | Val | Ser | Met | Ala |
| 225 | | | | | 230 | | | | | 235 | | | | | 240 |
| Leu | Leu | Thr | Gly | Ala | Thr | Leu | Val | Val | Ala | Pro | Arg | Glu | Arg | Leu | Leu |
| | | | | 245 | | | | | 250 | | | | | 255 | |
| Pro | Gly | Pro | Glu | Phe | Ser | Ala | Leu | Ala | Ala | Glu | Glu | Gly | Ile | Thr | His |
| | | | 260 | | | | | 265 | | | | | 270 | | |
| Phe | Thr | Leu | Pro | Ala | Ser | Thr | Leu | Ala | Ala | Leu | Pro | Asp | Gly | Ala | Leu |
| | | 275 | | | | | 280 | | | | | 285 | | | |
| Pro | Ala | Gly | Ala | Thr | Val | Val | Asn | Val | Gly | Glu | Ala | Cys | Asn | Ser | Glu |
| | 290 | | | | | 295 | | | | | 300 | | | | |
| Leu | Val | Arg | Arg | Trp | Ser | Pro | Gly | Arg | Leu | Leu | Val | Asn | Ala | Tyr | Gly |
| 305 | | | | | 310 | | | | | 315 | | | | | 320 |
| Pro | Thr | Glu | Ser | Thr | Val | Ser | Ala | Thr | Met | Ser | Gly | Pro | Leu | Ala | Gly |
| | | | | 325 | | | | | 330 | | | | | 335 | |
| Ala | Gly | Ile | Pro | Pro | Ile | Gly | Arg | Pro | Leu | Ser | Asp | Thr | Arg | Ile | His |
| | | | 340 | | | | | 345 | | | | | 350 | | |
| Val | Leu | Asp | Glu | Arg | Leu | Arg | Pro | Val | Pro | Pro | Gly | Ala | Val | Gly | Glu |
| | | 355 | | | | | 360 | | | | | 365 | | | |
| Ile | His | Ile | Ala | Gly | Ala | Gly | Leu | Ala | Arg | Gly | Tyr | Leu | Gly | Arg | Pro |

```
                370             375             380
Ala Leu Thr Ala Glu Arg Phe Val Ala Asp Pro Phe Gly Thr Pro Gly
385             390             395             400

Glu Arg Met Tyr Arg Thr Gly Asp Arg Val Arg Val Arg Asp Asp Gly
                405             410             415

Gln Leu Glu Phe Val Gly Arg Val Asp Asp Gln Ala Lys Ile Arg Gly
                420             425             430

Phe Arg Val Glu Pro Gly Glu Val Ala Val Leu Arg Asp His Pro
            435             440             445

Glu Val Ala Gln Ala Ala Val Val Arg Glu Asp Thr Pro Gly Asp
            450             455             460

Gln Arg Leu Val Ala Tyr Val Val Pro Asp His Pro Ala Val Arg Gln
465             470             475             480

Ala Asp Asp Thr Thr Ser Glu His Val Glu Glu Trp Gln Arg Leu Tyr
                485             490             495

Asp Glu Val Tyr Ser Ala Val Gly Ala Leu Pro Leu Gly Glu Asp Phe
                500             505             510

Ser Gly Trp Asn Ser Thr Tyr Asp Gly Glu Pro Ile Pro Val Pro Gln
                515             520             525

Met Gln Ala Trp Arg Asp Ala Thr Val Asp Ser Ile Arg Ala Leu Arg
                530             535             540

Pro Arg Arg Val Leu Glu Ile Gly Val Gly Thr Gly Leu Leu Leu Ser
545             550             555             560

Arg Leu Ala Gly Asp Cys Glu Ala Tyr Trp Ala Thr Asp Phe Ser Ala
                565             570             575

Glu Val Ile Glu Thr Leu Gly Lys Lys Val Asp Val Asp Pro Val Leu
                580             585             590

Arg Glu Lys Val His Leu Leu His Gly Pro Ala His Asp Leu Pro Gly
                595             600             605

Leu Pro Glu Gly Tyr Phe Asp Thr Val Val Leu Asn Ser Val Ile Gln
            610             615             620

Tyr Phe Pro Ser Ala Asp Tyr Leu Val Ser Val Leu Arg Glu Ala Ala
625             630             635             640

Arg Leu Leu Ala Pro Gly Gly Arg Val Phe Val Gly Asp Ile Arg His
                645             650             655

Leu Arg Leu Leu Arg Pro Leu Arg Ser Ala Val Arg Leu Arg Ser Ala
                660             665             670

Thr Arg Arg Glu Ala Ser Ala Ser Ala Val Arg Ala Ala Val Glu Gln
                675             680             685

Asp Leu Val Asp Glu Lys Glu Leu Leu Leu Asp Pro Ala Phe Phe Ala
            690             695             700

Ala Val Pro Arg Trp Ile Pro Gln Leu Arg Gly Val Arg Thr Ala Val
705             710             715             720

Gln Arg Gly Thr His His Asn Glu Leu Thr Arg Tyr Arg Tyr Asp Ala
                725             730             735

Val Leu Ile Lys Glu Pro Val Glu Thr Gly Thr Ala Ala Pro Asp Ala
                740             745             750

Gln Thr Leu Thr Trp Gly Thr Asp Val Ser Gly Leu Gln Glu Leu Ser
                755             760             765

Gly Leu Leu Ala Arg Thr Arg Thr Ser Leu Leu Arg Gly Val Pro
            770             775             780

Asn Ser Arg Ile Leu Gly Glu Ala Ser Ala Ala Thr Ala Leu Thr Thr
785             790             795             800
```

```
Ala Arg Ser Leu Asp Glu Pro Leu Arg Leu Leu Gln Glu Pro Ala Ala
            805                 810                 815

Gly Ile Asp Pro Glu Glu Leu His Ala Leu Gly Gly Ala Gly Cys
        820                 825                 830

Glu Val His Leu Thr Trp Ser Ala Gln Asp Pro Thr Arg Leu Asp Ala
        835                 840                 845

Cys Phe Thr Pro Val Gly Gly Glu Pro Gly Ala Val Pro Leu Ala Glu
    850                 855                 860

Ser Ala Asp Ser Gly Arg Thr Ser Pro Gly Asp His Ala Asn Gln Pro
865                 870                 875                 880

Thr Thr His Arg Thr Gly Asn Ala Leu Met Gly Lys Leu Pro Gly Tyr
                885                 890                 895

Leu Ala Ala Arg Leu Pro Ala Tyr Leu Arg Pro Ser Ala Val Val Arg
                900                 905                 910

Ile Ala Ser Leu Pro Leu Thr Val Asn Gly Lys Leu Asp Arg Thr Ala
                915                 920                 925

Leu Pro Arg Pro Ala Leu Phe Pro Arg Ala Asp Gly Gln Ala Pro Arg
    930                 935                 940

Thr Pro Arg Glu Glu Ile Leu Ala Asn Leu Phe Ala Asp Val Leu Gly
945                 950                 955                 960

Leu Pro Gly Val Pro Arg Asp Ala Asp Phe Phe Ala Leu Gly Gly Asn
                965                 970                 975

Ser Leu Leu Ala Thr Arg Leu Val Gly Arg Ile Ala Lys His Leu Glu
                980                 985                 990

Val Asp Val Pro Ile Ala Trp Ile Phe Glu Thr Pro Thr Val Glu Gly
                995                 1000                1005

Leu Ala Gly Arg Thr Ala Pro Ala Ser Arg Leu Arg Pro Leu Leu
    1010                1015                1020

Leu Cys Arg Asp Glu Asn His Ala Ala Val Pro Leu Ser His Ser
    1025                1030                1035

Gln Tyr Gly Met Trp Phe Ile Asn Gln Leu Gly Gly Pro Ala Ser
    1040                1045                1050

Arg Ile Tyr Asn Val Pro Tyr Cys Leu Arg Ile Thr Gly Arg Val
    1055                1060                1065

Asp Thr Gly Ala Leu Arg Thr Ala Leu Asp Asp Val Val Ala Arg
    1070                1075                1080

His Glu Pro Leu Arg Thr Val Phe Pro Asp Asp Gly Asp Gly Pro
    1085                1090                1095

Arg Gln Arg Val Leu Ala Pro Glu Asp Ala Ala Val Val Leu His
    1100                1105                1110

Glu Thr Asp Ala Ala Glu Asp Arg Leu Ala Gly His Leu Ala Arg
    1115                1120                1125

Ala Ala Ala Glu Pro Phe Glu Leu Arg Thr Asp Leu Pro Leu Arg
    1130                1135                1140

Ala Arg Leu Phe Arg His Gly Gln Asp Arg Tyr Thr Leu Leu Leu
    1145                1150                1155

Leu Met His His Ile Thr Val Asp Ala Trp Ser Leu Ala Pro Leu
    1160                1165                1170

Thr Ala Asp Leu Ala His Ala Tyr Arg Ala Arg Leu Gly Gln Arg
    1175                1180                1185

Ala Pro Gln Trp Gln Pro Leu Pro Val His Tyr Arg Asp Tyr Ala
    1190                1195                1200
```

| | | | | | | | | | | |
|---|---|---|---|---|---|---|---|---|---|---|
|Val|Trp|His|Asn|Glu|Gln|Ala|Ala|Glu|Ala|Gln|Asp|Arg|Gly|Ser|
| |1205| | | |1210| | | |1215| |

Val Trp His Asn Glu Gln Ala Ala Glu Ala Gln Asp Arg Gly Ser
    1205            1210            1215

Gly Phe Gly Arg Gln Leu Ala Phe Trp Glu Arg Thr Leu Arg Gly
    1220            1225            1230

Leu Pro Val Glu Thr Arg Leu Pro Ala Asp Arg Ser Arg Pro Ala
    1235            1240            1245

Arg Pro Thr Tyr Arg Gly Gly Thr Val His Thr His Val Glu Ala
    1250            1255            1260

Ser Leu His Gln Glu Leu Leu Asn Cys Ala Arg Glu Thr Gly Ala
    1265            1270            1275

Thr Leu Phe Met Val Leu His Ala Ala Leu Ala Ala Leu Leu Thr
    1280            1285            1290

Arg Leu Gly Gly Gly Thr Asp Ile Val Val Gly Thr Ala Ala Ala
    1295            1300            1305

Ala Arg Thr Asp Pro Ala Leu Asp Asp Leu Val Gly Leu Phe Ala
    1310            1315            1320

Asn Ser Val Val Leu Arg Val Asp Thr Ser Gly Asp Pro Thr Phe
    1325            1330            1335

Arg Thr Leu Leu Ala Arg Thr Arg Ala Val Asp Leu Asp Ala Phe
    1340            1345            1350

Thr His Gln Glu Val Pro Phe Asp Gln Val Val Asp Arg Val Asn
    1355            1360            1365

Pro Ala Arg His Pro Ala Arg His Pro Leu Tyr Gln Thr Ala Leu
    1370            1375            1380

Val Leu His Ala Pro Pro Gly Asp Gly His Arg Ala Asp Ser Val
    1385            1390            1395

Thr Leu Thr Pro Glu Pro Pro Asn Thr Gly Thr Ala Arg Phe
    1400            1405            1410

Asp Leu Met Phe Asn Trp Asp Glu Ser Arg Asp Ser Ala Gly Leu
    1415            1420            1425

Ala Gln Gly Leu Thr Gly Arg Thr Glu Tyr Ser Ser Asp Leu Phe
    1430            1435            1440

Ser Gln Glu Thr Val Glu Leu Leu Leu Glu Arg Tyr Leu Leu Leu
    1445            1450            1455

Leu Ser Ala Ala Val Arg Asp Pro Asp Ala Arg Leu His Thr Leu
    1460            1465            1470

Asp Ile Leu Thr Glu Pro Glu Arg Arg Ala Phe Ser Pro Arg Pro
    1475            1480            1485

<210> SEQ ID NO 5
<211> LENGTH: 1188
<212> TYPE: DNA
<213> ORGANISM: Streptomyces scabies

<400> SEQUENCE: 5

```
atggaatctc cggccaccca ggtcgacccg gcgaactcgc cgttggagcc ctatcacatc      60
tacccggagg ccaagtcctg cccggtggcg aaggtcggtc tgtggaacgg cacgccggcg     120
cacgtgttct ccgggtatga ggatgtgcgc accgtgctgc aggacaggcg gttcagctcg     180
gactcgcgcc gacccaactt caccgaactc actccgacgc tccagtcgca ggccgcggca     240
ccgccgttcg tacgcaccga caatcctgat caccggcgcc tgcgaggcac catcgcacgc     300
gagttcctgc ccaagcacat cgagctgctg cgccccgcga tccgcgagat cgtccagggt     360
gtgctcgacg ggctcgccga gaccgcgcct ccccaggaca tgctcgaggc cttcgccgta     420
```

| | | |
|---|---|---|
| ccggtcgcgt ccgcgaccgt cttccggctg ctggggattc cggccgagga ccgcgcgttg | 480 | |
| ctcacccgat gcgtcaaggg cgtggtctcg gcggtgggga gcgaggacga aggtgccgag | 540 | |
| gtgttccgga cactcggcga gtacatcggc gggctcgtcc aggacccctc cgaactgccc | 600 | |
| gaggacagcc tgatccggcg cctggtgacg ggcccgtacc aggagaagca gctcaccttc | 660 | |
| cacgagacca tcggcgtgat cctcatgctc atcgtcgggg gctacgacac gacggccagc | 720 | |
| accatctcgc tgtccttggt gagttatgca ctgcagccgg agaagttctc cgtcgtccac | 780 | |
| gaacacccgg agcggatacc cctgctcgtc gaggagttgc tgcgctatca caccgtctcg | 840 | |
| cagctcggac tgggcaggat cgccaccgag gacgtcgagg tgggcggcgt cacggtgcgg | 900 | |
| gccggccaga tggtggtggc ggcgctcccc ctggccaacc gggacgagag tgtcttcccg | 960 | |
| aacccggacg aactcgactt cgaccgcccg tccgtgcccc atgtcggctt cggttacgga | 1020 | |
| ccccaccagt gcgtcggcca ggcactggcc cgagtcgaac tccaggaggc cattcccgcg | 1080 | |
| gtgatccgac ggctgcccgg catgcggctc gcctgcgctc tggaagacct gccgttccgg | 1140 | |
| cacgacatgg ccacctacgg catccatgag ctgcccatga cctggtga | 1188 | |

<210> SEQ ID NO 6
<211> LENGTH: 395
<212> TYPE: PRT
<213> ORGANISM: Streptomyces scabies

<400> SEQUENCE: 6

```
Met Glu Ser Pro Ala Thr Gln Val Asp Pro Ala Asn Ser Pro Leu Glu
1               5                   10                  15

Pro Tyr His Ile Tyr Pro Glu Ala Lys Ser Cys Pro Val Ala Lys Val
                20                  25                  30

Gly Leu Trp Asn Gly Thr Pro Ala His Val Phe Ser Gly Tyr Glu Asp
            35                  40                  45

Val Arg Thr Val Leu Gln Asp Arg Arg Phe Ser Ser Asp Ser Arg Arg
        50                  55                  60

Pro Asn Phe Thr Glu Leu Thr Pro Thr Leu Gln Ser Gln Ala Ala Ala
65                  70                  75                  80

Pro Pro Phe Val Arg Thr Asp Asn Pro Asp His Arg Arg Leu Arg Gly
                85                  90                  95

Thr Ile Ala Arg Glu Phe Leu Pro Lys His Ile Glu Leu Leu Arg Pro
            100                 105                 110

Ala Ile Arg Glu Ile Val Gln Gly Val Leu Asp Gly Leu Ala Glu Thr
        115                 120                 125

Ala Pro Pro Gln Asp Met Leu Glu Ala Phe Ala Val Pro Val Ala Ser
    130                 135                 140

Ala Thr Val Phe Arg Leu Leu Gly Ile Pro Ala Glu Asp Arg Ala Leu
145                 150                 155                 160

Leu Thr Arg Cys Val Lys Gly Val Ser Ala Val Gly Ser Glu Asp
                165                 170                 175

Glu Gly Ala Glu Val Phe Arg Thr Leu Gly Glu Tyr Ile Gly Gly Leu
            180                 185                 190

Val Gln Asp Pro Ser Glu Leu Pro Glu Asp Ser Leu Ile Arg Arg Leu
        195                 200                 205

Val Thr Gly Pro Tyr Gln Glu Lys Gln Leu Thr Phe His Glu Thr Ile
    210                 215                 220

Gly Val Ile Leu Met Leu Ile Val Gly Gly Tyr Asp Thr Thr Ala Ser
225                 230                 235                 240
```

```
Thr Ile Ser Leu Ser Leu Val Ser Tyr Ala Leu Gln Pro Glu Lys Phe
            245                 250                 255

Ser Val Val His Glu His Pro Glu Arg Ile Pro Leu Leu Val Glu Glu
        260                 265                 270

Leu Leu Arg Tyr His Thr Val Ser Gln Leu Gly Leu Gly Arg Ile Ala
        275                 280                 285

Thr Glu Asp Val Glu Val Gly Gly Val Thr Val Arg Ala Gly Gln Met
    290                 295                 300

Val Val Ala Ala Leu Pro Leu Ala Asn Arg Asp Glu Ser Val Phe Pro
305                 310                 315                 320

Asn Pro Asp Glu Leu Asp Phe Asp Arg Pro Ser Val Pro His Val Gly
                325                 330                 335

Phe Gly Tyr Gly Pro His Gln Cys Val Gly Gln Ala Leu Ala Arg Val
            340                 345                 350

Glu Leu Gln Glu Ala Ile Pro Ala Val Ile Arg Arg Leu Pro Gly Met
        355                 360                 365

Arg Leu Ala Cys Ala Leu Glu Asp Leu Pro Phe Arg His Asp Met Ala
        370                 375                 380

Thr Tyr Gly Ile His Glu Leu Pro Met Thr Trp
385                 390                 395

<210> SEQ ID NO 7
<211> LENGTH: 1173
<212> TYPE: DNA
<213> ORGANISM: Streptomyces scabies

<400> SEQUENCE: 7
ttgcccgccc cgtccccgac agcgtgcccg gcactggggc ccgattcgtc ccttggcccg     60
gtcccgtcgg cggaaccggc gacgccgcag tcctgcggcg tcgccgatcc aaatgaggct    120
gaggagttcc tgcgccagtt ccacgcggag cagtccgatc agcccgtccc gctcgcccgg    180
cgcctggagc aggtccgcgc cgccatcgac gccacgggca cctaccggca caccaccgcc    240
gagctcgtgt acggtgcccg cgtcgcgtgg cgcaactcca gtcgctgcat cggccgcctg    300
tactggaaca gctgcgcgt cctggaccgc cgggacgcca cagcccccga tgagatccac    360
cggcacttgt gcacgcacct cgccaggcg accaacggcg ggcgcatcag gccggtgatt    420
tcggtcttcg ccccggactc cccggccgg ccggcccgc aggtgtggaa cgagcagctc    480
atccggtacg ccggctaccg ccgcgacgac ggcaccgtgc tcggtgaccc cgcgaccgcc    540
gacctcaccg aggccatcct ccgcctcggc tggcagggct gccccaagg gccgttcgac    600
gtcctgcccc tggtcatcga caccccgac gacaaacccc ggttcttcga gctgccgcgg    660
gagctggtct tggaggtccc tatcacccac cccgacgtcc cacgcctggc cgaactgggc    720
ctgcgctggc acgccgtacc cgtcatctcc aacatgcgcc tacgcatcgg cgggatggac    780
tacccgctcg ccccgttcaa cggctggtac atgggcacgg agatcggcgc cgcaacctc    840
gtcgacgagg accgctacaa catgctcccc gccgtcgccg cctgcctcca gctggacacc    900
accagcgagt caaccctgtg gcgcgaccgc gccctggtcg agctcaacgt cgccgtcctg    960
cactccttcg aggccgcagg tgtccggatc agcgaccacc acgaggagtc ccggcgcttc   1020
ctcgcccacc tggccaagga ggaacgccag gccgcaccg tatccgcaga ctggagctgg   1080
atcgtccccc cgctctccgg cggcatcacc ccgtgttcc accgttacta cgacaacgtc   1140
gaccagcgcc ccaacttcta cccccaccag tga                                1173
```

```
<210> SEQ ID NO 8
<211> LENGTH: 390
<212> TYPE: PRT
<213> ORGANISM: Streptomyces scabies

<400> SEQUENCE: 8

Leu Pro Ala Pro Ser Pro Thr Ala Cys Pro Ala Leu Gly Pro Asp Ser
1               5                   10                  15

Ser Leu Gly Pro Val Pro Ser Ala Glu Pro Ala Thr Pro Gln Ser Cys
            20                  25                  30

Gly Val Ala Asp Pro Asn Glu Ala Glu Phe Leu Arg Gln Phe His
        35                  40                  45

Ala Glu Gln Ser Asp Gln Pro Val Pro Leu Ala Arg Arg Leu Glu Gln
    50                  55                  60

Val Arg Ala Ala Ile Asp Ala Thr Gly Thr Tyr Arg His Thr Thr Ala
65                  70                  75                  80

Glu Leu Val Tyr Gly Ala Arg Val Ala Trp Arg Asn Ser Ser Arg Cys
                85                  90                  95

Ile Gly Arg Leu Tyr Trp Asn Ser Leu Arg Val Leu Asp Arg Arg Asp
            100                 105                 110

Ala Thr Ala Pro Asp Glu Ile His Arg His Leu Cys Thr His Leu Arg
        115                 120                 125

Gln Ala Thr Asn Gly Gly Arg Ile Arg Pro Val Ile Ser Val Phe Ala
    130                 135                 140

Pro Asp Ser Pro Gly Arg Pro Gly Pro Gln Val Trp Asn Glu Gln Leu
145                 150                 155                 160

Ile Arg Tyr Ala Gly Tyr Arg Arg Asp Asp Gly Thr Val Leu Gly Asp
                165                 170                 175

Pro Arg Thr Ala Asp Leu Thr Glu Ala Ile Leu Arg Leu Gly Trp Gln
            180                 185                 190

Gly Cys Pro Gln Gly Pro Phe Asp Val Leu Pro Leu Val Ile Asp Thr
        195                 200                 205

Pro Asp Asp Lys Pro Arg Phe Phe Glu Leu Pro Arg Glu Leu Val Leu
210                 215                 220

Glu Val Pro Ile Thr His Pro Asp Val Pro Arg Leu Ala Glu Leu Gly
225                 230                 235                 240

Leu Arg Trp His Ala Val Pro Val Ile Ser Asn Met Arg Leu Arg Ile
                245                 250                 255

Gly Gly Met Asp Tyr Pro Leu Ala Pro Phe Asn Gly Trp Tyr Met Gly
            260                 265                 270

Thr Glu Ile Gly Ala Arg Asn Leu Val Asp Glu Asp Arg Tyr Asn Met
        275                 280                 285

Leu Pro Ala Val Ala Ala Cys Leu Gln Leu Asp Thr Thr Ser Glu Ser
    290                 295                 300

Thr Leu Trp Arg Asp Arg Ala Leu Val Glu Leu Asn Val Ala Val Leu
305                 310                 315                 320

His Ser Phe Glu Ala Ala Gly Val Arg Ile Ser Asp His Glu Glu
                325                 330                 335

Ser Arg Arg Phe Leu Ala His Leu Ala Lys Glu Glu Arg Gln Gly Arg
            340                 345                 350

Thr Val Ser Ala Asp Trp Ser Trp Ile Val Pro Pro Leu Ser Gly Gly
        355                 360                 365

Ile Thr Pro Val Phe His Arg Tyr Tyr Asp Asn Val Asp Gln Arg Pro
    370                 375                 380
```

Asn Phe Tyr Pro His Gln
385                 390

<210> SEQ ID NO 9
<211> LENGTH: 1221
<212> TYPE: DNA
<213> ORGANISM: Streptomyces scabies

<400> SEQUENCE: 9

```
gtgaccgtcc cctcgccgct cgccgacccg tccatcgtgc ccgaccccta ccctgtctac      60
gccgacctgg cccagcgccg ccccgtccac tgggtcgagc gcctgaacgc ctgggcggtc     120
ttgacgtacg ccgactgcgc cgccgggctg aaggatcccc ggctcaccgc cgaccggggg     180
acggaagtgc tggccgcgaa gttccccgga cagccgctgc cgccggacaa catcttccac     240
cgctggacca agaacgtggt gatgtacacg gacccgccgc tccacgacgc gctacgccgg     300
tccgtccgcg caggcttcac ccgtgccgcg caccagcact acgaccaagt cctccagaag     360
gtcgcgcacg acctggtcgc ttccatcccg gccggtgcca ccgagatcga cgccgtcccc     420
gccctggctg ccgaactccc cgtacgctcc gccgtgcacg ccttcggggt ccccgaggag     480
gacctcggat tcctcatccc gcgcgtgaat acgatcatga cgtaccactc cggtccgaag     540
gatcagccgg tgacgcagga gataatcctg gaaaagctca ccgacctgca cacgtacgcc     600
tccgaactcc tccagggcat gcggggcaag gtcctgccgg acaccgtcat cgcccgcctg     660
gcagccgccc aggacggcct gaccgagacc acgccggaac agaccgtgca ccagctggcg     720
ctggtgttca tcgcgttgtt cgcgcccacg acgccgggct ctctcagcag cggcacgctc     780
gcgttcgccc gcaacccgcg gcaggtcgaa cgcttcctgg cggaccaggc gtgcgtggac     840
aacacggcga acgaggtcct ccgctacaac gcctcgaacc agttcacctg gcgcgtcgcg     900
gccaaggacg tcgagatggg cggcgtacgg atcgaggccg ggcagactct cgccctgttc     960
ctgggctcgg ccaaccggga cgccaacatg ttcgagcgac cgaacgactt cgacctcgac    1020
cgtcccaaca gcgctcggca cctgtcgttc ggccaagggg tgcacgcctg tctcgccgcg    1080
cagctcatct ccctgcagct gaagtggttc tacgtcgccc tgctgaaccg cttcccgggc    1140
atccggacgg cgggcgagcc gatctggaac gagaacctcg aattccgctc ccttcgctcc    1200
ctgccgctca gcctccgctg a                                              1221
```

<210> SEQ ID NO 10
<211> LENGTH: 406
<212> TYPE: PRT
<213> ORGANISM: Streptomyces scabies

<400> SEQUENCE: 10

Val Thr Val Pro Ser Pro Leu Ala Asp Pro Ser Ile Val Pro Asp Pro
1               5                   10                  15

Tyr Pro Val Tyr Ala Asp Leu Ala Gln Arg Arg Pro Val His Trp Val
            20                  25                  30

Glu Arg Leu Asn Ala Trp Ala Val Leu Thr Tyr Ala Asp Cys Ala Ala
        35                  40                  45

Gly Leu Lys Asp Pro Arg Leu Thr Ala Asp Arg Gly Thr Glu Val Leu
    50                  55                  60

Ala Ala Lys Phe Pro Gly Gln Pro Leu Pro Pro Asp Asn Ile Phe His
65                  70                  75                  80

Arg Trp Thr Lys Asn Val Val Met Tyr Thr Asp Pro Pro Leu His Asp
                85                  90                  95

```
Ala Leu Arg Arg Ser Val Arg Ala Gly Phe Thr Arg Ala Ala His Gln
                100                 105                 110

His Tyr Asp Gln Val Leu Gln Lys Val Ala His Asp Leu Val Ala Ser
            115                 120                 125

Ile Pro Ala Gly Ala Thr Glu Ile Asp Ala Val Pro Ala Leu Ala Ala
        130                 135                 140

Glu Leu Pro Val Arg Ser Ala Val His Ala Phe Gly Val Pro Glu Glu
145                 150                 155                 160

Asp Leu Gly Phe Leu Ile Pro Arg Val Asn Thr Ile Met Thr Tyr His
                165                 170                 175

Ser Gly Pro Lys Asp Gln Pro Val Thr Gln Glu Ile Ile Leu Glu Lys
            180                 185                 190

Leu Thr Asp Leu His Thr Tyr Ala Ser Glu Leu Leu Gln Gly Met Arg
        195                 200                 205

Gly Lys Val Leu Pro Asp Thr Val Ile Ala Arg Leu Ala Ala Ala Gln
210                 215                 220

Asp Gly Leu Thr Glu Thr Thr Pro Glu Gln Thr Val His Gln Leu Ala
225                 230                 235                 240

Leu Val Phe Ile Ala Leu Phe Ala Pro Thr Thr Pro Gly Ser Leu Ser
                245                 250                 255

Ser Gly Thr Leu Ala Phe Ala Arg Asn Pro Arg Gln Val Glu Arg Phe
            260                 265                 270

Leu Ala Asp Gln Ala Cys Val Asp Asn Thr Ala Asn Glu Val Leu Arg
        275                 280                 285

Tyr Asn Ala Ser Asn Gln Phe Thr Trp Arg Val Ala Ala Lys Asp Val
290                 295                 300

Glu Met Gly Gly Val Arg Ile Glu Ala Gly Gln Thr Leu Ala Leu Phe
305                 310                 315                 320

Leu Gly Ser Ala Asn Arg Asp Ala Asn Met Phe Glu Arg Pro Asn Asp
                325                 330                 335

Phe Asp Leu Asp Arg Pro Asn Ser Ala Arg His Leu Ser Phe Gly Gln
            340                 345                 350

Gly Val His Ala Cys Leu Ala Ala Gln Leu Ile Ser Leu Gln Leu Lys
        355                 360                 365

Trp Phe Tyr Val Ala Leu Leu Asn Arg Phe Pro Gly Ile Arg Thr Ala
370                 375                 380

Gly Glu Pro Ile Trp Asn Glu Asn Leu Glu Phe Arg Ser Leu Arg Ser
385                 390                 395                 400

Leu Pro Leu Ser Leu Arg
                405

<210> SEQ ID NO 11
<211> LENGTH: 198
<212> TYPE: DNA
<213> ORGANISM: Streptomyces scabies

<400> SEQUENCE: 11
gtgccctcac ccttcgacga ccatgacggg cagttccatg tgctccgcaa cgaggaaggc      60
cagttctcac tctggccgaa tttcgccgac atcccctccg ggtggcgttc cgtgagcggg     120
ccgagccccc gcggaagcgc ccttgagtac atcgagaagg aatggacgga catgcgcccg     180
gcgtccgtcc gtgaatga                                                  198

<210> SEQ ID NO 12
<211> LENGTH: 65
```

```
<212> TYPE: PRT
<213> ORGANISM: Streptomyces scabies

<400> SEQUENCE: 12

Val Pro Ser Pro Phe Asp Asp His Asp Gly Gln Phe His Val Leu Arg
1               5                   10                  15

Asn Glu Glu Gly Gln Phe Ser Leu Trp Pro Asn Phe Ala Asp Ile Pro
            20                  25                  30

Ser Gly Trp Arg Ser Val Ser Gly Pro Ser Arg Gly Ser Ala Leu
        35                  40                  45

Glu Tyr Ile Glu Lys Glu Trp Thr Asp Met Arg Pro Ala Ser Val Arg
    50                  55                  60

Glu
65

<210> SEQ ID NO 13
<211> LENGTH: 834
<212> TYPE: DNA
<213> ORGANISM: Streptomyces scabies

<400> SEQUENCE: 13
atgcagataa aatctttcaa ggccggcggg gtcaaggtga cgatcataga ttccggtcca     60
gccgtcatcg agttcgaggc aatcaactcg gaggcggcct tgacgccgca gagaacagtc   120
atatgcgtac tgtcaggaat ggcgttcatc gctggtaccg aaacggtac ggagatcgac    180 gcggggacgc tggttatgac ggacggcgac gttccctttt cgatgaatgt gcccgttgct   240
tcgcgactcc tcgtactgcg tttcgccgac gaagcgaagg atggactccc ggtgtcgcct   300
cgggggactt tatcgtgac ggatgctgcc aagggtcccg gatccggatt tcttttttcg    360
ttcttgaata ccctggctgt ggagatgatg aaaaccgatg ggattctgtc ctcgtatatg   420
gaggaggtcg tgcgcatcct ggcgatctcc gcgacgcgaa tcgcatatgc cgagctcgga   480
aagcattact ctgggggatg cgatccactt ctgatcgcgg ttcaggagtc gatcgaccgg   540
cagttggccg accccgagat cagcccggcg accctcgcgg ccgaacacaa catatcggtg   600
cgtcagttac atcgagtttt cggaccgatc ggggaaagcg tcatgagcta tgtcaaacgc   660
cgtcgcctgg agcgtttcgc atgcgatctg agggatccga gcctggggca cggaagatc    720 aatgagctgg cggcggactg ggggatgctg atgccgcga tgctgagcag acacttccgc    780
tgcgcctacg aatgtcgcc ccgcgattac cggaagcagc actgtttcac ctga           834

<210> SEQ ID NO 14
<211> LENGTH: 277
<212> TYPE: PRT
<213> ORGANISM: Streptomyces scabies

<400> SEQUENCE: 14

Met Gln Ile Lys Ser Phe Lys Ala Gly Gly Val Lys Val Thr Ile Ile
1               5                   10                  15

Asp Ser Gly Pro Ala Val Ile Glu Phe Glu Ala Ile Asn Ser Glu Ala
            20                  25                  30

Ala Leu Thr Pro Gln Arg Thr Val Ile Cys Val Leu Ser Gly Met Ala
        35                  40                  45

Phe Ile Ala Gly Thr Gly Asn Gly Thr Glu Ile Asp Ala Gly Thr Leu
    50                  55                  60

Val Met Thr Asp Gly Asp Val Pro Phe Ser Met Asn Val Pro Val Ala
65                  70                  75                  80
```

```
Ser Arg Leu Leu Val Leu Arg Phe Ala Asp Glu Ala Lys Asp Gly Leu
                85                  90                  95

Pro Val Ser Pro Arg Gly Thr Phe Ile Val Thr Asp Ala Ala Lys Gly
            100                 105                 110

Pro Gly Ser Gly Phe Leu Phe Ser Phe Leu Asn Thr Leu Ala Val Glu
        115                 120                 125

Met Met Lys Thr Asp Gly Ile Leu Ser Ser Tyr Met Glu Glu Val Val
    130                 135                 140

Arg Ile Leu Ala Ile Ser Ala Thr Arg Ile Ala Tyr Ala Glu Leu Gly
145                 150                 155                 160

Lys His Tyr Ser Gly Gly Cys Asp Pro Leu Leu Ile Ala Val Gln Glu
                165                 170                 175

Ser Ile Asp Arg Gln Leu Ala Asp Pro Glu Ile Ser Pro Ala Thr Leu
            180                 185                 190

Ala Ala Glu His Asn Ile Ser Val Arg Gln Leu His Arg Val Phe Gly
        195                 200                 205

Pro Ile Gly Glu Ser Val Met Ser Tyr Val Lys Arg Arg Arg Leu Glu
    210                 215                 220

Arg Phe Ala Cys Asp Leu Arg Asp Pro Ser Leu Gly His Arg Lys Ile
225                 230                 235                 240

Asn Glu Leu Ala Ala Asp Trp Gly Met Leu Asp Ala Ala Met Leu Ser
                245                 250                 255

Arg His Phe Arg Cys Ala Tyr Gly Met Ser Pro Arg Asp Tyr Arg Lys
                260                 265                 270

Gln His Cys Phe Thr
            275

<210> SEQ ID NO 15
<211> LENGTH: 1059
<212> TYPE: DNA
<213> ORGANISM: Streptomyces scabies

<400> SEQUENCE: 15
atggtgacag gccacgggc acggggccgg agcggtgggc ggccgacgtt ggaggaggtc    60
gccgcacggg ccggagtggg ccgggggacg gtgtcccggg tgatcaacgg ctcgccccgg   120
gtgagcgacg cgacccgcgc ggcggtcgag gcggccgtcg cggagctggg ttacgtcccg   180
aacacggcgg cccgcgcgct cgcggcgaac cgtaccgacg cgatcgcgat ggtcgtgccc   240
gaaccggaga cccgcttctt ctcggagccg tacttctccg acatcctcaa gggtgtcgga   300
gcgcaactgt ccgacaccga gatgcagctc ctgctgatct cgcgggcaa cgaccgggag   360 cgccggcgcc tcgcccagta cctggccgcg caccgcgtcg acggtgtcct cctggtctcc   420 gtccacgcg acgacccgct ccccgatctg ctgtcgcaac tggaaatccc ggccgtcatc   480
agcggccccc gctccgagca cgagacgctc ccctcggtcg actccgacaa ctacggcggc   540
ggccgctcgg cggtcgagca cctcatcgca cggggcgcg cccggatcgc acgatcacc    600 ggccggctgg acgtctacgg cgcccagcgg cgcatcgagg gctaccgcga cgccctggag   660
gacgcgggcc gcgaggtgga cgagcgcctg atcgccccg gtgacttcac ggaggagggc   720
ggccgccgag cgatgcgcga actcctggcc gctgccccg acctcgacgc ggtcttcgcc   780
gagtcggacg tcatggccgc cggcgcccgc caggtgctcc gcgaggaggg ccgccgcata   840
cccgacgacg tggcgctggt cggctacgac gactcggcga tcgcccgcca catggacccg   900
ccgctcacca gcgtccgcca gccgatagag gagatgggcc gcgcgatgat cgacctcctc   960
```

```
ctggacgaga tcgcggaccg ccgcccggcg gtgtcgaggg gcttggaacg acgccaggtg    1020
gtgctgccga cggagctggt ggggcgggat tcttcctga                           1059
```

<210> SEQ ID NO 16
<211> LENGTH: 352
<212> TYPE: PRT
<213> ORGANISM: Streptomyces scabies

<400> SEQUENCE: 16

```
Met Val Thr Gly His Gly Ala Arg Gly Arg Ser Gly Gly Arg Pro Thr
1               5                   10                  15

Leu Glu Glu Val Ala Ala Arg Ala Gly Val Gly Arg Gly Thr Val Ser
                20                  25                  30

Arg Val Ile Asn Gly Ser Pro Arg Val Ser Asp Ala Thr Arg Ala Ala
            35                  40                  45

Val Glu Ala Ala Val Ala Glu Leu Gly Tyr Val Pro Asn Thr Ala Ala
        50                  55                  60

Arg Ala Leu Ala Ala Asn Arg Thr Asp Ala Ile Ala Met Val Val Pro
65                  70                  75                  80

Glu Pro Glu Thr Arg Phe Phe Ser Glu Pro Tyr Phe Ser Asp Ile Leu
                85                  90                  95

Lys Gly Val Gly Ala Gln Leu Ser Asp Thr Glu Met Gln Leu Leu Leu
                100                 105                 110

Ile Phe Ala Gly Asn Asp Arg Glu Arg Arg Leu Ala Gln Tyr Leu
            115                 120                 125

Ala Ala His Arg Val Asp Gly Val Leu Leu Val Ser Val His Ala Asp
        130                 135                 140

Asp Pro Leu Pro Asp Leu Leu Ser Gln Leu Glu Ile Pro Ala Val Ile
145                 150                 155                 160

Ser Gly Pro Arg Ser Glu His Glu Thr Leu Pro Ser Val Asp Ser Asp
                165                 170                 175

Asn Tyr Gly Gly Gly Arg Ser Ala Val Glu His Leu Ile Ala Arg Gly
                180                 185                 190

Arg Ala Arg Ile Ala Thr Ile Thr Gly Arg Leu Asp Val Tyr Gly Ala
            195                 200                 205

Gln Arg Arg Ile Glu Gly Tyr Arg Asp Ala Leu Glu Asp Ala Gly Arg
        210                 215                 220

Glu Val Asp Glu Arg Leu Ile Ala Pro Gly Asp Phe Thr Glu Glu Gly
225                 230                 235                 240

Gly Arg Arg Ala Met Arg Glu Leu Leu Ala Arg Cys Pro Asp Leu Asp
                245                 250                 255

Ala Val Phe Ala Glu Ser Asp Val Met Ala Ala Gly Ala Arg Gln Val
                260                 265                 270

Leu Arg Glu Glu Gly Arg Arg Ile Pro Asp Asp Val Ala Leu Val Gly
            275                 280                 285

Tyr Asp Asp Ser Ala Ile Ala Arg His Met Asp Pro Pro Leu Thr Ser
        290                 295                 300

Val Arg Gln Pro Ile Glu Glu Met Gly Arg Ala Met Ile Asp Leu Leu
305                 310                 315                 320

Leu Asp Glu Ile Ala Asp Arg Arg Pro Ala Val Ser Arg Gly Leu Glu
                325                 330                 335

Arg Arg Gln Val Val Leu Pro Thr Glu Leu Val Gly Arg Asp Ser Ser
            340                 345                 350
```

<210> SEQ ID NO 17
<211> LENGTH: 1443
<212> TYPE: DNA
<213> ORGANISM: Streptomyces scabies

<400> SEQUENCE: 17

```
atgcctgaac cgtgaatcc ggccaccccg gtgacctttc ctcccgcctt cctctggggc     60
gcggccacct ccgcgtacca gatcgagggg gcggtgcggg aggacggccg tacgccctcc    120
atctgggaca ccttcagtca cacgccgggc aagaccgccg gcggcgagaa cggtgacatc    180
gctgtcgacc actaccaccg ctaccgcgac gacgtggcga tgatggcgga cctgggcctc    240
aacgcgtacc gcttctccgt ctcctggtcg cgggtgcagc cgacggggcg gggcccggcc    300
gtccagaagg ggctcgactt ctaccgacgg ctggtcgacg agctgctggc caagggcatc    360
aagcccgccg tcaccctcta ccactgggac ctcccgcagg agctggagga cgccggcggc    420
tggcccgagc gggacatcgt gcaccggttc gccgagtacg cgcggatcat gggcgaggcg    480
ctcggcgacc gcgtcgagca gtggatcacc ctcaacgagc cgtggtgcac cgcgttcctg    540
ggctacggct ccggggtgca cgcgccgggc cgtacggacc cggtggcgtc cctgcgcgcg    600
gcccaccatc tgaacgtggc gcacggcctc ggcgtctcgg cgctgcggtc ggcgatgccc    660
gcccgcaact cgatcgcggt gagcctcaac tcctcggtgg tgcggccgat caccagctcc    720
ccggaggacc gggccgcggc ccggaagatc gacgacctcg cgaacggcgt cttccacgga    780
ccgatgctgc acggggccta cccggagacc ctgttcgccg cgacctcgtc gctgacggac    840
tggtcgttcg tgcgggacgg tgacgtggcg acggcccatc agccgctgga cgctctgggg    900
ctgaactact acacgccggc gctggtcggc gcggcggacg ccggcctgga gggccccgc    960
gcggacggcc acggggcgag cgagcactcg ccgtggccgg ccgcggacga cgtcctgttc   1020
caccagaccc cgggcgagcg tacggagatg ggctggacca tcgacccgac gggcctgcac   1080
gagctgatca tgcggtacgc gcgggaggct ccgggcctgc cgatgtacgt gacggagaac   1140
ggcgccgcgt acgacgacaa gatggacgcg gacgccgtg tccacgaccc cgagcgcatc   1200
gcctacctgc acggccacct gcgggcggtc cggcgcgcga tcgccgaggg gcggacgtg   1260
cgcgggtact acctgtggtc cctgatggac aacttcgagt gggcgtacgg ctacggcaag   1320
cgcttcggcg cggtgtacgt cgactacgcg accctgaccc gcacaccgaa gtcgagcgcg   1380
cactggtacg gcaggcggc gaagacgggc gccctcccgc cgctggcgcc ggcgccggcg   1440
tag                                                                 1443
```

<210> SEQ ID NO 18
<211> LENGTH: 480
<212> TYPE: PRT
<213> ORGANISM: Streptomyces scabies

<400> SEQUENCE: 18

```
Met Pro Glu Pro Val Asn Pro Ala Thr Pro Val Thr Phe Pro Pro Ala
1               5                   10                  15

Phe Leu Trp Gly Ala Ala Thr Ser Ala Tyr Gln Ile Glu Gly Ala Val
            20                  25                  30

Arg Glu Asp Gly Arg Thr Pro Ser Ile Trp Asp Thr Phe Ser His Thr
        35                  40                  45

Pro Gly Lys Thr Ala Gly Gly Glu Asn Gly Asp Ile Ala Val Asp His
    50                  55                  60

Tyr His Arg Tyr Arg Asp Asp Val Ala Met Met Ala Asp Leu Gly Leu
65                  70                  75                  80
```

```
Asn Ala Tyr Arg Phe Ser Val Ser Trp Ser Arg Val Gln Pro Thr Gly
                85                  90                  95

Arg Gly Pro Ala Val Gln Lys Gly Leu Asp Phe Tyr Arg Arg Leu Val
            100                 105                 110

Asp Glu Leu Leu Ala Lys Gly Ile Lys Pro Ala Val Thr Leu Tyr His
        115                 120                 125

Trp Asp Leu Pro Gln Glu Leu Glu Asp Ala Gly Gly Trp Pro Glu Arg
130                 135                 140

Asp Ile Val His Arg Phe Ala Glu Tyr Ala Arg Ile Met Gly Glu Ala
145                 150                 155                 160

Leu Gly Asp Arg Val Glu Gln Trp Ile Thr Leu Asn Glu Pro Trp Cys
                165                 170                 175

Thr Ala Phe Leu Gly Tyr Gly Ser Gly Val His Ala Pro Gly Arg Thr
            180                 185                 190

Asp Pro Val Ala Ser Leu Arg Ala Ala His His Leu Asn Val Ala His
        195                 200                 205

Gly Leu Gly Val Ser Ala Leu Arg Ser Ala Met Pro Ala Arg Asn Ser
    210                 215                 220

Ile Ala Val Ser Leu Asn Ser Ser Val Val Arg Pro Ile Thr Ser Ser
225                 230                 235                 240

Pro Glu Asp Arg Ala Ala Arg Lys Ile Asp Asp Leu Ala Asn Gly
                245                 250                 255

Val Phe His Gly Pro Met Leu His Gly Ala Tyr Pro Glu Thr Leu Phe
                260                 265                 270

Ala Ala Thr Ser Ser Leu Thr Asp Trp Ser Phe Val Arg Asp Gly Asp
            275                 280                 285

Val Ala Thr Ala His Gln Pro Leu Asp Ala Leu Gly Leu Asn Tyr Tyr
        290                 295                 300

Thr Pro Ala Leu Val Gly Ala Ala Asp Ala Gly Leu Glu Gly Pro Arg
305                 310                 315                 320

Ala Asp Gly His Gly Ala Ser Glu His Ser Pro Trp Pro Ala Ala Asp
                325                 330                 335

Asp Val Leu Phe His Gln Thr Pro Gly Glu Arg Thr Glu Met Gly Trp
            340                 345                 350

Thr Ile Asp Pro Thr Gly Leu His Glu Leu Ile Met Arg Tyr Ala Arg
        355                 360                 365

Glu Ala Pro Gly Leu Pro Met Tyr Val Thr Glu Asn Gly Ala Ala Tyr
    370                 375                 380

Asp Asp Lys Met Asp Ala Asp Gly Arg Val His Asp Pro Glu Arg Ile
385                 390                 395                 400

Ala Tyr Leu His Gly His Leu Arg Ala Val Arg Arg Ala Ile Ala Glu
                405                 410                 415

Gly Ala Asp Val Arg Gly Tyr Tyr Leu Trp Ser Leu Met Asp Asn Phe
            420                 425                 430

Glu Trp Ala Tyr Gly Tyr Gly Lys Arg Phe Gly Ala Val Tyr Val Asp
        435                 440                 445

Tyr Ala Thr Leu Thr Arg Thr Pro Lys Ser Ser Ala His Trp Tyr Gly
    450                 455                 460

Gln Ala Ala Lys Thr Gly Ala Leu Pro Pro Leu Ala Pro Ala Pro Ala
465                 470                 475                 480

<210> SEQ ID NO 19
<211> LENGTH: 1369
```

```
<212> TYPE: DNA
<213> ORGANISM: Artificial Sequence
<220> FEATURE:
<223> OTHER INFORMATION: chemically synthesized apramycin resistance
      gene deletion cassette

<400> SEQUENCE: 19
attccgggga tccgtcgacc tgcagttcga agttcctatt ctctagaaag tataggaact      60
tcgaagttcc cgccagcctc gcagagcagg attcccgttg agcaccgcca ggtgcgaata     120
agggacagtg aagaaggaac acccgctcgc gggtgggcct acttcaccta tcctgcccgg    180
ctgacgccgt tggatacacc aaggaaagtc tacacgaacc cttttggcaaa atcctgtata    240 tcgtgcgaaa aaggatggat ataccgaaaa aatcgctata atgaccccga agcagggtta    300
tgcagcggaa aatgcagctc acggtaactg atgccgtatt tgcagtacca gcgtacggcc    360
cacagaatga tgtcacgctg aaaatgccgg cctttgaatg ggttcatgtg cagctccatc    420
agcaaaaggg gatgataagt ttatcaccac cgactatttg caacagtgcc gttgatcgtg    480
ctatgatcga ctgatgtcat cagcggtgga gtgcaatgtc gtgcaatacg aatggcgaaa    540
agccgagctc atcggtcagc ttctcaacct tggggttacc cccggcggtg tgctgctggt    600
ccacagctcc ttccgtagcg tccggcccct cgaagatggg ccacttggac tgatcgaggc    660
cctgcgtgct gcgctgggtc cgggagggac gctcgtcatg ccctcgtggt caggtctgga    720
cgacgagccg ttcgatcctg ccacgtcgcc cgttacaccg gaccttggag ttgtctctga    780
cacattctgg cgcctgccaa atgtaaagcg cagcgcccat ccatttgcct tgcggcagc    840 ggggccacag gcagagcaga tcatctctga tccattgccc ctgccacctc actcgcctgc    900
aagcccggtc gcccgtgtcc atgaactcga tgggcaggta cttctcctcg gcgtgggaca    960
cgatgccaac acgacgctgc atcttgccga gttgatggca aaggttccct atggggtgcc   1020
gagacactgc accattcttc aggatggcaa gttggtacgc gtcgattatc tcgagaatga   1080
ccactgctgt gagcgctttg ccttggcgga caggtggctc aaggagaaga gccttcagaa   1140
ggaaggtcca gtcggtcatg cctttgctcg gttgatccgc tcccgcgaca ttgtggcgac   1200
agccctgggt caactgggcc gagatccgtt gatcttcctg catccgccag aggcgggatg   1260
cgaagaatgc gatgccgctc gccagtcgat tggctgagct cataagttcc tattccgaag   1320
ttcctattct ctagaaagta taggaacttc gaagcagctc agcctaca                 1369

<210> SEQ ID NO 20
<211> LENGTH: 20
<212> TYPE: DNA
<213> ORGANISM: Artificial Sequence
<220> FEATURE:
<223> OTHER INFORMATION: chemically synthesized primer to detect
      integration of TR in aviX1

<400> SEQUENCE: 20
tccacctcct gaccaccaag                                                    20

<210> SEQ ID NO 21
<211> LENGTH: 19
<212> TYPE: DNA
<213> ORGANISM: Artificial Sequence
<220> FEATURE:
<223> OTHER INFORMATION: chemically synthesized primer to detect
      integration of TR in aviX1

<400> SEQUENCE: 21
aagatccccg aaccgacct                                                     19
```

<210> SEQ ID NO 22
<211> LENGTH: 24
<212> TYPE: DNA
<213> ORGANISM: Artificial Sequence
<220> FEATURE:
<223> OTHER INFORMATION: chemically synthesized primer for amplification
     of integrase in TR2

<400> SEQUENCE: 22
gtagcgaagg cgagagtctc actg                                          24

<210> SEQ ID NO 23
<211> LENGTH: 24
<212> TYPE: DNA
<213> ORGANISM: Artificial Sequence
<220> FEATURE:
<223> OTHER INFORMATION: chemically synthesized primer for amplification
     of integrase in TR2

<400> SEQUENCE: 23
gagccgacga acaagtacta cccg                                          24

<210> SEQ ID NO 24
<211> LENGTH: 24
<212> TYPE: DNA
<213> ORGANISM: Artificial Sequence
<220> FEATURE:
<223> OTHER INFORMATION: chemically synthesized primer to detect
     site-integration of TR2 or TR into aviX1

<400> SEQUENCE: 24
cgaagatcga gaacgtcagg aagg                                          24

<210> SEQ ID NO 25
<211> LENGTH: 24
<212> TYPE: DNA
<213> ORGANISM: Artificial Sequence
<220> FEATURE:
<223> OTHER INFORMATION: chemically synthesized primer to detect
     site-integration of TR2 or TR into aviX1

<400> SEQUENCE: 25
gaccgacgag gacttcaaga acga                                          24

<210> SEQ ID NO 26
<211> LENGTH: 20
<212> TYPE: DNA
<213> ORGANISM: Artificial Sequence
<220> FEATURE:
<223> OTHER INFORMATION: chemically synthesized primer sequence for
     amplification of txtH in TR1 region

<400> SEQUENCE: 26
tacgagacca tcggcaggga                                               20

<210> SEQ ID NO 27
<211> LENGTH: 20
<212> TYPE: DNA
<213> ORGANISM: Artificial Sequence
<220> FEATURE:
<223> OTHER INFORMATION: chemically synthesized primer sequence for
     amplificaiton of txtH in TR1 region

<400> SEQUENCE: 27
acatcctcac cgagccggaa                                               20

<210> SEQ ID NO 28
<211> LENGTH: 57
<212> TYPE: DNA
<213> ORGANISM: Artificial Sequence
<220> FEATURE:
<223> OTHER INFORMATION: chemically synthesized primer sequence for txtH redirect deletion cassette

<400> SEQUENCE: 28
tgccgggccc tctttgccga ctaggagaaa ttcaccgtgt gtaggctgga gctgctt    57

<210> SEQ ID NO 29
<211> LENGTH: 59
<212> TYPE: DNA
<213> ORGANISM: Artificial Sequence
<220> FEATURE:
<223> OTHER INFORMATION: hemically synthesized primer sequence for txtH redirect deletion cassette

<400> SEQUENCE: 29
ggcgacccgt ggccccgctc gatgttattg gccgggtcaa ttccggggat ccgtcgacc    59

<210> SEQ ID NO 30
<211> LENGTH: 58
<212> TYPE: DNA
<213> ORGANISM: Artificial Sequence
<220> FEATURE:
<223> OTHER INFORMATION: chemically synthesized primer sequence for lanA and lanB redirect deletion cassette

<400> SEQUENCE: 30
atgaagaact tcgaagccgc gaccactcag gtcgatgtgt gtaggctgga gctgcttc    58

<210> SEQ ID NO 31
<211> LENGTH: 59
<212> TYPE: DNA
<213> ORGANISM: Artificial Sequence
<220> FEATURE:
<223> OTHER INFORMATION: chemically synthesized primer sequence for lanA and lanB redirect deletion cassette

<400> SEQUENCE: 31
tcacggcgtc ctccagtgtt cgcgggcgct ctggcgcaga ttccggggat ccgtcgacc    59

<210> SEQ ID NO 32
<211> LENGTH: 27
<212> TYPE: DNA
<213> ORGANISM: Artificial Sequence
<220> FEATURE:
<223> OTHER INFORMATION: chemically synthesized forward primer for amplificaiton of 1kb upstream of thaxtomin gene cluster

<400> SEQUENCE: 32
gcgcgctagc gattcacggc aaactgc    27

<210> SEQ ID NO 33
<211> LENGTH: 46
<212> TYPE: DNA
<213> ORGANISM: Artificial Sequence
<220> FEATURE:
<223> OTHER INFORMATION: chemically synthesized reverse primer for amplificaiton of 1kb upstream of thaxtomin gene cluster

<400> SEQUENCE: 33
gcacctgatt tcgcgatccg ttaacaggtc gtcgaaaccc agatcg    46

<210> SEQ ID NO 34
<211> LENGTH: 46
<212> TYPE: DNA
<213> ORGANISM: Artificial Sequence
<220> FEATURE:
<223> OTHER INFORMATION: chemically synthesized forward primer for
      amplification of 1kb downstream of thaxtomin gene cluster

<400> SEQUENCE: 34
cgatctgggt tcgacgacc tgttaacgga tcgcgaaatc aggtgc                        46

<210> SEQ ID NO 35
<211> LENGTH: 30
<212> TYPE: DNA
<213> ORGANISM: Artificial Sequence
<220> FEATURE:
<223> OTHER INFORMATION: chemically synthesized reverse primer for
      amplification of 1kb downstream of thaxtomin gene cluster

<400> SEQUENCE: 35
gcgcgcatgc ctcaaaggcc aggttgtagg                                         30

<210> SEQ ID NO 36
<211> LENGTH: 22
<212> TYPE: DNA
<213> ORGANISM: Artificial Sequence
<220> FEATURE:
<223> OTHER INFORMATION: chemically synthesized forward primer for
      9828-vector

<400> SEQUENCE: 36
tctagagtcg acctgcagcc ca                                                 22

<210> SEQ ID NO 37
<211> LENGTH: 22
<212> TYPE: DNA
<213> ORGANISM: Artificial Sequence
<220> FEATURE:
<223> OTHER INFORMATION: chemically synthesized reverse primer for
      9828-vector

<400> SEQUENCE: 37
gtaatcatgt catagctgtt tc                                                 22

<210> SEQ ID NO 38
<211> LENGTH: 44
<212> TYPE: DNA
<213> ORGANISM: Artificial Sequence
<220> FEATURE:
<223> OTHER INFORMATION: chemically synthesized forward primer for
      Thx-fragment-1

<400> SEQUENCE: 38
gaaacagcta tgacatgatt acacgtatcg gcgacctgct cctg                         44

<210> SEQ ID NO 39
<211> LENGTH: 22
<212> TYPE: DNA
<213> ORGANISM: Artificial Sequence
<220> FEATURE:
<223> OTHER INFORMATION: chemically synthesized reverse primer for
      Thx-fragment-1

<400> SEQUENCE: 39
ttcaccaaca ggccggcgtt cg                                                 22

<210> SEQ ID NO 40

```
<211> LENGTH: 21
<212> TYPE: DNA
<213> ORGANISM: Artificial Sequence
<220> FEATURE:
<223> OTHER INFORMATION: chemically synthesized forward primer for
      Thx-fragment-2

<400> SEQUENCE: 40
aagagaggcc atcgtctggg a                                              21

<210> SEQ ID NO 41
<211> LENGTH: 42
<212> TYPE: DNA
<213> ORGANISM: Artificial Sequence
<220> FEATURE:
<223> OTHER INFORMATION: chemically synthesized reverse primer for
      Thx-fragment-2

<400> SEQUENCE: 41
tgggctgcag gtcgactcta gagacgagta cctggcggac ta                       42

<210> SEQ ID NO 42
<211> LENGTH: 22
<212> TYPE: DNA
<213> ORGANISM: Artificial Sequence
<220> FEATURE:
<223> OTHER INFORMATION: chemically synthesized forward primer for
      2828deltaC vector

<400> SEQUENCE: 42
catgttcgag cgaccgaacg ac                                             22

<210> SEQ ID NO 43
<211> LENGTH: 22
<212> TYPE: DNA
<213> ORGANISM: Artificial Sequence
<220> FEATURE:
<223> OTHER INFORMATION: chemically synthesized reverse primer for
      2828deltaC vector

<400> SEQUENCE: 43
gtaatcatgt catagctgtt tc                                             22

<210> SEQ ID NO 44
<211> LENGTH: 44
<212> TYPE: DNA
<213> ORGANISM: Artificial Sequence
<220> FEATURE:
<223> OTHER INFORMATION: chemically synthesized forward primer for
      thxdeltaC-fragment-1

<400> SEQUENCE: 44
gaaacagcta tgacatgatt acggtgtcgt ttcctttcca agac                     44

<210> SEQ ID NO 45
<211> LENGTH: 22
<212> TYPE: DNA
<213> ORGANISM: Artificial Sequence
<220> FEATURE:
<223> OTHER INFORMATION: chemically synthesized reverse primer for
      thxdeltaC-fragment-1

<400> SEQUENCE: 45
gtgatccagt actttccctc ag                                             22

<210> SEQ ID NO 46
<211> LENGTH: 22
```

```
<212> TYPE: DNA
<213> ORGANISM: Artificial Sequence
<220> FEATURE:
<223> OTHER INFORMATION: chemically synthesized forward primer for
      thxdeltaC-fragment-2

<400> SEQUENCE: 46
cagtaggtcg aacaggtaat cg                                              22

<210> SEQ ID NO 47
<211> LENGTH: 23
<212> TYPE: DNA
<213> ORGANISM: Artificial Sequence
<220> FEATURE:
<223> OTHER INFORMATION: chemically synthesized reverse primer for
      thxdeltaC-fragment-2

<400> SEQUENCE: 47
gtcgaggtcg aagtcgttcg gtc                                             23

<210> SEQ ID NO 48
<211> LENGTH: 22
<212> TYPE: DNA
<213> ORGANISM: Artificial Sequence
<220> FEATURE:
<223> OTHER INFORMATION: chemically synthesized forward primer for
      9828deltaABCH-vector

<400> SEQUENCE: 48
tctagagtcg acctgcagcc ca                                              22

<210> SEQ ID NO 49
<211> LENGTH: 22
<212> TYPE: DNA
<213> ORGANISM: Artificial Sequence
<220> FEATURE:
<223> OTHER INFORMATION: chemically synthesized reverse primer for
      9828deltaABCH-vector

<400> SEQUENCE: 49
gtaatcatgt catagctgtt tc                                              22

<210> SEQ ID NO 50
<211> LENGTH: 43
<212> TYPE: DNA
<213> ORGANISM: Artificial Sequence
<220> FEATURE:
<223> OTHER INFORMATION: chemically synthesized forward primer for
      thxdeltaABCH

<400> SEQUENCE: 50
gaaacagcta tgacatgatt acaggtatcc gttcctctct gtc                       43

<210> SEQ ID NO 51
<211> LENGTH: 43
<212> TYPE: DNA
<213> ORGANISM: Artificial Sequence
<220> FEATURE:
<223> OTHER INFORMATION: chemically synthesized reverse primer for
      thxdeltaABCH

<400> SEQUENCE: 51
tgggctgcag gtcgactcta gagacgagta cctggcggac tac                       43

<210> SEQ ID NO 52
<211> LENGTH: 22
<212> TYPE: DNA
```

```
<213> ORGANISM: Artificial Sequence
<220> FEATURE:
<223> OTHER INFORMATION: chemically synthesized forward primer for txtA

<400> SEQUENCE: 52
cttctcgtcc ccgagtttcg ac                                              22

<210> SEQ ID NO 53
<211> LENGTH: 22
<212> TYPE: DNA
<213> ORGANISM: Artificial Sequence
<220> FEATURE:
<223> OTHER INFORMATION: chemically synthesized reverse primer for txtA

<400> SEQUENCE: 53
gatcgctcat ggtggcgcag ac                                              22

<210> SEQ ID NO 54
<211> LENGTH: 20
<212> TYPE: DNA
<213> ORGANISM: Artificial Sequence
<220> FEATURE:
<223> OTHER INFORMATION: chemically synthesized forward primer for txtB

<400> SEQUENCE: 54
gtcatctaca cctcgggttc                                                 20

<210> SEQ ID NO 55
<211> LENGTH: 20
<212> TYPE: DNA
<213> ORGANISM: Artificial Sequence
<220> FEATURE:
<223> OTHER INFORMATION: chemically synthesized reverse primer for txtB

<400> SEQUENCE: 55
ccaacggtcc gctcatggtc                                                 20

<210> SEQ ID NO 56
<211> LENGTH: 21
<212> TYPE: DNA
<213> ORGANISM: Artificial Sequence
<220> FEATURE:
<223> OTHER INFORMATION: chemically synthesized forward primer for txtC

<400> SEQUENCE: 56
tgttctccgg gtatgaggat g                                               21

<210> SEQ ID NO 57
<211> LENGTH: 21
<212> TYPE: DNA
<213> ORGANISM: Artificial Sequence
<220> FEATURE:
<223> OTHER INFORMATION: chemically synthesized reverse primer for txtC

<400> SEQUENCE: 57
gttcgggaag acactctcgt c                                               21

<210> SEQ ID NO 58
<211> LENGTH: 20
<212> TYPE: DNA
<213> ORGANISM: Artificial Sequence
<220> FEATURE:
<223> OTHER INFORMATION: chemically synthesized forward primer for txtD

<400> SEQUENCE: 58
gcaactccag tcgctgcatc                                                 20
```

<210> SEQ ID NO 59
<211> LENGTH: 22
<212> TYPE: DNA
<213> ORGANISM: Artificial Sequence
<220> FEATURE:
<223> OTHER INFORMATION: chemically synthesized reverse primer for txtD

<400> SEQUENCE: 59
cgaagaaccg gggtttgtcg tc                                             22

<210> SEQ ID NO 60
<211> LENGTH: 21
<212> TYPE: DNA
<213> ORGANISM: Artificial Sequence
<220> FEATURE:
<223> OTHER INFORMATION: chemically synthesized forward primer for txtE

<400> SEQUENCE: 60
caagaacgtg gtgatgtaca c                                              21

<210> SEQ ID NO 61
<211> LENGTH: 21
<212> TYPE: DNA
<213> ORGANISM: Artificial Sequence
<220> FEATURE:
<223> OTHER INFORMATION: chemically synthesized reverse primer for txtE

<400> SEQUENCE: 61
gagcttttcc aggattatct c                                              21

<210> SEQ ID NO 62
<211> LENGTH: 12
<212> TYPE: DNA
<213> ORGANISM: Streptomyces scabies

<400> SEQUENCE: 62
ttgaagcgga ac                                                        12

<210> SEQ ID NO 63
<211> LENGTH: 12
<212> TYPE: DNA
<213> ORGANISM: Streptomyces acidiscabies

<400> SEQUENCE: 63
ttgaaccgga ac                                                        12

<210> SEQ ID NO 64
<211> LENGTH: 12
<212> TYPE: DNA
<213> ORGANISM: Streptomyces sp. 96-12

<400> SEQUENCE: 64
ttgaacctga ac                                                        12

METHODS FOR THAXTOMIN PRODUCTION AND ENGINEERED NON-NATIVE *STREPTOMYCES* WITH INCREASED THAXTOMIN PRODUCTION

CROSS-REFERENCE TO RELATED APPLICATIONS

This application is the 35 U.S.C. § 371 national stage application of PCT Application No. PCT/US2018/034071, filed May 23, 2018, where the PCT claims priority to, and the benefit of, U.S. provisional application entitled "METHODS FOR THAXTOMIN PRODUCTION AND ENGINEERED NON-NATIVE *STREPTOMYCES* WITH INCREASED THAXTOMIN PRODUCTION" having Ser. No. 62/646,626, filed Mar. 22, 2018, and U.S. provisional application entitled "METHODS FOR THAXTOMIN PRODUCTION AND ENGINEERED NON-NATIVE *STREPTOMYCES* WITH INCREASED THAXTOMIN PRODUCTION" having Ser. No. 62/509,792, filed May 23, 2017, all of which are herein incorporated by reference in their entireties.

STATEMENT REGARDING FEDERALLY SPONSORED RESEARCH OR DEVELOPMENT

This invention was made with government support under Grant No. FA9550-16-1-0186 awarded by the US Air Force Office of Scientific Research and Grant No. 2010-65110-20416 awarded by the United States Department of Agriculture. The government has certain rights in the invention.

SEQUENCE LISTING

This application contains a sequence listing filed in electronic form as an ASCII.txt file entitled 222110-2290_ST25.txt, created on May 23, 2018 and having a size of 77 KB. The content of the sequence listing is incorporated herein in its entirety.

BACKGROUND

The thaxtomins are a group of phytotoxins generated by some species of *Streptomyces* bacteria, such as *Streptomyces scabiei* (the main causal organism of potato common scab). The thaxtomins can cause plant cell necrosis of various plant species and thus have broad spectrum herbicidal activity.

Thaxtomins, also known as virulence factor in common scab potato disease, induce the formation of scabs on potato tubers and have been isolated from *S. scabiei*. These toxins, including thaxtomin A, thaxtomin B and at least 10 other analogs, are cyclic dipeptides classed as 2,5-Diketopiperazines, with thaxtomin A, the most abundant, having the chemical formula $C_{22}H_{22}N_4O_6$. Individual thaxtomins appear to differ only in the presence or absence of N-methyl and hydroxyl groups and their respective substitution sites.

The pathogenicity of *Streptomyces* strains is believed to be related to the production of thaxtomin. The genes involved in thaxtomin biosynthesis are located on a part of the genome called the pathogenicity island, present in the pathogenic *Streptomyces* strains *S. acidiscabies* and *S. turgidiscabies*. Although more than 800 *Streptomyces* species are known to date, only about ten species are known to be phytopathogenic (Loria et al. 2006). The best characterized pathogenic species are *S. scabiei*, *S. acidiscabies*, *S. turgidiscabies*, and *S. ipomoeae* (Loria et al. 2008).

Thaxtomins inhibit the synthesis of cellulose, the major component of the plant cell wall, and cause dramatic plant cell hypertrophy and seedling stunting at the nM level (Bischoff et al. 2009; Fry and Loria 2002; King et al. 2001). The attractive bioactivities of thaxtomins makes them desirable candidates for development and use as natural, commercial herbicides for weed control (Koivunen et al. 2013; Leep et al. 2010). Thaxtomins have been explored as effective herbicides to control the germination and growth of broadleaved, sedge, and grass weeds (Koivunen et al. 2013). In addition, thaxtomins have also been applied to control algae growth in algae contaminated environments (Kang et al. 2008). However, the limited productivity of thaxtomins in existing *Streptomyces* species, with isolation yields of less than 10 mg/L from native producers, results in a costly production process. Current synthetic routes to thaxtomin compounds and analogs are lengthy and inefficient for production on an industrial scale.

SUMMARY

Briefly described, the present disclosure provides genetically engineered, non-pathogenic *Streptomyces* bacterium with exogenous, non-native thaxtomin biosynthetic gene clusters conferring the genetically engineered, non-pathogenic *Streptomyces* bacterium with the ability to produce thaxtomin compounds, derivatives, and intermediates such as thaxtomin A, thaxtomin C, thaxtomin D, nitrotryptophan compounds, and fluorinated derivatives of these compounds. Also included are methods of providing thaxtomin-producing capability in non-native *Streptomyces* bacterial strains, methods of producing thaxtomin compounds with the genetically engineered *Streptomyces* bacteria of the present disclosure, and methods of producing thaxtomin compounds and nitrotryptophan analogs, and fluorinated thaxtomin compounds, analogs, and intermediates Embodiments of genetically engineered *Streptomyces* bacteria of the present disclosure include: a *Streptomyces* bacterium from a non-pathogenic *Streptomyces* strain, the *Streptomyces* bacterium having an exogenous, non-native Thaxtomin A (ThxA) biosynthetic gene cluster from a pathogenic *Streptomyces* strain, where the presence of the non-native ThxA biosynthetic cluster provides the genetically engineered *Streptomyces* bacterium with the ability to produce thaxtomin A, where the non-pathogenic *Streptomyces* strain without the exogenous non-native ThxA biosynthetic cluster does not have the ability to produce thaxtomin.

The present disclosure also provides, in embodiments, genetically engineered *Streptomyces* bacteria of the including: a *Streptomyces* bacterium from a non-pathogenic *Streptomyces* strain, the *Streptomyces* bacterium having an exogenous, non-native engineered thaxtomin biosynthetic gene cluster from a pathogenic *Streptomyces* strain, where the engineered thaxtomin biosynthetic gene cluster does not include the txtC gene, where the presence of the non-native, engineered thaxtomin biosynthetic cluster provides the genetically engineered *Streptomyces* bacterium with the ability to produce thaxtomin biosynthetic intermediates selected from thaxtomin D, thaxtomin C, N-acetyl-nitro-L-tryptophan, and N-methyl-nitro-L-tryptophan, where the non-pathogenic *Streptomyces* strain without the exogenous non-native, engineered thaxtomin biosynthetic cluster does not have the ability to produce the thaxtomin intermediates.

Embodiments of methods of the present disclosure include methods for providing a non-native *Streptomyces* bacterium with the ability to product thaxtomin compounds, derivatives thereof, or intermediates thereof. Embodiments of such methods include: providing a *Streptomyces* bacterium from a naturally non-pathogenic species that does not produce thaxtomin, and genetically engineering the *Streptomyces* bacterium by introducing a non-native nucleic acid molecule encoding for a non-native thaxtomin biosynthetic gene cluster from a pathogenic *Streptomyces* strain, such that the non-native thaxtomin biosynthetic gene cluster is integrated into the genome of the *Streptomyces* bacterium such that the genetically engineered *Streptomyces* bacterium is capable of producing one or more thaxtomin compounds, intermediates thereof, or derivatives thereof. In some embodiments, introducing the non-native nucleic acid molecule includes: providing a genetically engineered pathogenic *Streptomyces* bacterium having an exogenous nucleic acid encoding a selectable marker operably linked to a TR nucleic acid encoding a native TR1 and TR2; performing conjugal mating of the genetically engineered pathogenic *Streptomyces* bacterium with the naturally non-pathogenic *Streptomyces* bacterium such that the selectable marker, TR1, and TR2 are transferred from the pathogenic *Streptomyces* bacterium to the naturally non-pathogenic *Streptomyces* bacterium; and selecting for transconjugants and detecting for integration of the TR into a genome of the naturally non-pathogenic *Streptomyces* bacterium to produce a genetically engineered *Streptomyces* bacterium capable of producing thaxtomin. In some other embodiments, introducing the non-native nucleic acid molecule includes: cloning a thaxtomin biosynthetic gene cluster from a pathogenic *Streptomyces* strain, transforming the thaxtomin biosynthetic gene cluster into the *Streptomyces* bacterium from the naturally non-pathogenic species, and selecting for transformants to provide genetically engineered *Streptomyces* bacterium capable of producing thaxtomin. The present disclosure also provides genetically engineered *Streptomyces* bacteria produced by the methods of the present disclosure.

Methods of producing thaxtomin compounds, thaxtomin derivatives, and thaxtomin intermediates of the present disclosure, in embodiments, include: culturing genetically engineered *Streptomyces* bacteria from a non-pathogenic *Streptomyces* strain, the genetically engineered *Streptomyces* bacterium having an exogenous, non-native thaxtomin biosynthetic gene cluster from a pathogenic *Streptomyces* strain, such that the genetically engineered *Streptomyces* bacteria produce thaxtomin compounds, derivatives or intermediates. In embodiments, the genetically engineered *Streptomyces* bacteria of the present disclosure have about the same or increased production of a thaxtomin compound, derivative, or intermediate as compared to a wild type *S. scabiei* bacteria under the same culture conditions.

In embodiments of the present disclosure, methods of producing thaxtomin compounds and nitrotryptophan analogs include: providing a *Streptomyces* bacterium from a naturally non-pathogenic species that does not produce thaxtomin and genetically engineering the *Streptomyces* bacterium by introducing a non-native nucleic acid molecule encoding for a genetically modified, non-native thaxtomin biosynthetic gene cluster from a pathogenic *Streptomyces* strain, where the genetically modified, non-native thaxtomin biosynthetic gene cluster is integrated into the genome of the *Streptomyces* bacterium such that the genetically engineered *Streptomyces* bacterium is capable of producing thaxtomin, thaxtomin intermediates, and/or thaxtomin analogs.

Other systems, methods, features, and advantages of the present disclosure will be or will become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A is an image of *Streptomyces scabiei*, FIG. 1B shows potato scab lesions caused by *Streptomyces scabiei*, and FIG. 1C shows the structure of thaxtomin A.

Figures 3A, 3B:
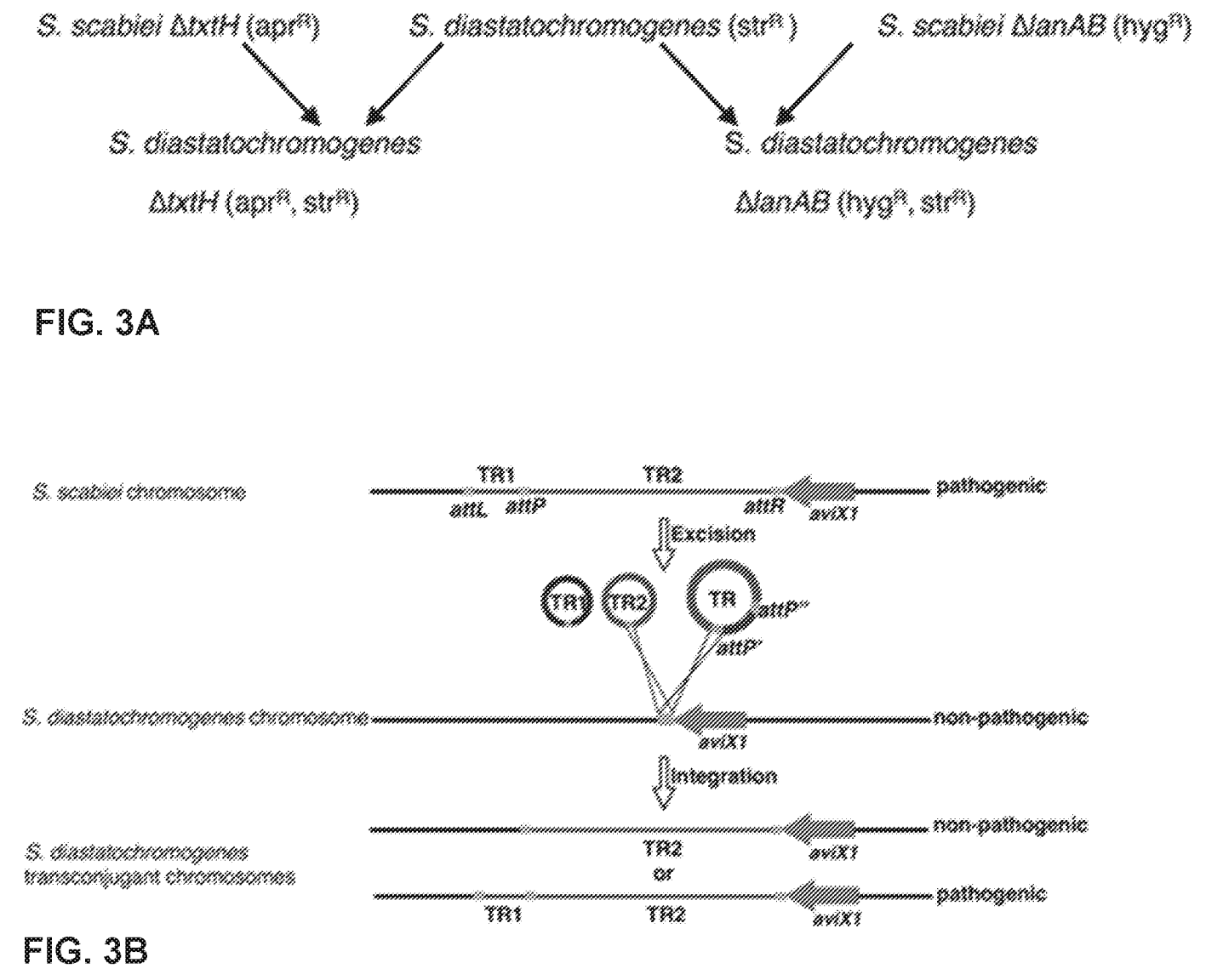

FIGS. 3A-3B illustrate the excision and site-specific integration of the *S. scabiei* thaxtomin biosynthetic cluster into the *S. diastatochromogenes* chromosome. FIG. 3A is a schematic representation of the mating experiments between *S. scabiei* 87-22 deletion mutants and *S. diastatochromogenes*. FIG. 3B illustrates the three excision forms and two site-specific integration forms of *S. scabiei* thaxtomin biosynthetic cluster: TR1 alone, TR2 alone, and the whole TR (TR1 and TR2) can excise from the *S. scabiei* chromosome, but only TR2 alone and the whole TR can integrate into the *S. diastatochromogenes* chromosome.

FIG. 6A illustrates HPLC traces of C18 SPE, 25% methanol washes of TDMc medium for analysis of nitrated precursors of thaxtomin A. The top chromatogram is from the S. albus J1074 extract seven days after inoculation, and the bottom chromatogram is from the S. scabiei 87-22 extract seven days after inoculation. FIG. 6B is a set of graphs illustrating accumulation of 4-nitrotryptophan of S. albus J1074 (left) and S. scabiei 87-22 (right), in TDMc liquid medium. The final yield of N-methyl-4-nitrotryptophan of S. scabiei 87-22 is set to %100. The average % production of nitrated precursors for two strains at each time points relative to S. scabiei 87-22 final yields of N-methyl-4-nitrotryptophan is shown, and the errors bars represent the standard deviation from the mean. Spores were cultured on TSB at 30° C. for 48 hours.

Figure 1A:
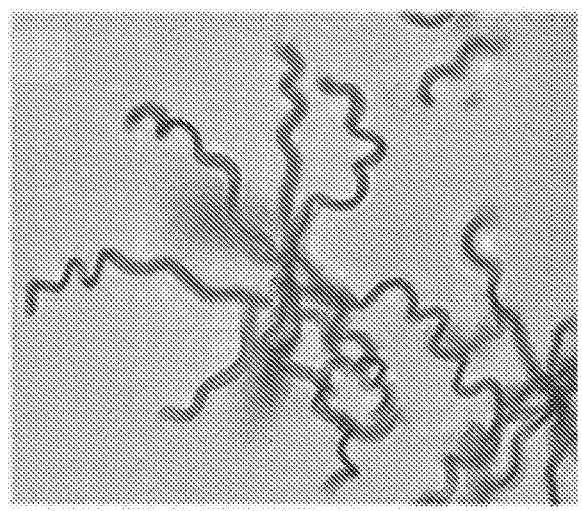
FIGS. 1A-C illustrate *Streptomyces* scabies and thaxtomin A.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, botany, biochemistry, biology, molecular biology, genetics, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

All publications and patents cited in this specification are cited to disclose and describe the methods and/or materials in connection with which the publications are cited. Publications and patents that are incorporated by reference, where noted, are incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. Any terms not specifically defined within the instant application, including terms of art, are interpreted as would be understood by one of ordinary skill in the relevant art; thus, is not intended for any such terms to be defined by a lexicographical definition in any cited art, whether or not incorporated by reference herein, including but not limited to, published patents and patent applications. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

It must be noted that, as used in the specification and the appended claims, the singular forms "a," "an," and "the" include plural referents unless the context clearly dictates otherwise. Thus, for example, reference to "a cell" includes a plurality of cells. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

The terms "nucleic acid" and "polynucleotide" are terms that generally refer to a string of at least two base-sugar-phosphate combinations. As used herein, the terms include deoxyribonucleic acid (DNA) and ribonucleic acid (RNA) and generally refer to any polyribonucleotide or polydeoxyribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" and "oligonucleotide" also encompasses a nucleic acid and polynucleotide as defined above.

In addition, polynucleotide as used herein refers to double-stranded regions comprising RNA or DNA or both RNA and DNA. The strands in such regions may be from the same molecule or from different molecules. The regions may include all of one or more of the molecules, but more typically involve only a region of some of the molecules. One of the molecules of a double-helical region often is an oligonucleotide.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein.

The term also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotides" as that term is intended herein.

A "gene" typically refers to a hereditary unit corresponding to a sequence of DNA that occupies a specific location on a chromosome and that contains the genetic instruction for a characteristic(s) or trait(s) in an organism.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome. A "transformed" cell is thus a cell transfected with a nucleic acid sequence. The term "transformation" refers to the introduction of a nucleic acid (e.g., DNA or RNA) into cells in such a way as to allow expression of the coding portions of the introduced nucleic acid.

As used herein, "transformation" or "transformed" refers to the introduction of a nucleic acid (e.g., DNA or RNA) into cells in such a way as to allow expression of the coding portions of the introduced nucleic acid.

As used herein a "transformed cell" is a cell transfected with a nucleic acid sequence. As used herein, a "transgene" refers to an artificial gene or portion thereof that is used to transform a cell of an organism, such as a bacterium or a plant.

As used herein, "transgenic" refers to a cell, tissue, or organism that contains a transgene.

As used herein, "exogenous nucleic acid sequence" or "exogenous polynucleotide" refers to a nucleic acid sequence that was introduced into a cell, organism, or organelle via transfection. Exogenous nucleic acids originate from an external source, for instance, the exogenous nucleic acid may be from another cell or organism and/or it may be synthetic and/or recombinant, e.g., a "non-native" nucleic acid. While an exogenous nucleic acid sometimes originates from a different organism or species, it may also originate from the same species (e.g., an extra copy or recombinant form of a nucleic acid that is introduced into a cell or organism in addition to or as a replacement for the naturally occurring nucleic acid). Typically, the introduced exogenous sequence is a recombinant sequence.

The term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a "fusion protein" (e.g., a protein or polypeptide formed from the combination of two different proteins or protein fragments)), the combination of a nucleic acid encoding a polypeptide to a promoter sequence, where the coding sequence and promoter sequence are from different sources or otherwise do not typically occur together naturally). Recombinant also refers to the polypeptide encoded by the recombinant nucleic acid. Non-naturally occurring nucleic acids or polypeptides include nucleic acids and polypeptides modified by man.

As used herein, "isolated" means removed or separated from the native environment. Therefore, isolated DNA can contain both coding (exon) and noncoding regions (introns) of a nucleotide sequence corresponding to a particular gene. An isolated peptide or protein indicates the protein is separated from its natural environment. Isolated nucleotide sequences and/or proteins are not necessarily purified. For instance, an isolated nucleotide or peptide may be included in a crude cellular extract or they may be subjected to additional purification and separation steps.

With respect to nucleotides, "isolated nucleic acid" refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example but not limited to, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, e.g., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

It is advantageous for some purposes that a nucleotide sequence is in purified form. The term "purified" in reference to nucleic acid represents that the sequence has increased purity relative to the natural environment.

The term "polypeptides" and "protein" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

As used herein "functional variant" refers to a variant of a protein or polypeptide (e.g., a thaxtomin compound) that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, N.J., 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

The term "expression" as used herein describes the process undergone by a structural gene to produce a polypeptide. It can refer to transcription or the combination of transcription and translation. Expression generally refers to the transcription of a gene to produce messenger RNA, as used herein expression may refer to the entire process of "expression" of a nucleic acid to produce a polypeptide (e.g., transcription plus translation). If "expression" is used in reference to a polypeptide, it indicates that the polypeptide is being produced via expression of the corresponding nucleic acid.

As used herein, the term "over-expression" and "up-regulation" or "increasing" production of a polypeptide refers to the expression of a nucleic acid encoding a polypeptide (e.g., a gene) in a modified cell at higher levels (therefore producing an increased amount of the polypeptide encoded by the gene) as compared to a "wild type" cell (e.g., a substantially equivalent cell that is not modified in the manner of the modified cell) under substantially similar conditions. Thus, to over-express or increase expression of thaxtomin refers to increasing or inducing the production of the thaxtomin dipeptide by one or more enzymes encoded by the thaxtomin biosynthetic genes, which may be done by a variety of approaches, such as, but not limited to: increasing the transcription of the genes (such as by placing the genes under the control of a constitutive promoter) responsible for synthesis of thaxtomin, or increasing the translation of such genes, inhibiting or eliminating a repressor of thaxtomin production (e.g., CebR or β-glucosidase enzyme), or a combination of these and/or other approaches.

Conversely, "under-expression" and "down-regulation" refers to expression of a polynucleotide (e.g., a gene) at lower levels (producing a decreased amount of the polypeptide encoded by the polynucleotide) than in a "wild type" cell. As with over-expression, under-expression can occur at different points in the expression pathway, such as by decreasing the number of gene copies encoding for the polypeptide; removing, interrupting, or inhibiting (e.g., decreasing or preventing) transcription and/or translation of the gene (e.g., by the use of antisense nucleotides, suppressors, knockouts, antagonists, etc.), or a combination of such approaches. "Suppression" refers to the inhibition of production and/or activity functional gene product. Thus, the suppression of a gene or protein may indicate that the expression of the gene and/or activity of the encoded peptide has been inhibited such as by transcription and/or translation being inhibited, thus resulting in low to no production of the encoded protein, or production of a non-functional product, or production of an interfering nucleic acid that otherwise suppresses activity of the target protein.

Similarly, with respect to a gene product, such as a protein, "reduced activity" indicates that the activity of the protein is reduced relative to activity in a "wild type cell". Such reduction in activity can be the result of inhibition/suppression/down-regulation/under-expression of the gene encoding the protein, the result of inhibition of translation of the messenger RNA into a functional gene product, or the result of production of a non-functional protein with reduced or no activity, or the direct suppression of the protein activity (e.g., preventing binding to a target), or the like. "Reduced production" of a gene product (e.g., a protein), such as by suppression, interruption, or other inhibition of transcription or translation, may result in reduced activity, but "reduced activity" of a protein or other gene product may result from other causes other than "reduced production", such as set for the above.

As used herein, the term "genetically engineered," with respect to a living organism, refers to an organism that has had its genetic makeup directly manipulated by techniques of biotechnology (as opposed to random changes occurring in nature). Genetically engineered organisms can include mutations involving changes only of the genetically engineered organisms' own genetic material as well as mutations involving insertions of exogenous genetic material, such as insertions resulting in either cisgenic (including exogenous genetic material from the same or a closely related organism) or transgenic (including exogenous genetic material from a non-closely related organism) organisms.

As used herein a "mutation" refers to a heritable change in genetic material, which may include alteration of single base pairs of a nucleic acid, or the deletion, insertion, or rearrangement of larger sections of genes or chromosomes. An "engineered mutation" refers to a mutation created by human design (e.g., the mutation did not spontaneously occur by natural causes and/or was the result of intentional human manipulation). A "genetically modified" organism is an organism whose genetic material has been altered by one or more engineered mutations (e.g., human induced mutations).

Similarly, with respect to genes or other nucleic acids, "silencing" or "deletion" of a gene may include complete deletion of the nucleic acid/gene encoding a target peptide, complete suppression of translation or transcription of the target nucleic acid such that the target peptide is not produced, but the terms may also include some of the methods for "suppression" and "down-regulation" discussed above, where the "suppression" is significant enough to reduce expression of the target gene to the extent that the resulting peptide is inactive or the activity of the resulting peptide is so minimal as to be virtually undetected.

The term "null mutation" refers to a mutation in which the gene product (e.g., the protein encoded by the gene) is either not produced (or produced at significantly reduced levels, so as to be negligible) or is non-functional. Typically, a null mutation will involve a mutation of the native gene, such that the gene is not transcribed into RNA, the RNA product cannot be translated, or the protein produced by gene expression is non-functional.

The term "plasmid" as used herein refers to a non-chromosomal double-stranded DNA sequence including an intact "replicon" such that the plasmid is replicated in a host cell. A plasmid may include exogenous nucleic acid sequences and/or recombinant sequences.

As used herein, the term "vector" or "expression vector" is used in reference to a vehicle used to introduce an exogenous nucleic acid sequence into a cell. A vector may include a DNA molecule, linear or circular, which includes a segment encoding a polypeptide of interest operably linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. As such, expression vectors typically contain recombinant nucleic acid sequences having different sequences linked together to effect expression of a target sequence. Expression vectors are generally derived from yeast DNA, bacterial genomic or plasmid DNA, or viral DNA, or may contain elements of more than one of these.

As used herein, the term "expression system" includes a biologic system (e.g., a cell based system) used to express a polynucleotide to produce a protein. Such systems generally employ a plasmid or vector including the polynucleotide of interest (e.g., an exogenous nucleic acid sequence, a recombinant sequence, etc.), where the plasmid or expression vector is constructed with various elements (e.g., promoters, selectable markers, etc.) to enable expression of the protein product from the polynucleotide. Expression systems use the host system/host cell transcription and translation mechanisms to express the product protein. Common expression systems include, but are not limited to, bacterial expression systems (e.g., *Streptomyces* strains), yeast expression systems, viral expression systems, animal expression systems, and plant expression systems.

As used herein, the term "promoter" or "promoter region" includes all sequences capable of driving transcription of a coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

The term "operably linked" indicates that the regulatory sequences necessary for expression of the coding sequences of a nucleic acid are placed in the nucleic acid molecule in the appropriate positions relative to the coding sequence so as to effect expression of the coding sequence. This same definition is sometimes applied to the arrangement of coding sequences and transcription control elements (e.g. promoters, enhancers, and termination elements), and/or selectable markers in an expression vector.

As used herein, the term "selectable marker" refers to a gene whose expression allows one to identify cells that have been transformed or transfected with a vector containing the marker gene (e.g., by antibiotic resistance on antibiotic medium, fluorescence, color generation, or other detectable signal). For instance, a recombinant nucleic acid may include a selectable marker operably linked to a gene of interest and a promoter, such that expression of the select-able marker indicates the successful transformation of the cell with the gene of interest.

The terms "native," "wild type", or "unmodified" in reference to a polypeptide/protein/enzyme, polynucleotide, cell, or organism, are used herein to provide a reference point for a variant/mutant of a polypeptide/protein/enzyme, polynucleotide, cell, or organism prior to its mutation and/or modification/engineering (whether the mutation and/or modification occurred naturally or by human design). On the other hand, "non-native" refers to a polypeptide/protein/enzyme, polynucleotide, cell, or organism that has a sequence or feature not found naturally in that peptide/cell/organism/etc., but that has been genetically engineered/manipulated to have such non-native feature.

Figure 1B:

As used herein, "thaxtomin" or "thaxtomin compound" refers to one or more compounds from a family of cyclic dipeptide phytotoxins, 4-nitroindol-3-yl-containing 2,5-dioxopiperazines, generated by some species of *Streptomyces* bacteria (and possibly by other actinomycetes) and exhibiting toxicity to various plant species. Thaxtomin compounds of the present disclosure have the general formula of Formula I below, and variants thereof. At least 5 thaxtomin compounds have been characterized, including thaxtomin A, A ortho analog, B, C, and D, and up to at least 12 different variants identified. Thaxtomin A, the most abundant of the thaxtomins and also believed to be the most physiologically active, has the chemical formula $C_{22}H_{22}N_4O_6$ (chemical structure illustrated in FIG. 1C). The thaxtomins, such as those isolated from *S. scabiei* (FIG. 1A), can cause plant cell necrosis of various plant species and can induce the formation of scabs on potato tubers (FIG. 1B). As used herein "thaxtomin" and "thaxtomin compound" refers generally to any of the members of this chemical group. Much of the discussion of thaxtomin in the present disclosure is in reference to thaxtomin A. However, as thaxtomin A may be a precursor to other thaxtomin compounds and/or the production of thaxtomin A is interwoven with production of other thaxtomin compound's, to the extent the methods and compositions of the present disclosure also modulate the production of other thaxtomin compounds, this is also intended to fall within the scope of the present disclosure. The general structure of a thaxtomin compound is shown below as Formula I, where R1 and R3 are independently selected from methyl or H and where R2, R4, R5, and R6 are each independently selected from hydroxyl or H.

Formula I

The term "thaxtomin A (ThxA) biosynthetic gene cluster" refers to a gene cluster responsible for production of thatxtomin A (ThxA) in a pathogenic organism. In pathogenic *Streptomyces* species, the native ThxA gene cluster includes genes involved in ThxA production, such as, but not limited to, TxtA (SEQ ID NO: 1), TxtB (SEQ ID NO: 3), TxtC (SEQ ID NO: 5), TxtD (SEQ ID NO: 7), TxtE (SEQ ID NO: 9), TxtH (SEQ ID NO: 11), TxtR (SEQ ID NO: 13), which encode the peptides TxtA (SEQ ID NO: 2), TxtB (SEQ ID NO: 4), TxtC (SEQ ID NO: 6), TxtD (SEQ ID NO: 8), TxtE (SEQ ID NO: 10), TxtH (SEQ ID NO: 12), and TxtR (SEQ ID NO: 14), respectively). The sequences listed above are from *Streptomyces scabiei* and are representative of the ThxA genes of pathogenic *Streptomyces* species; however, the genes encoding the thaxtomin peptides may vary slightly in different species. Thus, in the present disclosure, the genes involved in production of thaxtomin A and the encoded peptides in different species are also intended to be included in the scope of the disclosure, such as polynucleotide sequences having sequence similarity with the sequences above from *Streptomyces scabiei* and still having the same function (e.g., sequences having about 70% or greater, 80% or greater, 90% or greater, 95% or greater, 99% or greater sequence identity with SEQ ID Nos: 1, 3, 5, 7, 9, 11, and 13) and peptide sequences having sequence identity with the peptide sequences from *Streptomyces scabiei* and still having the same function (e.g., sequences having about 70% or greater, 80% or greater, 90% or greater, 95% or greater, 99% or greater sequence identity with SEQ ID Nos: 2, 4, 6, 8, 10, 12, and 14).

Figure 1C:
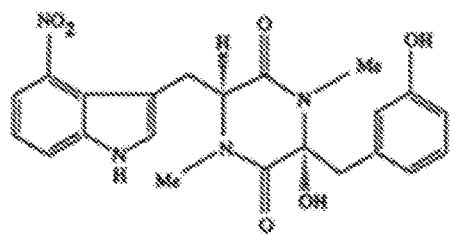
Figure 2:
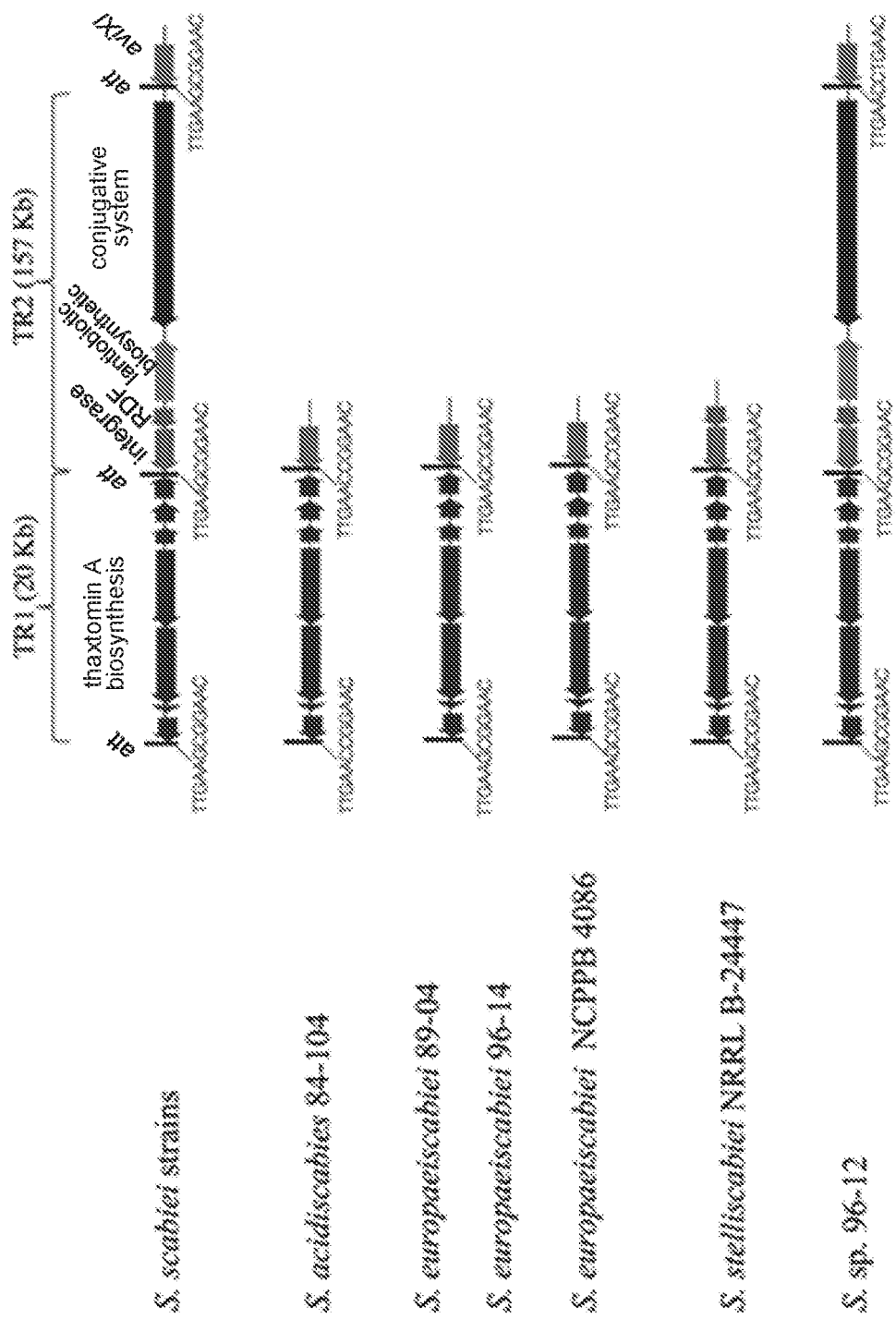
FIG. 2 is a schematic of genetic organization of genomic islands from different plant pathogenic *Streptomyces* species. Arrowed boxes represent the location and orientation of the open reading frames (ORFs) of thaxtomin biosynthetic genes, integrase and recombination directionality factor (RDF), lantibiotic biosynthetic genes, conjugative system genes, and aviX1. The sequences of attachment (att) sites (either TTGAAGCGGAAC (SEQ ID NO: 62) or TTGAACCGGAAC (SEQ ID NO: 63), or TTGAACCT-GAAC (SEQ ID NO: 64) at the junctions for TR1/TR2 are also shown.

The ThxA gene cluster of the present disclosure may include all of the above genes or any subset/variant of these needed to confer a recipient organism with the ability to produce thaxtomin. Thus the ThxA gene cluster or thaxtomin gene cluster can be engineered to include a subset or variant of the thaxtomin genes. The term "minimal thaxtomin biosynthetic gene cluster" refers to the minimal subset of the Thx A biosynthetic gene cluster needed to confer a recipient organism with the ability to produce thaxtomin. A minimal thaxtomin A biosynthetic gene cluster includes a minimal subset of the ThxA gene cluster needed to confer the ability to produce thaxtomin A, whereas other engineered thaxtomin biosynthetic gene clusters may include subsets of the ThxA gene cluster that confer the ability to produce other thaxtomin compounds or variants (e.g., thaxtomin C, thaxtomin D) or intermediates, such as nitrotryptophan intermediates (e.g., N-acetyl-nitro-L-tryptophan, and N-methyl-nitro-L-tryptophan), such engineered thaxtomin biosynthetic gene clusters may or may not also confer the ability to produce thaxtomin A.

The term "toxigenic region (TR)", refers to a mobile genomic island in some *Streptomyces* species that can include "toxigenic region 1 (TR1)" (see FIG. 2), that includes the thaxtomin A biosynthetic cluster, described above, and typically confers pathogenicity, and "toxigenic region 2 (TR2)" (see FIG. 2) that includes integrative and conjugative elements that can mobilize itself (TR2) or an entire TR element (TR1 and TR2) between species (e.g., between pathogenic and non-pathogenic species) as described in greater detail below).

The terms "thaxtomin-inducing conditions" indicates certain environmental conditions (e.g., natural or cell culture conditions) known to induce thaxtomin production in wild-type *Streptomyces* bacterial species known to be capable of thaxtomin production. For instance, wild type *Streptomyces* are induced to produce thaxtomin in the presence of certain products of cellulose degradation, such as, but not limited to, cellobiose, as well as xylan-degradation products (Wach et al. 2007), such as, but not limited to suberin (Lauzier et al. 2008). In embodiments, "thaxtomin-inducing conditions" may include specific conditions or cell culture media (such as but not limited to, Oat Bran Broth (OBB), Oat Bran Agar (OBA), etc.) known to induce thaxtomin production in cell culture of wild-type *Streptomyces* species (such as, but not limited to *S. scabiei, S. acidiscabies*, and *S. turgidiscabies*). In embodiments, "thaxtomin-inducing conditions" may also include a standard cell culture growth medium supplemented with a known thaxtomin-inducing compound, such as, but not limited to cellobiose.

The term "cebR gene" as used in the present disclosure indicates a nucleic acid sequence encoding a CebR protein in a *Streptomyces* or other thaxtomin-producing Actinomycete species that is a modulator of thaxtomin production. In embodiments, "cebR genes" include the cebR gene of *S. scabiei* (SEQ ID NO: 15) and variants and/or homologs (e.g., orthologs and paralogs) thereof retaining the function of modulation of thaxtomin production. In embodiments "cebR genes" include nucleic acids having a sequence of SEQ ID NO: 15 as well as sequences having about 60% or more, about 70% or more, about 80% or more, about 90% or more, about 95% or more, or about 99% or more (including any intervening ranges) sequence identity with SEQ ID NO: 15. In embodiments, cebR genes include nucleic acids having a sequence identity to SEQ ID NO: 15 of about 60% or more and having a sequence coverage to SEQ ID NO: 15 of about 70% or more, where sequence coverage indicates the percent of the total length of nucleic acids that are aligned.

The term "bglC gene" as used in the present disclosure indicates a nucleic acid sequence encoding a β-glucosidase enzyme in a *Streptomyces* or thaxtomin-producing Actinomycete species that is a modulator of thaxtomin production. In embodiments, "bglC genes" include the bglC gene of *S. scabiei* (SEQ ID NO: 17) and variants and/or homologs (e.g., orthologs and paralogs) thereof retaining the function of modulating thaxtomin production. In embodiments "bglC genes" include nucleic acids having a sequence of SEQ ID NO: 17 as well as sequences having about 60% or more, about 70% or more, about 80% or more, about 90% or more, about 95% or more, or about 99% or more (including any intervening ranges) sequence identity with SEQ ID NO: 17. In embodiments, bglC genes include nucleic acids having a sequence identity to SEQ ID NO: 17 of about 60% or more and also having a sequence coverage of about 70% with SEQ ID NO: 17.

Discussion

In accordance with the purpose(s) of the present disclosure, as embodied and broadly described herein, embodiments of the present disclosure, in some aspects, relate to genetically engineered *Streptomyces* bacteria from a naturally non-pathogenic *Streptomyces* species capable of increased thaxtomin production, genetically engineered *Streptomyces* bacteria with non-native thaxtomin pathogenicity clusters capable of producing about the same or a greater amount of thaxtomin than *S. scabiei* under the same culture conditions. In aspects, embodiments of the present disclosure also relate to methods of producing thaxtomins, thaxtomin analogs, nitro-tryptophan analogs, fluorinated thaxtomin compounds, analogs and intermediate, and the thaxtomin compounds, analogs, and intermediates produced by the methods of the present disclosure.

*Streptomyces* is a very large genus of filamentous Gram-positive, high G+C content bacteria that are mostly saprophytes and best known for the production of pharmaceutically- and agriculturally-important secondary metabolites, including two-thirds of currently-used antibiotics (Hopwood 2007, Bentley et al. 2002). Although several hundred species are known to date, only about ten are known to be phytopathogenic (Loria et al. 2006). The best characterized pathogens are *Streptomyces scabiei, S. acidiscabies, S. turgidiscabies* and *S. ipomoeae*, which cause raised or pitted scab lesions on economically-important root and tuber crops like potato, radish, beet, peanut, and sweet potato (FIG. 1A, 1B). The primary virulence determinant of *S. scabiei, S. acidiscabies* and *S. turgidiscabies* is the phytotoxin thaxtomin A (Loria et al. 2008) (FIG. 1C). It is member of a family of nitrated 2,5-diketopiperazines formed by non-ribosomal peptide synthases out of the main components tryptophan, phenylalanine and nitric oxide derived from arginine (Loria et al. 2008; Barry et al. 2012), with 11 members of the family differing only in the presence or absence of hydroxyl and N-methyl groups at specific sites.

The biosynthesis of ThxA involves two nonribosomal peptide synthetases (NRPSs) encoded by the txtA and txtB genes, a P450 monooxygenase (TxtC), a nitric oxide synthase (TxtD), and a novel cytochrome P450 (TxtE) that site specifically nitrates tryptophan prior to cyclization (Bignell et al. 2014b). The thaxtomin biosynthetic cluster also contains a txtH gene encoding a 65-amino-acid MbtH-like protein potentially regulating NRPS activity (Herbst et al. 2013; Stegmann et al. 2006). The production of thaxtomin A is under strict controls, including both the pathway-specific transcriptional activator TxtR (Joshi et al. 2007) and global regulators belonging to the bld gene family (Bignell et al. 2014a) and the cellulose utilization repressor CebR (Francis et al. 2015). This group of genes, called the thaxtomin A biosynthetic gene cluster, resides on a portion of a mobile genomic island in pathogenic *Streptomyces* species, known as toxigenic region 1 (TR1). Many *Streptomyces* species also include another toxigenic region (TR2) that has integrative and conjunctive elements and has the ability to mobilize TR2 alone or the whole TR element (TR1 and TR2) between *Streptomyces* species as described in Zhang & Loria 2016 ("Emergence of Novel Pathogenic *Streptomyces* Species by Site-Specific Accretion and cis-Mobilization of Pathogenicity Islands", December 2016) and Zhang, et al. 2016 ("Promiscuous Pathogenicity Islands and Phylogeny of Pathogenic *Streptomyces* spp." July 2016), both of which are hereby incorporated by reference herein in their entirety.

Thaxtomin A (and other toxic thaxtomin compounds) primarily targets the cell wall in dividing and expanding plant cells through an alteration of expression of cell wall biosynthesis-related genes and depletion of cellulose synthase complexes from the plasma membrane. This causes extensive cell wall remodeling, characterized by reduced incorporation of crystalline cellulose into the plant cell wall, and is compensated by an increased amount of pectins and hemicelluloses (Scheible et al. 2003; Bischoff et al. 2009). Data have shown that thaxtomin provokes the same effects on plants, qualitatively as well as quantitatively, as the synthetic cellulose biosynthesis inhibitor isoxaben, making thaxtomin an excellent candidate as a natural herbicide (Heim et al. 1990; Bischoff et al. 2009). In 2001, King and Lawrence reported a study in collaboration with James A. Gray from Dow Agrosciences, Inc. to evaluate the potential of thaxtomin for use as a commercial herbicide. The biological properties of this novel phytotoxin raised an interest in using thaxtomin as a biological compound to control weeds (Marrone Bio Innovations 2009, 2010; Novozymes Biologicals 2011, 2012); however, thaxtomin production in wild type *Streptomyces* requires specialized cell culture media (such as media supplemented with cellobiose or other thaxtomin-inducing compounds), which can be expensive. Thus, these methods of production of thaxtomin in wild type *Steptomyces*, such as *S. scabiei*, are insufficient. The present disclosure provides genetically engineered non-native *Streptomyces* bacteria with the ability to produce thaxtomin compounds at an increase over wild type bacteria and/or in species that do not naturally produce thaxtomin and are not naturally pathogenic to plants. In embodiments, the present disclosure provides genetically engineered bacteria as well as methods to produce thaxtomin in non-native species and at greater amounts than in wild type, native, thaxtomin-producing *Steptomyces*, such as *S. scabiei*, as well as methods for producing thaxtomin using such genetically modified bacteria.

Mobilization of pathogenicity islands (PAIs) can drive the evolution of plant pathogenic *Streptomyces* species (Loria et al. 2006). This disclosure describes the purposeful mobilization of a thaxtomin biosynthetic cluster (the full thaxtomin biosynthetic gene cluster, a subset of the cluster, or minimal thaxtomin biosynthetic gene cluster) of *S. scabiei*, and its application for the heterologous production of thaxtomin in non-pathogenic *Streptomyces* species. The present disclosure describes that the thaxtomin biosynthetic cluster is located on a mobile genomic island and that the mating of *S. scabiei* with non-pathogenic *Streptomyces* species resulted in the acquisition of the thaxtomin biosynthetic cluster by non-pathogenic *Streptomyces* species. Some of the recipient *Streptomyces* spp. do not produce thaxtomins, or produce lower amounts than *S. scabiei* upon the acquisition of the thaxtomin cluster, indicating that the genetic backgrounds of recipients affect the thaxtomin production considerably.

Acquisition of genes required for virulence is one step on the way to pathogenicity. Indeed, more subtle genetic changes are involved in adapting the expression of newly acquired genes to the environment and the life cycle of the recipient microorganism. For instance, a limited number of mutations in intergenic regulatory regions can transform a harmless strain into a pathogen. The distribution of cis-acting elements in the gene is an element involved in development of a strain-specific transcriptional response. These DNA motifs are targeted by transcription factors, which themselves are informed of the presence of environmental signals through direct interaction with membrane sensors or indirect association with elicitor transporters. The production of thaxtomin A itself is under transcriptional regulatory control including at least five global regulators belonging to the bld gene family involved in secondary metabolism and/or morphological differentiation of *Streptomyces* (Bignell et al. 2014) in addition to the thaxtomin biosynthesis pathway-specific transcriptional activator, TxtR. The multiplicity of global and specific regulators associated with thaxtomin production suggests that *S. scabiei* may respond to multiple triggers that originate from plant material such as xylan-degradation products (Wach et al. 2007), suberin (Lauzier et al. 2008), and cellobiose, a product of cellulose degradation and the best-known elicitor of thaxtomin biosynthesis (Wach et al. 2007; Johnson et al. 2009) by directly targeting TxtR (Joshi et al. 2007).

Remarkably, *S. albus* J1074 acquires the cluster via mating with *S. scabiei* and produces a significantly higher concentration of thaxtomins in comparison to *S. scabiei*. Furthermore, in embodiments, described in greater detail in the Examples below, a cloned thaxtomin cluster from the mobile genomic island is inserted, via a transformation-associated recombination (TAR) cloning approach (Kouprina et al. 2006; Mathee et al. 2008), into *S. albus* J1074 conferred a similar increase in thaxtomin production over wild type *S. scabiei*. The growth rate and thaxtomin production of the strain carrying the cloned thaxtomin cluster were similar to the *S. albus* strain created by the mobilization of the genomic island. The data provided in the Examples below indicated that non-pathogenic *Streptomy-* ces strains can be genetically engineered to produce thaxtomin and that these engineered strains, such as *S. albus* J1074, can provide a premium host for the heterologous production of thaxtomin for commercial applications.

Thus, as described in more detail in the discussion and the examples below, the present disclosure includes genetically engineered *Streptomyces* bacterium from non-pathogenic species (or other non-pathogenic gram-positive bacteria) that have been genetically engineered to express an exogenous, non-native thaxtomin gene from a pathogenic *Streptomyces* strain. The present disclosure also provides methods of providing thaxtomin-producing capability in non-native *Streptomyces* bacterium that are naturally non-pathogenic, and methods of making the genetically engineered *Streptomyces* bacterium. Additionally, the present disclosure provides methods of producing thaxtomin compounds by culturing the genetically engineered *Streptomyces* bacteria of the present disclosure.

In additional embodiments, and as described in application PCT/US2015/050582 (WO 2016/044527 A1), which is hereby incorporated by reference in its entirely, the genetically engineered non-native, thaxtomin producing *Streptomyces* of the present disclosure can also include additional engineered mutations affecting the production of proteins involved in regulation of thaxtomin regulation, such as cebR and bglC (e.g., by engineered mutations in the genes encoding the proteins and/or by inhibition of the proteins themselves), to further increase thaxtomin production. In embodiments, genetically engineered *Streptomyces* bacteria have non-native thaxtomin producing gene clusters as well as modifications to cebR and bglC to decrease production of and/or activity of CebR protein and/or β-glucosidase enzyme to further increase production of thaxtomin compounds, such as, but not limited to, thaxtomin A. In an embodiment, the genetically engineered non-native *Streptomyces* bacteria are capable of thaxtomin production in non-inducing conditions and on non-inducing media (e.g., conditions in which wild type thaxtomin producing *Streptomyces* do not produce thaxtomin or produce only trace amounts of thaxtomin).

The genetically modified bacteria of the present disclosure, methods of increasing production of thaxtomin compounds in *Streptomyces* bacteria, methods of producing thaxtomin, and thaxtomin produced by methods of the present disclosure are described in greater detail in the discussion below and following examples.

Genetically Modified Bacteria

Embodiments of the present disclosure include genetically engineered *Streptomyces* bacterium including a *Streptomyces* bacterium from a non-pathogenic *Streptomyces* strain (e.g., *Streptomyces* strain that, in its native, unmodified form, does not produce thaxtomin and is not pathogenic to plants), that has been engineered to have and express an exogenous, non-native Thaxtomin A (ThxA) biosynthetic gene cluster from a pathogenic *Streptomyces* strain. While the present disclosure primarily discusses the engineering of non-pathogenic *Streptomyces* bacteria, the same approach could be extended to other types of bacterial hosts, such as other non-pathogenic gram-positive bacteria. In embodiments, the presence of the non-native ThxA biosynthetic cluster in the modified genome of the genetically engineered *Streptomyces* bacterium provides the naturally non-pathogenic strain with the ability to produce thaxtomin A, unlike corresponding wild type strains of the bacterium. Thus, although a wild-type version of this non-pathogenic *Streptomyces* strain without the exogenous non-native ThxA biosynthetic cluster does not have the ability to produce thaxtomin, the genetically engineered strain that harbors the exogenous ThxA cluster can express the ThxA biosynthetic genes and thus produce thaxtomin.

As discussed above, all known pathogenic *Streptomyces* species carry TR1, which carries the thaxtomin biosynthetic cluster, while some pathogenic and non-pathogenic species carry TR2. TR1 and TR2 together are referred to herein as the toxigenic region (TR). Some species, such as, but not limited to *Streptomyces scabiei* (also referred to herein as *S. scabiei*), include both TR1 and TR2. Some non-pathogenic species include TR2, but naturally non-pathogenic species do not contain TR1. Thus, in embodiments, the exogenous, non-native ThxA biosynthetic cluster includes toxigenic region 1 (TR1). In some embodiments the exogenous, non-native thaxtomin biosynthetic gene cluster includes a subset of TR1 capable of conferring thaxtomin-producing ability to the recipient species. In some embodiments, the exogenous thaxtomin biosynthetic gene cluster includes a minimal thaxtomin biosynthetic gene cluster (e.g., the minimal portion of the thaxtomin biosynthetic gene cluster needed to confer the ability to produce thaxtomin). In some embodiments, the genetically engineered *Streptomyces* bacterium also includes exogenous, non-native TR2.

In embodiments, the non-native ThxA biosynthetic cluster is from a pathogenic *Streptomyces* strain including, but not limited to, *Streptomyces scabiei, Streptomyces acidiscabies*, and *Streptomyces turgidiscabies*. In embodiments, the *Streptomyces* bacterium from a non-pathogenic *Streptomyces* strain can be, but is not limited to, one of the following strains: *S. albus, S. diastatochromogenes, S. lividans, S. coelicolor*, and *S. avermitilis*. In embodiments, the non-pathogenic bacteria may be from a different gram positive bacterial species, such as *Norcardia*, or other species compatible with receipt of the ThxA biosynthetic cluster from the pathogenic *Streptomyces* species. In embodiments, the pathogenic *Streptomyces* strain is *S. scabiei* and the non-pathogenic strain is *S. albus* J1074.

In order to select for successful integration of the exogenous, non-native ThxA biosynthetic gene cluster from the pathogenic strain into the genome of the recipient non-pathogenic *Streptomyces* bacteria, in embodiments, the ThxA biosynthetic gene cluster from a pathogenic *Streptomyces* strain is operably linked to a nucleotide encoding a selectable marker. Thus, in such embodiments, the expression of the selectable marker indicates integration and expression of the genes in the non-native ThxA gene cluster. In embodiments, the selectable marker is antibiotic resistance, such as known to those of skill in the art, and described in greater detail in the examples below.

In embodiments the genetically engineered *Streptomyces* bacterium of the present disclosure produces about the same or a greater amount of thaxtomin than *S. scabiei* under the same culture conditions. Thus, in some conditions the genetically engineered *Streptomyces* bacterium of the present disclosure "overproduces" thaxtomin, as compared to a wild-type, thaxtomin producing, pathogenic species, such as *S. scabiei*.

In embodiments, the genetically engineered *Streptomyces* bacterium also includes at least one additional mutation, in addition to the addition of the exogenous ThxA gene cluster, to increase thaxtomin production, such as those discussed above and described in detail in PCT/US2015/050582 (WO 2016/044527 A1). In embodiments, this mutation is one or more mutations, affecting the production of proteins involved in regulation of thaxtomin regulation, such as cebR and bglC. For instance, in embodiments, the genetically engineered *Streptomyces* bacterium of the present disclosure further includes at least one of a mutation of a native cebR gene and a mutation of a native bglC gene, where the mutation reduces production or functionality of at least one of a CebR repressor encoded by the cebR gene and a β-glucosidase enzyme encoded by the bglC gene. In embodiments the cebR gene has a nucleotide sequence of SEQ ID NO: 15 or a nucleotide sequence having about 60% or more sequence identity with SEQ ID NO: 15. In embodiments, the bglC gene has a nucleotide sequence of SEQ ID NO: 17 or a nucleotide sequence having about 60% or more sequence identity with SEQ ID NO: 17.

Methods of Providing Thaxtomin-Production in Non-Native *Streptomyces*

The present disclosure also provides methods of providing thaxtomin-producing capability in a non-native *Streptomyces* bacterium (or other Actinomycete capable of receiving and integrating the thaxtomin gene cluster into its genome). In general, methods of the present disclosure for providing thaxtomin-producing capability in a non-native *Streptomyces* bacterium include providing a *Streptomyces* bacterium from a naturally non-pathogenic species that does not produce thaxtomin and genetically engineering the bacterium for thaxtomin production. In embodiments the genetic engineering includes introducing a non-native nucleic acid molecule encoding for non-native Thaxtomin A (ThxA) biosynthetic gene cluster from a pathogenic *Streptomyces* strain, such that the non-native ThxA is integrated into the genome of the *Streptomyces* bacterium such that the genetically engineered *Streptomyces* bacterium is capable of producing thaxtomin. In embodiments, the exogenous, non-native nucleic acid molecule encoding for the non-native ThxA gene cluster includes all of TR1, as described above. In embodiments the exogenous, non-native nucleic acid molecule also includes exogenous, TR2, where TR1 and TR2 are operably linked. In other embodiments, as described above, the exogenous, non-native nucleic acid molecule encoding for the non-native ThxA gene cluster includes a subset of TR1.

In embodiments, the process of introducing the non-native nucleic acid molecule is done via conjugal mating of a recombinant pathogenic strain and a naturally non-pathogenic strain, such that the exogenous, non-native nucleic acid molecule encoding for the non-native ThxA gene cluster is transferred to the naturally non-pathogenic strain. In embodiments the method includes providing a pathogenic *Streptomyces* bacterium that includes a TR nucleic acid encoding a native TR1, a subset thereof, and TR2 (TR) and conjugally mating this pathogenic *Streptomyces* bacterium with a naturally non-pathogenic *Streptomyces* bacterium lacking TR1, such that TR1 and TR2 are transferred from the pathogenic *Streptomyces* bacterium to the naturally non-pathogenic *Streptomyces* bacterium. In embodiments, the process includes providing a genetically engineered pathogenic *Streptomyces* bacterium that has been engineered to include an exogenous nucleic acid encoding a selectable marker operably linked to a TR nucleic acid encoding a native TR1, a subset thereof, and TR2 (TR). Then this genetically engineered pathogenic *Streptomyces* bacterium is conjugally mated with a naturally non-pathogenic *Streptomyces* bacterium lacking TR1, such that the selectable marker, TR1, and TR2 are transferred from the pathogenic *Streptomyces* bacterium to the naturally non-pathogenic *Streptomyces* bacterium. Then the selectable marker can be used to select for transconjugants that harbor the TR. Additional methods (such as PCR) can be used to confirm integration of the TR into a genome of the naturally non-pathogenic *Streptomyces* bacterium. The resulting genetically engineered transformants express the ThxA gene cluster (e.g., the whole cluster or subset thereof) and are able to produce thaxtomin. In embodiments the genetically engineered *Streptomyces* bacterium made according to the methods of the present disclosure are able to produce about as much or more thaxtomin than a wild type pathogenic species, such as the species from which the ThxA gene cluster originated.

In other methods, introducing the non-native nucleic acid molecule does not include bacterial conjugation, due to possible instability of the conjugates. In embodiments, the method includes cloning a ThxA biosynthetic gene cluster from a pathogenic *Streptomyces* strain, optionally operably linking the ThxA biosynthetic gene cluster to a selectable marker, and then transforming the ThxA biosynthetic gene cluster into the *Streptomyces* bacterium from the naturally non-pathogenic species using methods such as yeast cloning systems and bacterial transforming systems, such as *E. coli* (as described in greater detail in Examples 1 and 2, below). In embodiments, after transforming, the recipient, naturally non-pathogenic species includes the ThxA biosynthetic cluster and optional selectable marker, and successful transformants can be identified using the selectable marker or other method known to those of skill in the art. The successful transformants can be further tested (e.g., genetic analysis or thaxtomin production tests) to confirm integration of the ThxA gene cluster into the recipient bacterial genome. Other methods known to those of skill in the art can be used to introduce the exogenous non-native ThxA gene cluster into the *Streptomyces* bacteria resulting in integration of the ThxA gene cluster and consequent production of thaxtomin. Such methods are intended to be included in the scope of the present application.

These methods provide genetically engineered *Streptomyces* bacterium capable of producing thaxtomin. In embodiments, the genetically engineered *Streptomyces* bacterium are capable of producing thaxtomin produces in about the same or a greater amount of thaxtomin than *S. scabiei* under the same culture conditions.

In the various methods described herein, in embodiments, the non-native ThxA biosynthetic cluster is from a pathogenic *Streptomyces* strain including, but not limited to, *Streptomyces scabiei*, *Streptomyces acidiscabies*, and *Streptomyces turgidiscabies*. In embodiments, the *Streptomyces* bacterium from a non-pathogenic *Streptomyces* strain can be, but is not limited to, one of the following strains: *S. albus*, *S. diastatochromogenes*, *S. lividans*, *S. coelicolor*, and *S. avermitilis*. As mentioned above, in some embodiments the non-pathogenic recipient bacterial species is another non-pathogenic species compatible with transformation with and expression of the ThxA biosynthetic cluster from a pathogenic *Streptomyces* strain, such as, but not limited to *Norcardia*. In embodiments, the pathogenic *Streptomyces* strain is *S. scabiei* and the non-pathogenic strain is *S. albus* J1074.

In some embodiments, the methods also include introducing a non-naturally occurring mutation into the *Streptomyces* bacterium, such as discussed above that affect the production of CebR protein β-glucosidase enzyme, and thus the production of thaxtomin. In embodiments, the non-naturally occurring mutation can include a mutation of a cebR gene that reduces production or functionality of a CebR protein encoded by the cebR gene, a mutation of a bglC gene that reduces production or functionality of a β-glucosidase enzyme encoded by the bglC gene, or both.

The present disclosure also includes genetically engineered *Streptomyces* bacterium produced by the methods described in the present disclosure.

Methods of Producing Thaxtomin

The present disclosure also includes methods of producing thaxtomin. Embodiments of such methods include culturing the genetically engineered *Streptomyces* bacteria of the present disclosure described above, so that the modified *Streptomyces* bacteria produce thaxtomin.

In the methods of producing thaxtomin of the present disclosure, the genetically engineered *Streptomyces* bacteria exhibit about the same or increased production of thaxtomin compounds as compared to a wild type *Streptomyces scabiei* bacteria. As described above, in some embodiments, the genetically engineered *Streptomyces* bacteria of the present disclosure produce thaxtomin in environmental conditions (e.g., standard growth medium) where the native or wild type *Streptomyces* bacteria would not be able to produce thaxtomin or may only produce trace amounts. In embodiments of the methods of the present disclosure for producing thaxtomin, the thaxtomin produced by the genetically engineered *Streptomyces* bacteria is collected and/or extracted from the cell culture. After collection/extraction of the thaxtomin from the cell culture, the thaxtomin may be further extracted/separated from the culture media, and/or the extracted thaxtomin may then be subject to further isolation and/or purification steps as needed or desired.

The present disclosure also includes the thaxtomin compounds produced by the methods and genetically engineered bacteria of the present disclosure described above. The isolated and/or purified thaxtomin compound isolated from the genetically engineered *Streptomyces* bacteria of the present disclosure can then be used for various purposes, such as in the production of certain herbicides. Thus, the methods of the present disclosure also include methods of making herbicides including thaxtomin by producing thaxtomin according to the methods of the present disclosure and using the thaxtomin to produce the herbicide. The present disclosure also includes thaxtomin compounds produced by the methods of making thaxtomin of the present disclosure described above.

Methods of Producing Thaxtomin Analogs and Intermediates

The present disclosure also provides methods of producing thaxtomin derivatives, analogs and/or intermediates and genetically engineered *Streptomyces* bacterium capable of producing the thaxtomin derivatives, analogs and/or intermediates. In embodiments, methods of the present disclosure, include methods such as those described above for producing thaxtomin compounds, by providing a *Streptomyces* bacterium from a naturally non-pathogenic species that does not produce thaxtomin compounds or intermediates and genetically engineering the *Streptomyces* bacterium by introducing a non-native nucleic acid molecule encoding for a genetically modified, non-native thaxtomin biosynthetic gene cluster from a pathogenic *Streptomyces* strain, where the non-native thaxtomin biosynthetic gene cluster can confer the ability to produce thaxtomin compounds, derivatives, or intermediates. In embodiments, the genetically modified, non-native thaxtomin biosynthetic gene cluster is integrated into the genome of the *Streptomyces* bacterium such that the genetically engineered *Streptomyces* bacterium is capable of producing thaxtomin, thaxtomin intermediates, and/or thaxtomin analogs.

In embodiments for making thaxtomin intermediates or other thaxtomin compounds other than thaxtomin A, such as thaxtomin D, thaxtomin C, N-acetyl-nitro-L-tryptophan, and N-methyl-nitro-L-tryptophan, the non-native thaxtomin biosynthetic gene cluster from a pathogenic *Streptomyces* strain is engineered such that instead of producing thaxtomin A, the genetically engineered *Streptomyces* bacterium produces one or more of the intermediates. Although other native, pathogenic *Streptomyces* bacterium and other genetically engineered *Streptomyces* bacterium of the present disclosure may produce some of these intermediates, in embodiments, the genetically engineered *Streptomyces* bacterium can produce a greater amount of intermediates/derivatives than a native pathogenic or other engineered strain.

In embodiments, the non-native thaxtomin biosynthetic gene cluster from a pathogenic *Streptomyces* strain comprises an engineered thaxtomin biosynthetic gene cluster that has a deletion or other silencing mutation of the txtC gene and therefore does not include/does not include txtC and/or does not produce TxtC. This deletion of txtC provides the genetically engineered *Streptomyces* bacterium with the capability of producing thaxtomin biosynthetic intermediates such as, but not limited to, thaxtomin D, thaxtomin C, N-acetyl-nitro-L-tryptophan, and N-methyl-nitro-L-tryptophan. In some embodiments the engineered thaxtomin biosynthetic gene cluster also has a deletion or other silencing mutation of other txt genes from the TR1 region, such as deletion of one or more of txtC, txtA, txtB, and txtH. In embodiments these engineered thaxtomin biosynthetic gene clusters that do not include one or more of txtC, txtA, txtB, and txtH, confer the genetically engineered *Streptomyces* bacterium with the capability of producing thaxtomin biosynthetic intermediates such as, but not limited to, thaxtomin D, thaxtomin C, N-acetyl-nitro-L-tryptophan, and N-methyl-nitro-L-tryptophan.

The present disclosure also includes the genetically engineered *Streptomyces* bacterium that include these exogenous, non-native engineered thaxtomin biosynthetic gene cluster from a pathogenic *Streptomyces* strain, wherein the engineered thaxtomin biosynthetic gene cluster does not include one or more of txtC, txtA, txtB, and txtH.

In yet other embodiments, methods of the present disclosure also include methods of making halogenated derivatives of thaxtomin compounds, intermediates, and/or analogs. In embodiments, such halogenated derivatives include, but are not limited to, fluorinated derivatives. In embodiments, methods include culturing any of the genetically engineered *Streptomyces* bacterium of the present disclosure having the non-native thaxtomin biosynthetic gene clusters in a culture media including a halogenated compound, (e.g., fluorinated compound 5-F-L-tryptophan or other fluorinated enzyme substrate, or other halogenated compound), such that the genetically engineered *Streptomyces* bacterium incorporates the halogenated substrates into the thaxtomin compounds/intermediates to produce fluorinated derivatives of these compounds, such as, but not limited to, 5-F-thaxtomin A.

Additional details regarding the methods, compositions, and organisms of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Aspects

The following listing of exemplary aspects supports and is supported by the disclosure provided herein.

Aspect 1. A genetically engineered *Streptomyces* bacterium comprising:
a *Streptomyces* bacterium from a non-pathogenic *Streptomyces* strain, the *Streptomyces* bacterium comprising an exogenous, non-native Thaxtomin A (ThxA) biosynthetic gene cluster from a pathogenic *Streptomyces* strain, wherein the presence of the non-native ThxA biosynthetic cluster provides the genetically engineered *Streptomyces* bacterium with the ability to produce thaxtomin A, wherein the non-pathogenic *Streptomyces* strain without the exogenous non-native ThxA biosynthetic cluster does not have the ability to produce thaxtomin.

Aspect 2. The genetically engineered *Streptomyces* bacterium of aspect 1, wherein the exogenous, non-native ThxA biosynthetic cluster comprises toxigenic region 1 (TR1).

Aspect 3. The genetically engineered *Streptomyces* bacterium of aspect 1 or 2, wherein the non-native ThxA biosynthetic cluster is from a pathogenic *Streptomyces* strain selected from the group of pathogenic *Streptomyces* species consisting of: *Streptomyces scabiei, Streptomyces acidiscabies*, and *Streptomyces turgidiscabies*.

Aspect 4. The genetically engineered *Streptomyces* bacterium of aspect 3, wherein the pathogenic *Streptomyces* species is *S. scabiei* 87-22 or other strain of *S. scabiei*.

Aspect 5. The genetically engineered *Streptomyces* bacterium of any of aspects 1-4, wherein the *Streptomyces* bacterium from a non-pathogenic *Streptomyces* strain is selected from the group of non-pathogenic *Streptomyces* species consisting of: *S. albus, S. diastatochromogenes, S. lividans, S. coelicolor*, and *S. avermitilis*.

Aspect 6. The genetically engineered *Streptomyces* bacterium of aspect 5, wherein the *Streptomyces* bacterium from a non-pathogenic *Streptomyces* strain is *S. albus* J1074.

Aspect 7. The genetically engineered *Streptomyces* bacterium of any of aspects 1-6, wherein the genetically engineered *Streptomyces* bacterium further comprises exogenous, non-native toxigenic region 2 (TR2).

Aspect 8. The genetically engineered *Streptomyces* bacterium of any of aspects 1-7, wherein the exogenous, non-native Thaxtomin A (ThxA) biosynthetic gene cluster from a pathogenic *Streptomyces* strain is operably linked to a nucleotide encoding a selectable marker.

Aspect 9. The genetically engineered *Streptomyces* bacterium of aspect 8, wherein the selectable marker is antibiotic resistance.

Aspect 10. The genetically engineered *Streptomyces* bacterium of any of aspects 1-9, wherein the genetically engineered *Streptomyces* bacterium produces about the same or a greater amount of thaxtomin than *S. scabiei* under the same culture conditions.

Aspect 11. The genetically engineered *Streptomyces* bacterium of any of aspects 1-10, wherein the non-native ThxA biosynthetic cluster is from a pathogenic *Streptomyces* strain of *S. scabiei* and wherein the *Streptomyces* bacterium from a non-pathogenic *Streptomyces* strain of *S. albus*.

Aspect 12. A genetically engineered *Streptomyces* bacterium comprising: a *Streptomyces* bacterium from a non-pathogenic *Streptomyces* strain, the *Streptomyces* bacterium comprising an exogenous, non-native engineered thaxtomin biosynthetic gene cluster from a pathogenic *Streptomyces* strain, wherein the engineered thaxtomin biosynthetic gene cluster does not include the txtC gene, wherein the presence of the non-native, engineered thaxtomin biosynthetic cluster provides the genetically engineered *Streptomyces* bacterium with the ability to produce thaxtomin biosynthetic intermediates selected from thaxtomin D, thaxtomin C, N-acetyl-nitro-L-tryptophan, and N-methyl-nitro-L-tryptophan, wherein the non-pathogenic *Streptomyces* strain without the exogenous non-native, engineered thaxtomin biosynthetic cluster does not have the ability to produce the thaxtomin intermediates.

Aspect 13. The genetically engineered *Streptomyces* bacterium of aspect 12, wherein the engineered thaxtomin biosynthetic gene cluster further does not include any of the txtA, txtB, and txtH genes.

Aspect 14. A method of providing a non-native *Streptomyces* bacterium with the ability to product thaxtomin compounds, derivatives thereof, or intermediates thereof, the method comprising: providing a *Streptomyces* bacterium from a naturally non-pathogenic species that does not produce thaxtomin; and genetically engineering the *Streptomyces* bacterium by introducing a non-native nucleic acid molecule encoding for a non-native thaxtomin biosynthetic gene cluster from a pathogenic *Streptomyces* strain, such that the non-native thaxtomin biosynthetic gene cluster is integrated into the genome of the *Streptomyces* bacterium such that the genetically engineered *Streptomyces* bacterium is capable of producing one or more thaxtomin compounds, intermediates thereof, or derivatives thereof.

Aspect 15. The method of aspect 14, wherein the non-native thaxtomin biosynthetic gene cluster from a pathogenic *Streptomyces* strain comprises toxigenic region 1 (TR1) and provides the genetically engineered *Streptomyces* bacterium with the capability of producing thaxtomin A.

Aspect 16. The method of aspect 14 or 15, wherein the non-native nucleic acid molecule further comprises exogenous, toxigenic region 2 (TR2), wherein TR1 and TR2 are operably linked.

Aspect 17. The method of aspect 16, wherein introducing the non-native nucleic acid molecule includes: providing a genetically engineered pathogenic *Streptomyces* bacterium comprising an exogenous nucleic acid encoding a selectable marker operably linked to a TR nucleic acid encoding a native TR1 and TR2; performing conjugal mating of the genetically engineered pathogenic *Streptomyces* bacterium with the naturally non-pathogenic *Streptomyces* bacterium such that the selectable marker, TR1, and TR2 are transferred from the pathogenic *Streptomyces* bacterium to the naturally non-pathogenic *Streptomyces* bacterium; and selecting for transconjugants and detecting for integration of the TR into a genome of the naturally non-pathogenic *Streptomyces* bacterium to produce a genetically engineered *Streptomyces* bacterium capable of producing thaxtomin.

Aspect 18. The method of any of aspects 14-16, wherein introducing the non-native nucleic acid molecule comprises: cloning a thaxtomin biosynthetic gene cluster from a pathogenic *Streptomyces* strain; transforming the thaxtomin biosynthetic gene cluster into the *Streptomyces* bacterium from the naturally non-pathogenic species; and selecting for transformants to provide genetically engineered *Streptomyces* bacterium capable of producing thaxtomin.

Aspect 19. The method of aspect 18 further comprising: operably linking the thaxtomin biosynthetic gene cluster to a selectable marker and using the selectable marker to select for transformants having the thaxtomin biosynthetic gene cluster.

Aspect 20. The method of any of aspects 14-19, wherein the pathogenic *Streptomyces* strain is selected from the group of pathogenic *Streptomyces* species consisting of: *Streptomyces scabiei, Streptomyces acidiscabies*, and *Streptomyces turgidiscabies*.

Aspect 21. The method of any of aspects 14-20, wherein the *Streptomyces* bacterium from a non-pathogenic *Streptomyces* strain is selected from the group of non-pathogenic *Streptomyces* species consisting of: *S. albus, S. diastatochromogenes*, and *S. avermitilis*.

Aspect 22. The method of aspect 21, wherein the *Streptomyces* bacterium from a non-pathogenic *Streptomyces* strain is *S. albus* J1074.

Aspect 23. The method of any of aspects 14-22, wherein the genetically engineered *Streptomyces* bacterium capable of producing thaxtomin produces about the same or a greater amount of thaxtomin than *S. scabiei* under the same culture conditions.

Aspect 24. The method of any of aspects 18-23, wherein the non-native thaxtomin biosynthetic gene cluster from a pathogenic *Streptomyces* strain comprises an engineered ThxA biosynthetic gene cluster comprising less than the full toxigenic region 1 (TR1) and provides the genetically engineered *Streptomyces* bacterium with the capability of producing thaxtomin A.

Aspect 25. The method of any of aspects 18-23, wherein the non-native thaxtomin biosynthetic gene cluster from a pathogenic *Streptomyces* strain comprises an engineered thaxtomin biosynthetic gene cluster that does not include txtC gene and provides the genetically engineered *Streptomyces* bacterium with the capability of producing thaxtomin biosynthetic intermediates selected from thaxtomin D, thaxtomin C, N-acetyl-nitro-L-tryptophan, and N-methyl-nitro-L-tryptophan.

Aspect 26. The method of aspect 25, wherein the engineered thaxtomin biosynthetic gene cluster also does not include any of the txtA, txtB, and txtH genes and provides the genetically engineered *Streptomyces* bacterium with the capability of producing thaxtomin biosynthetic intermediates selected from thaxtomin D, thaxtomin C, N-acetyl-nitro-L-tryptophan, and N-methyl-nitro-L-tryptophan.

Aspect 27. A genetically engineered *Streptomyces* bacterium produced by the method of any of aspects 14-26.

Aspect 28. A method of producing thaxtomin compounds, thaxtomin derivatives, and thaxtomin intermediates, the method comprising: culturing genetically engineered *Streptomyces* bacteria from a non-pathogenic *Streptomyces* strain, the genetically engineered *Streptomyces* bacterium comprising an exogenous, non-native thaxtomin biosynthetic gene cluster from a pathogenic *Streptomyces* strain, such that the genetically engineered *Streptomyces* bacteria produce thaxtomin compounds, derivatives or intermediates, wherein the genetically engineered *Streptomyces* bacteria have about the same or increased production of a thaxtomin compound, derivative, or intermediate as compared to a wild type *S. scabiei* bacteria under the same culture conditions.

Aspect 29. The method of aspect 28, wherein the non-native thaxtomin biosynthetic gene cluster from a pathogenic *Streptomyces* strain comprises toxigenic region 1 (TR1) and provides the genetically engineered *Streptomyces* bacterium with the capability of producing thaxtomin A.

Aspect 30. The method of aspect 28, wherein the non-native thaxtomin biosynthetic gene cluster from a pathogenic *Streptomyces* strain comprises an engineered ThxA biosynthetic gene cluster comprising less than the full toxigenic region 1 (TR1) and provides the genetically engineered *Streptomyces* bacterium with the capability of producing thaxtomin A.

Aspect 31. The method of aspect 28, wherein the non-native thaxtomin biosynthetic gene cluster from a pathogenic *Streptomyces* strain comprises an engineered thaxtomin biosynthetic gene cluster that does not include txtC gene and provides the genetically engineered *Streptomyces* bacterium with the capability of producing thaxtomin biosynthetic intermediates selected from thaxtomin D, thaxtomin C, N-acetyl-nitro-L-tryptophan, and N-methyl-nitro-L-tryptophan.

Aspect 32. The method of aspect 31, wherein the engineered thaxtomin biosynthetic gene cluster also does not include any of the txtA, txtB, and txtH genes and provides the genetically engineered *Streptomyces* bacterium with the capability of producing thaxtomin biosynthetic intermediates selected from thaxtomin D, thaxtomin C, N-acetyl-nitro-L-tryptophan, and N-methyl-nitro-L-tryptophan.

Aspect 33. The method of any of aspects 28-33, wherein culturing the genetically engineered *Streptomyces* bacterium comprising the non-native thaxtomin biosynthetic gene cluster comprises culturing in a culture media comprising a halogenated compound, such that the genetically engineered *Streptomyces* bacterium produces halogenated thaxtomin derivatives, halogenated thaxtomin intermediates, and/or halogenated thaxtomin analogs.

Aspect 34. The method of aspect 33, wherein the halogenated thaxtomin analog comprises 5-F-thaxtomin A.

Aspect 35. The method of any of aspects 27-34, further comprising extracting the thaxtomin compound from the culture media.

Aspect 36. A method of producing thaxtomin compounds and nitrotryptophan analogs, the method comprising: providing a *Streptomyces* bacterium from a naturally non-pathogenic species that does not produce thaxtomin; and genetically engineering the *Streptomyces* bacterium by introducing a non-native nucleic acid molecule encoding for a genetically modified, non-native thaxtomin biosynthetic gene cluster from a pathogenic *Streptomyces* strain, such that the genetically modified, non-native thaxtomin biosynthetic gene cluster is integrated into the genome of the *Streptomyces* bacterium such that the genetically engineered *Streptomyces* bacterium is capable of producing thaxtomin, thaxtomin intermediates, and/or thaxtomin analogs.

Aspect 37. The method of aspect 36, wherein the non-native thaxtomin biosynthetic gene cluster from a pathogenic *Streptomyces* strain comprises toxigenic region 1 (TR1) and provides the genetically engineered *Streptomyces* bacterium with the capability of producing thaxtomin A.

Aspect 38. The method of aspect 36, wherein the non-native thaxtomin biosynthetic gene cluster from a pathogenic *Streptomyces* strain comprises an engineered ThxA biosynthetic gene cluster comprising less than the full toxigenic region 1 (TR1) and provides the genetically engineered *Streptomyces* bacterium with the capability of producing thaxtomin A.

Aspect 39. The method of aspect 36, wherein the non-native thaxtomin biosynthetic gene cluster from a pathogenic *Streptomyces* strain comprises an engineered thaxtomin biosynthetic gene cluster that does not include txtC gene and provides the genetically engineered *Streptomyces* bacterium with the capability of producing thaxtomin biosynthetic intermediates selected from thaxtomin D, thaxtomin C, N-acetyl-nitro-L-tryptophan, and N-methyl-nitro-L-tryptophan.

Aspect 40. The method of aspect 39, wherein the engineered thaxtomin biosynthetic gene cluster also does not include any of the txtA, txtB, and txtH genes and provides the genetically engineered *Streptomyces* bacterium with the capability of producing thaxtomin biosynthetic intermediates selected from thaxtomin D, thaxtomin C, N-acetyl-nitro-L-tryptophan, and N-methyl-nitro-L-tryptophan.

Aspect 41. The method of any of aspects 36-40, further comprising culturing the genetically engineered *Streptomyces* bacterium comprising the non-native thaxtomin biosynthetic gene cluster in a culture media comprising a halogenated compound, such that the genetically engineered *Streptomyces* bacterium produces halogenated thaxtomin compounds, halogenated thaxtomin intermediates, and/or halogenated thaxtomin analogs.

From the foregoing, it will be seen that aspects herein are well adapted to attain the ends and objectives hereinabove set forth together with other advantages which are obvious and which are inherent to the systems and methods.

It will be understood that certain features and subcombinations are of utility and may be employed without reference to other features and subcombinations. This is contemplated by and is within the scope of the aspects.

While specific elements and steps are discussed in connection to one another, it is understood that any element and/or steps provided herein is contemplated as being combinable with any other elements and/or steps regardless of explicit provision of the same while still being within the scope provided herein. Since many possible aspects may be made of the disclosure without departing from the scope thereof, it is to be understood that all matter herein set forth or shown in the accompanying drawings is to be interpreted as illustrative and not in a limiting sense.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1—Overproduction of Thaxtomin in Non-Native *Streptomyces* Species

Thaxtomins are metabolites of several plant pathogenic *Streptomyces* species and have broad spectrum herbicidal activity. This example describes the overproduction of thaxtomins in nonpathogenic *Streptomyces* species that carry the genomic island of the plant pathogen *S. scabiei* 87-22; this island contains the thaxtomin biosynthetic cluster. Also provided herein are strategies for enhancing thaxtomin production in microbial fermentation.

Materials and Methods

Bacterial Strains and Culture Conditions

*Escherichia coli* strains were cultured in Luria-Bertani (LB) medium at 37° C. *Streptomyces* strains were cultured at 30° C. on the International *Streptomyces* Project medium 4 (ISP4) agar medium or in tryptic soy broth (TSB; BD Biosciences). All liquid cultures were shaken at 250 rpm. When required, media were supplemented with the following antibiotics at the indicated final concentrations: hygromycin B (100 µg/ml), apramycin (50 µg/ml), kanamycin (50 µg/ml), chloramphenicol (25 µg/ml), and nalidixic acid (50 µg/ml). All *S. scabiei* 87-22 deletion mutants used in this study were generated by intergeneric conjugation from the non-methylating *E. coli* strain ET12567/pUZ8002. Strains and plasmids used in this study are described in Table 2.

Insertion of Antibiotic Resistance Markers in the PAI

Insertion of the antibiotic resistance markers into the TR1 or TR2 region of *S. scabiei* 87-22 was accomplished by replacing txtH (SCAB_31771) with the apramycin resistance gene or replacing the lantibiotic biosynthesis genes lanA (SCAB_32021) and lanB (SCAB_32031) with the hygromycin B resistance gene using the Redirect PCR targeting system (Gust et al. 2003).

The cosmid 1989 (harboring the txtH gene) or the cosmid 2757 (harboring the lantibiotic biosynthesis genes) was introduced to the *Escherichia coli* BW25113 strain harboring the arabinose-inducible λ red expression plasmid pIJ790 (aac(3)IV+oriT) or pIJ10700 (hyg+oriT) (Table 2). The deletion cassette for txtH was PCR amplified using pIJ773 as the template and using primers DRB201 and DRB202 (Table 7); the deletion cassette for lanA and lanB was PCR amplified using pIJ10700 as the template and using primers DRB431 and DRB432 (Table 7). The gel-purified deletion cassettes were electroporated into the *E. coli* BW25113 cells that contained either the cosmid 1989 or cosmid 2757 and which had been induced with arabinose (20 mM final concentration). The ΔtxtH and ΔlanAB mutant cosmids were then isolated and confirmed by PCR and sequencing. Following transformation of each cosmid into the non-methylating *E. coli* ET12567 strain (Table 2) (MacNeil et al. 1992), which contains the plasmid pUZ8002 as a driver for transfer (Bierman et al. 1992), the cosmids were conjugated into *S. scabiei* 87-22 on soy flour mannitol (SFM) agar (Kieser et al. 2000). Resulting exconjugants for ΔtxtH were selected for resistance to apramycin (apr$^R$) and sensitive to kanamycin, and exconjugants for ΔlanAB were selected for resistance to hygromycin B (hyg$^R$) and sensitive to kanamycin. The mutant strains were confirmed using PCR and were stored as spore stocks in 20% vol/vol glycerol at −80° C.

Selection of Transconjugant Strains

Conjugal mating was carried out by co-culturing donor and recipient strains on SFM plates (Kieser et al. 2000) for 2 days at 30° C. A soft nutrient agar overlay containing antibiotics was used to select for transconjugants. Qualitative PCR assays were conducted to detect the integration of S. scabiei TR into the chromosome of non-pathogenic strains (Table 7). Primers a+b flanking the att site located at the 3' end of the aviX1 gene were used to detect the site-specific integration of TR in aviX1. Primers e+f were used to amplify the chromosomal junction formed by integration of the whole TR or TR2 into aviX1. Primers c+d that are located within the integrase gene (SCAB_31871) of TR2 were used to confirm TR2 integration. Primers g+h flanking txtH (SCAB_31771) were used to confirm TR1 integration. All PCR products were sequenced.

The Procedure of Fermentation and Isolation Thaxtomins and Nitro-Tryptophans

Mycelial suspensions of *S. scabiei* and *S. albus* J1074 strains were prepared from 48-hour-old 20 ml TSB-grown cultures by pelleting the mycelia, washing twice with sterile water, and resuspending in 20 ml sterile water. For analysis of thaxtomin production, TDM medium with 1% cellobiose (Johnson et al. 2007) was used. Three times 500 ml medium in 2 Liter flasks were inoculated with 15 ml of mycelial suspension of $OD_{600\ nm}$ 1.0. After incubation for 7 days at 30° C. with shaking at 250 rpm, the culturing media were centrifuged with 5000 rpm to pellet the mycelium. The supernatants of centrifugation were added to C18 columns (waters-2 g). Nitrotrptophans were eluted with 25% methanol while thaxtomins were eluted with 100% methanol. The eluted solvents containing targeted compounds were further evaporated to dryness and then were further purified by semi-prep HPLC column to give isolation yields in Table 1. Experiments were repeated with at least three technical replicates per strain and per medium. Thaxtomins could also be extracted by ethyl acetate directly from supernatant which could provide the same amount of thaxtomins from the same volume of supernatant. Experiments were repeated using different biological replicates of the *Streptomyces* strains with three technical replicates per strain.

Analytical HPLC Analysis

Thaxtomins: the HPLC column (ZORBAX RX-C18, 5.0 μm, 4.6×250 mm) kept at 30° C. was eluted with 40% solvent B acetonitrile for 15 min. The flow rate was set as 1.0 ml/min, and the products were detected at 380 nm with a PDA detector.

Tryptophans: the HPLC column (Agilent Poroshell 120 EC-C18, 2.7 μm, 4.6×50 mm) kept at 30° C. was eluted first with 10% solvent B (acetonitrile with 0.1% formic acid) for 2 min and then with a linear gradient of 10-50% solvent B in 8 min, followed by another linear gradient of 50-99% solvent B in 5 min. After eluting in 99% solvent B for 3 min, the liner gradient of 99-10% solvent B in 1 min was used. The column was further re-equilibrated with 10% solvent B for 1 min. The flow rate was set as 0.5 ml/min, and the products were detected at 380 nm with a PDA detector.

Semi-Preparative HPLC Isolation

For semi-preparative analysis, the column (ZORBAX SB-C18, 5.0 μm, 9.4×250 mm) kept at 40° C. was eluted first with 10% solvent B (acetonitrile with 0.1% formic acid) for 2 min and then with a linear gradient of 10-50% solvent B for 8 min, followed by a linear gradient of 50-99% solvent B for 5 min. The column was then cleaned by 99% solvent B for 3 min and re-equilibrated with 10% solvent B for 1 min. The flow rate was set at 3 ml/min, and the products were detected at 380 nm with a PDA detector. All isolates were combined, concentrated, freeze-dried, and then weighed.

LC-MS Analysis of Isolated Products

A SHIMADZU Prominence UPLC system fitted with an Agilent Poroshell 120 EC-C18 column (2.7 μm, 4.6×50 mm) coupled with a Linear Ion Trap Quadrupole LC/MS/MS Mass Spectrometer system was used in the studies. The column was eluted with 10% solvent B (acetonitrile with 0.1% formic acid) for 2 min and then with a linear gradient of 10-50% solvent B in 8 min, followed by another linear gradient of 50-99% solvent B in 5 min. After eluting in 99% solvent B for 3 min, the liner gradient of 99-10% solvent B in 1 min was used. The column was further re-equilibrated with 10% solvent B for 1 min. The flow rate was set as 0.5 ml/min. For MS detection, the turbo spray conditions were identical for all chemicals (curtain gas: 30 psi; ion spray voltage: 5500 V; temperature: 600° C.; ion source gas 1: 50 psi; ion source gas 2: 60 psi).

Results

Comparative Genomic Analysis Suggests the Thaxtomin Cluster is Located on a Genomic Island To understand the emergence and evolution of thaxtomin biosynthetic cluster, we sequenced the genomes of 10 isolates of plant pathogenic streptomycetes from different locations. Comparative genomic analysis of these newly sequenced pathogenic *Streptomyces* genomes together with those available in the public database indicates that pathogenic isolates share a 20 Kb genomic region, designated TR1. TR1 contains the thaxtomin biosynthetic cluster and is flanked by two identical attachment (att) sites (FIG. 2). Moreover, a nearby 157 Kb genomic region is conserved only in *S. scabiei* and S. sp. 96-12, which belongs to a novel pathogenic species (Zhang et al. 2016). This region has been named TR2 by a previous study (Chapleau et al. 2016). TR2 is also flanked by two identical att sites, and includes putative integrative and conjugative elements (ICEs). ICEs are genomic islands that can be excised from chromosome to form a circular molecule, which is then transferred by conjugation and integrated into another genome by site-specific recombination (Burrus et al. 2002). Since S. sp. 96-12 is phylogenetically distant from *S. scabiei* (Zhang et al. 2016), the same organization and contents of TR1 and TR2 between S. sp. 96-12 and *S. scabiei* suggested an in vivo mobilization of the TR1 and TR2.

The *S. scabiei* Thaxtomin Biosynthetic Cluster is Site-Specifically Mobilized into the Chromosome of Non-Pathogenic Species To investigate the mobilization of thaxtomin biosynthetic cluster from *S. scabiei* to non-pathogenic species, two *S. scabiei* 87-22 deletion mutants were created, one with the apramycin resistance ($apr^R$) marker inserted in its TR1 [*S. scabiei* ΔtxtH ($apr^R$)] and the other with the hygromycin B ($hyg^R$) resistance marker inserted in its TR2 [*S. scabiei* ΔlanAB ($hyg^R$)]. In mating experiments, these mutants served as the genomic island donors. A naturally streptomycin resistant ($str^R$) nonpathogenic strain, *S. diastatochromogenes* ATCC 12309, was used as the recipient (FIG. 3A). Following selection with apramycin or hygromycin B, together with streptomycin, a number of *S. diastatochromogenes* mutants were isolated. Using PCR-based genotypic diagnosis with primers shown in Table 7, integration of *S. scabiei* TR1 and TR2 regions into the att site (TTGAAGCGGAAC, SEQ ID NO: 62) of the *S. diastatochromogenes* aviX1 gene (FIG. 3B) was detected. Mating of *S. scabiei* ΔlanAB with *S. diastatochromogenes* resulted in the acquisition of TR2 alone or of the complete TR (TR1 and TR2) element by *S. diastatochromogenes*; however, all transconjugants from the mating of *S. scabiei* ΔtxtH with *S. diastatochromogenes* acquired the entire TR element, but not TR1 alone. These observations suggested that the integrative and conjugative element of the TR2 region is important for the mobilization and site-specific integration of TR2 or the entire TR region into a new host chromosome via conjugation. In contrast, the TR1 region carrying the thaxtomin biosynthetic cluster does not appear to be mobile alone; its transfer appears to depend on the integrative and conjugative elements in the TR2 region. Acquisition of both TR1 and TR2, but not TR2 alone, conferred a pathogenic phenotype and thaxtomin production ability on *S. diastatochromogene* (data not shown).

Engineering of Non-Pathogenic *Streptomyces* Species for the Heterologous Production of Thaxtomin After characterizing the mobilization of the *S. scabiei* genomic island containing the thaxtomin biosynthetic cluster, the extent to which non-pathogenic *Streptomyces* sp. can act as the heterologous hosts for thaxtomin production was investigated. First, the apramycin-resistant ($apr^R$) integrative plasmid pSET152 from *Escherichia coli* was transferred into *S. albus* J1074, *S. coelicolor* M145, *S. lividans* 1326, and *S. avermitilis* NRRL 8165 to provide them with the apramycin-resistance for selection during the mating experiment. These non-pathogenic *Streptomyces* isolates comprising pSET52 ($apr^R$) were mated with *S. scabiei* ΔlanAB ($hyg^R$), which contains the hygromycin B ($hyg^R$) resistance marker in its TR2 region. After selection with apramycin together with hygromycin B, *S. albus* J1074, *S. coelicolor* M145, *S. lividans* 1326, and *S. avermitilis* NRRL 8165 transconjugants with the *S. scabiei* thaxtomin biosynthetic cluster were identified by the PCR screening with primers within TR1 and TR2 (Table 7).

Figure 4:
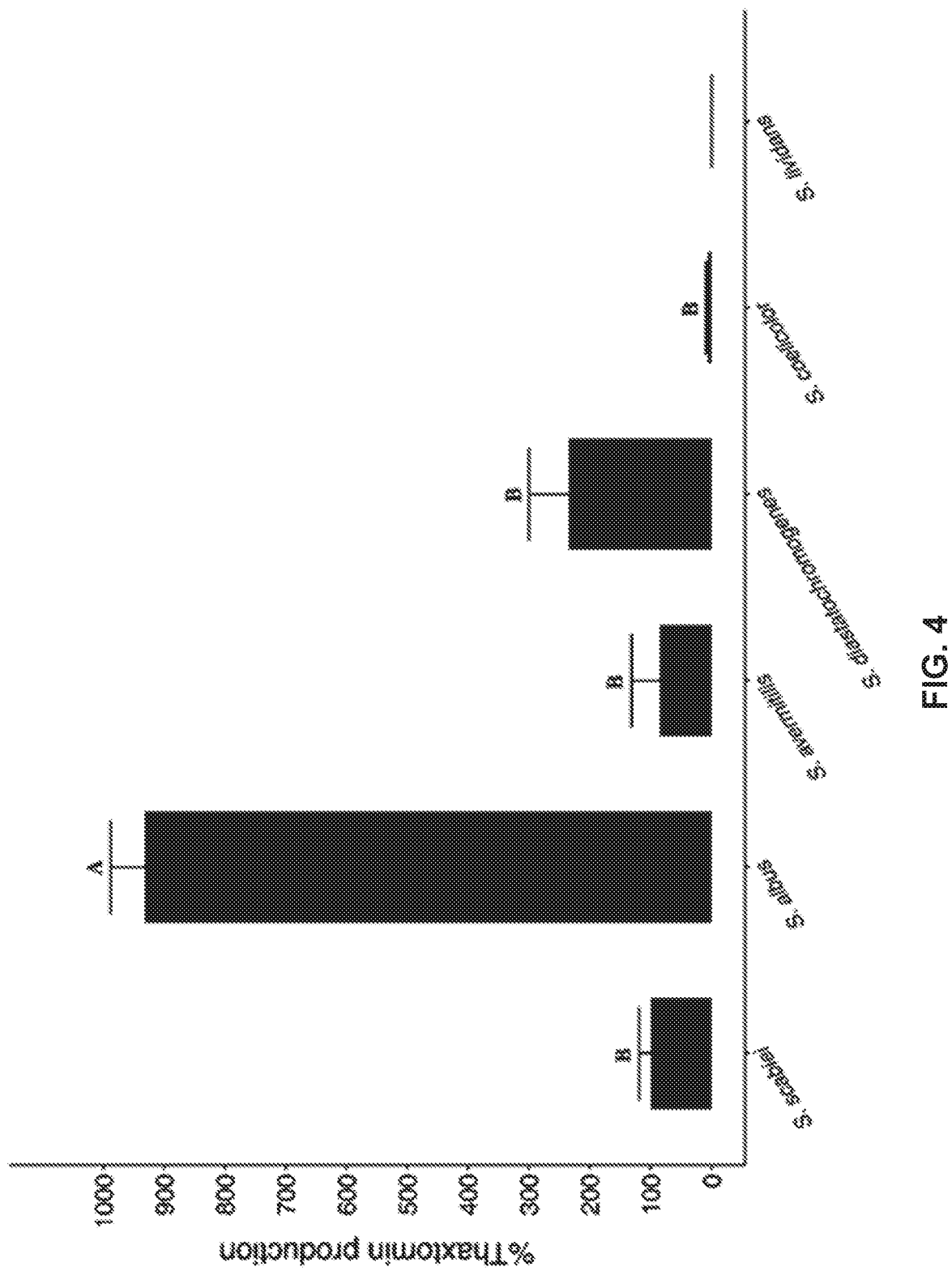
FIG. 4 illustrates a graph of the production of thaxtomin by heterologous hosts. *Streptomyces* strains were grown in triplicate TDM medium with 1% cellobiose for 6 days at 30° C. Spores were cultured on TSB at 30° C. for 48 hr. Vegetative culture was diluted to OD600=1 and 0.5 ml portion of the diluted culture was inoculated into 50 ml TDMc liquid medium and incubated at 30° C. with shaking (250 rpm). The average thaxtomin production of *S. scabiei* 87-22 is set to 100%. The average % production for each strain relative to *S. scabiei* 87-22 is shown, and the errors bars represent the standard deviation from the mean. Letters represent results of a one-way ANOVA with Tukey's HSD test; bars not sharing letters are significantly different at $P<0.05$.

Thaxtomin production of these four newly created heterologous hosts was then assessed along with the engineered *S. diastatochromogenes* ATCC 12309 created in the above studies in TDM medium supplemented with cellobiose (TDMc). The five heterologous hosts (*S. albus* J1074, *S. coelicolor* M145, *S. lividans* 1326, *S. avermitilis* NRRL 8165, and *S. diastatochromogenes* ATCC 12309) carrying the thaxtomin cluster produce thaxtomin at different levels (FIG. 4). *S. diastatochromogenes* and *S. avermitilis* produced a similar level of thaxtomin to *S. scabiei*; however, *S. coelicolor* only produced a trace amount of thaxtomin and *S. lividans* did not produce a detectable level of thaxtomin (FIG. 4). These data indicate that subtle differences in genetic backgrounds of these recipients can influence thaxtomin production. Remarkably, *S. albus* produced a significantly higher level of thaxtomin (about 9-fold) than *S. scabiei*.

Early Metabolic Switch of *S. albus* J1074 Leads to Early Thaxtomin Production

Figure 5:
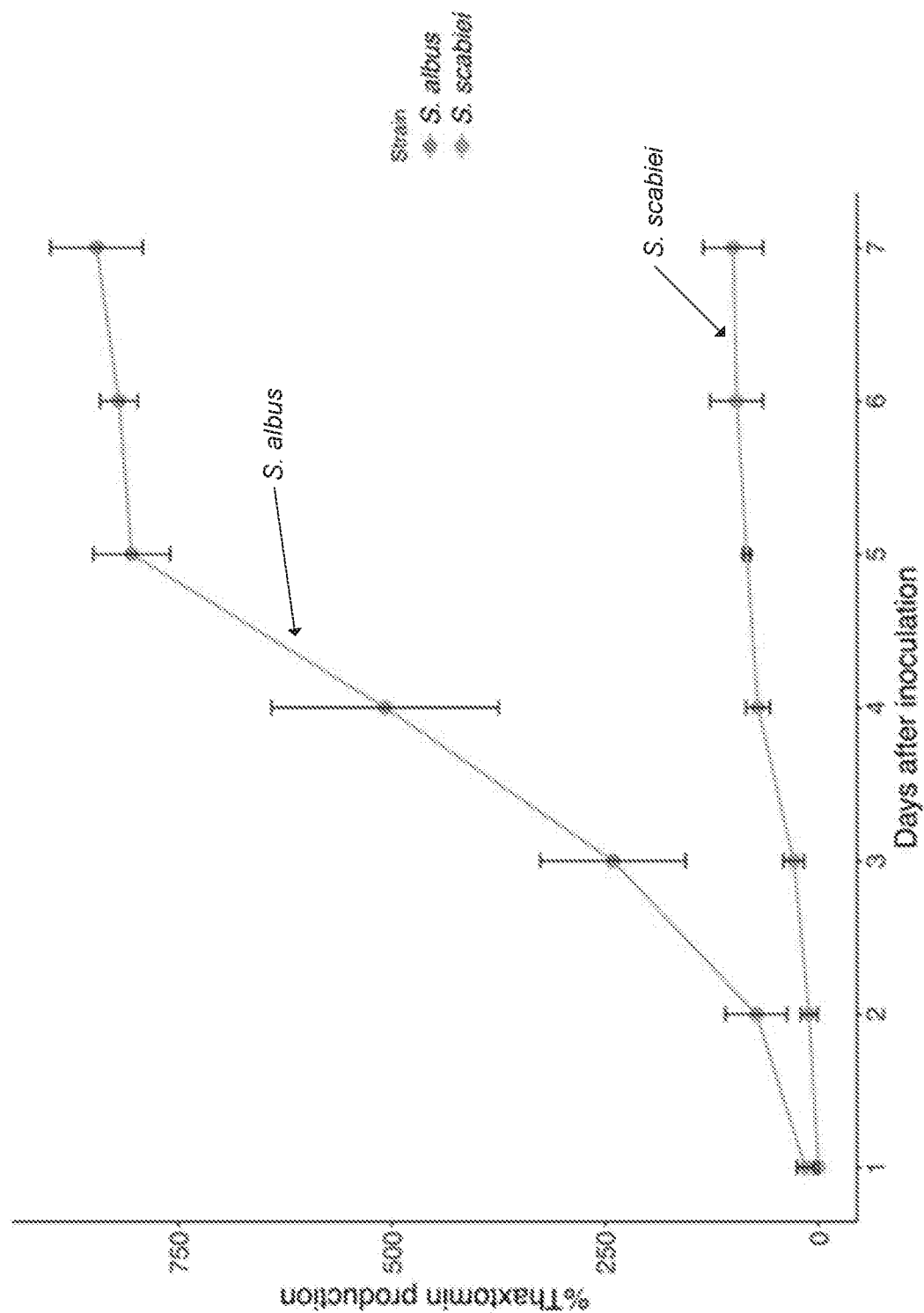
FIG. 5 illustrates a graph of the thaxtomin production of *S. albus* J1074 and *S. scabiei* 87-22, in TDMc liquid medium. The final yield of thaxtomin of *S. scabiei* 87-22 is set to 100%. The average % production of thaxtomin for two strains at each time points relative to *S. scabiei* 87-22 final yield is shown, and the errors bars represent the standard deviation from the mean. Spores were cultured on TSB at 30° C. for 48 hours. Vegetative culture was diluted to OD600=1 and 1 ml portion of the diluted culture was inoculated into 100 ml TDMc liquid medium and incubated at 30° C. with shaking (250 rpm). Samples (3 ml) of cultures were collected every 24 hours to determine the concentration of thaxtomin.

To further characterize the overproduction of thaxtomins in *S. albus*, the production of thaxtomin and its precursor 4-nitrotryptophan in TDMc medium was quantified at different time points (FIG. 5). *S. scabiei* was used as the control. Thaxtomin A was detected from the *S. albus* fermentation medium within 24 hours by HPLC analysis. By contrast, *S. scabiei* produced thaxtomin A two days after inoculation. The thaxtomin A level in the *S. albus* fermentation medium linearly increased until day five and remained stable from day five to seven (FIG. 5). At day two, *S. albus* already produces the same level of thaxtomin A as the final yield of *S. scabiei*.

Figure 6A:
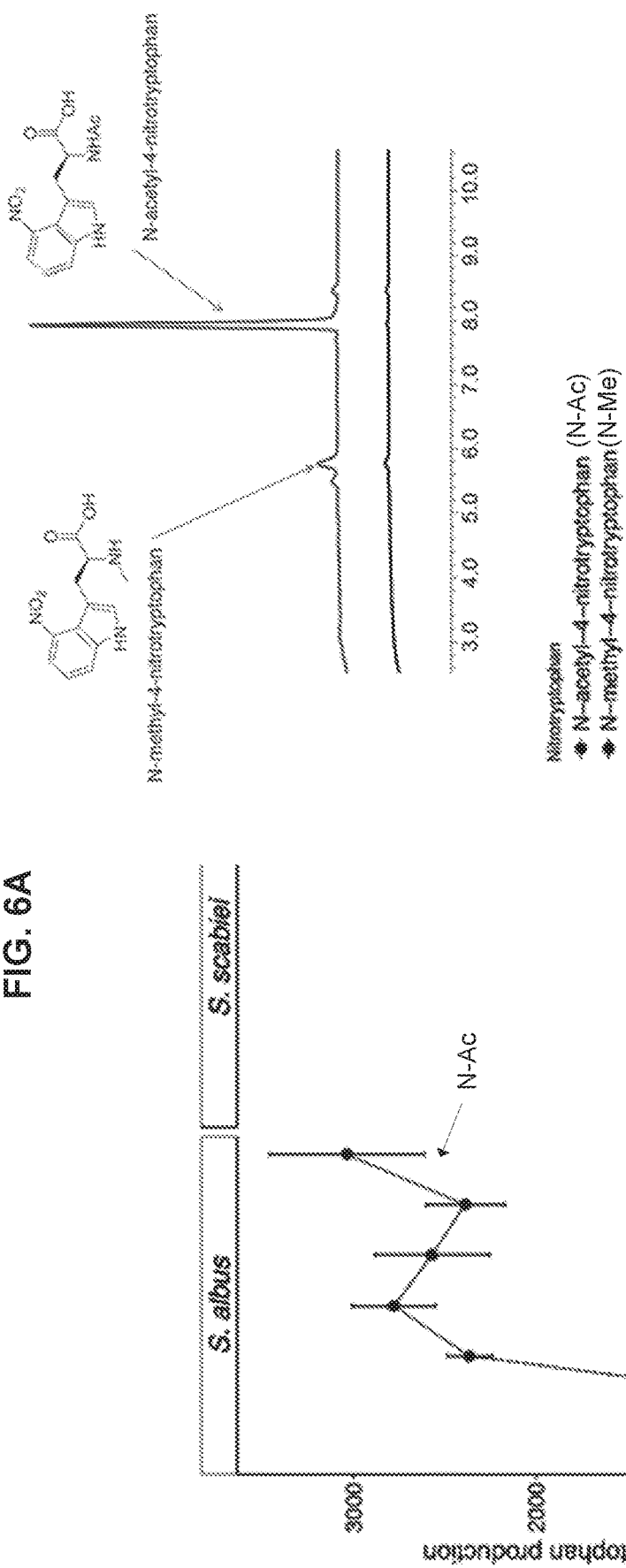
FIGS. 6A-6B are graphs illustrating the nitrated precursors of S. albus J1074 and S. scabiei 87-22, in TDMc liquid medium.
Figure 6B:
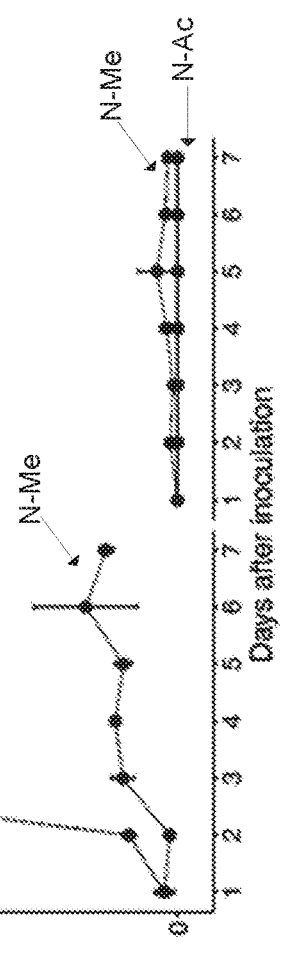

The accumulation of the biosynthetic intermediate in the thaxtomin biosynthetic pathway, 4-nitrotryptophan, was also monitored during the fermentation of *S. albus* J1074 and *S. scabiei* 87-22. A significant peak with the retention time of 7.93 min in the HPLC analysis was observed in the *S. albus* J1074 culture extract; this peak occurred in the *S. scabiei* 87-22 extract but was much smaller (FIG. 6A; $t_R$=7.93 min). LC-MS analysis revealed the peak content as N-acetyl-4-nitrotryptophan. HPLC analysis further detected a minor peak (FIG. 6A; $t_R$=5.77 min) in both extracts, which was determined as N-methyl-4-nitrotryptophan in the LC-MS analysis. The concentration of N-Methyl-4-nitrotryptophan was low in both transformed *S. albus* J1074 and *S. scabiei* 87-22 extracts (FIG. 6B); however, N-acetyl-4-nitrotryptophan accumulated in the culture of transformed *S. albus* J1074 over time (FIG. 6B). The level of N-acetyl-4-nitrotryptophan was about 100-fold of that of N-methyl-4-nitrotryptophan in the transformed *S. albus* J1074 and about 300-fold of that of N-methyl-4-nitrotryptophan in *S. scabiei* 87-22 seven days after inoculation.

Creating a Genetically Stable *S. albus* Strain for Thaxtomin Production

Figure 7:
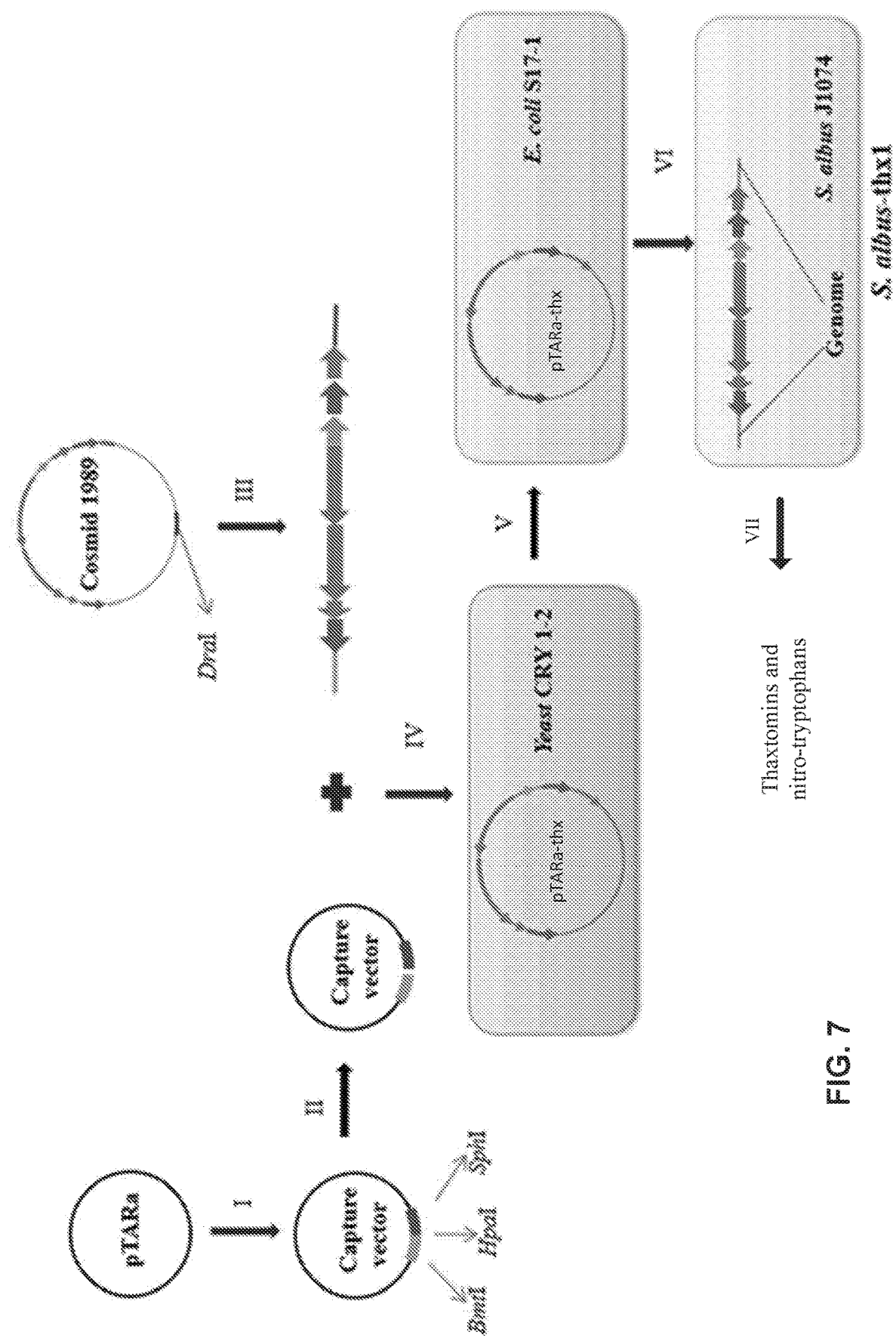

The mobility of the genomic island was leveraged as described above to engineer *S. albus* J1074 for thaxtomin overproduction. However, given the inherent instabilities of genomic islands, use of this strain for commercial production could raise concerns about this strain's genetic stability. In this regard, it was desired to engineer a strain to express only the thaxtomin gene cluster in *S. albus* J1074. Specifically, as illustrated in FIG. 7, a transformation-associated recombination (TAR) approach was employed to clone the thaxtomin gene cluster into pTARa vector using yeast as the assembly host. The pTARa plasmid carrying the thaxtomin cluster was transformed into *E. coli* S17 cells. The conjugation of the transformed *E. coli* S17 with *S. albus* J1074 enabled the transfer of the thaxtomin biosynthetic cluster into *S. albus* J1074. Detailed characterization of the strain carrying only the thaxtomin gene cluster revealed yields of thaxtomins and nitro-tryptophan derivatives to the strain with the genomic island, in the tested media, as described in greater detail in Example 2, below.

Quantification of Thaxtomin and 4-Nitrotryptophan Production in Different Media

To evaluate the effects of culture media on thaxtomin production, the transformed *S. albus* J1074 was cultured in ISP4, TDM, R5 and PDB with sea salt (PDBS) media supplemented with 1% cellobiose. ISP4c (ISP4 with 1% cellobiose), R5c (R5 with 1% cellobiose) and PDBSc (Potato Dextrose Broth with 3.7% sea salt and 1% cellobiose) supported higher production of thaxtomins by the transformed *S. albus* (ThxA, ~150 to ~170 mg/L) than did TDMc (ThxA, ~90 mg/L) (Table 1). Among these media, PDBSc can be prepared directly from raw potato and thus is a cost-effective option for the commercial production of thaxtomins.

Example 2—High-Yield Production of Herbicidal Thaxtomins and Analogs in a Nonpathogenic *Streptomyces* Strain The present example describes heterologous expression of a thaxtomin gene cluster in *S. albus* J1074, which resulted in the highest yield of thaxtomins ever reported. Furthermore, current synthetic routes to thaxtomins and analogs are lengthy, and two thaxtomin biosynthetic intermediates produced at high yields in this example can provide precursors and building blocks to advanced synthetic routes. The production of 5-F-thaxtomin A in engineered S. albus J1074 in this example demonstrated a viable alternative to chemical methods in the synthesis of new thaxtomin analogs. This work represents an attractive synthetic biology strategy to improve the supply of herbicidal thaxtomins.

Figure 8A:
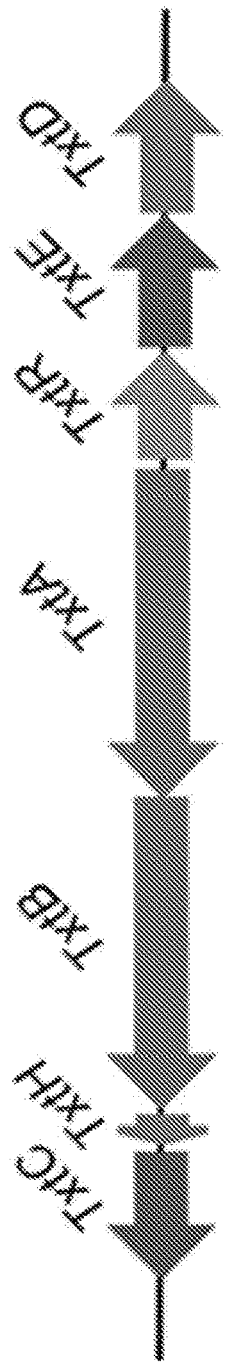
Figure 8B:
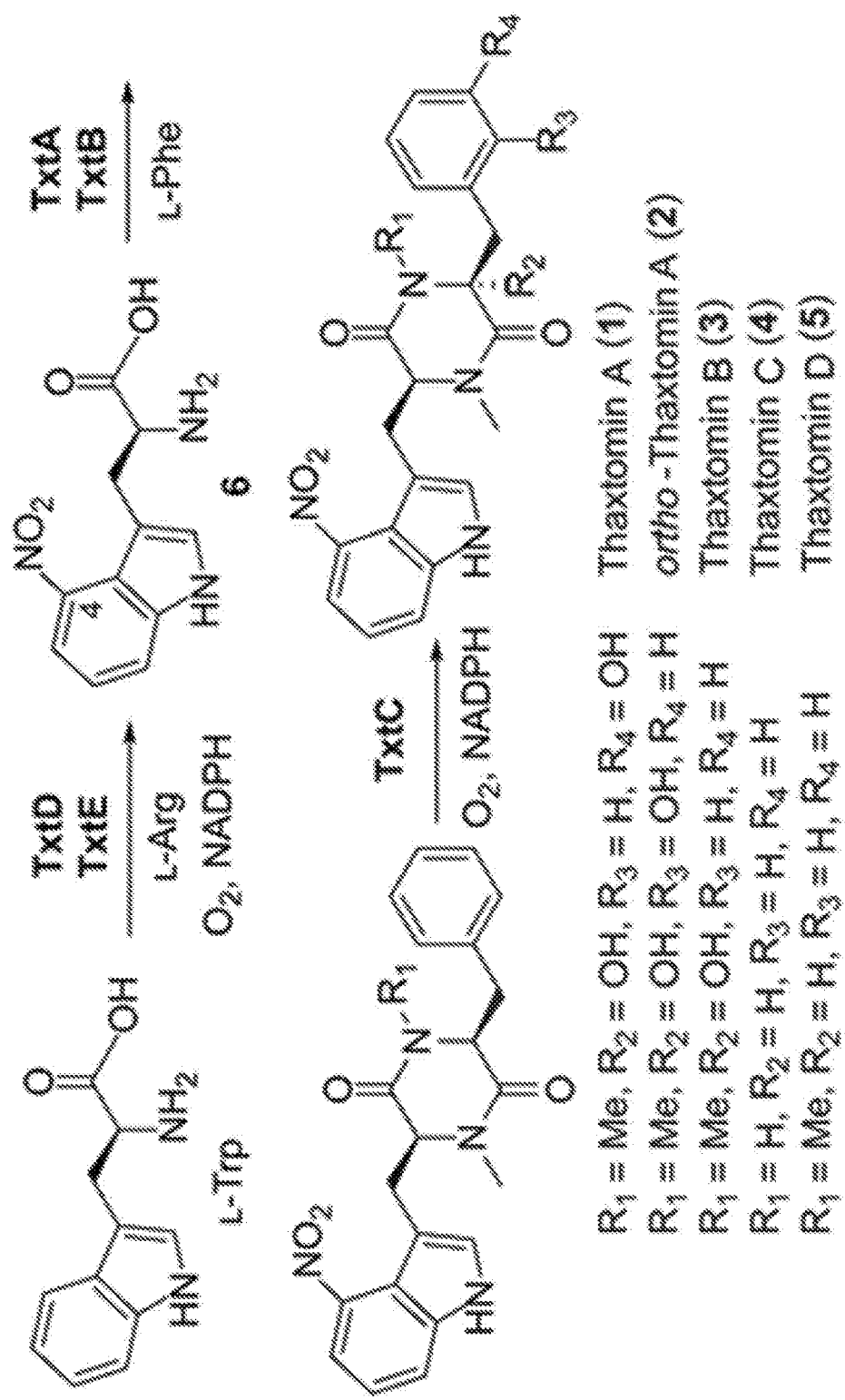

Herbicides play a crucial role in agricultural production all over the world but their extensive and broad uses have resulted in the herbicide resistance in weeds. The situation is further exaggerated by the fact that no new class of herbicides has been commercialized in the past decades. Known as a virulence factor in the common scab potato disease, thaxtomins, including the major metabolite thaxtomin A and 10 other analogs, are produced by tens of pathogenic *Streptomyces* strains (FIGS. 8A-8B). Thaxtomin A (1) inhibits cellulose biosynthesis in the nM range, a unique mechanism of plant pathogenicity. As weeds have a significantly higher demand of cellulose for the rapid growth, a bioherbicide with 1 as the main active ingredient has been approved by the United States Environmental Protection Agency for pre- and post-emergence weed control on various crops at a ppm concentration. Economically and environmentally acceptable production of thaxtomins will foster and sustain their agricultural applications. Accordingly, several synthetic routes have been developed but generally generate environmentally damaging wastes, produce racemic products, and experience a low overall yield, therefore being impractical to industrial production. On the other hand, the isolation yield of 1 from its native producers (e.g., *S. scabiei* and *S. acidiscabie*) is lower than 10 mg/L, rendering a costly production process.

The gene cluster of 1 has been elucidated and contains seven genes encoding two P450s (TxtC and TxtE), two nonribosomal peptide synthetases (NRPSs, TxtA and TxtB), one MbtH-like protein (TxtH), one positive regulator (TxtR) and one nitric oxide synthase (TxtD) (FIG. 8A). TxtD generates nitric oxide (NO) from l-arginine, which is then used by TxtE to nitrate C4 of l-tryptophan, resulting in 4-NO$_2$-l-tryptophan (6). Compound 6 is then cyclized with l-phenylalanine by TxtA and TxtB to form a diketopiperazine thaxtomin D (5), which is further hydroxylated twice to produce thaxtomin A, likely by TxtC (FIG. 8B). The expression of the thaxtomin gene cluster is regulated by TxtR, which is known to be activated by cellobiose.

This disclosure seeks to address the thaxtomin supply issue, by expressing the thaxtomin cluster in capable hosts to achieve overproduction. *Streptomyces* strains including *S. coelicolor, S. lividans, S. avermitilis*, and *S. albus* J1074 have been used to express active and silent natural product gene clusters. *S. albus* J1074 has the smallest genome within the genus streptomycetes, indicating fewer competing pathways for efficient heterologous expression. Indeed, *S. albus* J1074 has been used to produce structurally diverse natural products of actinomycete and nonstreptomycete origins, and can demonstrate high productivity.

Example 1, above, and Zhang, Y., et al., (2018, incorporated by reference herein) described expression of mobile pathogenicity islands (PAIs, 177 kb and 674 kb) from two pathogenic *Streptomyces* strains, which contain the thaxtomin gene cluster, mobile elements and others, in five nonpathogenic *Streptomyces* hosts, including *S. albus* J1074, *S. avermitilis* NRRL8165, *S. coelicolor* M145, *S. diastatochromogenes* ATCC12309, and *S. lividans* 1326. Strikingly, *S. albus* J1074 expressing the 177-kb PAI from *S. scabiei* produced the highest level of thaxtomins among all engineered strains and two native producers when cultured in TDMc. This result indicates the influences of genetic backgrounds of expression hosts on the gene cluster expression and illustrates the attractive capability of *S. albus* J1074 in heterologous production of natural products. However, the PAI-based production of thaxtomins in *S. albus* J1074 has potential limitations to developing industrial processes, e.g., the mobility nature of PAI, leading to the possible genetic instability of production strain, technique difficulties in engineering the biosynthetic gene cluster for further improving the production yield, and the cost and safety concerns on the use of two antibiotics in the fermentation media.

This example describes the high-yield production of thaxtomins in *S. albus* J1074 after chromosomal integration of only its biosynthetic gene cluster. The yield of thaxtomins was improved by about 12 times in comparison with the native producer in TDMc. Further engineering of the cluster produced key biosynthetic intermediates, which can be used as precursors for chemical synthesis of thaxtomin analogs. Moreover, feeding 5-F-l-tryptophan into the culture medium led to the generation of one unnatural analog 5-F-thaxtomin A. Natural and unnatural thaxtomins demonstrated potent herbicidal activity and possessed weak cytotoxicity.

Materials and Methods

Microorganisms, Fermentation and Analysis.

Molecular biology reagents and enzymes were purchased from Fisher Scientific. Primers were ordered from Sigma-Aldrich. Other chemicals and solvents were purchased from Sigma-Aldrich and Fisher Scientific. *E. coli* EP1300 competent cells were purchased from Epicenter. DNA sequencing was performed at Eurofins. The plasmids and strains used in this study were listed in Table 6. *Streptomyces* strains were cultivated on soybean flour-mannitol agar plates and ISP4 agar plates (BD Biosciences, San Jose, Calif., USA) for sporulation and conjugation, respectively. Spores were collected, suspended in 20% (v/v) glycerol and stored at −80° C. Trypticase soy broth (TSB) was used to prepare seed culture for fermentation. A Shimadzu Prominence UHPLC system (Kyoto, Japan) fitted with an Agilent Poroshell 120 EC-C18 column (2.7 μm, 4.6×50 mm), coupled with a PDA detector was used for HPLC analysis. Agilent ZORBAX SB-C18, (5 μm, 9.4×250 mm) or YMC-Pack Ph column (5 μm, 4.6×250 mm) was used for semi-preparative HPLC analysis to isolate the metabolite. 1D and 2D NMR spectra were recorded in CDOD$_3$ on Bruker 400 MHz or Bruker 500 MHz instruments at the University of Florida, Gainesville, Fla., USA. Spectroscopy data were collected using Topspin 3.5 software. HRMS data were obtained using a Thermo Fisher Q Exactive Focus mass spectrometer equipped with electrospray probe on Universal Ion Max API source. Unless special instruction, all the samples were analyzed at the end of 6-day fermentation.

Preparation of Thaxtomin-Producing *S. albus* Strains

The transformation-associated recombination (TAR) approach (Kim, J H, et al., 2010, and Kallifidas, et al., 2012, both of which are hereby incorporated by reference herein) was followed to clone the thaxtomin gene cluster into pTARa vector as shown in FIG. 7. Primers used were included in Table 8. The resultant pTARa-thx was transformed into *E. coli* S17-1. The conjugation of the transformed *E. coli* S17-1 with *S. albus* J1074 led to the creation of S. albus-thx1. To create *S. albus*-thx2 and strains with the engineered thaxtomin clusters, end-overlapped DNA fragments (1 kb/each) of whole or partial thaxtomin synthetic gene clusters were PCR amplified using the cosmid 1989 as template and assembled with the conjugative vector pLST9828 following the protocols of NEBuilder HiFi DNA Assembly Cloning Kit. The assembled mixtures were transformed into *E. coli* EP1300. The constructed plasmids were isolated and confirmed by restriction digestion and DNA sequencing. The validated construct was then transformed into *E. coli* S17-1 for conjugating with *S. albus* J1074 to create *S. albus*-thx2, *S. albus*-thx2-ΔC and *S. albus*-thx2-ΔABCH.

Isolation of Thaxtomins and Nitro-Tryptophan Analogs

*Streptomyces* strains were cultured in TSB for 2 days. Mycelial pellets were collected after centrifugation, washed twice with sterile water, and then resuspended in an equal volume of sterile water to prepare mycelial suspension solutions. Fermentation medium (500 mL) in one 2-L flask was inoculated with 15 mL of mycelial suspension solutions and then incubated at 30° C., 250 rpm for 6 days. Clean supernatants were collected after centrifugation at 5000 rpm for 10 min and then passed through Sep-Pak C18 columns (Waters, 2 g). The columns were washed with one volume of water. Nitrotryptophan analogs were eluted with 25% MeOH while thaxtomins were eluted with 100% MeOH. The eluted solvents containing targeted compounds were further dried in vacuo evaporation. Microscale balance (Mettler Toledo) was used to measure the weights of isolated compounds. To determine the yields of thaxtomin A and other analogs, thaxtomins were further purified by semi-prep HPLC. After drying corresponding fractions in vacuo evaporation, the weights of thaxtomins were measured by microscale balance. Alternatively, the concentrations of thaxtomins were calculated on the basis of their areas under peak in HPLC traces using an established standard curve of authentic thaxtomin A. Experiments were repeated with at least three technical replicates per strain and per medium. Isolated thaxtomins and nitro-tryptophans were analyzed in HR-MS and MS/MS studies.

HPLC Analysis

The HPLC program included the column elution first with 10% solvent B (acetonitrile with 0.1% formic acid, FA) for 2 min and then with a linear gradient of 10-50% solvent B in 8 min, followed by another linear gradient of 50-99% solvent B in 5 min. The column was further cleaned with 99% solvent B for 3 min and then re-equilibrated with 10% solvent B for 1 min. Solvent A was water with 0.1% FA. The flow rate was set as 0.5 mL/min, and the products were detected at 254 nm with a PDA detector. For semi-preparative HPLC analysis, the column at 40° C. was first eluted with 10% solvent B (acetonitrile with 0.1% FA) for 2 min and then with a linear gradient of 10-50% solvent B for 8 min, followed by a linear gradient of 50-99% solvent B for 5 min. The column was then cleaned by 99% solvent B for 1 min and re-equilibrated with 10% solvent B for 1 min. The flow rate was set at 3 mL/min, and the products were detected at 380 nm with a PDA detector. All metabolites were well separated, and corresponding fractions were combined, concentrated, dried, and then weighed.

LC-MS Analysis

A SHIMADZU Prominence UPLC system fitted with an Agilent Poroshell 120 EC-C18 column (2.7 µm, 4.6×50 mm) coupled with a Linear Ion Trap Quadrupole LC/MS/MS Mass Spectrometer system was used in the studies. The HPLC conditions were the same as described above. For MS detection, the turbo spray conditions included curtain gas: 30 psi; ion spray voltage: 5500 V; temperature: 600° C.; ion source gas 1: 50 psi; ion source gas 2: 60 psi). For MS/MS analysis, the collision energy was 12 eV. LC-HR-MS analysis was performed on a Thermo Fisher Q Exactive Focus mass spectrometer. Acetonitrile (B)/water (A) containing 0.1% FA were used as mobile phases with a linear gradient program (10-90% solvent B over 15 min) to separate chemicals at a flow rate of 0.3 mL/min. A pre-wash phase of 15 min with 10% solvent B was added at the beginning of each run, in which the elute was diverted to the waste by a diverting valve. MS1 were acquired under Full Scan mode of Orbitrap, in which a mass range of m/z 150-2000 was covered and data were collected in the positive ion mode. Fragmentation was introduced by HCD technique with optimized collision energy ranging from 6 to 15 eV. Other settings for the Orbitrap scan were as follows: resolution 15000, AGC target $5\times10^5$. Full scan mass spectra and targeted MS/MS spectra for each of the pre-selected parental ion were extracted from the raw files of the HPLC-MS/MS Experiment II using Xcalibur™ 2.1 (Thermo Scientific).

Feeding Experiment with 5-F-I-tryptophan

*S. albus*-thx2 were cultured in TDMc under the same conditions described above for 2 days, and filter sterilized 5-F-I-tryptophan solutions (0 to 50 µM final concentrations) were added to the culture medium. After fermentation for 5 additional days, the cultures were centrifuged to prepare clean supernatants that were extracted with the equal volume of ethyl acetate three times. The combined organic layers were washed, dried over sodium sulfate, and then evaporated to the dryness in vacuo. The residues were suspended in methanol for HPLC analysis as described above. To purify 5F-thaxtomin A (compound 9) for structural determination, the mixture was separated on one C18 column (Agilent ZORBAX SB-C18, 5 µm, 9.4×250 mm). The column was first eluted with 30% solvent B (acetonitrile with 0.1% FA) for 18 min, followed by another linear gradient of 50-99% solvent B in 0.5 min. After eluting in 99% solvent B for 0.5 min, the liner gradient of 99-10% solvent B in 0.5 min was used. The column was further re-equilibrated with 30% solvent B for 0.5 min. The flow rate was set at 3 mL/min, and the products were detected at 380 nm with a PDA detector. The fraction 8 (F8) with a retention time of 18.1 min was collected and dried for further purification with one analytical column (YMC-Pack Ph column, 5 µm, 4.6×250 mm). The column at 30° C. was eluted with 50% solvent B (methanol with 0.1% FA) for 13.5 min and then with a linear gradient of 50-99% solvent B in 0.5 min, followed by another linear gradient of 50-99% solvent B in 0.5 min. After eluting in 99% solvent B for 0.5 min, the liner gradient of 99-50% solvent B in 1.0 min was used. The flow rate was set at 1 mL/min, and the product was detected at 380 nm with a PDA detector. The compound 9 was eluted and collected for NMR analysis.

5F-thaxtomin A (9): yellow solid; $[\alpha]^{20}_D$+148.3 (c 0.0022, MeOH); HRMS (ESI-TOF) m/z 457.1497 $[M+H]^+$ (calcd. for $C_{22}H_{21}FN_4O_6$, 457.1523); $^{19}F$ NMR (500 MHz, $CD_3OD$) δ−137.41 (dd, J=10.9 Hz, 4.5 Hz, 1F); $^1H$ and $^{13}C$ NMR data were described in Table 4.

Herbicidal Activity Assay of Thaxtomins

Serial concentrations (0 to 4 µM) of thaxtomins in DMSO were added into 20 mL of 1.5% warm agar solution with gentle agitation. DMSO was included as the negative control. The solution was then poured into the plate for solidification at room temperature for 30 min. Radish seeds (Burpee) were surface disinfested, pregerminated and selected when the radicle was 1±2 mm and just emerged from the seed coat. Six radish seedlings were equally located on the surface of each plate with the root ends all pointed in the same direction. Agar plates were covered, sealed with Parafilm. The seedlings in the agar plates grew at room temperature under fluorescent lighting (12 h per day for 6 days), and total seedling lengths were then recorded. Three plates were set up for each dosage of each compound. Percent inhibition relative to the mean growth response in DMSO treated control plates was then calculated. Dose-response curves were fit to a four-parameter logistic model as described in Streibig, J C, et al., 1993 (which is hereby incorporated by reference herein), and Iso values were estimated from these curves.

MTT Assay to Characterize Cytotoxicity of Thaxtomins

PC-3 and Jurkat cells were cultured in DMEM or RPM11640 medium containing 10% fetal bovine serum and 100 U/mL penicillin and streptomycin, and maintained at 37° C. in a humidified incubator under 5% $CO_2$. The cells ($1\times10^4$ for Jurkat, and 5,000 for PC-3 in 100 µL) were seeded into 96-well plates and incubated overnight. Varying concentrations of purified compounds (0 µM, 12.5 µM, 25 µM, 50 µM and 100 µM) were added to the wells. After incubation at 37° C. for 48 to 72 h, 10 µL of MTT (5 mg/mL) in PBS was added and incubated for 4 h, followed by aspiration of the medium. DMSO (100 µL) was added to each well to dissolve the MTT in the wells, and the plates were agitated for 1 h for recording the absorbance at 570 nm using UV/vis microplate spectrophotometer (BioTek). Three to six replications were performed per treatment of each sample.

Statistic Analysis

Statistical significance among multiple groups was analyzed by one-way ANOVA followed by Student's t-test for comparison of the results between two groups using Prism 5 (Graphpad Software, Inc). P value of <0.05 is considered to be statistically significant.

Results and Discussion

Thaxtomin Production in *S. albus*

Transformation-associated recombination approach described in Kim, J H, et al., 2010 and Kallifidas, D. et al., 2012, hereby incorporated by reference herein) was used to capture the 18-kb thaxtomin gene cluster of *S. scabiei* 87.22. The resultant integrative construct pTARa-thx was then conjugated into *S. albus* J1074 to create *S. albus*-thx1 (FIG. 7). This strain was cultured along with the untransformed *S. albus* J1074 as a control in the minimal medium TDMc. TDMc contains 1% cellobiose that induces the production of thaxtomin in native producers as described in Joshi, M V, et all, 2007 and Francis, I M, 2015 (hereby incorporated by reference herein) presumably by its binding to the pathway-specific regulator TxtR and likely one global regulator CebR.

Figure 9B:
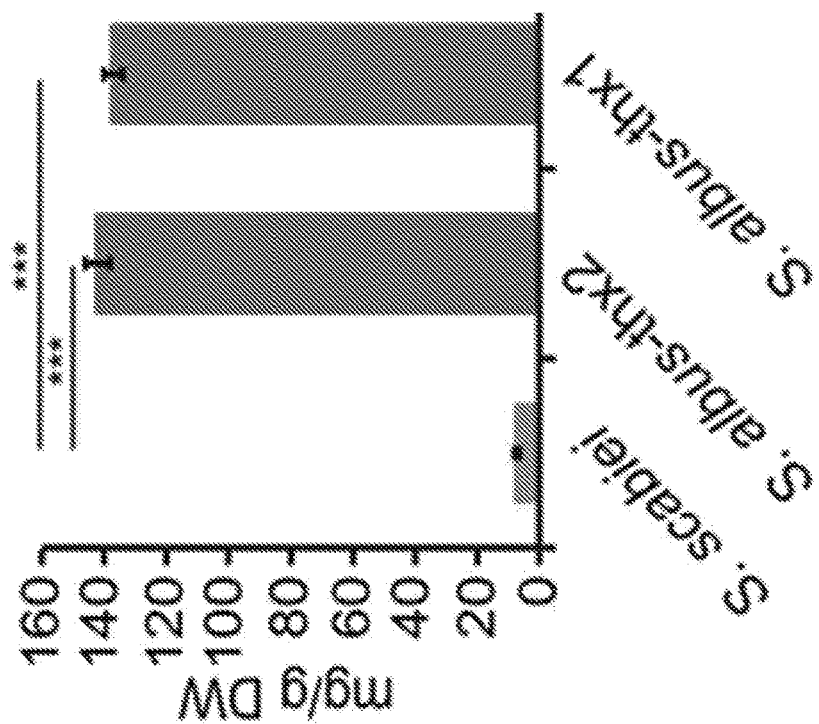
Figure 9A:
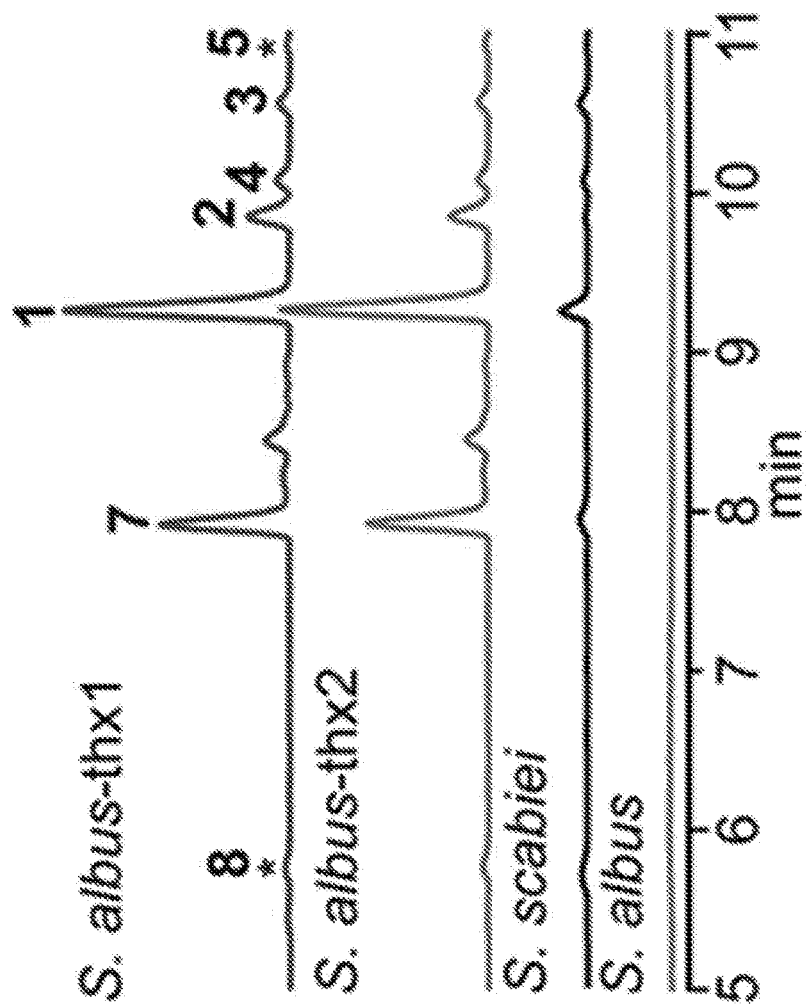
Figure 10A:
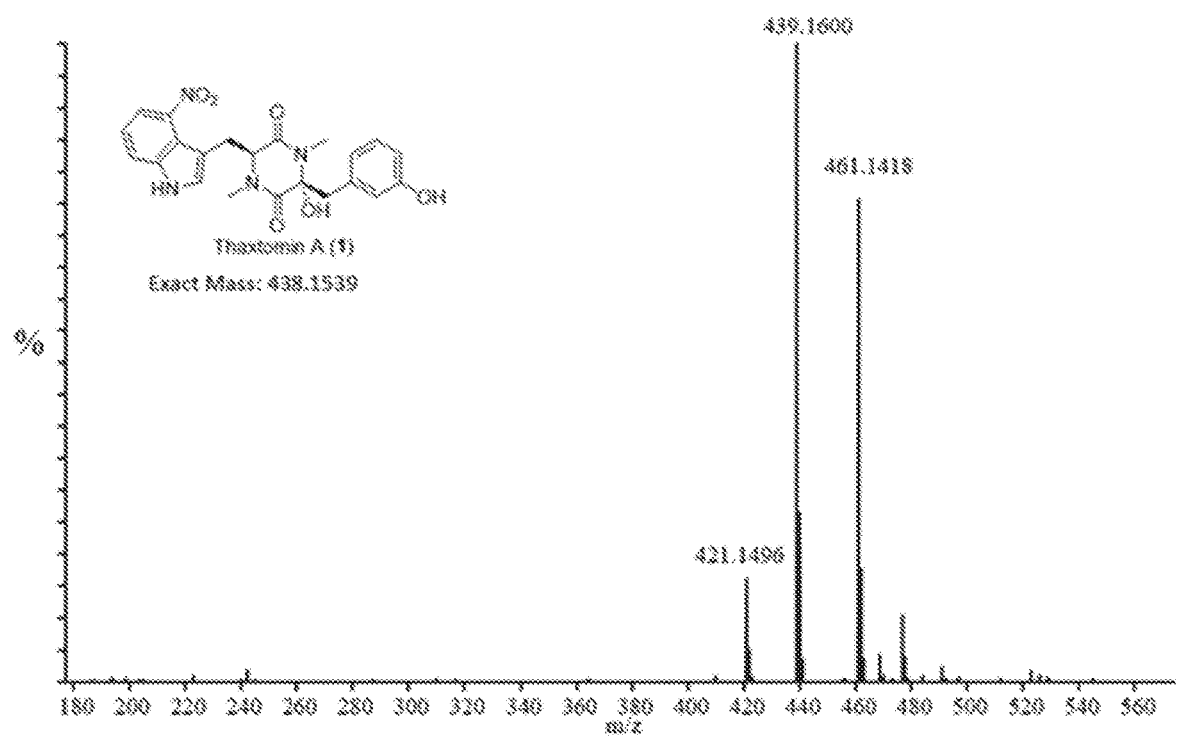
Figure 10B:
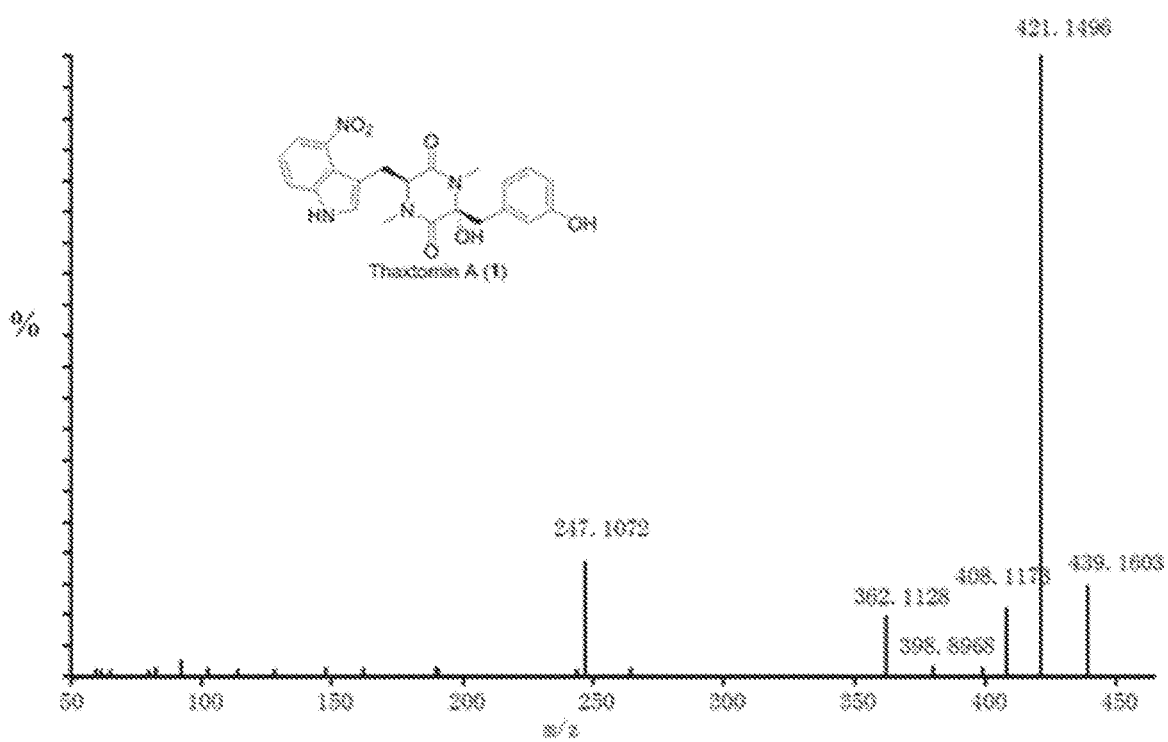
Figure 10C:
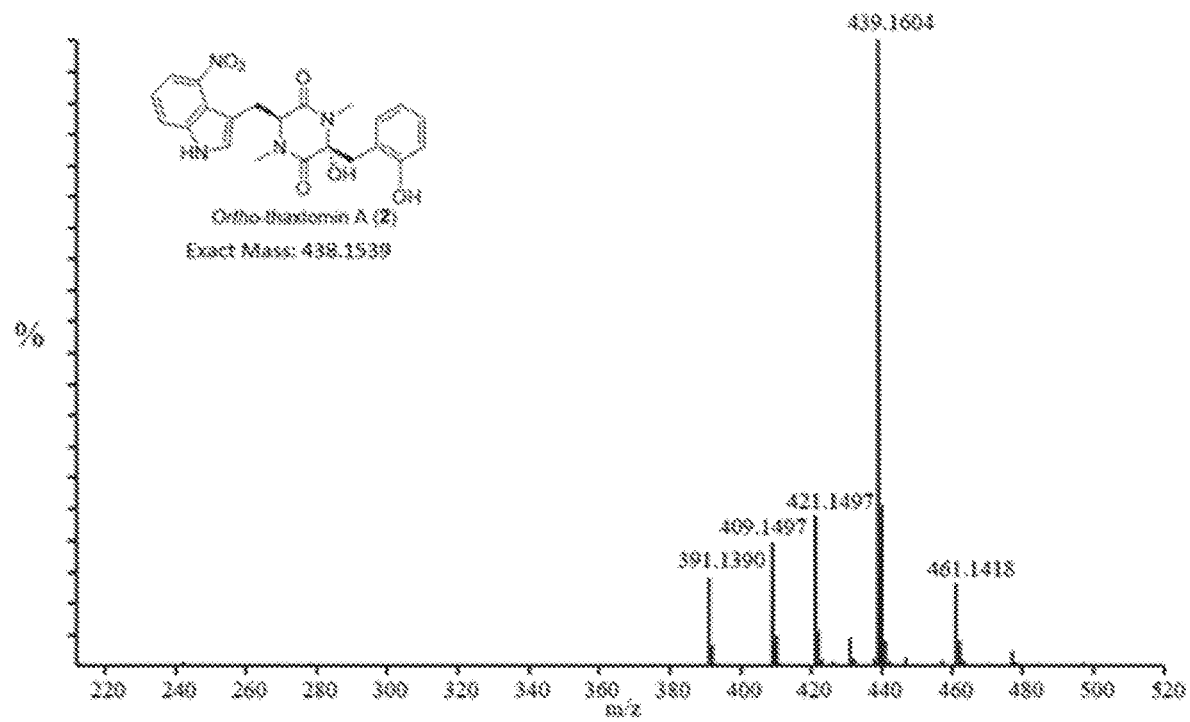
Figure 10D:
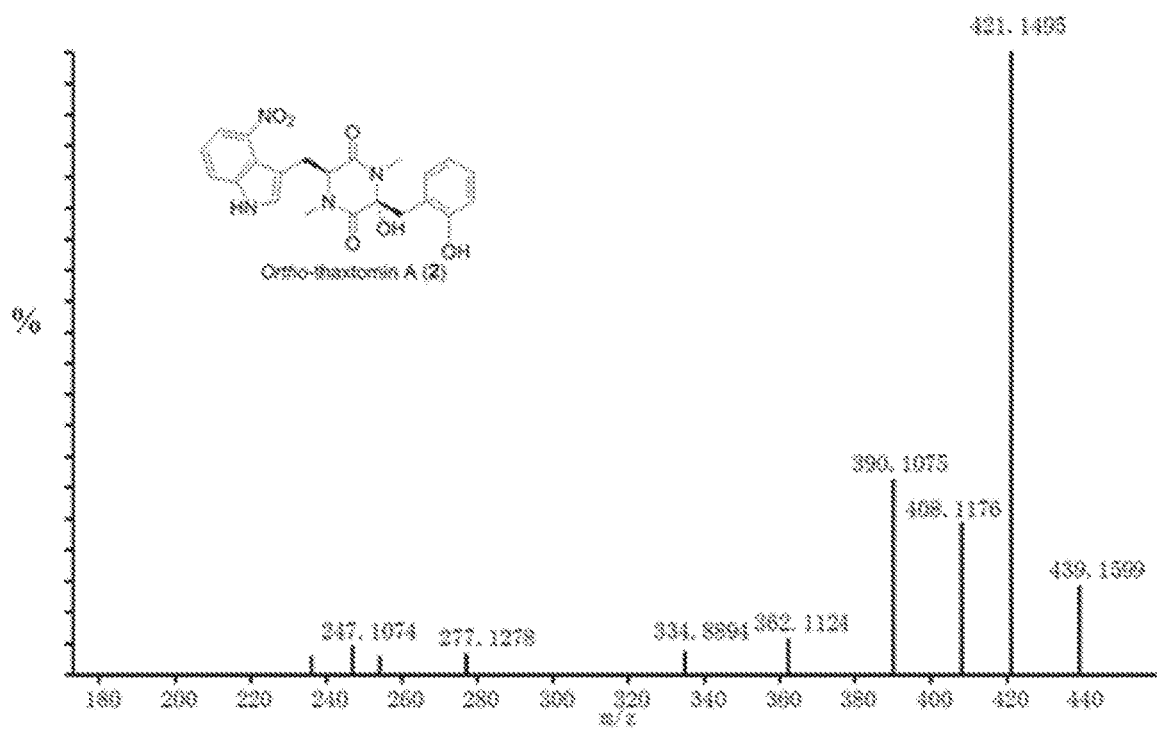
Figure 10E:
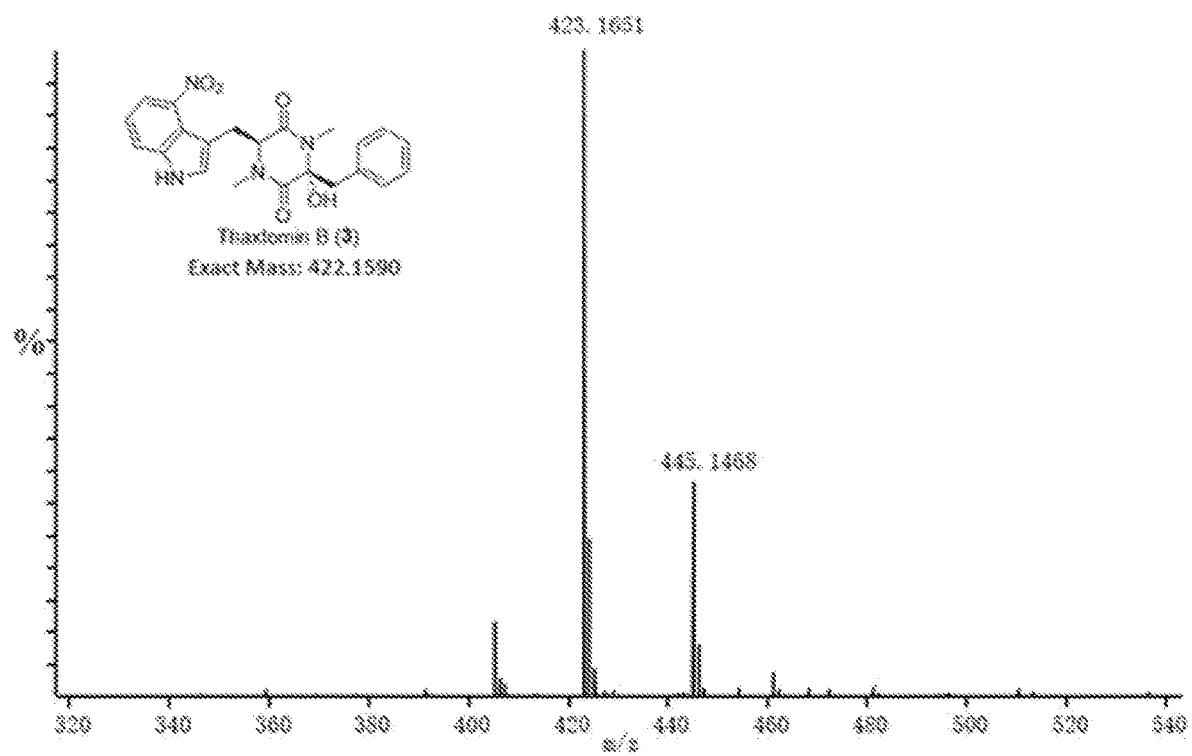
Figure 10F:
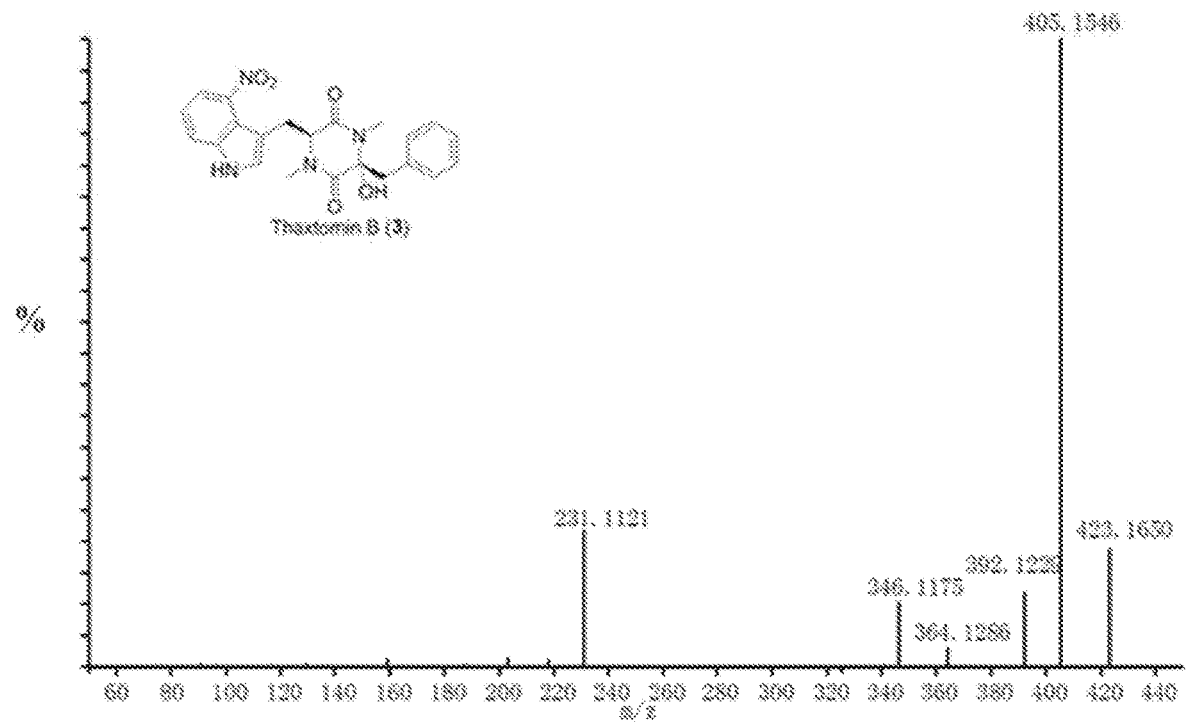
Figure 10G:
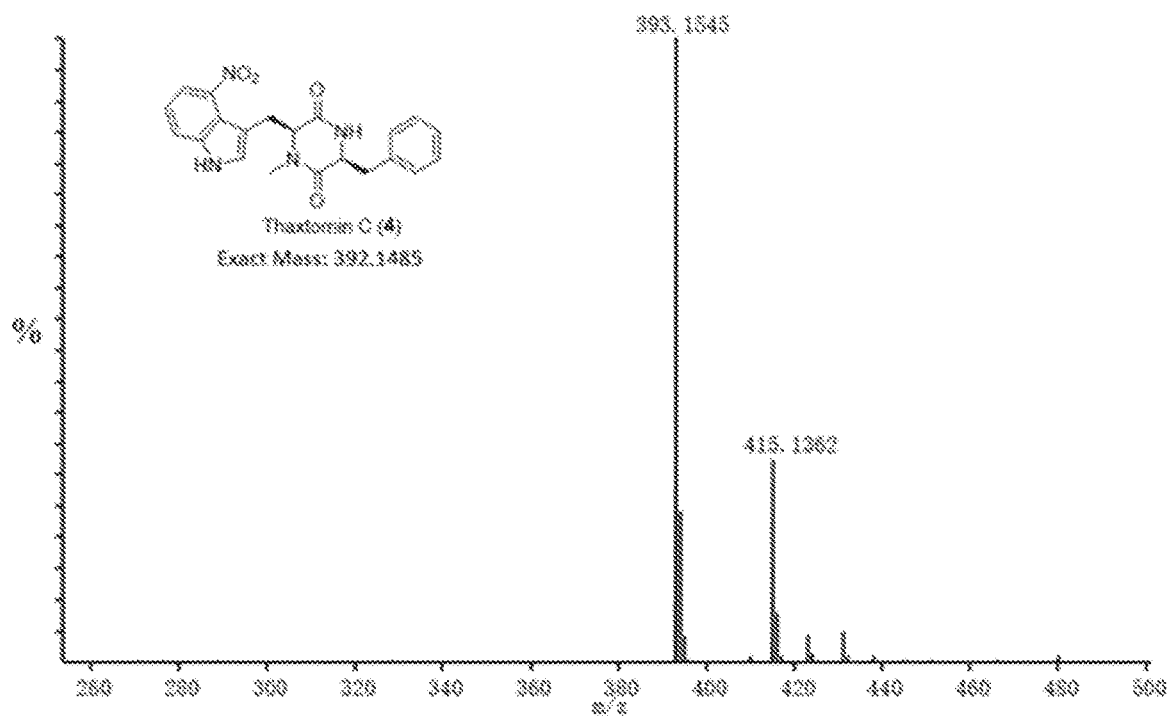
Figure 10H:
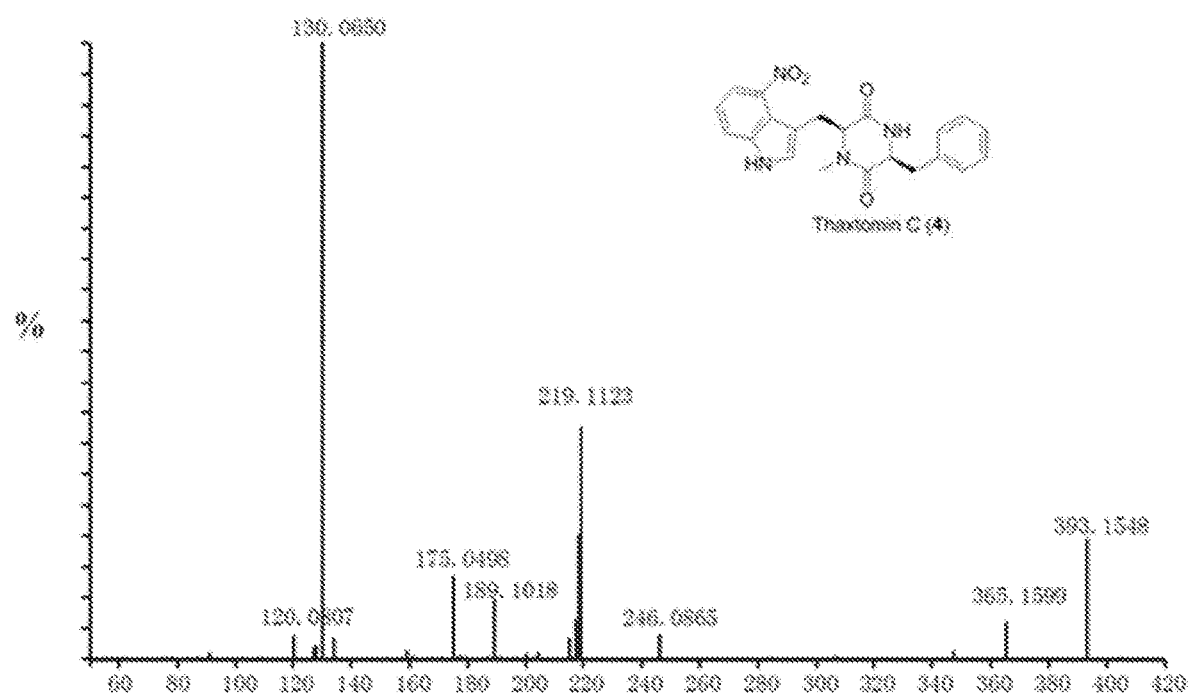
Figure 10I:
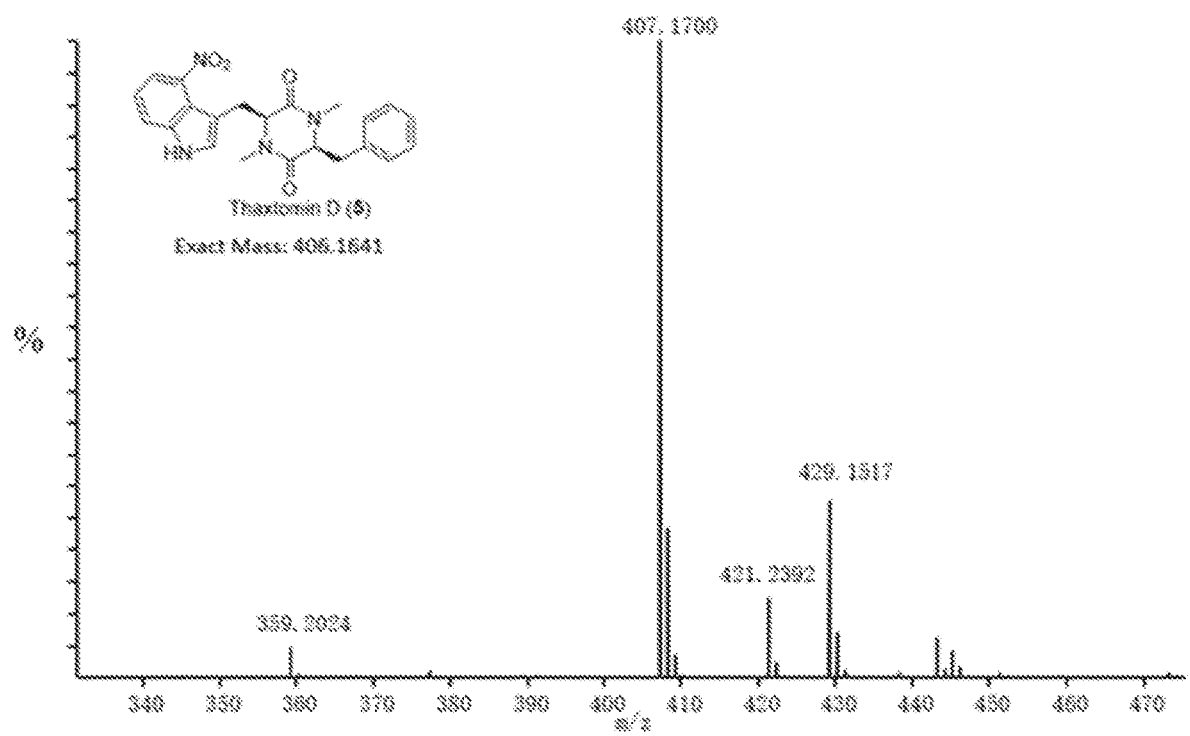
Figure 10J:
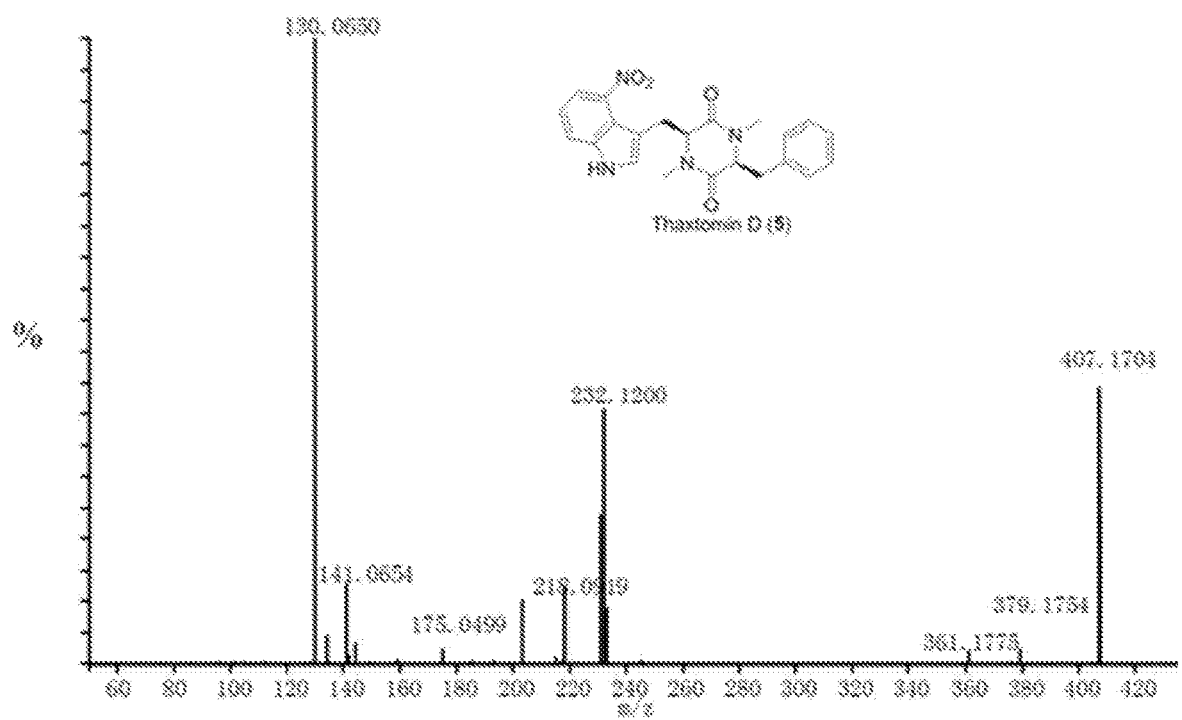
Figure 10K:
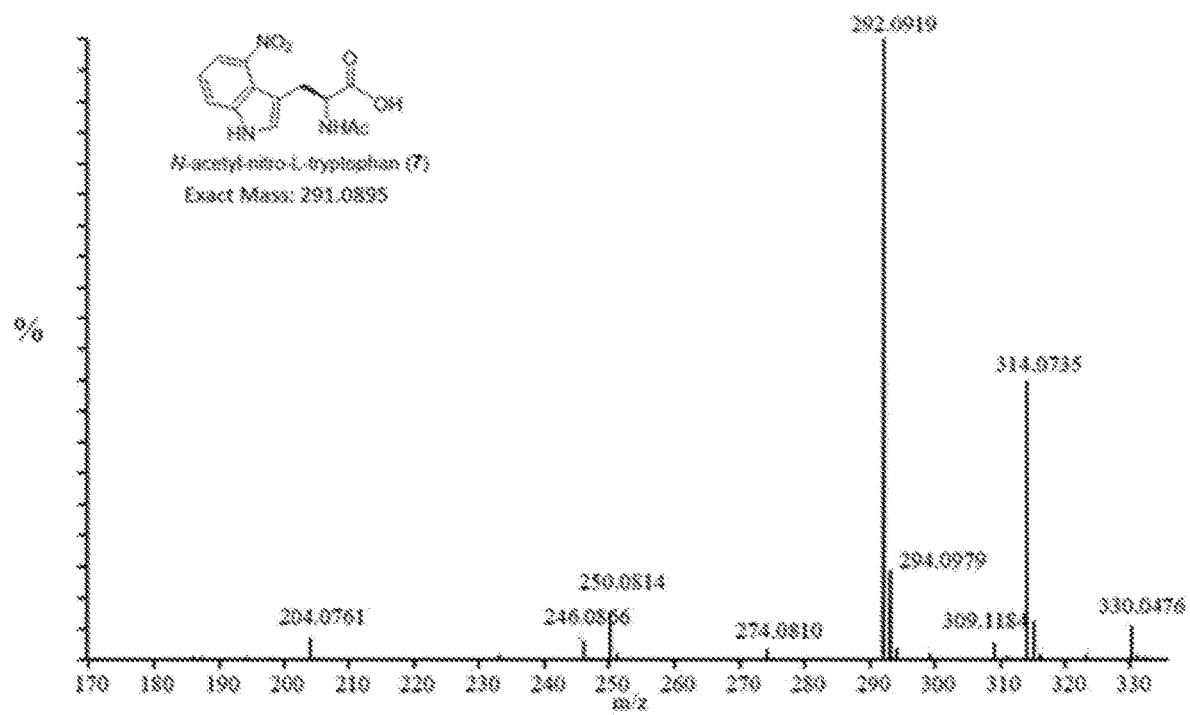
Figure 10L:
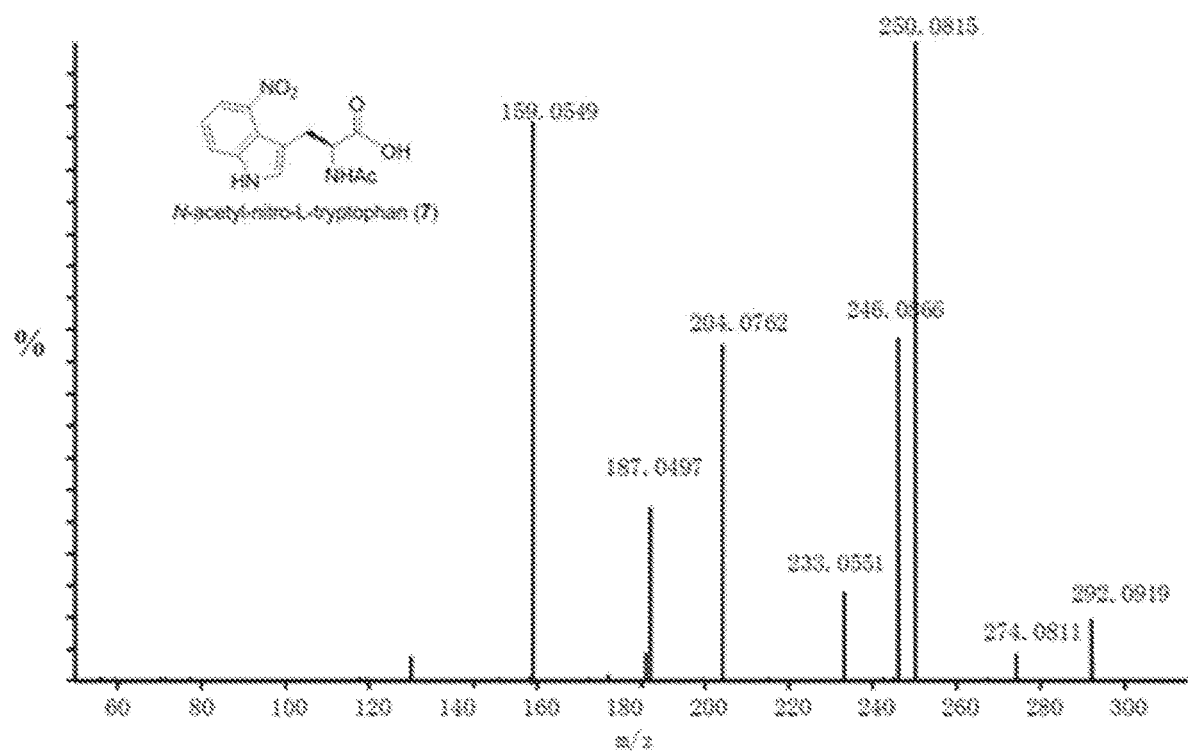
Figure 10M:
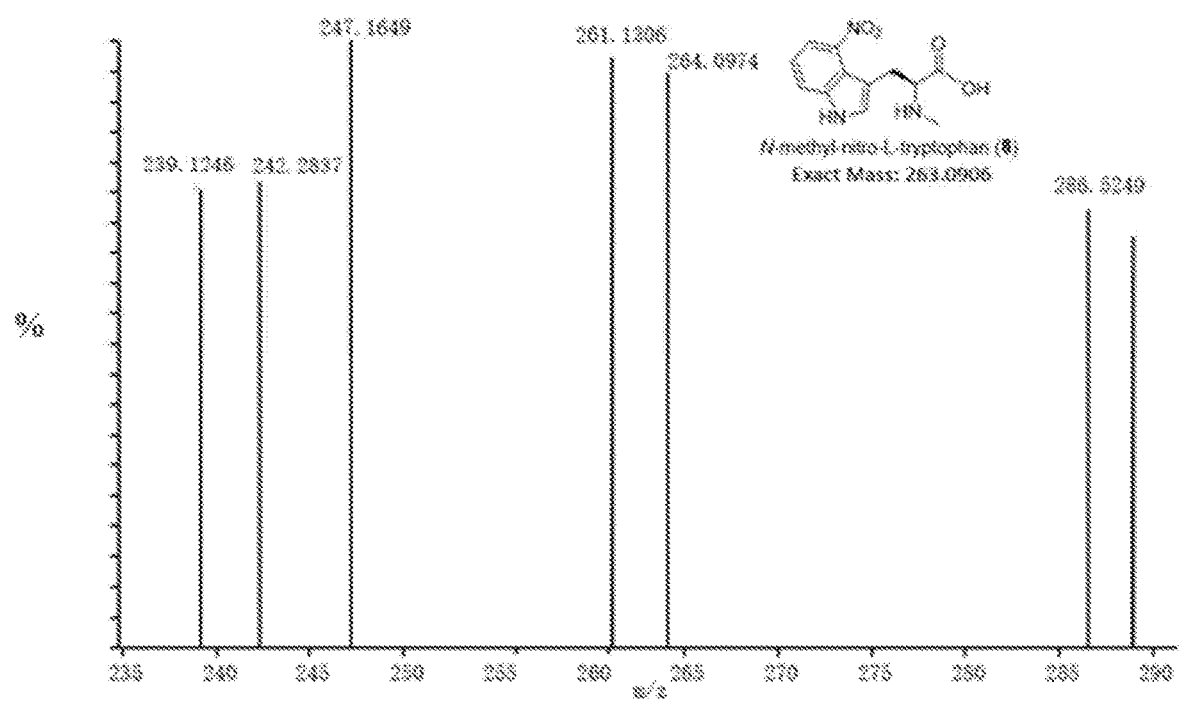
Figure 10N:
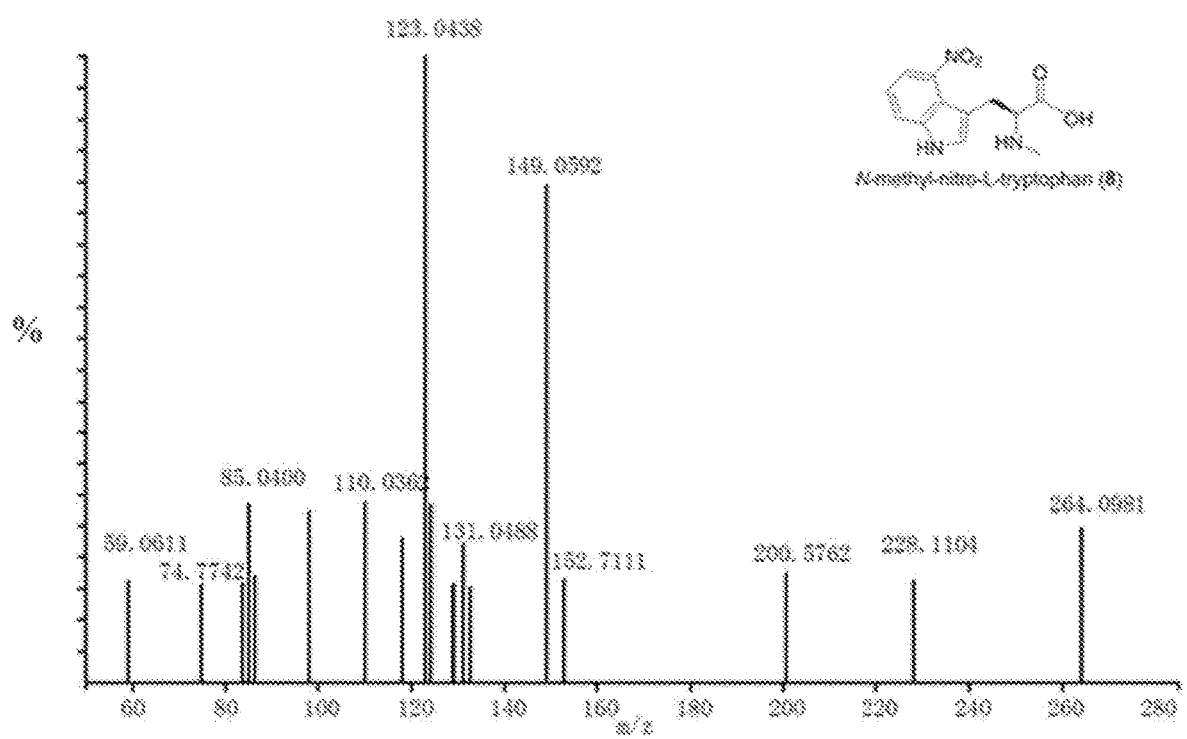
Figure 11:
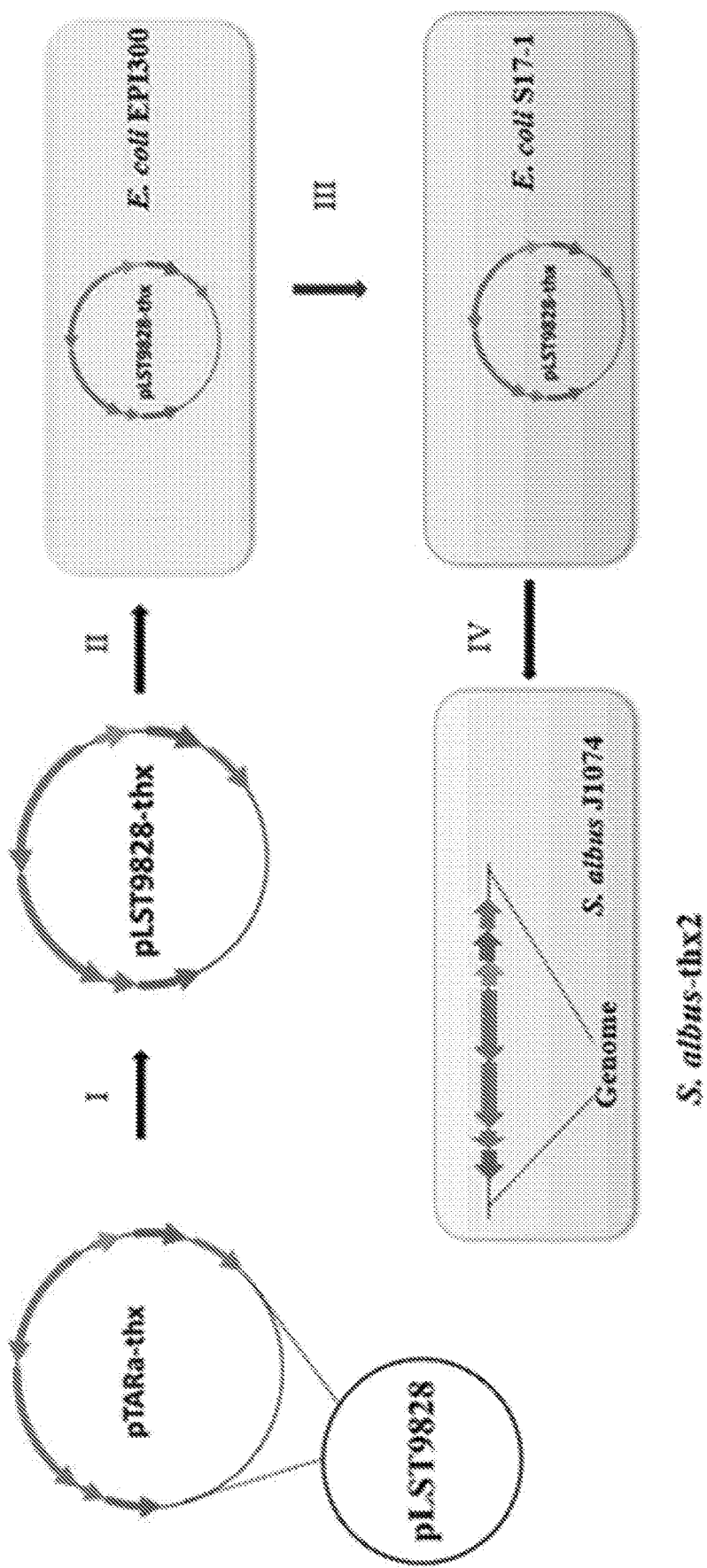
Figure 12:
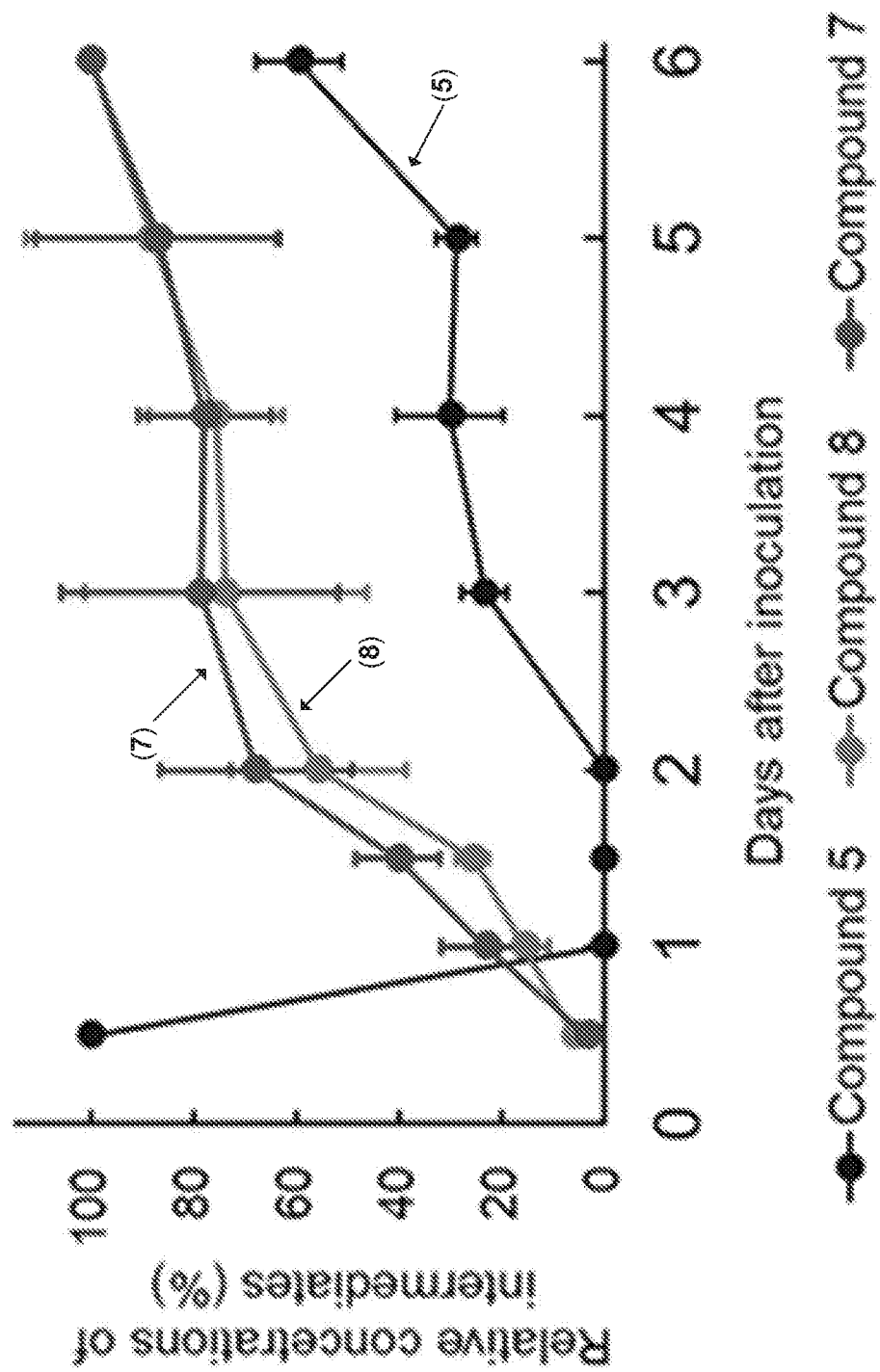
Figure 13A:
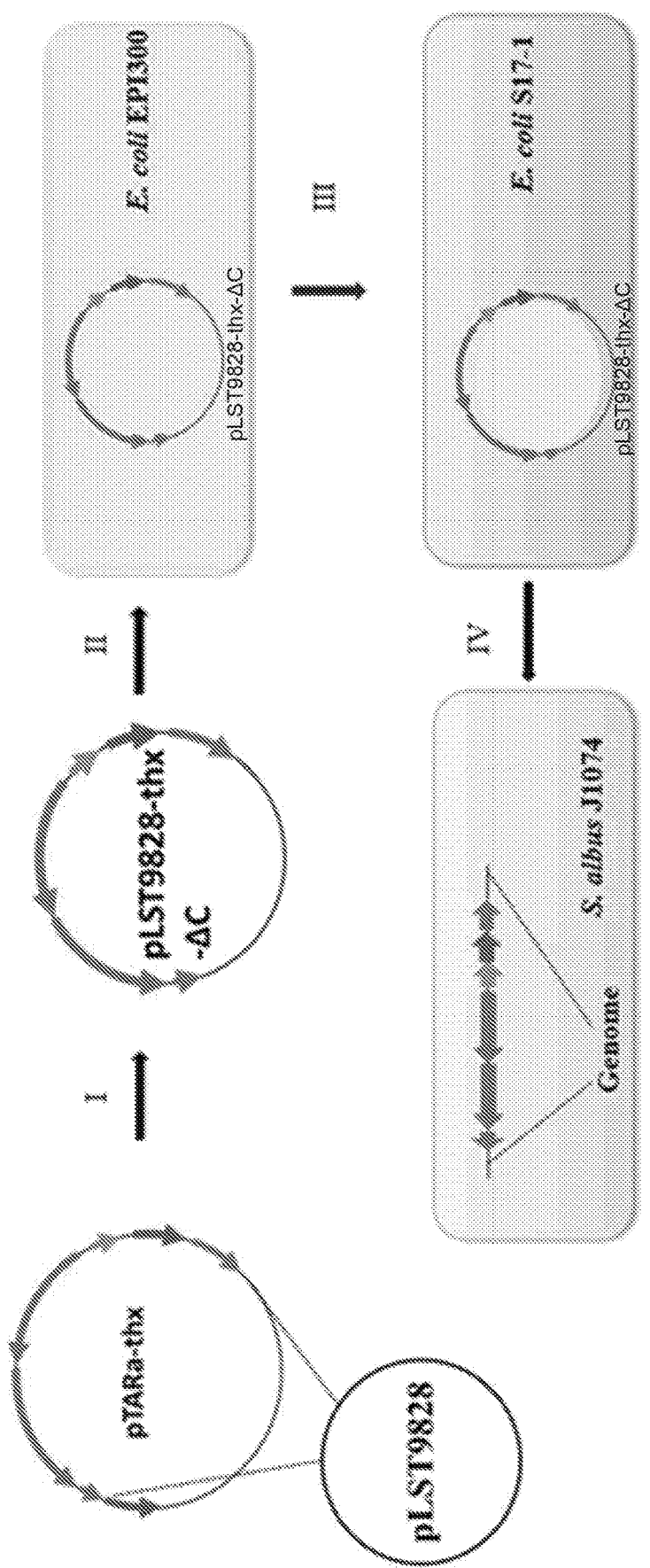
Figure 13B:
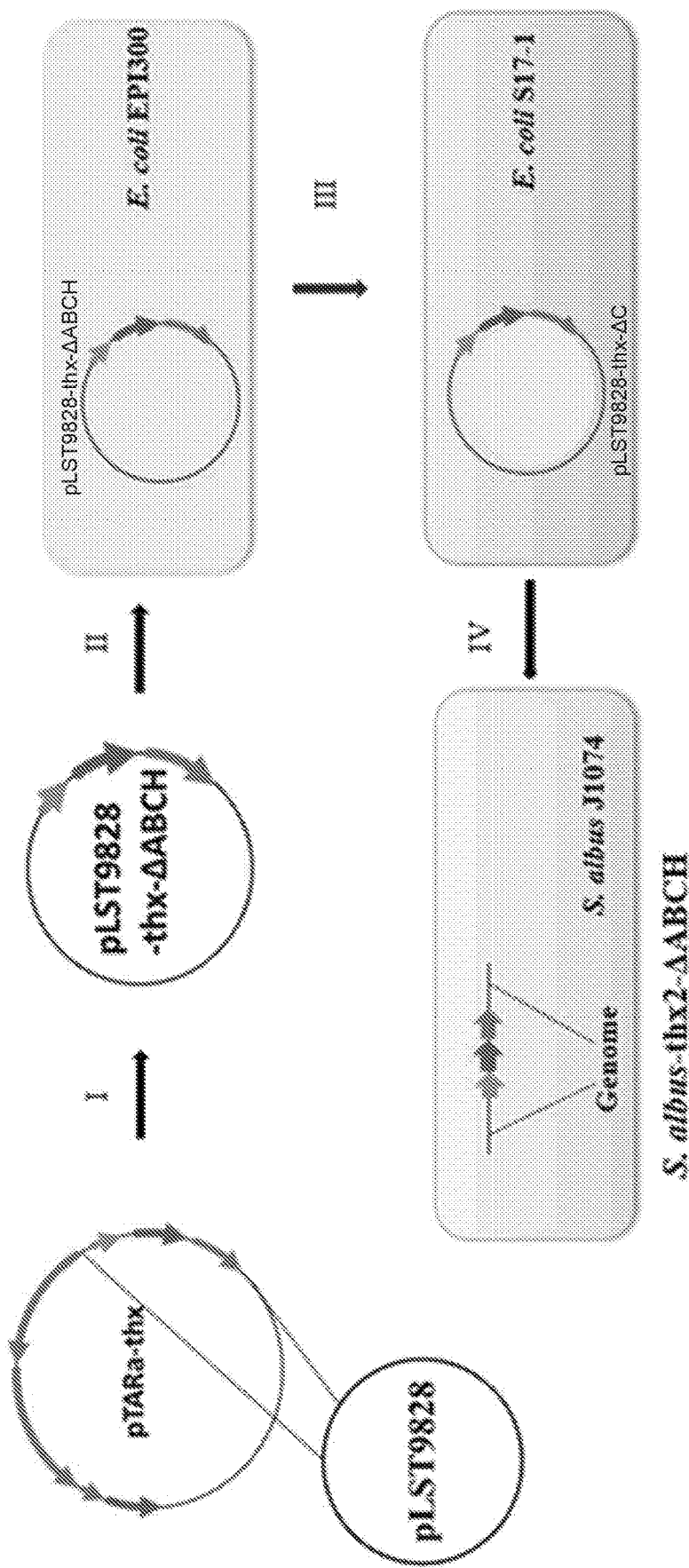
Figure 15:
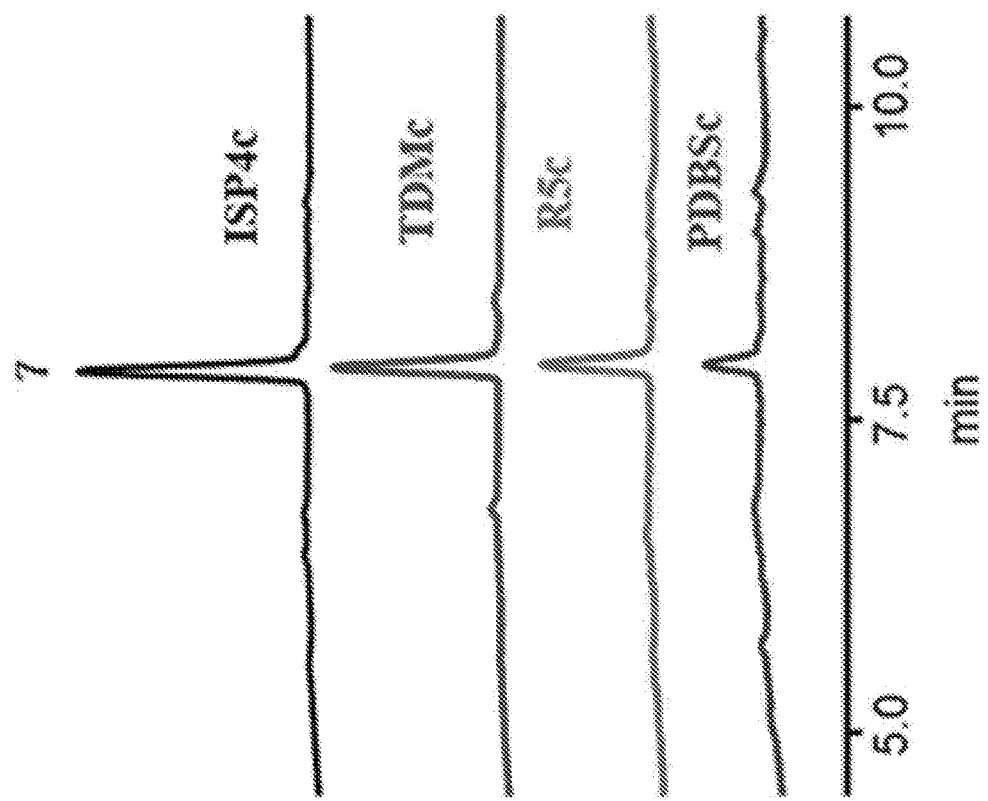
Figure 14:
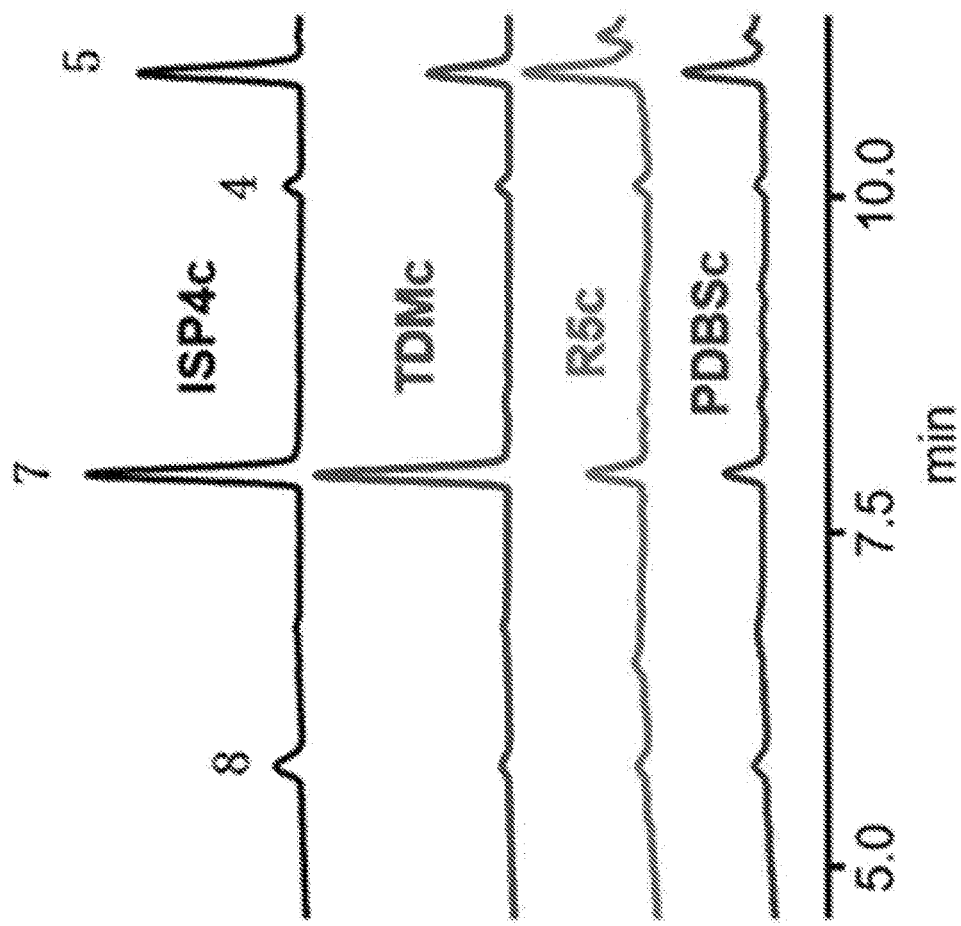
Figure 16A:
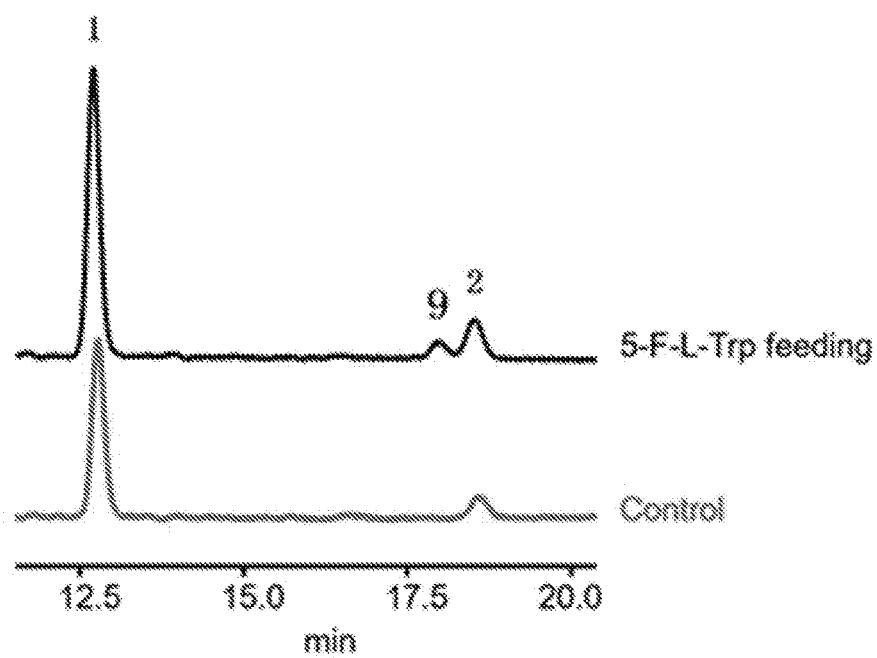
Figure 16B:
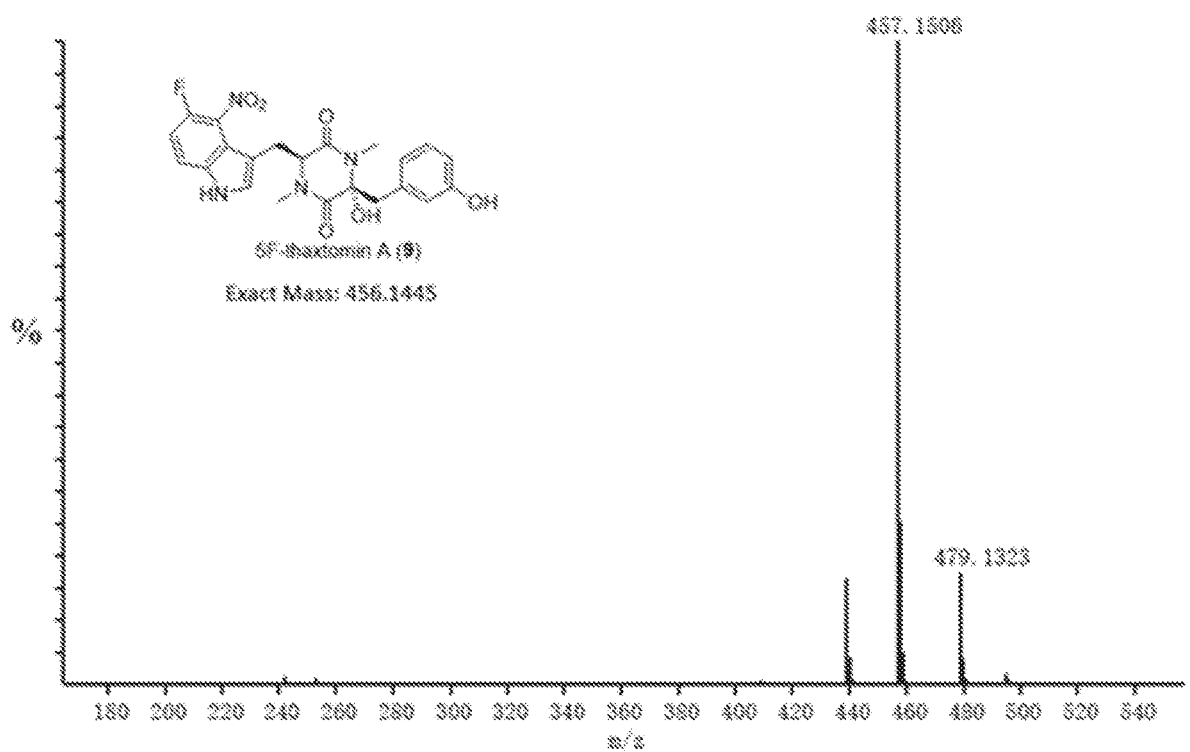
Figure 16C:
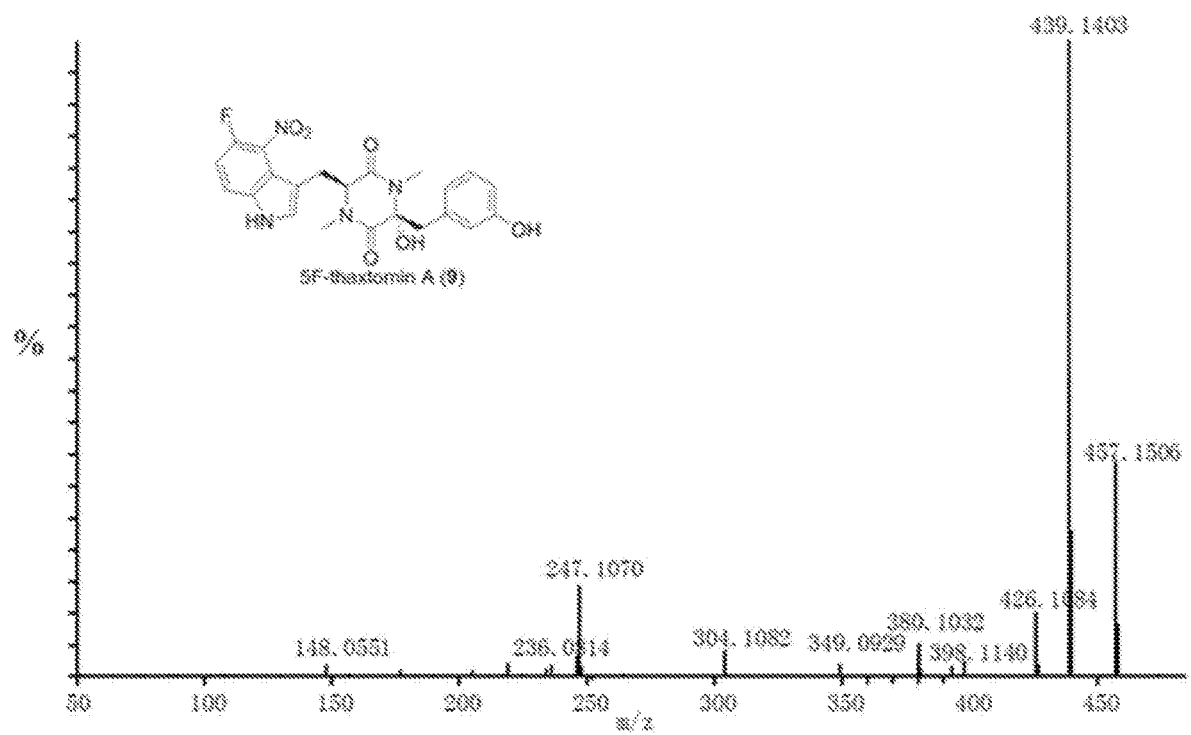
Figure 17:
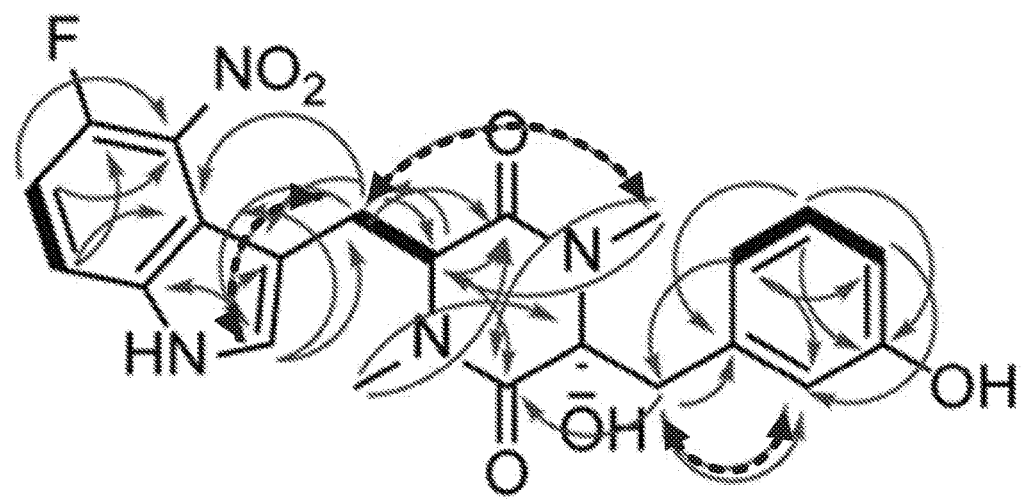
Figure 18A:
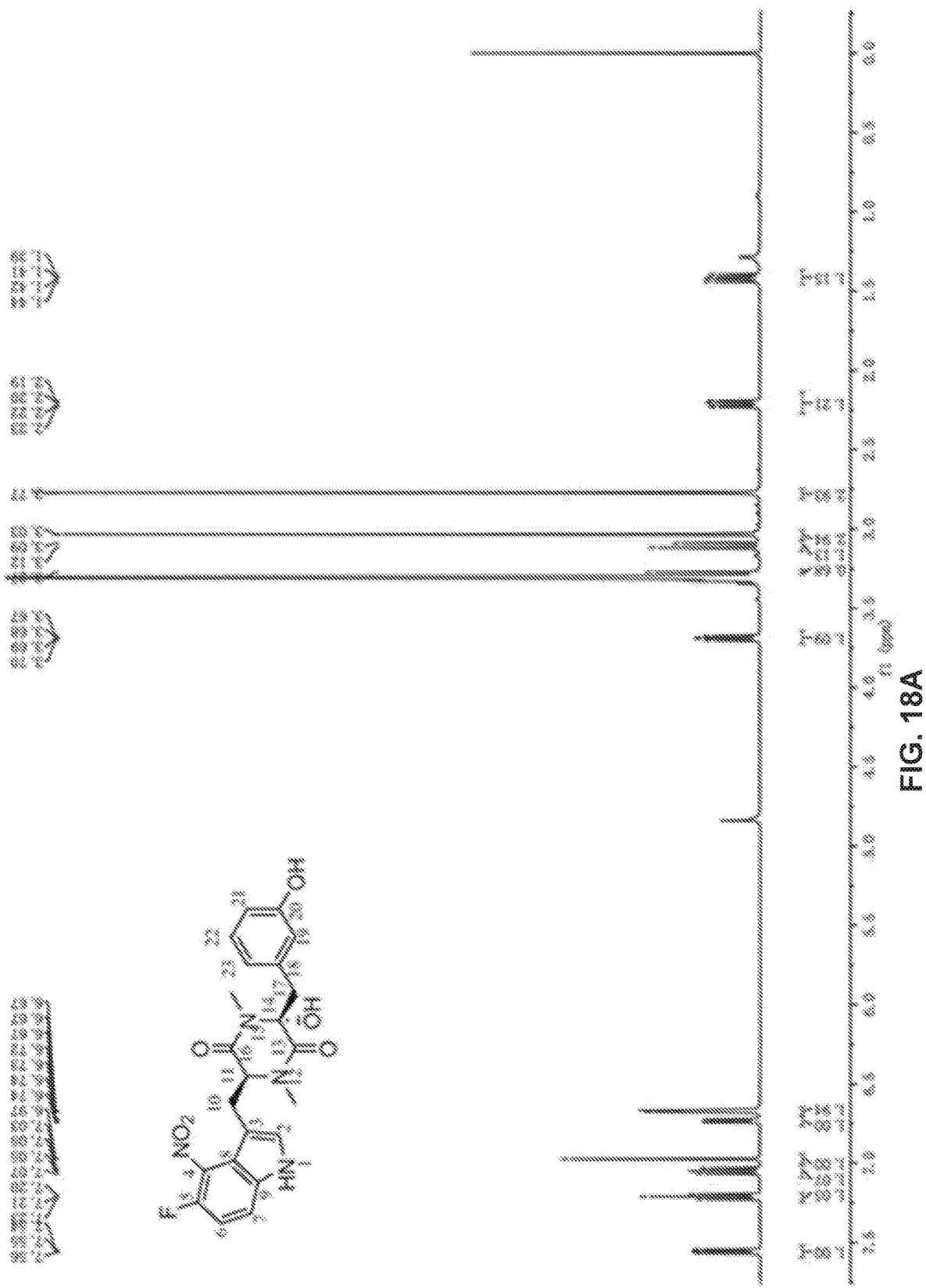
Figure 18B:
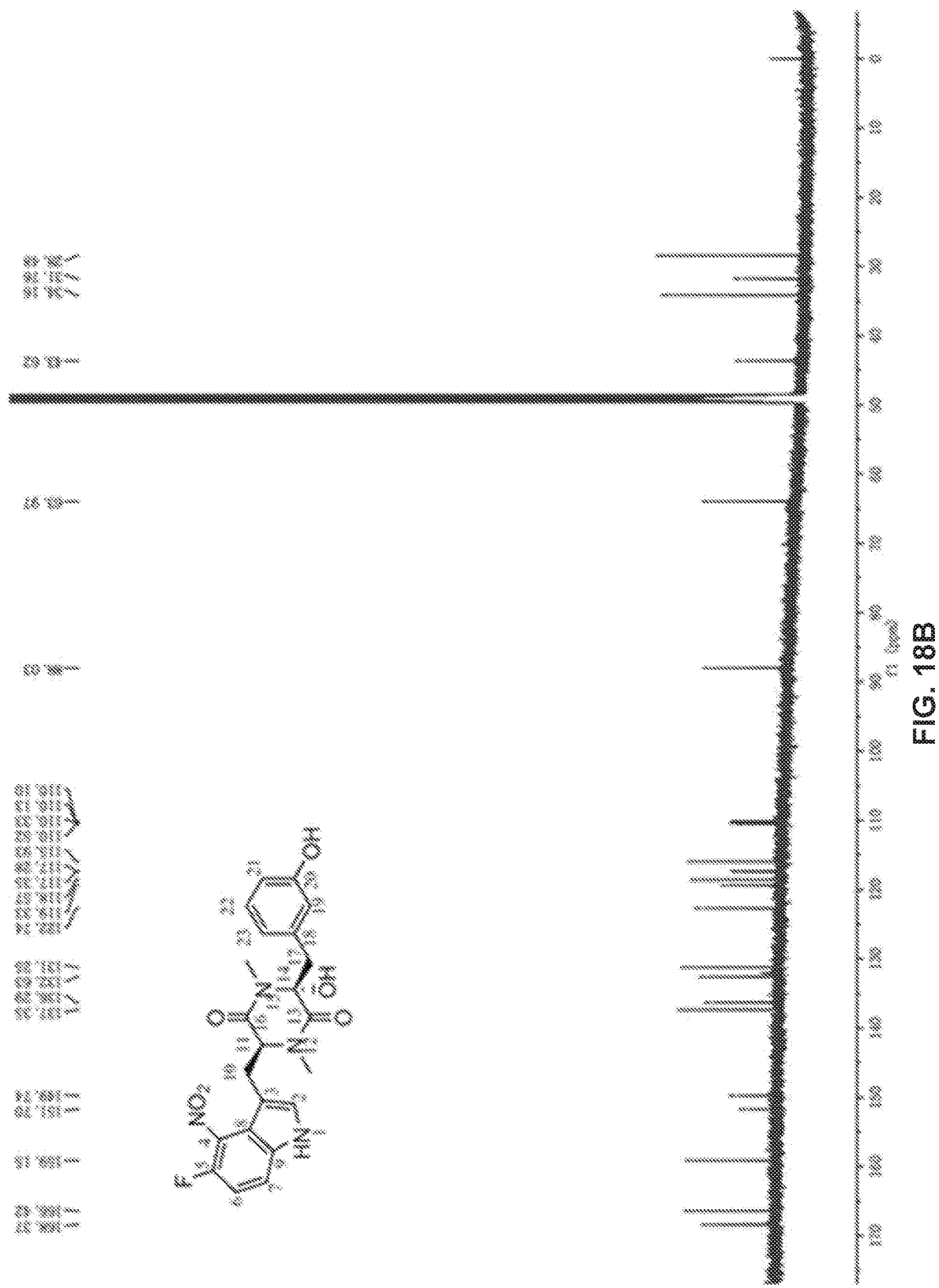
Figure 18C:
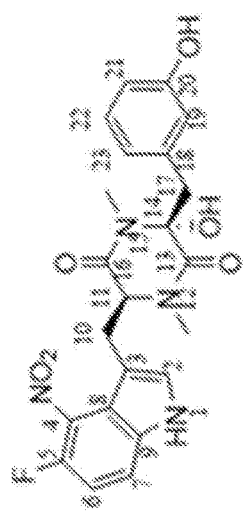
Figure 18C:
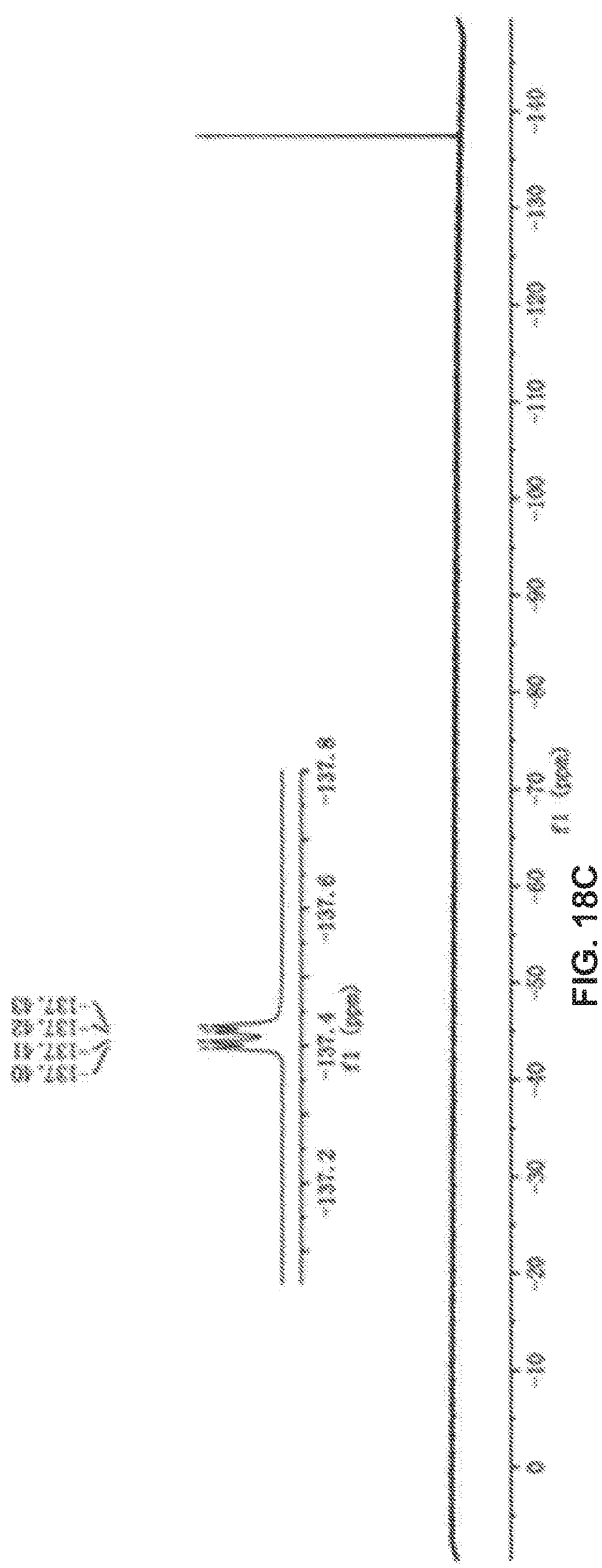

After 6-day fermentation, *S. albus*-thx1 produced thaxtomin A (1), four thaxtomin analogs as minor metabolites (2-5), N-acetyl-4-nitrotryptophan (7) and a trace amount of N-methyl-4-nitrotryptophan (8) as shown in HPLC trace (FIG. 9A). The identities of these compounds were revealed by high resolution-mass spectrometry (HR-MS) analysis including the fragmentation of target ions (FIGS. 10A-10N). None of these metabolites were detected from the culture medium extract of wild type *S. albus* J1074. The production of these thaxtomin-related metabolites suggested that *S. albus* J1074 properly recognized the native promoters of the thaxtomin gene cluster of *S. scabiei* 87.22.

Remarkably, the yield of the most abundant metabolite thaxtomin A (1) reached about 23 mg/L after only 24 hours, highlighting a rapid and highly efficient production. Compounds 7 and 8 are the derivatives of $4\text{-}NO_2$-I-tryptophan, and have been isolated from the culture medium of *S. scabiei* 87.22 at low titers. Nitrotryptophan analogs can be valuable building blocks for the synthesis of bioactive chemicals such as the protein kinase C activator indolactam V and new analogs of numerous tryptophan-containing compounds. However, chemical synthesis of optically pure $4\text{-}NO_2$-I-tryptophan (6) is complicated. *S. albus*-thx1 produced a high amount of N-acetyl-nitrotryptophan (7, >50.0 mg/L) and can provide a green route to nitrotryptophan analogs.

The integrative bacterial artificial chromosome (BAC) vector pTARa is specific for assembling natural product gene clusters and is over 15 kb in size. To assess the potential size effect of integrative vectors on the production of thaxtomins and to ease the cluster engineering as detailed below, the assembled thaxtomin gene cluster was cloned from pTARa-thx into a smaller integrative vector pLST9828 (~5.7 kb) to generate pLST9828-thx via Gibson assembly approach (FIG. 11) (see gibson, DG., et al., 2009 and Butler, A R, et al., 1999, which are hereby incorporated by reference herein). This new construct was used to create *S. albus*-thx2. The metabolite profile of *S. albus*-thx2 cultured in TDMc was identical to *S. albus*-thx1 (FIG. 9A), including the increasing accumulation of compounds 7 and 8 during the fermentation (FIG. 12). This result suggested that the vector size minimally affects the thaxtomin production.

Compared with *S. scabiei* 87.22 cultured under the same conditions, *S. albus*-thx1 and -thx2 produced significantly higher concentrations of 1, 2 and 7 (FIG. 9A). Of note, the engineered *S. albus* strains produced about 10 times more thaxtomin A (1) than *S. scabiei* 87.22 (91.2±6.8 mg/L vs 9.1±0.4 mg/L, Table 3) after 6-day fermentation in TDMc. The productivity of thaxtomin A (1) was determined per biomass, and two *S. albus* strains demonstrated even greater improvement (FIG. 9B). *S. albus*-thx2 showed a slightly, statistically insignificantly higher yield of thaxtomin A (1) than *S. albus*-thx1 (142±4 mg/g vs 137±3 mg/g of dry weight, DW, FIG. 9B), both of which were about 20 times higher than the native producer (7.2±0.7 mg/g DW). Collectively, these results indicate the superior production of thaxtomins in *S. albus*.

Screening of Culture Media for Improving Thaxtomin Yield

To further improve the productivity of thaxtomins in *S. albus*, we screened a total of seven fermentation media. Specifically, both oat bran broth (OBB) and TDMc support the production of thaxtomins by pathogenic *Streptomyces* strains, while TSB, ISP4 and R5 are common media for growing a number of *Streptomyces* strains. Additionally, although potato dextrose broth (PDB) is a fungal culture medium, it was prepared in water or artificial seawater (PDBS) for screening because it contains ingredients of plant origin, as does OBB. *S. albus*-thx2 was selected for the culturing in these media under the same conditions. HPLC analysis revealed that in addition to TDMc, only PDBS was able to induce the production of thaxtomin A (1) at a low level (about 0.5 mg/L) (Table 3). This result presumably suggested that cellobiose remains indispensable for the induction of thaxtomin biosynthesis in *S. albus*. Consequently, these media (except TDMc) were supplemented with 1% cellobiose, which is indicated by a lowercase c (e.g., ISP4c). It was found that ISP4c, R5c and PDBSc supported the production of ~150 to ~170 mg/L of thaxtomin A (1) by *S. albus*-thx2 after 6-day fermentation, 1.7 to 1.9 times higher than TDMc (Table 3). Furthermore, when PDBSc was prepared directly from raw potato materials, *S. albus*-thx2 was able to produce~142 mg/L of thaxtomin A (1), providing a highly economical option for the production of thaxtomins. In these cellobiose-containing media, *S. albus*-thx2 also produced compounds 2-5, whose total productivity was about one third of thaxtomin A (1), 50 to 80 mg/L of N-acetyl-4-nitrotryptophan (7) and a trace amount of 8 (Table 3).

Engineering the Thaxtomin Gene Cluster by Gene Deletion to Produce Biosynthetic Intermediates Thaxtomin biosynthetic intermediates can be valuable for developing advanced synthetic approaches (e.g., semi-synthesis) to produce thaxtomins and analogs. Thaxtomin D (5) is an advanced intermediate carrying a featured diketopiperazine core (FIG. 8B), but only a trace amount was produced by both native producers and two engineered *S. albus* strains (FIG. 9A). To overproduce this compound, the txtC gene was deleted from the thaxtomin cluster cloned in pLST9828 and then created *S. albus*-thx2-ΔC (FIG. 13A). This new strain was cultured in thaxtomin production media TDMc, ISP4c, R5c and PDBSc for 6 days. All selected media supported the production of thaxtomin D (5) (FIG. 14), and the highest yield at 76 mg/L was achieved in ISP4c (Table 5). This strain also produced a low concentration of thaxtomin C (4) in all media (FIG. 14) and 55 to 65 mg/L of 7-8 in TDMc, R5c and ISP4c (Table 5). However, only about 11 mg/L of nitrotryptophans were produced when the stain was cultured in PDBSc (Table 5), strikingly different compared to that of *S. albus*-thx2, which produced~80 mg/L of 7-8 in PDBSc (Table 3). It remains unclear how the removal of txtC influences the production of nitrotryptophan analogs in some media.

Next, txtABCH genes were deleted from the thaxtomin gene cluster (FIG. 13B), and *S. albus*-thx2-ΔABCH was created, which can potentially overproduce nitrotryptophans. Indeed, about 50 mg/L of 7 was produced by *S. albus*-thx2-ΔABCH when cultured in TMDc and ISP4c for 6 days (Table 5 and FIG. 15). R5c and PDBSc were less effective production media (about less than 18 mg/L). Interestingly, no 8 was detected from any extract of *S. albus*-thx2-ΔABCH (FIG. 15). Future studies can investigate the potential role of the methyltransferase domain of TxtB/TxtA in the formation of 8. *S. albus*-thx2-ΔABCH is not able to produce thaxtomin analogs, therefore having no competing pathway using 4-$NO_2$-I -tryptophan (6) as substrate (FIG. 8B). The comparable amounts of 7 with *S. albus*-thx2 and *S. albus*-thx2-ΔC indicated that the cellular availability of 4-$NO_2$-I-tryptophan (6) may not limit the productivity of thaxtomins in *S. albus*, suggesting potential synthetic biology approaches to further overproduce thaxtomins, e.g., the overexpression of txtABCH genes under stronger promoters.

Production of 5-F-thaxtomin A

The impressive substrate promiscuity of TxtE was previously demonstrated in in vitro studies, and 5-F-I-tryptophan was identified as the best enzyme substrate as described in Zuo, R. et al., 2016 and Zuo, R. et al., 2017, incorporated herein by reference. To further probe the feasibility of the thaxtomin biosynthetic system as an alternative to chemical methods in synthesizing thaxtomin analogs, it was desired to produce unnatural thaxtomin analogs by feeding tryptophan analogs. Specifically, serial concentrations (0 to 50 μM) of 5-F-I-tryptophan were included in TDMc to culture *S. albus*-thx2. HPLC analysis of culture extract revealed the appearance of a new peak with a retention time of 18.1 min (FIG. 16A). The peak content showed a molecular ion of 457.1497 in HRMS analysis (FIG. 16B), matching the value of 5-F-thaxtomin A (9, calculated: 457.1523) (HR-MS/MS analysis shown in FIG. 16C). This compound (1.8 mg/L) was further isolated by semi-prep HPLC analysis and its structure as 5-F-thaxtomin A (9) (FIG. 17) was determined by multiple 1D ($^1H$, $^{19}F$, and $^{13}C$) (FIGS. 18A-18C) and 2D (COSY, HMBC, HSQC, and NOESY) NMR analyses (data not shown). Of note, the purified compound showed a chemical shift (δ) of −137.41 ppm (dd, J=10.9 Hz and 4.5 Hz, 1F) in $^{19}F$ NMR analysis, confirming the aromatic C5-F substitution. Compared with reported NMR spectra of thaxtomin A (1), this new analog lost a proton signal at its C5 and possessed an increased chemical shift of its C5 (δ=151.7 ppm vs 119.2 ppm in thaxtomin A) caused by the deshielding of C5-F substitution (Table 4). These results illustrated the remarkable plasticity of thaxtomin biosynthetic system and the use of *S. albus* as host to produce new thaxtomin analogs. In addition, fluorine substitution is an effective strategy to improve other properties (e.g., metabolism) of bioactive compounds.

Bioactivities of Natural and Unnatural Thaxtomin Analogs

Thaxtomins have potent herbicidal activity, and their analogs can possess additional bioactivities including antifungal and antiviral activities. So, the herbicidal activity of 5-F-thaxtomin A (9) was measured in a radish seedling assay (FIG. 19). Its $I_{50}$ at 0.56±0.03 μM was statistically insignificantly weaker than thaxtomin A (1) ($I_{50}$=0.45±0.05 μM, P value=0.04) but significantly stronger than ortho-thaxtomin A (2) ($I_{50}$=0.81±0.04 μM, P value=0.0005). The cytotoxicity of compound 9 was further examined along with compounds 1-3, and weak growth inhibition toward human T-cell leukemia Jurkat and prostate cancer PC-3 cell lines was observed in a dose-dependent manner (FIGS. 20A-20B). $IC_{30}$ values (i.e., 30% inhibitory concentrations) of compounds 1, 2, 3, and 9 toward Jurkat cells were 70.84±16.68 μM, 56.46±12.04 μM, 50.92±13.17 μM and 63.26±9.29 μM, respectively (FIG. 20A). For PC-3 cells, the corresponding values were 80.28±10.50 μM, 42.38±13.62 μM, 37.87±13.46 μM and 56.76±17.12 μM (FIG. 20B). The $IC_{30}$ values of 2 and 3 were significantly different to $IC_{30}$ value of 1, with P values=0.019 and 0.013, respectively, while $IC_{30}$ value difference of 9 with 1 was statistically insignificant (P value=0.112).

In conclusion, despite the promising agricultural applications of thaxtomins, there has, thus far, been a lack of cost-effective production approaches. The present examples describes the heterologous production of thaxtomins in *S. albus*. Through medium optimization, the expression of the chromosomally integrated biosynthetic gene cluster resulted in the highest yield of thaxtomin A ever reported, at about 170 mg/L. This significant achievement can lay a solid basis toward the wide agricultural use of this novel class of bioherbicide. Furthermore, the thaxtomin biosynthetic gene cluster was engineered to produce two valuable biosynthetic intermediates at high yields, both of which can act as precursors and building blocks for the development of advanced synthetic strategies of chemicals. This work also demonstrated the versatility and feasibility of the thaxtomin biosynthetic system by the production of 5-F-thaxtomin A (9), which showed potent herbicidal activity similar to thaxtomin A (1) and ortho-thaxtomin A (2). Overall, this disclosure, as evidenced by this Example, presents an attractive synthetic biology strategy to address the insufficient supply of herbicidal thaxtomins and analogs, which can find general applications in translating genomes into chemicals.

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

TABLE 1

Tables and Sequences from Examples
Production of thaxtomins and nitrotryptophan derivatives by S. albus
J1074 transformed with a minimal gene cluster in different media.

| Media | Thaxtomin A (mg/L) | Other thaxtomins (mg/L) | 4-Nitrotryptophans (mg/L) |
|---|---|---|---|
| TDMc | 91.2 ± 6.8 | 33.6 ± 2.4 | 58.2 ± 1.4 |
| ISP4c | 151.2 ± 12.2 | 48.4 ± 3.6 | 50.4 ± 2.1 |
| R5c | 168.2 ± 13.2 | 54.2 ± 3.8 | 56.6 ± 2.3 |
| PDBSc | 157.6 ± 8.8 | 48.0 ± 2.2 | 80.2 ± 3.2 | mean ± standard deviation, n = 3

TABLE 2

Bacterial strains, plasmids, and cosmids used in this study

| Strain or plasmid | Description[†] | Source or reference |
|---|---|---|
| *E. coli* strains | | |
| DH5α | General cloning host | Gibco-BRL |
| BW25113 | Host for the REDIRECT © PCR targeting system | (Gust et al. 2003) |
| ET12567 | dam⁻, dcm⁻, hsdS⁻; non-methylating host for transfer of DNA into *Streptomyces* spp. (cml$^R$, tet$^R$) | (MacNeil et al. 1992) |
| S 17-1 | General cloning and conjugation donor strain (tmp$^R$) | (Simon et al. 1983) |
| Plasmids or cosmids | | |
| pIJ790 | λ Red plasmid (t$^S$, cml$^R$) | (Gust et al. 2003) |
| pUZ8002 | Supplies transfer functions for mobilization of oriT-containing vectors from *E. coli* to *Streptomyces* (kan$^R$) | (Kieser et al. 2000) |
| pIJ773 | Template for the REDIRECT © PCR targeting system, contains the [aac(3)IV + oriT] disruption cassette (amp$^R$, apr$^R$) | (Gust et al. 2003) |
| Cosmid 1989 | SuperCos1 derivative containing the S. scabiei 87-22 txtH locus (kan$^R$, amp$^R$) | This study |
| Cosmid 2757 | SuperCos1 derivative containing the S. scabiei 87-22 lanAB locus (kan$^R$, amp$^R$) | This study |
| pTARa | Bacterial artificial chromosome (BAC) plasmid (chl$^R$, amp$^R$) | (Dimitris Kallifidas 2012) |

[†]apr$^R$, apramycin resistance; cml$^R$, chloramphenicol resistance; tet$^R$, tetracyclin resistance; t$^S$, temperature sensitive; kan$^R$, kanamycin resistance; amp$^R$, ampicillin resistance; thio$^R$, thiostrepton resistance; chl$^R$, chloramphenicol resistance; tmp$^R$, Trimethoprim resistance.

TABLE 3

The yields of thaxtomins (1-5) and nitrotryptophan derivatives (7, 8) by S. albus-thx2 in different media and by S. scabiei 87.22 in TMDc[a]

| Media | 1 | 2-5 | 7, 8 |
|---|---|---|---|
| TDMc[b] | 9.1 ± 0.4 | 1.5 ± 0.1 | 2.1 ± 0.1 |
| TDMc | 91.2 ± 6.8 | 33.6 ± 2.4 | 58.2 ± 1.4 |
| PDBS | 0.50 ± 0.03 | 0.40 ± 0.02 | Trace |
| ISP4c | 151.2 ± 12.2 | 48.4 ± 3.6 | 50.4 ± 2.1 |
| R5c | 168.2 ± 13.2 | 54.2 ± 3.8 | 56.6 ± 2.3 |
| PDBSc | 157.6 ± 8.8 | 48.0 ± 2.2 | 80.2 ± 3.2 |
| PDBSc[c] | 142.1 ± 5.4 | 44.1 ± 1.3 | 76.2 ± 2.1 |

[a]data represented mean ± s. d. (n = 3). The concentration unit was mg/L;
[b]S. scabiei 87.22 was cultured in TDMc;
[c]home-made PDBS with 1% cellobiose.

TABLE 4

$^1$H and $^{13}$C NMR data comparison of compounds 1 and 9

| Position | Thaxtomin A[a] δ$_C$, type | Thaxtomin A[a] δ$_H$ (J in Hz) | 9[b] δ$_C$, type | 9[b] δ$_H$ (J in Hz) |
|---|---|---|---|---|
| 2 | 132.5, CH | 6.95, s | 132.6, CH | 6.97, s |
| 3 | 110.5, C | | 110.3, C | |
| 4 | 143.6, C | | 149.7, C | |
| 5 | 119.2, CH | 7.84 (7.9, 1.0, dd) | 151.7, C | |
| 6 | 121.0, CH | 7.19 (8.0, t) | 110.4, CH | 7.05, (12.0, t) |
| 7 | 118.6, CH | 7.68 (8.1, 1.0, dd) | 117.3, CH | 7.56 (12.0, 4.0, dd) |

TABLE 4-continued

¹H and ¹³C NMR data comparison of compounds 1 and 9

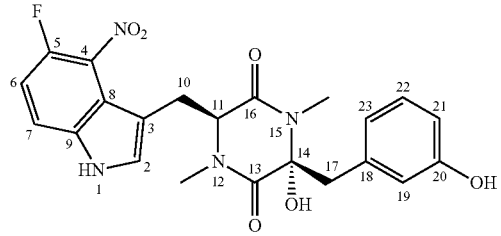

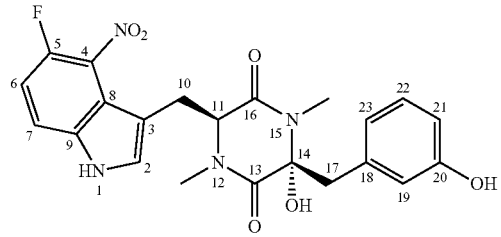 [SMILES: CN1C(=O)[C@](O)(Cc2cccc(O)c2)N(C)C(=O)[C@@H]1Cc1c[nH]c2ccc(F)c([N+](=O)[O-])c12]

| Posi-tion | Thaxtomin A[a] | | 9[b] | |
|---|---|---|---|---|
| | $\delta_C$, type | $\delta_H$ (J in Hz) | $\delta_C$, type | $\delta_H$ (J in Hz) |
| 8 | 119.8, C | | 119.3, C | |
| 9 | 141.1, C | | 136.3, C | |
| 10 | 33.5, CH$_2$ | 1.62 (14.2, 8.9, dd); 2.60 (14.1, 6.2, 0.5, ddd) | 31.8, CH$_2$ | 1.40 (16.0, 8.0, dd); 2.21 (12.0, 4.0, dd) |
| 11 | 64.6, CH | 3.86 (8.9, 6.3, dd) | 64.0, CH | 3.69 (8.0, 4.0, dd) |
| 13 | 168.3, C | | 168.4, C | |
| 14 | 88.0, C | | 88.0, C | |
| 16 | 166.8, C | | 166.4, C | |
| 17 | 45.4, CH$_2$ | 3.11 (13.4, d); 3.32 (13.5, d) | 43.6, CH$_2$ | 3.11 (12.0, d); 3.29 (12.0, d) |
| 18 | 137.4, C | | 137.4, C | |
| 19 | 118.4, CH | 6.71, m | 118.6, CH | 6.67, m |
| 20 | 159.1, C | | 159.2, C | |
| 21 | 115.8, CH | 6.71, m | 115.9, CH | 6.74, m |
| 22 | 131.2, CH | 7.23 (8.1, t) | 131.3, CH | 7.21 (8.0, t) |
| 23 | 122.7, CH | 6.71, m | 122.7, CH | 6.67, m |
| N-12 | 28.5, CH$_3$ | 3.03, s | 28.5, CH$_3$ | 3.03, s |
| N-15 | 34.2, CH$_3$ | 2.81, s | 34.2, CH$_3$ | 2.77, s |

[a]NMR data were reported in King, RR., et al., 1992;
[b]NMR spectra were recorded in CDOD$_3$.

TABLE 5

The yields of thaxtomin biosynthetic intermediates 5, 7, and 8 by two engineered strains in different media[a]

| | S. albus-thx2-ΔC | | S. albus-thx2-ΔABCH |
|---|---|---|---|
| Media | 5 | 7, 8 | 7 |
| TDMc | 36.1 ± 0.3 | 54.9 ± 1.5 | 48.2 ± 2.2 |
| ISP4c | 75.9 ± 1.1 | 65.8 ± 2.1 | 56.2 ± 3.5 |
| R5c | 63.9 ± 1.2 | 64.8 ± 1.3 | 17.5 ± 0.8 |
| PDBSc | 27.2 ± 0.4 | 11.3 ± 0.3 | 11.5 ± 0.4 |

[a]data represented mean ± s. d. (n = 3). The concentration unit was mg/L.

TABLE 6

Microbial strains, plasmids, and cosmid used in this study

| Strains or plasmids | Features[†] | Source |
|---|---|---|
| *E. coli* strains | | |
| EPI300 | General cloning host | Epicentre |
| S17-1 | General cloning and conjugation donor strain (tmp[R]) | 59 |
| *Streptomyces* strains | | |
| *S. albus* J1074 | Isoleucine and valine auxotrophic derivative of *S. albus* G lacking Sa/l-restriction activity | 60 |
| *S. albus*-thx1 | *S. albus* J1074 transformed with pTARa-thx | This study |
| *S. albus*-thx2 | *S. albus* J1074 transformed with pLST9828-thx | This study |
| *S. albus*-thx2-ΔC | TxtC gene was deleted from the thaxtomin gene cluster | This study |
| *S. albus*-thx2-ΔABCH | TxtA-C and H genes were deleted from the thaxtomin gene cluster | This study |
| *S. scabiei* 87.22 | Native thaxtomin producer | 18 |
| Yeast strain | | |
| *Saccharomyces cerevisiae* CRY1-2 | Uracil-deficient (MATa, ura3Δ, cyh2[R]) | 43 |
| Plasmids | | |
| Cosmid 1989 | SuperCos1 derivative containing the thaxtomin gene cluster of *S. scabiei* 87-22 (kan[R], amp[R]) | This study |
| pTARa | Bacterial artificial chromosome vector (chl[R], amp[R]) | 42 |
| pTARa-thx | pTARa was cloned with the thaxtomin gene cluster | This study |
| pLST9828 | E.coli-Streptomyces integrative shuttle vector (apr[R]) | 52 |
| pLST9828-thx | pLST9828 was cloned with the thaxtomin gene cluster | This study |
| pLST9828-thx-ΔC | TxtC gene was deleted from the thaxtomin cluster in pLST9828 | This study |

TABLE 6-continued

Microbial strains, plasmids, and cosmid used in this study

| Strains or plasmids | Features[†] | Source |
|---|---|---|
| pLST9828-thx-ΔABCH | TxtA-C and H genes were deleted from the thaxtomin cluster in pLST9828 | This study |

[†]apr[R], apramycin resistance; cml[R], chloramphenicol resistance; kan[R], kanamycin resistance; amp[R], ampicillin resistance; chl[R], chloramphenicol resistance; tmp[R], Trimethoprim resistance; cyh2[R], cycloheximide resistance.

LISTING OF SEQUENCES:

txtA (scab31791) (SEQ ID NO: 1)
GTGTCGCACCTGACCGGTGAAGATCTCCCGGAGGGAGCGCTCGCCACGACGTGGCCGAGTCTCCTCGAAGCGCGGGTGGCC
GACACACCTGACGCCATCGCGCTCGTCGCCGGGGACACGGCGCTCACGTACGCGCAGTTCAATGCCCGTGCGAACCGGCTC
GCCCGGTGGCTGAAGTACCTCGGCGCCGGGCCGGAGCGGTCGGTCGGGCTGGTGCTGGGCAGGTCCGCGGACTTCTTCCTG
TGCGCGACGGCCGTGCTCAAGTGCGGGGCCGCGTACCTGCCGCTGGATCCGAACTACCCCGTGGAGCGACTGTCCTTCATG
GCCCGGGACGCAGCACCCGTGGTGCTGGTGACGACGTCGGACGTCCGGGGCGACCTTCTGGGCCAGCTGCCCACCGGCAGC
CTCGTGGTACTGGACGACGAGGCCACCGAGGACGTACTGCGCCGTCTGCCGGACCATGGAGGACGGGGAACGTTTG
GAGCCACTGCGCCCCGCGAGTCCCGCCTACATCATCTACACCTCCGGCTCCACGGGGATCCCCAAGGGAGTCGTCGTCACC
CACCAAGGCGTCGCGAGCCTGATCGCGACCCAGCGTCGTCGCCTCGCCGTCACCGGCGCCTCACGCGTGCTCGCCTTCTCG
TCCCCGAGTTTCGACGCCAGTTTCTGGGAGATGTCGATGGCGCTGCTGGCCGGGGCCGCGCTCGTGGTCGGCAGGCCGGGG
CGGCTGCTGCCCGACGCCGAACTGGCCGCGTTGATCGCGGACCACGGAGTCACTCATGTCACTCTCCCGCCCTCGGTCGCG
GGTGCGCTGGGCCCCGACATGCTGCCTCCGAGCGTGACGCTGGTCGTCGCGGGCGAAGCGTGCCCGGCGGCTCTCGTGCAG
CGCTGGCGCCCGCACCGGACGATGGTGAACGCCTACGGCCCGACGGAGTCCACCGTCTGCGCCACCATGAGCGATCCGCTG
GCCGACGACGTGGCGCCGCCGGTCGGCCGGGCGGTGGACGGCACCCGGATCCATGTCCTCGACGACCGCCTCGCACCGGTT
GTGCCGGGAGCGGTCGGCGAGATCTACATCGCGGGGCACAGCCTGGCACGCGGGTACCTCGAGCGGCCGGGTCTGACCGCG
CAGCGGTTCGTGGCGGACCCCTTCGGCCCGGCGGCAGCCGTATGTACCGCAGCGGTGACCTCGGCCGCTGGACCCGTTCA
GGAGACCTGGAGTTCGTCGGCAGGGCGGACGACCAGGTCAAGGTACGGCTTCCGTATCGAGCCGGGCGAGATCGAATCC
GTCATCGCCGGGTGCCGCGGGGTCCGGCAGGCCGCCGTCGTCCTGCGTGAGGACCGGCCCGGAGAGCCATACCTCGCCGCC
TACGTCATACCCGAGAACGCGGCCGCCGACGAGGCGGCCGGCGAGGAACCGGACGGTCAACTCGATGCCTGGCGACGGCTC
TACGACGATCTGTACGGCCGAGCCGACACCGCCGACTTCGGCGAGGACTTCTCCGGCTGGGTGAGCAGTTATGGCGGGCGG
CCGATCGAGGGGATGCGCGAATGGCGTGAGCAGACCGTGCGACAGATCCGCGAACTGGCTCCGCGCCGCGTACTGGAGATC
GGCTGCGGTTCCGGTCTGCTGCTCTCGCAGCTGGCGGGTGACTGCGAAAGCTACTGGGGCACCGACATCTCCGGGGCCCTG
ATCGAGCGGCTGCGCGGGCAGGTCGCCGAGCGCCCCGGCCTCGCGGACCGGGTCGTCCTGCATCAGCTCTCCGCCCATGAG
CTGGGGAGTCTGCCCAGCGGCGGCTTCGACACCGTCGTGCTCAACTCCGTGATCCAGTACTTTCCCTCAGGCGATTACCTG
TTCGACCTACTGCGCGAGGTGTCCCGGCTCCTGGTACCCGGGGGCGCGGTGTTCCTCGGCGACGTCCGTAACCTTCGTCTG
CTGCGCACCCTTCCACGCCGGGGGGCTGCTGGCGGCGGCCACGCACACCGACACTCCGCAGACGGTCTGCGCGGCGATCGAC
CGGGCCATGGCGCAGGAGAAGGAACTGCTCGTGGACCCGGAGTTCTTCACGACGGCCGTCGGCGCGCTGCCCGGCATGACG
CTGGAGTCGTGCACGCTCAAACGGGGCGGGTACGACAACGAACTCAGCCGCTATCGCTACGAGGTGGTGCTGCGCAAGCAT
GCCGGGCCTGCCGATGACACCGGGCCCACGGACGACGCGGGGCCGGTCGTGCGACTGCGGTGGGACGGCGAGATGGCGAGC
CTGGCCGACGTCGCCGATCGGCTGCGTCGTGGGAAACCGAGCGGTTGTGCGTCACCGGGATCCCCAACGGCCGGGTGGCC
GGCGAGCATGCCGCGACACTCGCGCTGTTCGACCGGCGCCCCCTGCACGAGGTGCTGTCCCTGGGGCAGGCTCCGGCGGGC
GTGGCACCGGAGGACCTGCGCCGGCTGGGCGCGGAACTGGGCTACCACCTGCACCTGGTCGTCCGAGGACGACGCC
CTGATCGACGCTTCCTTCACACGCGCCGGAGCGCTCGTGCCGCGTCCCGCCCCCCGGACCGACGCGGAGCCGGACGGTTTC
TCCCCGGCCCGGTTCACCAACAGGCCGGCGTTCGCCCGCCCCGACTCCCAGACGATGGCCTCTCTTCCCGGGCAGGTCGCG
GCGAAGCTGCCGGCCTTCATGGTCCCGGAGGTCTTCGTCCCGCTCGACAGGCTGCCGGTCACGGTGAACGGAAAGCTCGAC
CGCGGCGCCCTGCCCCGGCCGCGGGCGCCGCCGCCCATGCCTCGGGACGTCGCAGGACCGCCCGCGAGGAGGTACTGGCG
GCGATCTTCGCCGACGTACTCGCGACAGCCGACGTCACAGCCGACAGCGACTTCTTCGCCGTCGGCGGCAACTCCCTGCTG
GCCACCCGACTCGCCGCCGAGGTCCGGCGGCGCCTGAACACCGAGATGCCGCTGTCGTGGCTGTTCGAGTCGCCCACCGTC
GGCGCGCTCGCCGCCCGCTTCGACGCGGGGACGAGGCCAGGCCGCTGCCCGTGCCGAGCGAGTACGCCTCCGGCAGCACG
GCGCCGTTGTCGGCCCAGCAGATGCAGATGTGGCACGAGTACGCCGAAGCCTGTGTCGCGACATGTTCAACGTGCCGCTG
TCGCAGCGGCTGACCGGTGCCGTCGACGCCGAGGCACTGCGCGCCGCCTCGCCGATGTCGTCACCCGGCACGTTCCGCTG
CGCACGCTCGTCCAGGACGACGGCAGCGGTCCGTGTGCGGTGATCACGGAAGCCACCGCGGACGACATCCCATGGACGGAG
ACCAGGACCACGCCCGAGCGGCTGTCCGAGGATCTCGCGCACGCCGCCCGCCGCCACTTCGACCTCGAGACCGAGATCCCG
CTGCGGGCCGTACTGTTCACGCTCGGCCCGGACGAGTCCGTACTGCTGCTGGTCATGCATCACATCGCCGCCGACGGCTGG
TCCTTCGGCCCCCCTGCTGGAGGACCTGGTCCGCGCCTACCGCGCCCGGACCGAGGGGCGCGCACCACAGTGGGAGCCGCTG
TCCTTCGGCTACCTCGACTACGTCGCCTGGCAGCGCCGGCTGCTCGGCGCCACGGGACCCGAGCGACGTCGCGCTGCGC
CAGGCGGAGTACTGGAGGAAGACGCTGCACGGTGCCGACGACAGGCCGGTCCTGGAGACCGACAGCCCGGCGCCGGCCCAG
CAGGACTTTGCCGGCAGGTCCCTCGATCTTCCGCTCGAAGTCGGCGGCCACCGGGTGCTGACAGCCGCGGCCCGTGAGCAC
GGTGTCACCGTCTTCATGATCCTGCACGCCGCGCTCGTCGCACTGCTCGCCCGCAGGGGAGCAGGAGGGGACGTCACCGTC
GTGACCGCGGTGGCCGGCCGGACCGACACCCAGTTCGAACCGCTGGTGGGCCTCTTCGCCAACACCTTGGCGCTGCGCACC
GACACGTCGGGCAACCCCACCTTCCGCGAACTGCTGGACCGGGTCCGCGTGACCGATCTCGGTGCCTATGCCCACCAGGAC
CTGCTCTTCGAGCGCCTGGCCGACGTGCCACCGCCCAGGTGTCACTCGTCCTGCGCACGGTCGCAGCTCCGCCGGCCGAC
CTGCCGGGCCTCACCATCAGTCCCGGCCCACGGCCGGCGAGCGAATCCGCCCGCTATCCGGTGCTGTGGACCGTGGAGCAT
CTGGCCTCCGCCGCGGACGGCGGGACGCTGCGCAGCCACATCCAGTACCAGAGCGGGCTGCTGCGCGACACGGTCGTC
CGGCTCGCCCAGCAGTACGAAGTCGTGCTGTCCCTGTTGTTGAAGGATCCCGATCTCCGCGTCCAGGACCTCCCACTGCAG
TGA TxtA (scab31791) (SEQ ID NO: 2)
VSHLTGEDLPEGALATTWPSLLEARVADTPDAIALVAGDTALTYAQFNARANRLARWLKYLGAGPERSVGLVLGRSADFFL
CATAVLKCGAAYLPLDPNYPVERLSFMARDAAPVVLVTTSDVRGDLLGQLPTGSLVVLDDEATEDVLRRLPDHDMEDGERL
EPLRPASPAYIIYTSGSTGIPKGVVVTHQGVASLIATQRRRLAVTGASRVLAFSSPSFDASFWEMSMALLAGAALVVGRPG
RLLPDAELAALIADHGVTHVTLPPSVAGALGPDMLPPSVTLVVAGEACPAALVQRWRPHRTMVNAYGPTESTVCATMSDPL
ADDVAPPVGRAVDGTRIHVLDDRLAPVVPGAVGEIYIAGHSLARGYLERPGLTAQRFVADPFGPAGSRMYRSGDLGRWTRS
GDLEFVGRADDQVKVRGFRIEPGEIESVIAGCRGVRQAAVVLREDRPGEPYLAAYVIPENAAADEAAGEEPDGQLDAWRRL
YDDLYGRADTADFGEDFSGWVSSYGGRPIEGMREWREQTVRQIRELAPRRVLEIGCGSGLLLSQLAGDCESYWGTDISGAL
IERLRGQVAERPGLADRVVLHQLSAHELGSLPSGGFDTVVLNSVIQYFPSGDYLFDLLREVSRLLVPGGAVFLGDVRNLRL -continued

LISTING OF SEQUENCES:

LRTFHAGGLLAAATHTDTPQTVCAAIDRAMAQEKELLVDPEFFTTAVGALPGMTLESCTLKRGGYDNELSRYRYEVVLRKH
AGPADDTGPTDDAGPVVRLRWDGEMASLADVADRLRRGKPERLCVTGIPNGRVAGEHAATLALFDRRPLHEVLSLGQAPAG
VAPEDLRRLGAELGYRVDCTWSSEDDALIDASFTRAGALVPRPAPRTDAEPDGFSPARFTNRPAFARPDSQTMASLPGQVA
AKLPAFMVPEVFVPLDRLPVTVNGKLDRGALPRPRRAAHASGRPPRTAREEVLAAIFADVLATADVTADSDFFAVGGNSLL
ATRLAAEVRRRLNTEMPLSWLFESPTVGALAARFDAGDEARPLPVPSEYASGSTAPLSAQQMQMWHEYRRSLCRDMFNVPL
SQRLTGAVDAEALRAALADVVTRHVPLRTLVQDDGSGPCAVITEATADDIPWTETRTTPERLSEDLAHAARRHFDLETEIP
LRAVLFTLGPDESVLLLVMHHIAADGWSFGPLLEDLVRAYRARTEGRAPQWEPLSFGYLDYVAWQRRLLGATDDPSDVALR
QAEYWRKTLHGADDRPVLETDSPAPAQQDFAGRSLDLPLEVGGHRVLTAAAREHGVTVFMILHAALVALLARRGAGGDVTV
VTAVAGRTDTQFEPLVGLFANTLALRTDTSGNPTFRELLDRVRVTDLGAYAHQDLLFERLADVPPPQVSLVLRTVAAPPAD
LPGLTISPGPRPASESARYPVLWTVEHLASAADGGTLRSHIQYQSGLLRDDTVVRLAQQYEVVLSLLLKDPDLRVQDLPLQ txtB (scab31781) (SEQ ID NO: 3)
ATGTCCATGCTGCCGCCGGGGCGAAGCCGCACCACGGCCTCGCCCGCCGGGGCCCAGGCCGGCCCCGAGTTCACCCCCGGC
CTATGGGGACGGCTCTTCGAAGCCCGTGTCGACGCCGCCCCCGAATCCACCGCGATCAACTCCGCGAGCGAGCGGCTGAGT
TACGCCGAACTGAACCGGCGGGCCAACCGCCTCGCCAGGTTGCTCATCGCACGTGGCGCCGGCCCGGAGAGCCTGGTCGGT
CTCGCCCTGCCGCGCTCGACCGACTTCGTGGTGGCCGTGGCGGCCGTACTGAAATCGGGCGCCGGCTACTTCCCGATGGAT
CCGGACTATCCTCCGCAGCGGCTGGCGTTCATGCTCGCCGACGCCGCTCCCATGCTGGTGCTGACCAGGAGTGACATCGAG
CCCGAGCTGCCGGCCGAGGCGGCCTCCCGCACGGTGGTGCTGGACGACCCGGCCGTCGTACGGACCCTGGCCGACTGCTCC
GCGGCGGATGTGGCGGACGACGAACGCGGCGCCCCGCTCCGGACCCGGCATCCGGCCTATGTCATCTACACCTCGGGTTCC
ACCGGTACTCCCAAAGGAGTGGTCCTCACCCACCACGGCATCGCCAGCCTGGTGGGCAGCCATGCGCGGGACCTGGGGATC
GGGCCGTCCAGCCGGTTGCTGCTCTTTTCCTCGCCGAGTTTCGACGGCGCCTTCTGGGACGTGTCGATGGCCTTGCTCACT
GGCGCCACGCTGGTGGTCGCACCGCGTGAACGGCTCCTGCCCGGACCGGAGTTCAGTGCGCTCGCCGCCGAGGAGGGCATC
ACCCACTTCACCCTGCCGGCCTCCACGCTCGCCGCCCTGCCGGACGGCGCTCTGCCCGCCGGGGCCACCGTCGTCAATGTG
GGCGAGGCCTGCAACAGCGAGCTGGTGCGCCGCTGGTCGCCGGGCCGGCTGCTGGTGAACGCGTACGGACCGACCGAATCG
ACCGTCTCCGCGACCATGAGCGGACCGTTGGCCGGGGCAGGCATCCCGCCCATCGGCCGTCCGCTCTCGGACACCCGCATC
CACGTCCTCGACGAGCGGCTCCGGCCGGTACCGCCGGGAGCGGTCGGAGAGATCCACATCGCCGGAGCGGGGCTGGCCCGC
GGGTACCTGGGGCGGCCCGCGCTGACCGCCGAGCGGTTCGTGGCCGACCCCTTCGGGACGCCGGGCGAGCGGATGTACCGG
ACCGGCGACCGGGTGAGGGTGCGTGACGACGGGCAACTGGAGTTCGTGGGCCGGGTCGACGACCAGGCGAAGATACGGGGT
TTCCGAGTGGAGCCCGGCGAGGTCGAAGCCGTGCTGCGCGACCATCCCGAGGTCGCGCAGGCCGCGGTGGTGGTCCGGGAG
GACACTCCGGGAGACCAGAGGCTCGTCGCCTATGTCGTGCCGGACCACCCGGCCGTGCGGCAGGCCGACGACACCACCTCG
GAGCACGTCGAGGAATGGCAACGGCTCTACGACGAGGTCTACAGCGCAGTGGGAGCGCTCCCCCTGGGGGAGGACTTCAGC
GGCTGGAACAGCACCTACGACGGCGAGCCCATTCCCGTGCCTCAGATGCAAGCCTGGCGGGACGCCACGGTCGACAGCATC
CGTGCCCTGCGACCGCGCCGGGTACTGGAGATCGGCGTGGGCACCGGGCTGCTGCTGTCCCGCCTCGCCGGTGACTGCGAG
GCGTACTGGGCCACCGACTTCTCCGCCGAGGTGATCGAGACACTCGGCAAGAAGGTGGACGTCGACCCGGTGCTGCGGGAG
AAGGTCCACCTGCTGCACGGTCCCGCACACGACCTCCCCGGCCTCCCCGAGGGGTACTTCGACACCGTTGTCCTCAACTCG
GTGATCCAGTACTTTCCGTCGGCCGACTACCTGGTGAGCGTCCTGCGCGAGGCGGCACGCCTGCTGGCGCCGGGCGGCCGG
GTGTTCGTCGGCGACATCCGGCACCTGCGTCTGCTGCGCCCGCTGCGCAGCGCCGTCCGGCTGCGCTCCGCCACCCGGCGG
GAAGCCTCTGCCTCCGCCGTCCGCGCGGCGGTCGAGCAGGACCTGGTGGATGAGAAGGAGTTGCTCCTCGACCCCGCGTTC
TTCGCCGCGGTACCCCGGTGGATCCCGCAGCTCCGCGGGGTACGCACAGCGGTGCAGCGCGGCACGCACCACAACGAACTG
ACCCGCTACCGGTACGACGCGGTGCTCATCAAGGAGCCGGTGGAAACCGGTACCGCTGCGCCGGACGCGCAGACACTGACC
TGGGGCACGGATGTCAGCGGACTGCAGGAGTTGTCCGGCCTGCTGGCCCGCACCCGCACGTCGCTGCTGCTGCGCGGCGTG
CCGAACAGCCGGATCCTCGGTGAGGCATCGGCCGCGACGGCGCTGACCACGGCCCGGTCGCTCGACGAGCCGTTGCGGTTG
CTGCAAGAACCGGCGGCAGGGATCGACCCCGAGGAACTGCACGCCCTGGGCGGGGGCGCCGGCTGCGAGGTCCACCTCACG
TGGTCGGCGCAGGACCCCACGCGACTGGACGCCTGTTTCACACCCGTGGGCGGTGAACCGGGCGCCGTCCCGCTGGCGGAG
TCCGCCGACAGCGGCAGGACGTCGCCCGGTGACCACGCCAACCAGCCGACCACGCACCGGACCGGCAACGCCCTGATGGGC
AAGCTCCCCGGCTATCTGGCCGCCAGGCTCCCCGCGTACCTGCGGCCCAGCGCCGTGGTACGCATCGCGTCGCTCCCCCTC
ACCGTCAACGGCAAGCTCGACCGCACGGCGCTGCCCCGTCCCGCCCTGTTCCCGCGGGCTGACGGGCAGGCGCCCCGCACT
CCGCGCGAGGAGATCCTCGCCAATCTCTTCGCCGATGTGCTCGGCCTGCCCGGGGTGCCGAGGGACGCCGACTTCTTCGCC
CTGGGCGGCAACTCGCTACTGGCCACGCGCCTCGTCGGCCGTATCGCGAAACACCTCGAAGTCGATGTTCCGATCGCCTGG
ATCTTCGAGACACCGACCGTCGAGGGCCTGGCCGGGCGTACCGCTCCGGCGAGCAGGCTCCGCCCGCTGTTGCTCTGCCGC
GACGAGAACCACGCGGCGGTGCCGCTCTCGCACAGCCAGTACGGCATGTGGTTCATCAACCAACTCGGCGGACCCGCGAGC
CGGATCTACAACGTGCCGTACTGCCTGCGGATCACGGGCCGGGTGGACACCGGGGCGCTGCGGACCGCACTCGATGACGTC
GTGGCTCGTCACGAACCCCTGCGTACCGTCTTCCCCGATGACGGTGACGGCCCCCGCCAACGGGTCCTCGCCCCCGAGGAC
GCCGCGGTGGTCCTTCATGAGACCGACGCCGCCGAAGACCGTCTGGCCGGCCACCTGGCGCGGGCCGCGGCGGAACCCTTC
GAGCTCAGGACGGACCTTCCCCTGCGCGCACGCCTGTTCCGGCACGGACAGGACCGGTACACGCTCCTGCTCCTGATGCAC
CACATCACCGTGGACGCCTGGTCGCTGGCCCCCCTGACGGCGGACCTGGCGCACGCCTACCGGGCGCGGCTGGGGCAGCGG
GCCCCGCAGTGGCAGCCGCTGCCGGTTCACTATCGCGACTACGCCGTATGGCACAACGAGCAAGCAGCCGAGGCGCAGGAC
CGCGGCAGCGGCTTCGGGCGCCAGCTCGCCTTCTGGGAGCGGACGCTGCGCGGTCTTCCGGTCGAGACGCGGCTGCCGGCC
GACCGGAGCCGTCCGGCCAGACCTACCTATCGTGGCGGCACCGTCCACACCCACGTCGAAGCCTCCCTCCATCAGGAACTG
CTCAACTGCGCGCGGGAGACGGGCGCGACGCTCTTCATGGTGCTGCACGCCGCGCTCGCGGCACTGCTGACCCGGCTGGGC
GGCGGCACCGACATCGTCGTCGGCACCGCTGCCGCGGCGCGCACGGACCCCGCGCTGGACGACCTCGTCGGGCTGTTCGCC
AACAGTGTCGTCCTTCGCGTCGACACCTCGGGCGACCCGACGTTCCGCACCCTGCTCGCTCGGACCCGGGCCGTGGACCTC
GACGCCTTCACCCACCAGGAGGTCCCGTTCGACCAGGTGGTGGATCGCGTCAACCCGGCACGCCACCCGGCACGTCACCCG
CTCTACCAGACGGCCCTCGTCCTGCACGCACCGCCCGGCGACGGCCATCGGGCCGACTCCGTCACCCTCACCCCCGAACCG
CCCCCGAACACCGGAACGGCCCGCTTCGATCTGATGTTCAACTGGGACGAGAGCCGGGACAGCGCCGGCCTCGCCCAGGGC
CTCACCGGCCGTACCGAGTACAGCTCGGACCTCTTCTCCCAGGAGACAGTCGAACTGCTCCTGGAGCGGTATCTCCTGCTG
CTGTCCGCCGCGGTCCGCGACCCGGACGCACGCCTTCACACCCTGGACATCCTCACCGAGCCGGAACGGCGGGCCTTCTCA
CCACGGCCGTAG TxtB (scab31781) (SEQ ID NO: 4)
MSMLPPGRSRTTASPAGAQAGPEFTPGLWGRLFEARVDAAPESTAINSASERLSYAELNRRANRLARLLIARGAGPESLVG
LALPRSTDFVVAVAAVLKSGAGYFPMDPDYPPQRLAFMLADAAPMLVLTRSDIEPELPAEAASRTVVLDDPAVVRTLADCS
AADVADDERGAPLRTRHPAYVIYTSGSTGTPKGVVLTHHGIASLVGSHARDLGIGPSSRLLLFSSPSFDGAFWDVSMALLT
GATLVVAPRERLLPGPEFSALAAEEGITHFTLPASTLAALPDGALPAGATVVNVGEACNSELVRRWSPGRLLVNAYGPTES
TVSATMSGPLAGAGIPPIGRPLSDTRIHVLDERLRPVPPGAVGEIHIAGAGLARGYLGRPALTAERFVADPFGTPGERMYR
TGDRVRVRDDGQLEFVGRVDDQAKIRGFRVEPGEVEAVLRDHPEVAQAAVVVREDTPGDQRLVAYVVPDHPAVRQADDTTS
EHVEEWQRLYDEVYSAVGALPLGEDFSGWNSTYDGEPIPVPQMQAWRDATVDSIRALRPRRVLEIGVGTGLLLSRLAGDCE

LISTING OF SEQUENCES:

AYWATDFSAEVIETLGKKVDVDPVLREKVHLLHGPAHDLPGLPEGYFDTVVLNSVIQYFPSADYLVSVLREAARLLAPGGR
VFVGDIRHLRLLRPLRSAVRLRSATRREASASAVRAAVEQDLVDEKELLLDPAFFAAVPRWIPQLRGVRTAVQRGTHHNEL
TRYRYDAVLIKEPVETGTAAPDAQTLTWGTDVSGLQELSGLLARTRTSLLLRGVPNSRILGEASAATALTTARSLDEPLRL
LQEPAAGIDPEELHALGGGAGCEVHLTWSAQDPTRLDACFTPVGGEPGAVPLAESADSGRTSPGDHANQPTTHRTGNALMG
KLPGYLAARLPAYLRPSAVVRIASLPLTVNGKLDRTALPRPALFPRADGQAPRTPREEILANLFADVLGLPGVPRDADFFA
LGGNSLLATRLVGRIAKHLEVDVPIAWIFETPTVEGLAGRTAPASRLRPLLLCRDENHAAVPLSHSQYGMWFINQLGGPAS
RIYNVPYCLRITGRVDTGALRTALDDVVARHEPLRTVFPDDGDGPRQRVLAPEDAAVVLHETDAAEDRLAGHLARAAAEPF
ELRTDLPLRARLFRHGQDRYTLLLLMHHITVDAWSLAPLTADLAHAYRARLGQRAPQWQPLPVHYRDYAVWHNEQAAEAQD
RGSGFGRQLAFWERTLRGLPVETRLPADRSRPARPTYRGGTVHTHVEASLHQELLNCARETGATLFMVLHAALAALLTRLG
GGTDIVVGTAAAARTDPALDDLVGLFANSVVLRVDTSGDPTFRTLLARTRAVDLDAFTHQEVPFDQVVDRVNPARHPARHP
LYQTALVLHAPPGDGHRADSVTLTPEPPPNTGTARFDLMFNWDESRDSAGLAQGLTGRTEYSSDLFSQETVELLLERYLLL
LSAAVRDPDARLHTLDILTEPERRAFSPRP txtC (scab31761) (SEQ ID NO: 5)
ATGGAATCTCCGGCCACCCAGGTCGACCCGGCGAACTCGCCGTTGGAGCCCTATCACATCTACCCGGAGGCCAAGTCCTGC
CCGGTGGCGAAGGTCGGTCTGTGGAACGGCACGCCGGCGCACGTGTTCTCCGGGTATGAGGATGTGCGGACCGTGCTGCAG
GACAGGCGGTTCAGCTCGGACTCGCGCCGACCCAACTTCACCGAACTCACTCCGACGCTCCAGTCGCAGGCCGCGGCACCG
CCGTTCGTACGCACCGACAATCCTGATCACCGGCGCCTGCGAGGCACCATCGCACGCGAGTTCCTGCCCAAGCACATCGAG
CTGCTGCGCCCCGCGATCCGCGAGATCGTCCAGGGTGTGCTCGACGGGCTCGCCGAGACCGCGCCTCCCCAGGACATGCTC
GAGGCCTTCGCCGTACCGGTCGCGTCCGCGACCGTCTTCCGGCTGCTGGGGATTCCGGCCGAGGACCGCGCGTTGCTCACC
CGATGCGTCAAGGGCGTGGTCTCGGCGGTGGGGAGCGAGGACGAAGGTGCCGAGGTGTTCCGGACACTCGGCGAGTACATC
GGCGGGCTCGTCCAGGACCCCTCCGAACTGCCCGAGGACAGCCTGATCCGGCGCCTGGTGACGGGCCCGTACCAGGAGAAG
CAGCTCACCTTCCACGAGACCATCGGCGTGATCCTCATGCTCATCGTCGGGGGCTACGACACGACGGCCAGCACCATCTCG
CTGTCCTTGGTGAGTTATGCACTGCAGCCGGAGAAGTTCTCCGTCGTCCACGAACACCCGGAGCGGATACCCCTGCTCGTC
GAGGAGTTGCTGCGCTATCACACCGTCTCGCAGCTCGGACTGGGCAGGATCGCCACCGAGGACGTCGAGGTGGGCGGCGTC
ACGGTGCGGGCCGGCCAGATGGTGGTGGCGGCGCTCCCCCTGGCCAACCGGGACGAGAGTGTCTTCCCGAACCCGGACGAA
CTCGACTTCGACCGCCCGTCCGTGCCCCATGTCGGCTTCGGTTACGGACCCCACCAGTGCGTCGGCCAGGCACTGGCCCGA
GTCGAACTCCAGGAGGCCATTCCCGCGGTGATCCGACGGCTGCCCGGCATGCGGCTCGCCTGCGCTCTGGAAGACCTGCCG
TTCCGGCACGACATGGCCACCTACGGCATCCATGAGCTGCCCATGACCTGGTGA TxtC (scab31761) (SEQ ID NO: 6)
MESPATQVDPANSPLEPYHIYPEAKSCPVAKVGLWNGTPAHVFSGYEDVRTVLQDRRFSSDSRRPNFTELTPTLQSQAAAP
PFVRTDNPDHRRLRGTIAREFLPKHIELLRPAIREIVQGVLDGLAETAPPQDMLEAFAVPVASATVFRLLGIPAEDRALLT
RCVKGVVSAVGSEDEGAEVFRTLGEYIGGLVQDPSELPEDSLIRRLVTGPYQEKQLTFHETIGVILMLIVGGYDTTASTIS
LSLVSYALQPEKFSVVHEHPERIPLLVEELLRYHTVSQLGLGRIATEDVEVGGVTVRAGQMVVAALPLANRDESVFPNPDE
LDFDRPSVPHVGFGYGPHQCVGQALARVELQEAIPAVIRRLPGMRLACALEDLPFRHDMATYGIHELPMTW txtD (scab31841) (SEQ ID NO: 7)
TTGCCCGCCCCGTCCCCGACAGCGTGCCCGGCACTGGGGCCCGATTCGTCCCTTGGCCCGGTCCCGTCGGCGGAACCGGCG
ACGCCGCAGTCCTGCGGCGTCGCCGATCCAAATGAGGCTGAGGAGTTCCTGCGCCAGTTCCACGCGGAGCAGTCCGATCAG
CCCGTCCCGCTCGCCCGGCGCCTGGAGCAGGTCCGCGCCGCCATCGACGCCACGGGCACCTACCGGCACACCACCGCCGAG
CTCGTGTACGGTGCCCGCGTCGCGTGGCGCAACTCCAGTCGCTGCATCGGCCGCCTGTACTGGAACAGCCTGCGCGTCCTG
GACCGCCGGGACGCCACAGCCCCCGATGAGATCCACCGGCACTTGTGCACGCACCTGCGCCAGGCGACCAACGGCGGGCGC
ATCAGGCCGGTGATTTCGGTCTTCGCCCCGGACTCCCCCGGCCGGCCCGGCCCGCAGGTGTGGAACGAGCAGCTCATCCGG
TACGCCGGCTACCGCCGCGACGACGGCACCGTGCTCGGTGACCCGCGCACCGCCGACCTCACCGAGGCCATCCTCCGCCTC
GGCTGGCAGGGCTGCCCCCAAGGGCCGTTCGACGTCCTGCCCCTGGTCATCGACACCCCCGACGACAAACCCCGGTTCTTC
GAGCTGCCGCGGGAGCTGGTCTTGGAGGTCCCTATCACCCACCCCGACGTCCCACGCCTGGCCGAACTGGGCCTGCGCTGG
CACGCCGTACCCGTCATCTCCAACATGCGCCTACGCATCGGCGGGATGGACTACCCGCTCGCCCCGTTCAACGGCTGGTAC
ATGGGCACGGAGATCGGCGCCCGCAACCTCGTCGACGAGGACCGCTACAACATGCTCCCCGCCGTCGCCGCCTGCCTCCAG
CTGGACACCACCAGCGAGTCAACCCTGTGGCGCGACCGCGCCCTGGTCGAGCTCAACGTCGCCGTCCTGCACTCCTTCGAG
GCCGCAGGTGTCCGGATCAGCGACCACCACGAGGAGTCCCGGCGCTTCCTCGCCCACCTGGCCAAGGAGGAACGCCAGGGC
CGCACCGTATCCGCAGACTGGAGCTGGATCGTCCCCCCGCTCTCCGGCGGCATCACCCCCGTGTTCCACCGTTACTACGAC
AACGTCGACCAGCGCCCCAACTTCTACCCCCACCAGTGA TxtD (scab31841) (SEQ ID NO: 8)
LPAPSPTACPALGPDSSLGPVPSAEPATPQSCGVADPNEAEEFLRQFHAEQSDQPVPLARRLEQVRAAIDATGTYRHTTAE
LVYGARVAWRNSSRCIGRLYWNSLRVLDRRDATAPDEIHRHLCTHLRQATNGGRIRPVISVFAPDSPGRPGPQVWNEQLIR
YAGYRRDDGTVLGDPRTADLTEAILRLGWQGCPQGPFDVLPLVIDTPDDKPRFFELPRELVLEVPITHPDVPRLAELGLRW
HAVPVISNMRLRIGGMDYPLAPFNGWYMGTEIGARNLVDEDRYNMLPAVAACLQLDTTSESTLWRDRALVELNVAVLHSFE
AAGVRISDHHEESRRFLAHLAKEERQGRTVSADWSWIVPPLSGGITPVFHRYYDNVDQRPNFYPHQ txtE (scab31831) (SEQ ID NO: 9)
GTGACCGTCCCCTCGCCGCTCGCCGACCCGTCCATCGTGCCCGACCCCTACCCTGTCTACGCCGACCTGGCCCAGCGCCGC
CCCGTCCACTGGGTCGAGCGCCTGAACGCCTGGGCGGTCTTGACGTACGCCGACTGCGCCGCCGGGCTGAAGGATCCCCGG
CTCACCGCCGACCGGGGGACGGAAGTGCTGGCCGCGAAGTTCCCCGGACAGCCGCTGCCGCCGGACAACATCTTCCACCGC
TGGACCAAGAACGTGGTGATGTACACGGACCCGCCGCTCCACGACGCGCTACGCCGGTCCGTCCGCGCAGGCTTCACCCGT
GCCGCGCACCAGCACTACGACCAAGTCCTCCAGAAGGTCGCGCACGACCTGGTCGCTTCCATCCCGGCCGGTGCCACCGAG
ATCGACGCCGTCCCCGCCCTGGCTGCCGAACTCCCCGTACGCTCCGCCGTGCACGCCTTCGGGGTCCCCGAGGAGGACCTC
GGATTCCTCATCCCGCGCGTGAATACGATCATGACGTACCACTCCGGTCCGAAGGATCAGCCGGTGACGCAGGAGATAATC
CTGGAAAAGCTCACCGACCTGCACACGTACGCCTCCGAACTCCTCCAGGGCATGCGGGGCAAGGTCCTGCCGGACACCGTC
ATCGCCCGCCTGGCAGCCGCCCAGGACGGCCTGACCGAGACCACGCCGGAACAGACCGTGCACCAGCTGGCGCTGGTGTTC
ATCGCGTTGTTCGCGCCCACGACGCCGGGCTCTCTCAGCAGCGGCACGCTCGCGTTCGCCCGCAACCCGCGGCAGGTCGAA
CGCTTCCTGGCGGACCAGGCGTGCGTGGACAACACGGCGAACGAGGTCCTCCGCTACAACGCCTCGAACCAGTTCACCTGG
CGCGTCGCGGCCAAGGACGTCGAGATGGGCGGCGTACGGATCGAGGCCGGGCAGACTCTCGCCCTGTTCCTGGGCTCGGCC
AACCGGGACGCCAACATGTTCGAGCGACCGAACGACTTCGACCTCGACCGTCCCAACAGCGCTCGGCACCTGTCGTTCGGC

LISTING OF SEQUENCES:

CAAGGGGTGCACGCCTGTCTCGCCGCGCAGCTCATCTCCCTGCAGCTGAAGTGGTTCTACGTCGCCCTGCTGAACCGCTTC
CCGGGCATCCGGACGGCGGGCGAGCCGATCTGGAACGAGAACCTCGAATTCCGCTCCCTTCGCTCCCTGCCGCTCAGCCTC
CGCTGA

TxtE (scab31831) (SEQ ID NO: 10)
VTVPSPLADPSIVPDPYPVYADLAQRRPVHWVERLNAWAVLTYADCAAGLKDPRLTADRGTEVLAAKFPGQPLPPDNIFHR
WTKNVVMYTDPPLHDALRRSVRAGFTRAAHQHYDQVLQKVAHDLVASIPAGATEIDAVPALAAELPVRSAVHAFGVPEEDL
GFLIPRVNTIMTYHSGPKDQPVTQEIILEKLTDLHTYASELLQGMRGKVLPDTVIARLAAAQDGLTETTPEQTVHQLALVF
IALFAPTTPGSLSSGTLAFARNPRQVERFLADQACVDNTANEVLRYNASNQFTWRVAAKDVEMGGVRIEAGQTLALFLGSA
NRDANMFERPNDFDLDRPNSARHLSFGQGVHACLAAQLISLQLKWFYVALLNRFPGIRTAGEPIWNENLEFRSLRSLPLSL
R txtH (scab31771) (SEQ ID NO: 11)
GTGCCCTCACCCTTCGACGACCATGACGGGCAGTTCCATGTGCTCCGCAACGAGGAAGGCCAGTTCTCACTCTGGCCGAAT
TTCGCCGACATCCCCTCCGGGTGGCGTTCCGTGAGCGGGCCGAGCCCCCGCGGAAGCGCCCTTGAGTACATCGAGAAGGAA
TGGACGGACATGCGCCCGGCGTCCGTCCGTGAATGA TxtH (scab31771) (SEQ ID NO: 12)
VPSPFDDHDGQFHVLRNEEGQFSLWPNFADIPSGWRSVSGPSPRGSALEYIEKEWTDMRPASVRE txtR (scab31801) (SEQ ID NO: 13)
ATGCAGATAAAATCTTTCAAGGCCGGCGGGGTCAAGGTGACGATCATAGATTCCGGTCCAGCCGTCATCGAGTTCGAGGCA
ATCAACTCGGAGGCGGCCTTGACGCCGCAGAGAACAGTCATATGCGTACTGTCAGGAATGGCGTTCATCGCTGGTACCGGA
AACGGTACGGAGATCGACGCGGGGACGCTGGTTATGACGGACGGCGACGTTCCCTTTTCGATGAATGTGCCCGTTGCTTCG
CGACTCCTCGTACTGCGTTTCGCCGACGAAGCGAAGGATGGACTCCCGGTGTGCGCCTCGGGGGACTTTTATCGTGACGGAT
GCTGCCAAGGGTCCCGGATCCGGATTTCTTTTTTCGTTCTTGAATACCCTGGCTGTGGAGATGATGAAAACCGATGGGATT
CTGTCCTCGTATATGGAGGAGGTCGTGCGCATCCTGGCGATCTCCGCGACGCGAATCGCATATGCCGAGCTCGGAAAGCAT
TACTCTGGGGGATGCGATCCACTTCTGATCGCGGTTCAGGAGTCGATCGACCGGCAGTTGGCCGACCCCGAGATCAGCCCG
GCGACCCTCGCGGCCGAACACAACATATCGGTGCGTCAGTTACATCGAGTTTTCGGACCGATCGGGGAAAGCGTCATGAGC
TATGTCAAACGCCGTCGCCTGGAGCGTTTCGCATGCGATCTGAGGGATCCGAGCCTGGGGCACCGGAAGATCAATGAGCTG
GCGGCGGACTGGGGGATGCTGGATGCCGCGATGCTGAGCAGACACTTCCGCTGCGCCTACGGAATGTCGCCCCGCGATTAC
CGGAAGCAGCACTGTTTCACCTGA TxtR (scab31801) (SEQ ID NO: 14)
MQIKSFKAGGVKVTIIDSGPAVIEFEAINSEAALTPQRTVICLVLSGMAFIAGTGNGTEIDAGTLVMTDGDVPFSMNVPVA
SRLLVLRFADEAKDGLPVSPRGTFIVTDAAKGPGSGFLFSFLNTLAVEMMKTDGILSSYMEEVVRILAISATRIAYAELGK
HYSGGCDPLLIAVQESIDRQLADPEISPATLAAEHNISVRQLHRVFGPIGESVMSYVKRRRLERFACDLRDPSLGHRKINE
LAADWGMLDAAMLSRHFRCAYGMSPRDYRKQHCFT cebR (scab57761) (SEQ ID NO: 15)
ATGGTGACAGGCCACGGGGCACGGGGCCGGAGCGGTGGGCGGCCGACGTTGGAGGAGGTCGCCGCACGGGCCGGAGTGGGC
CGGGGGACGGTGTCCCGGGTGATCAACGGCTCGCCCCCGGGTGAGCGACGCGACCCGCGCGGCGGTCGAGGCGGCCGTCGC
GGAGCTGGGTTACGTCCCGAACACGGCGGCCCGCGCGCTCGCGGCGAACCGTACCGACGCGATCGCGATGGTCGTGCCCGA
ACCGGAGACCCGCTTCTTCTCGGAGCCGTACTTCTCCGACATCCTCAAGGGTGTCGGAGCGCAACTGTCCGACACCGAGAT
GCAGCTCCTGCTGATCTTCGCGGGCAACGACCGGGAGCGCCGGCGCCTCGCCCAGTACCTGGCCGCGCACCTGGCCGACGG
TGTCCTCCTGGTCTCCGTCCACGCGGACGACCCGCTCCCCGATCTGCTGTCGCAACTGGAAATCCCGGCCGTCATCAGCGG
CCCCCGCTCCGAGCACGAGACGCTCCCCTCGGTCGACTCCGACAACTACGGCGGCGGCCGCTCGGCGGTCGAGCACCTCAT
CGCACGGGGCGCGCCCGGATCGCCACGATCACCGGCCGGCTGGACGTCTACGGCGCCCAGCGGCGCATCGAGGGCTACCG
CGACGCCCTGGAGGACGCGGGCCGCGAGGTGGACGAGCGCCTGATCGCCCCGGTGACTTCACGGAGGAGGCGGCGCCCG
AGCGATGCGCGAACTCCTGGCCCGCTGCCCCGACCTCGACGCGGTCTTCGCCGAGTCGGACGTCATGGCCGCGGCGCCCG
CCAGGTGCTCCGCGAGGAGGGCCGCCGCATACCCGACGACGTGGCGCTGGTCGGCTACGACGACTCGGCGATCGCCCGCCA
CATGGACCCGCCGCTCACCAGCGTCCGCCAGCCGATAGAGGAGATGGGCCGCGCGATGATCGACCTCCTCCTGGACGAGAT
CGCCGGACCGCCGCCCGGCGGTGTCGAGGGGCTTGAACGACGCCAGGTGGTGCTGCCGACGGAGCTGGTGGGGCGGGATTC
TTCCTGA CebR (SCAB57761) (SEQ ID NO: 16)
MVTGHGARGRSGGRPTLEEVAARAGVGRGTVSRVINGSPRVSDATRAAVEAAVAELGYVPNTAARALAANRTDAIAMVVPE
PETRFFSEPYFSDILKGVGAQLSDTEMQLLLIFAGNDRERRLAQYLAAHRVDGVLLVSVHADDPLPDLLSQLEIPAVISG
PRSEHETLPSVDSDNYGGGRSAVEHLIARGRARIATITGRLDVYGAQRRIEGYRDALEDAGREVDERLIAPGDFTEEGGRR
AMRELLARCPDLDAVFAESDVMAAGARQVLREEGRRIPDDVALVGYDDSAIARHMDPPLTSVRQPIEEMGRAMIDLLLDEI
ADRRPAVSRGLERRQVVLPTELVGRDSS bgIC (scab57721) (SEQ ID NO: 17)
ATGCCTGAACCCGTGAATCCGGCCACCCCGGTGACCTTTCCTCCCGCCTTCCTCTGGGGCGCGGCCACCTCCGCGTACCAG
ATCGAGGGGCGGTGCGGGAGGACGGCCGTACGCCCTCCATCTGGGACACCTTCAGTCACACGCCGGGCAAGACCGCCGGC
GGCGAGAACGGTGACATCGCTGTCGACCACTACCACCGCTACGCGCAGACGGCGATGGCGGACCTGGGCCTCAAC
GCGTACCGCTTCTCCGTCTCCTGGTCGCGGGTGCAGCCGACGGGGCGGGGCCCGGCCGTCCAGAAGGGGCTCGACTTCTAC
CGACGGCTGGTCGACGAGCTGCTGGCCAAGGGCATCAAGCCCGCCGTCACCCTCTACCACTGGGACCTCCCGCAGGAGCTG
GAGGACGCCGGCGGCTGGCCCGAGCGGGACATCGTGCACCGGTTCGCCGAGTACGCGCGGATCATGGGCGAGGCGCTCGGC
GACCGCGTCGAGCAGTGGATCACCCTCAACGAGCCGTGGTGCACCGCGTTCCTGGGCTACGGCTCCGGGGTGCACGCGCCG
GGCCGTACGGACCCGGTGGCGTCCCTGCGCGCGGCCCACCATCTGAACGTTGACCGGCAGTTCGGCGTCTCGGCGCTGCGG
TCGGCGATGCCCGCCGCAACTCGATCGCGGTGAGCCTCAACTCCTCGGTGGTGCGGCCGATCACCAGCTCCCCGGAGGAC
CGGGCCGCGGCCCGGAAGATCGACGACCTCGCGAACGGCGTCTTCCACGGACCGATGCTGCACGGGGCCTACCCGGAGACC
CTGTTCGCCGCGACCCTCGTCGCTGACGGACTGGTCGTTCGTGCGGGACGGTGACGTGGCGACGGCCCATCAGCCGCTGGAC
GCTCGGGGCTGAACTACTACACGCCGGCGCTGGTCGGCGCGGCGGACGCCGGCCTGAGGGCCCCCGCGCGGACGGCCAC
GGGCGAGCGAGCACTCGCCGTGGCCGGCCGCGGACGACGTCCTGTTCCACCAGACCCCGGGCGAGCGTACGGAGATGGGC
TGGACCATCGACCCGACGGGCCTGCACGAGCTGATCATGCGGTACGCGCGGGAGGCTCCGGGCCTGCCGATGTACGTGACG

LISTING OF SEQUENCES:

```
GAGAACGGCGCCGCGTACGACGACAAGATGGACGCGGACGGCCGTGTCCACGACCCCGAGCGCATCGCCTACCTGCACGGC
CACCTGCGGCGGTCCGGCGCGCGATCGCCGAGGGGGCGGACGTGCGCGGGTACTACCTGTGGTCCCTGATGGACAACTTC
GAGTGGGCGTACGGCTACGGCAAGCGCTTCGGCGCGGTGTACGTCGACTACGCGACCCTGACCCGCACACCGAAGTCGAGC
GCGCACTGGTACGGGCAGGCGGCGAAGACGGGCGCCCTCCCGCCGCTGGCGCCGGCGCCGGCGTAG
```

BgIC (SCAB57721) (SEQ ID NO: 18)

```
MPEPVNPATPVTFPPAFLWGAATSAYQIEGAVREDGRTPSIWDTFSHTPGKTAGGENGDIAVDHYHRYRDDVAMMADLGLN
AYRFSVSWSRVQPTGRGPAVQKGLDFYRRLVDELLAKGIKPAVTLYHWDLPQELEDAGGWPERDIVHRFAEYARIMGEALG
DRVEQWITLNEPWCTAFLGYGSGVHAPGRTDPVASLRAAHHLNVAHGLGVSALRSAMPARNSIAVSLNSSVVRPITSSPED
RAAARKIDDLANGVFHGPMLHGAYPETLFAATSSLTDWSFVRDGDVATAHQPLDALGLNYYTPALVGAADAGLEGPRADGH
GASEHSPWPAADDVLFHQTPGERTEMGWTIDPTGLHELIMRYAREAPGLPMYVTENGAAYDDKMDADGRVHDPERIAYLHG
HLRAVRRAIAEGADVRGYYLWSLMDNFEWAYGYGKRFGAVYVDYATLTRTPKSSAHWYGQAAKTGALPPLAPAPA
```

Apramycin resistance gene deletion cassette (SEQ ID NO: 19)

```
ATTCCGGGGATCCGTCGACCTGCAGTTCGAAGTTCCTATTCTCTAGAAAGTATAGGAACTTCGAAGTTCCCGCCAGCCTCG
CAGAGCAGGATTCCCGTTGAGCACCGCCAGGTGCGAATAAGGGACAGTGAAGAAGGAACACCCGCTCGCGGGTGGGCCTAC
TTCACCTATCCTGCCCGGCTGACGCCGTTGGATACACCAAGGAAAGTCTACACGAACCCTTTGGCAAAATCCTGTATATCG
TGCGAAAAAGGATGGATATACCGAAAAAATCGCTATAATGACCCCGAAGCAGGGTTATGCAGCGGAAAATGCAGCTCACGG
TAACTGATGCCGTATTTGCAGTACCAGCGTACGGCCCACAGAATGATGTCACGCTGAAAATGCCGGCCTTTGAATGGGTTC
ATGTGCAGCTCCATCAGCAAAAGGGGATGATAAGTTTATCACCACCGACTATTTGCAACAGTGCCGTTGATCGTGCTATGA
TCGACTGATGTCATCAGCGGTGGAGTGCAATGTCGTGCAATACGAATGGCGAAAAGCCGAGCTCATCGGTCAGCTTCTCAA
CCTTGGGGTTACCCCCGGCGGTGTGCTGCTGGTCCACAGCTCCTTCCGTAGCGTCCGGCCCCTCGAAGATGGGCCACTTGG
ACTGATCGAGGCCCTGCGTGCTGCGCTGGGTCCGGGAGGGACGCTCGTCATGCCCTCGTGGTCAGGTCTGGACGACGAGCC
GTTCGATCCTGCCACGTCGCCCGTTACACCGGACCTTGGAGTTGTCTCTGACACATTCTGGCGCCTGCCAAATGTAAAGCG
CAGCGCCCATCCATTTGCCTTTGCGGCAGCGGGGCCACAGGCAGAGCAGATCATCTCTGATCCATTGCCCCTGCCACCTCA
CTCGCCTGCAAGCCCGGTCGCCCGTGTCCATGAACTCGATGGGCAGGTACTTCTCCTCGGCGTGGGACACGATGCCAACAC
GACGCTGCATCTTGCCGAGTTGATGGCAAAGGTTCCCTATGGGGTGCCGAGACACTGCACCATTCTTCAGGATGGCAAGTT
GGTACGCGTCGATTATCTCGAGAATGACCACTGCTGTGAGCGCTTTGCCTTGGCGGACAGGTGGCTCAAGGAGAAGAGCCT
TCAGAAGGAAGGTCCAGTCGGTCATGCCTTTGCTCGGTTGATCCGCTCCCGCGACATTGTGGCGACAGCCCTGGGTCAACT
GGGCCGAGATCCGTTGATCTTCCTGCATCCGCCAGAGGCGGGATGCGAAGAATGCGATGCCGCTCGCCAGTCGATTGGCTG
AGCTCATAAGTTCCTATTCCGAAGTTCCTATTCTCTAGAAAGTATAGGAACTTCGAAGCAGCTCCAGCCTACA
```

Attachment site (att) sequence for *S. scabiei*, *S. europaeiscabiei*, and *S. stelliscabiei*, and *S.* sp. 96-12 (SEQ ID NO: 62)
TTGAAGCGGAAC Attachment site (att) sequence for *S. acidiscabies* (SEQ ID NO: 63)
TTGAACCGGAAC Third attachment site (att) sequence for *S.* sp. 96-12 (SEQ ID NO: 64)
TTGAACCTGAAC

TABLE 7

List of primers used in Example 1

| Primer | Sequence 5'-3' (SEQ ID NO (SEQ): 20-35) | Use |
|---|---|---|
| a | TCCACCTCCTGACCACCAAG (SEQ: 20) | Detect the site-specific |
| b | AAGATCCCCGAACCGACCT (SEQ: 21) | integration of TR in aviX1 |
| c | GTAGCGAAGGCGAGAGTCTCACTG (SEQ: 22) | PCR amplification of the |
| d | GAGCCGACGAACAAGTACTACCCG (SEQ: 23) | integrase gene (SCAB_31871) located in the TR2 region |
| e | CGAAGATCGAGAACGTCAGGAAGG (SEQ: 24) | Detect the site-integration of |
| f | GACCGACGAGGACTTCAAGAACGA (SEQ: 25) | TR2 or the whole TR in aviX1 |
| g | TACGAGACCATCGGCAGGGA (SEQ: 26) | PCR amplification of txtH |
| h | ACATCCTCACCGAGCCGGAA (SEQ: 27) | (SCAB_31771) located in the TR1 region |
| DRB201 | TGCCGGGCCCTCTTTGCCGACTAGGAGAAATTCACCGTG TGTAGGCTGGAGCTGCTT (SEQ: 28) | txtH (SCAB_31771) redirect deletion cassette |
| DRB202 | GGCGACCCGTGGCCCCGCTCGATGTTATTGGCCGGGTCA ATTCCGGGGATCCGTCGACC (SEQ: 29) | |
| DRB431 | ATGAAGAACTTCGAAGCCGCGACCACTCAGGTCGATGTG TGTAGGCTGGAGCTGCTTC (SEQ: 30) | lanA (SCAB_32021) and lanB (SCAB_32031) redirect |
| DRB432 | TCACGGCGTCCTCCAGTGTTCGCGGGCGCTCTGGCGCAG ATTCCGGGGATCCGTCGACC (SEQ: 31) | deletion cassette |

TABLE 7-continued

List of primers used in Example 1

| Primer | Sequence 5'-3' (SEQ ID NO (SEQ): 20-35) | Use |
|---|---|---|
| US-F | GCGCGCTAGCGATTCACGGCAAACTGC (SEQ: 32) | PCR amplification of 1 Kb upstream of thaxtomin biosynthetic gene cluster |
| US-R | GCACCTGATTTCGCGATCCGTTAACAGGTCGTCGAAACCCAGATCG (SEQ: 33) | |
| DS-F | CGATCTGGGTTTCGACGACCTGTTAACGGATCGCGAAATCAGGTGC (SEQ: 34) | PCR amplification of 1 Kb downstream of thaxtomin biosynthetic gene cluster |
| DS-R | GCGCGCATGCCTCAAAGGCCAGGTTGTAGG (SEQ: 35) | |

US-F/R: upstream forward/reverse primer; DS-F/R: downstream forward/reverse primer

TABLE 8

List of primers used in Example 2

| Primers | Sequence (5' → 3') (SEQ ID NO (SEQ): 32-61) |
|---|---|
| Plasmid construction (pTARa-thx) (SEQ ID Nos: 32-35 as in Table 7 above) | |
| Upstream-F | GCGCGCTAGCGATTCACGGCAAACTGC (SEQ: 32) |
| Upstream-R | GCACCTGATTTCGCGATCCGTTAACAGGTCGTCGAAACCCAGATCG (SEQ: 33) |
| Downstream-F | CGATCTGGGTTTCGACGACCTGTTAACGGATCGCGAAATCAGGTGC (SEQ: 34) |
| Downstream-R | GCGCGCATGCCTCAAAGGCCAGGTTGTAGG (SEQ: 35) |
| Plasmid construction (pLST9828-thx) | |
| 9828-Vector-F | TCTAGAGTCGACCTGCAGCCCA (SEQ: 36) |
| 9828-Vector-R | GTAATCATGTCATAGCTGTTTC (SEQ: 37) |
| Thx-fragment-1-F | GAAACAGCTATGACATGATTACACGTATCGGCGACCTGCTCCTG (SEQ: 38) |
| Thx-fragment-1-R | TTCACCAACAGGCCGGCGTTCG (SEQ: 39) |
| Thx-fragment-2-F | AAGAGAGGCCATCGTCTGGGA (SEQ: 40) |
| Thx-fragment-2-R | TGGGCTGCAGGTCGACTCTAGAGACGAGTACCTGGCGGACTA (SEQ: 41) |
| Plasmid construction (pLST9828-thx-ΔC) | |
| 9828ΔC-Vector-F | CATGTTCGAGCGACCGAACGAC (SEQ: 42) |
| 9828ΔC-Vector-R | GTAATCATGTCATAGCTGTTTC (SEQ: 43) |
| ThxΔC-fragment-1-F | GAAACAGCTATGACATGATTACGGTGTCGTTTCCTTTCCAAGAC (SEQ: 44) |
| ThxΔC-fragment-1-R | GTGATCCAGTACTTTCCCTCAG (SEQ: 45) |
| ThxΔC-fragment-2-F | CAGTAGGTCGAACAGGTAATCG (SEQ: 46) |
| ThxΔC-fragment-2-R | GTCGAGGTCGAAGTCGTTCGGTC (SEQ: 47) |
| Plasmid construction (pLST9828-thx-ΔABHC) | |
| 9828ΔABCH-Vector-F | TCTAGAGTCGACCTGCAGCCCA (SEQ: 48) |
| 9828ΔABCH-Vector-R | GTAATCATGTCATAGCTGTTTC (SEQ: 49) |
| ThxΔABCH-F | GAAACAGCTATGACATGATTACAGGTATCCGTTCCTCTCTGTC (SEQ: 50) |
| ThxΔABCH-R | TGGGCTGCAGGTCGACTCTAGAGACGAGTACCTGGCGGACTAC (SEQ: 51) |
| Colony PCR screening | |
| TxtA-F | CTTCTCGTCCCCGAGTTTCGAC (SEQ: 52) |
| TxtA-R | GATCGCTCATGGTGGCGCAGAC (SEQ: 53) |
| TxtB-F | GTCATCTACACCTCGGGTTC (SEQ: 54) |
| TxtB-R | CCAACGGTCCGCTCATGGTC (SEQ: 55) |
| TxtC-F | TGTTCTCCGGGTATGAGGATG (SEQ: 56) |
| TxtC-R | GTTCGGGAAGACACTCTCGTC (SEQ: 57) |
| TxtD-F | GCAACTCCAGTCGCTGCATC (SEQ: 58) |
| TxtD-R | CGAAGAACCGGGGTTTGTCGT (SEQ: 59) |
| TxtE-F | CAAGAACGTGGTGATGTACAC (SEQ: 60) |
| TxtE-R | GAGCTTTTCCAGGATTATCTC (SEQ: 61) |

REFERENCES

Barry S M, Kers J A, Johnson E G, Song L, Aston P R, Patel B, Krasnoff S B, Crane B R, Gibson D M, Loria R, Challis G L. 2012. Cytochrome P450-catalyzed 1-tryptophan nitration in thaxtomin phytotoxin biosynthesis. Nat Chem Biol 8:814-816.

Bentley, S. D., et al. 2002. Complete genome sequence of the model actinomycete *Streptomyces coelicolor* A3(2). Nature. 417:141-147.

Bibb M J. 2005. Regulation of secondary metabolism in streptomycetes. Curr Opin Microbiol. 8:208-215.

Bibb M, Hesketh A. 2009. Analyzing the regulation of antibiotic production in streptomycetes. Methods Enzymol 458:93-116.

Bierman, M., Logan, R., O'Brien, K., Seno, E. T., Rao, R. N., and Schoner, B. E. 1992. Plasmid cloning vectors for the conjugal transfer of DNA from *Escherichia coli* to *Streptomyces* spp. Gene. 116:43-49.

Bignell, D. R. D., Francis, I. M., Fyans, J. K., and Loria, R. 2014a. Thaxtomin A Production and Virulence Are Controlled by Several bld Gene Global Regulators in *Streptomyces scabies*. Mol Plant Microbe Interact. 27:875-885.

Bignell, D. R. D., Fyans, J. K., and Cheng, Z. 2014b. Phytotoxins produced by plant pathogenic *Streptomyces* species. J. Appl. Microbiol. 116:223-235.

Bischoff, V., Cookson, S. J., Wu, S., and Scheible, W.-R. 2009. Thaxtomin A affects CESA-complex density, expression of cell wall genes, cell wall composition, and causes ectopic lignification in *Arabidopsis thaliana* seedlings. J. Exp. Bot. 60:955-965.

Bourgault J P, Maddirala A R, Andreana P R. 2014. A one-pot multicomponent coupling/cyclization for natural product herbicide (±)-thaxtomin A. Org Biomol Chem 12:8125-8127.

Burrus, V., Pavlovic, G., Decaris, B., and Guedon, G. 2002. Conjugative transposons: the tip of the iceberg. Mol. Microbiol. 46:601-610.

Butler A R, Bate N, Cundliffe E. 1999. Impact of thioesterase activity on tylosin biosynthesis in *Streptomyces fradiae*. Chem Biol 6:287-292.

Cantrell C L, Dayan F E, Duke S O. 2012. Natural products as sources for new pesticides. J Nat Prod 75:1231-1242.

Chapleau, M., Guertin, J. F., Lerat, S., Burrus, V., and Beaulieu, C. 2016. Identification of genetic and environmental factors stimulating excision from *Streptomyces scabiei* chromosome of the toxicogenic region responsible for pathogenicity. Mol. Plant Pathol. 17:501-509.

Chater K F, Wilde L C. 1976. Restriction of a bacteriophage of *Streptomyces albus* G involving endonuclease SalI. J Bacteriol 128:644-650.

Chen Y, Wendt-Pienkowski E, Shen B. 2008. Identification and utility of FdmR1 as a *Streptomyces* antibiotic regulatory protein activator for fredericamycin production in *Streptomyces griseus* ATCC 49344 and heterologous hosts. J Bacteriol 190:5587-5596.

Copping L G, Duke S O. 2007. Natural products that have been used commercially as crop protection agents. Pest Manage Sci 63:524-554.

Dayan F E, Owens D K, Duke S O. 2012. Rationale for a natural products approach to herbicide discovery. Pest Manage Sci 68, 519-528.

Dimitris Kallifidas, S. F. B. 2012. Reassembly of functionally intact environmental DNA-derived biosynthetic gene clusters. Methods in enzymology. 517:225-239.

Duke S O, Cantrell C L, Meepagala K M, Wedge D E, Tabanca N, Schrader K K. 2010. Natural toxins for use in pest management. Toxins 2:1943-1962.

Goyer C, Charest P M, Toussaint V, Beaulieu C. 2000. Ultrastructural effects of thaxtomin A produced by *Streptomyces scabiei* on mature potato tuber tissues. Can J Bot 78:374-380.

Feng Z, Wang L, Rajski S R, Xu Z, Coeffet-LeGal M F, Shen B. 2009. Engineered production of iso-migrastatin in heterologous *Streptomyces* hosts. Bioorg Med Chem 17:2147-2153.

Francis, I. M., Jourdan, S., Fanara, S., Loria, R., and Rigali, S. 2015. The cellobiose sensor CebR is the gatekeeper of *Streptomyces* scabies pathogenicity. MBio. 6:e02018.

Fry, B. A., and Loria, R. 2002. Thaxtomin A: evidence for a plant cell wall target. Physiol Mol Plant Path. 60:1-8.

Gibson D G, Young L, Chuang Y, Venter J C, Hutchison III C A, Smith H O. 2009. Enzymatic assembly of DNA molecules up to several hundred kilobases. Nat Methods 6:343-345.

Goyer C, Charest P M, Toussaint V, Beaulieu C. 2000. Ultrastructural effects of thaxtomin A produced by *Streptomyces scabiei* on mature potato tuber tissues. Can J Bot 78:374-380.

Gullón S, Olano C, Abdelfattah M S, Braña A F, Rohr J, Méndez C, Salas J A. 2006. Isolation, characterization, and heterologous expression of the biosynthesis gene cluster for the antitumor anthracycline steffimycin. Appl Environ Microbiol 72:4172-4183.

Gust, B., Challis, G. L., Fowler, K., Kieser, T., and Chater, K. F. 2003. PCR-targeted *Streptomyces* gene replacement identifies a protein domain needed for biosynthesis of the sesquiterpene soil odor geosmin. Proc. Natl. Acad. Sci. U.S.A. 100:1541-1546.

Healy F, Krasnoff S B, Wach M, Gibson D M, Loria R. 2002. Involvement of a cytochrome P450 monooxygenase in thaxtomin A biosynthesis by *Streptomyces acidiscabiei*. J Bacteriol 184:2019-2029.

Herbst, D. A., Boll, B., Zocher, G., Stehle, T., and Heide, L. 2013. Structural basis of the interaction of MbtH-like proteins, putative regulators of nonribosomal peptide biosynthesis, with adenylating enzymes. J. Biol. Chem. 288: 1991-2003.

Hüter O F. 2011. Use of natural products in the crop protection industry. Phytochem Rev 10:185-194.

Johnson, E. G., Joshi, M. V., Gibson, D. M., and Loria, R. 2007. Cello-oligosaccharides released from host plants induce pathogenicity in scab-causing *Streptomyces* species. Physiol Mol Plant Path. 71:18-25.

Joshi, M. V., Bignell, D. R. D., Johnson, E. G., Sparks, J. P., Gibson, D. M., and Loria, R. 2007. The AraC/XylS regulator TxtR modulates thaxtomin biosynthesis and virulence in *Streptomyces scabiei*. Mol. Microbiol. 66:633-642.

Ju K S, Parales R E. 2010. Nitroaromatic compounds, from synthesis to biodegradation. Microbiol Mol Biol Rev 74:250-272.

Kallifidas D, Brady S F. 2012. Reassembly of functionally intact environmental DNA-derived biosynthetic gene clusters. Methods Enzymol 517:225-239.

Kang, Y., Semones, S., Leder, J., and Tran, A. 2008. Methods of controlling algae with thaxtomin and thaxtomin compositions. U.S. Patent Appl. Publ. WO2008124675.

Kers J A, Wach M J, Krasnoff S B, Widom J, Cameron K D, Bukhalid R A, Gibson D M, Crane B R, and Loria R. 2004. Nitration of a peptide phytotoxin by bacterial nitric oxide synthase. Nature 429:79-82.

Kieser, T., Bibb, M. J., Buttner, M. J., Chater, K. F., and Hopwood, D. A. 2000. Practical *Streptomyces* Genetics. Norwich, United Kindom.

Kim S Y, Zhao P, Igarashi M, Sawa R, Tomita T, Nishiyama M, Kuzuyama T. 2009. Cloning and heterologous expression of the cyclooctatin biosynthetic gene cluster afford a diterpene cyclase and two P450 hydroxylases. Chem Biol 16:736-743.

Kim J H, Feng Z, Bauer J D, Kallifidas D, Calle P Y, Brady S F. 2010. Cloning large natural product gene clusters from the environment: piecing environmental DNA gene clusters back together with TAR. Biopolymers 93:833-844.

King R R, Lawrence C H. 1995. 4-Nitrotryptophans associated with the in vitro production of thaxtomin A by *Streptomyces scabiei*. Phytochemistry 40:41-43.

King, R R, Lawrence C H, Calhoun L A. 1992. Chemistry of phytotoxins associated with *Streptomyces scabiei*, the causal organism of potato common scab. J Agric Food Chem 40:834-837.

King, R. R., and Calhoun, L. A. 2009. The thaxtomin phytotoxins: Sources, synthesis, biosynthesis, biotransformation and biological activity. Phytochemistry. 70:833-841.

King R R, Calhoun L A. 2009. Synthesis and NMR characteristics of N-acetyl-4-nitro, N-acetyl-5-nitro, N-acetyl-6-nitro and N-acetyl-7-nitrotryptophan methyl esters. Magn Reson Chem 47:273-276.

King R R, Lawrence C H, Clark M C, Calhoun L A. 1989. Isolation and characterization of phytotoxins associated with *Streptomyces scabiei*. J Chem Soc Chem Commun 0:849-850.

King R R, and Lawrence C H. 1994. Isolation and characterization of thaxtomin-type phytotoxins associated with *Streptomyces iponweae*. J Agric Food Chem 42:1791-1794.

King R R. 1997. Synthesis of thaxtomin C. Can J Chem 75:1172-1173.

King R R., and Lawrence C H. 1996. Characterization of new thaxtomin A analogues generated in vitro by *Streptomyces scabiei*. J Agric Food Chem 44:1108-1110.

King, R. R., Lawrence, C. H., and Gray, J. A. 2001. Herbicidal properties of the thaxtomin group of phytotoxins. J. Agric. Food Chem. 49:2298-2301.

Koivunen, M., Marrone, P., and Boddy, L. 2013. Uses of thaxtomin and thaxtomin compositions as herbicides. U.S. Patent Appl. Publ. US20130217573.

(a) Koivunen M, Marrone P. US 20100167930, 2010. (b) Leep D C, Doricchi L, Perez Baz M J, Millan F R, Fernandez Chimeno R I. WO 2010121079, 2010.

Kondoh S K, Nagasawa H K. 2009. Significance of nitroimidazole compounds and hypoxia-inducible factor-1 for imaging tumor hypoxia. Cancer Sci 100:1366-1373.

Kouprina, N., Noskov, V. N., and Larionov, V. 2006. Selective isolation of large chromosomal regions by transformation-associated recombination cloning for structural and functional analysis of mammalian genomes. Methods Mol. Biol. 349:85-101.

Krasnoff S B, Lobkovsky E B, Wach M J, Loria R, Gibson D M J. 2005. Chemistry and phytotoxicity of thaxtomin A alkyl ethers. J Agric Food Chem. 53:9446-9451.

Lawrence C H, Clark M C, King R R. 1990. Induction of common scab symptoms in aseptically cultured potato tubers by the vivotoxin, thaxtomin. Phytopathology 80:606-608.

Leep, D., Doricchi, L., Perez, B. M. J., Millan, F. R., Fernandez, C. R. I. 2010. Use of thaxtomin for selective control of rice and aquatic based weeds. U.S. Patent Appl. Publ. WO 2010121079.

Leiner R H, Fry B A. 1996. Probable involvement of thaxtomin A in pathogenicity of *Streptomyces scabiei* on seedlings. Phytopathology 86:709-713.

Ilardi E A, Vitaku E, Njardarson J T. 2014. Data-mining for sulfur and fluorine: An evaluation of pharmaceuticals to reveal opportunities for drug design and discovery. J Med Chem 57:2832-2842.

Lombó F, Velasco A, Castro A, De la Calle F, Braña A F, Sánchez-Puelles J M, Méndez C, Salas J A. 2006. Deciphering the biosynthesis pathway of the antitumor thiocoraline from a marine actinomycete and its expression in two *Streptomyces* species. Chem Bio Chem 7:366-376.

Loria, R., Bignell, D. R. D., Moll, S., Huguet-Tapia, J. C., Joshi, M. V., Johnson, E. G., Seipke, R. F., and Gibson, D. M. 2008. Thaxtomin biosynthesis: the path to plant pathogenicity in the genus *Streptomyces*. Antonie Van Leeuwenhoek. 94:3-10.

Loria, R., Kers, J., and Joshi, M. 2006. Evolution of Plant Pathogenicity in *Streptomyces*. Annu. Rev. Phytopathol. 44:469-487.

MacNeil, D. J., Gewain, K. M., Ruby, C. L., Dezeny, G., Gibbons, P. H., and MacNeil, T. 1992. Analysis of *Streptomyces avermitilis* genes required for avermectin biosynthesis utilizing a novel integration vector. Gene. 111:61-68.

Makitrynskyy R, Rebets Y, Ostash B, Zaburannyi N, Rabyk M, Walker S, Fedorenko V. 2010. Genetic factors that influence moenomycin production in streptomycetes. J Ind Microbiol Biotechnol 37:559-566.

Mathee, K., et al., 2008. Dynamics of *Pseudomonas aeruginosa* genome evolution. Proc. Natl. Acad. Sci. U.S.A. 105:3100-3105.

Molesworth P P, Gardiner M G, Jones R C, Smith J A, Tegg R S, Wilson C. 2010. Synthesis and phytotoxicity of structural analogues of thaxtomin natural products. Aust J Chem 63:813-820.

Sánchez, C., Butovich, I. A., Braña, A. F., Rohr, J., Méndez, C., and Salas, J. A. 2002. The biosynthetic gene cluster for the antitumor rebeccamycin: characterization and generation of indolocarbazole derivatives. Chem. Biol. 9:519-531.

Scheible W R, Fry B, Kochevenko A. 2003. An *arabidopsis* mutant resistant to thaxtomin A, a cellulose synthesis inhibitor from *Streptomyces* species. Plant Cell 15:1781-1794.

Simon, R., Priefer, U., and Pithier, A. 1983. A Broad Host Range Mobilization System for In Vivo Genetic Engineering: Transposon Mutagenesis in Gram Negative Bacteria. Nat. Biotechnol. 1:784-791.

Stegmann, E., Rausch, C., Stockert, S., Burkert, D., and Wohlleben, W. 2006. The small MbtH-like protein encoded by an internal gene of the balhimycin biosynthetic gene cluster is not required for glycopeptide production. FEMS Microbiol. Lett. 262:85-92.

Strauss M J. 1979. The nitroaromatic group in drug design: pharmacology and toxicology (for nonpharmacologists). Ind Eng Chem Prod Res Dev 18:158-166.

Streibig J C, Rudemo M, Jensen J E. 1993. Dose-response curves and statistical models. In herbicide bioassays; Streibig, J. C., Kudsk, P., Eds.; CRC Press: Boca Raton, Fla., 29-55.

Van Wezel G P, McKenzie N L, Nodwell J R. 2009. Applying the genetics of secondary metabolism in model actinomycetes to the discovery of new antibiotics. Methods Enzymol 458:117-141.

Xu Z, Zhang F, Zhang L, Jia Y. 2011. Total synthesis of (−)-indolactam V. Org. Biomol Chem 9:2512-2517.

Wach M J, Krasno S B, Loria R, Gibson D M. 2007. Effect of carbohydrates on the production of thaxtomin A by *Streptomyces* acidiscabiei. Arch Microbiol 188:81-88.

Wendt-Pienkowski E, Huang Y, Zhang J, Li B, Jiang H, Kwon H, Hutchinson C R, Shen B. 2005. Cloning, sequencing, analysis, and heterologous expression of the fredericamycin biosynthetic gene cluster from *Streptomyces griseus*. J Am Chem Soc 127:16442-16452.

Winter J M, Moffitt M C, Zazopoulos E, McAlpine J B, Dorrestein P C, Moore B S. 2007. Molecular basis for chloronium-mediated meroterpene cyclization: cloning, sequencing, and heterologous expression of the napyradiomycin biosynthetic gene cluster. J Biol Chem. 282: 16362-16368.

Zaburannyi N, Rabyk M, Ostash B, Fedorenko V, Luzhetskyy A. 2014. Insights into naturally minimised *Streptomyces albus* J1074 genome. BMC Genomics 15:97.

Zhang, Y., Bignell, D. R. D., Zuo, R., Fan, Q., Huguet-Tapia, J. C., Ding, Y., and Loria, R. 2016. Promiscuous Pathogenicity Islands and Phylogeny of Pathogenic *Streptomyces* spp. Mol. Plant Microbe Interact. 29:640-650.

Zhang H, Ning X, Hang H, Ru X, Li H, Li Y, Wang L, Zhang X, Yu S, Qiao Y, Wang X, Wang, P G. 2013. Total synthesis of thaxtomin A and its stereoisomers and findings of their biological activities. Org Lett 15:5670-5673.

Zhang H, Wang Q, Ning X, Hang H, Ma J, Yang X, Lu X, Zhang J, Li Y, Niu C, Song H, Wang X, and Wang P G. 2015. Synthesis and biological evaluations of a series of thaxtomin analogues. J Agric Food Chem 63:3734-3741.

Zhang Y, Jiang G, Ding Y, Loria R. 2018. Genetic background affects pathogenicity island function and pathogen emergence in *Streptomyces*. Mol Plant Pathol doi: 10.1111/mpp.12656.

Zuo R, Zhang Y, Huguet-Tapia J C, Mehta M, Dedic E, Bruner S D, Loria R, Ding Y. 2016. An artificial self-sufficient cytochrome P450 directly nitrates fluorinated tryptophan analogs with a different regio-selectivity. Biotechnol J 11:624-632.

Zuo R, Zhang Y, Jiang C, Hackett J C, Loria R, Bruner S D, Ding Y. 2017 Engineered P450 biocatalysts show improved activity and regio-promiscuity in aromatic nitration. Sci Rep 7:842.

We claim:

1. A genetically engineered *Streptomyces* bacterium comprising:
   a *Streptomyces* bacterium from a non-pathogenic *Streptomyces* strain, the *Streptomyces* bacterium comprising an exogenous, non-native thaxtomin biosynthetic gene cluster from a pathogenic *Streptomyces* strain, such that the exogenous non-native thaxtomin biosynthetic cluster provides the genetically engineered *Streptomyces* bacterium with the ability to produce thaxtomin compounds, thaxtomin intermediates, or combinations thereof, wherein the non-pathogenic *Streptomyces* strain without the exogenous non-native thaxtomin biosynthetic cluster does not have the ability to produce thaxtomin compounds, thaxtomin intermediates, or combinations thereof, and wherein the genetically engineered *Streptomyces* bacterium produces about the same or a greater amount of thaxtomin compounds, thaxtomin intermediates, or combinations thereof than *S. scabiei* under the same culture conditions.

2. The genetically engineered *Streptomyces* bacterium of claim 1, wherein the exogenous, non-native thaxtomin biosynthetic gene cluster from a pathogenic *Streptomyces* strain comprises at least a portion of toxigenic region 1 (TR1) that comprises a Thaxtomin A (TxtA) gene and provides the genetically engineered *Streptomyces* bacterium with the ability to produce thaxtomin A.

3. The genetically engineered *Streptomyces* bacterium of claim 1, wherein the non-native thaxtomin biosynthetic cluster is from a pathogenic *Streptomyces* strain selected from the group of pathogenic *Streptomyces* species consisting of: *Streptomyces scabiei*, *Streptomyces acidiscabies*, and *Streptomyces turgidiscabies*.

4. The genetically engineered *Streptomyces* bacterium of claim 3, wherein the pathogenic *Streptomyces* species is *S. scabiei* 87-22 or other strain of *S. scabiei*.

5. The genetically engineered *Streptomyces* bacterium of claim 1, wherein the *Streptomyces* bacterium from a non-pathogenic *Streptomyces* strain is selected from the group of non-pathogenic *Streptomyces* species consisting of: *S. albus*, *S. diastatochromogenes*, and *S. avermitilis*.

6. The genetically engineered *Streptomyces* bacterium of claim 5, wherein the *Streptomyces* bacterium from a non-pathogenic *Streptomyces* strain is *S. albus* J1074.

7. The genetically engineered *Streptomyces* bacterium of claim 2, wherein the genetically engineered *Streptomyces* bacterium further comprises exogenous, non-native toxigenic region 2 (TR2) and wherein TR1 and TR2 are operably linked.

8. The genetically engineered *Streptomyces* bacterium of claim 1, wherein the exogenous, non-native thaxtomin biosynthetic gene cluster from a pathogenic *Streptomyces* strain is operably linked to a nucleotide encoding a selectable marker.

9. The genetically engineered *Streptomyces* bacterium of claim 1, wherein the non-native ThxA biosynthetic cluster is from a pathogenic *Streptomyces* strain of *S. scabiei* and wherein the *Streptomyces* bacterium from a non-pathogenic *Streptomyces* strain is *S. albus*.

10. The genetically engineered *Streptomyces* bacterium of claim 1, wherein the non-native thaxtomin biosynthetic gene cluster from a pathogenic *Streptomyces* strain is an engineered thaxtomin biosynthetic gene cluster that does not include the txtC gene, wherein the presence of the non-native, engineered thaxtomin biosynthetic cluster provides the genetically engineered *Streptomyces* bacterium with the ability to produce thaxtomin biosynthetic intermediates selected from thaxtomin D, thaxtomin C, N-acetyl-nitro-L-tryptophan, and N-methyl-nitro-L-tryptophan.

11. The genetically engineered *Streptomyces* bacterium of claim 10, wherein the engineered thaxtom in biosynthetic gene cluster further does not include any of the txtA, txtB, and txtH genes and provides the genetically engineered *Streptomyces* bacterium with the capability of producing N-acetyl-nitro-L-tryptophan, N-methyl-nitro-L-tryptophan or both.

12. The genetically engineered *Streptomyces* bacterium of claim 1, wherein the non-native thaxtomin biosynthetic gene cluster from a pathogenic *Streptomyces* strain comprises an engineered ThxA biosynthetic gene cluster comprising less than the full toxigenic region 1 (TR1) but that comprises at least txtA, txtB, and txtC genes and provides the genetically engineered *Streptomyces* bacterium with the capability of producing thaxtomin A.

13. A method of producing thaxtomin compounds, and thaxtomin intermediates, the method comprising:
Culturing a plurality of genetically engineered *Streptomyces* bacteria of claim 1 such that the genetically engineered *Streptomyces* bacteria produce thaxtomin compounds, thaxtomin intermediates, or combinations thereof, wherein the genetically engineered *Streptomyces* bacteria have about the same or increased production of a thaxtomin compound, thaxtomin intermediate, or combinations thereof, as compared to a wild type *S. scabiei* bacteria under the same culture conditions.

14. The method of claim 13, wherein the non-native thaxtomin biosynthetic gene cluster from a pathogenic *Streptomyces* strain comprises toxigenic region 1 (TR1) and provides the genetically engineered *Streptomyces* bacterium with the capability of producing thaxtomin A.

15. The method of claim 13, wherein the non-native thaxtomin biosynthetic gene cluster from a pathogenic *Streptomyces* strain comprises an engineered ThxA biosynthetic gene cluster comprising less than the full toxigenic region 1 (TR1) and provides the genetically engineered *Streptomyces* bacterium with the capability of producing thaxtomin A.

16. The method of claim 13, wherein the non-native thaxtomin biosynthetic gene cluster from a pathogenic *Streptomyces* strain comprises an engineered thaxtomin biosynthetic gene cluster that does not include txtC gene and provides the genetically engineered *Streptomyces* bacterium with the capability of producing thaxtomin biosynthetic intermediates selected from thaxtomin D, thaxtomin C, N-acetyl-nitro-L-tryptophan, and N-methyl-nitro-L-tryptophan.

17. The method of claim 16, wherein the engineered thaxtomin biosynthetic gene cluster also does not include any of the txtA, txtB, and txtH genes and provides the genetically engineered *Streptomyces* bacterium with the capability of producing thaxtomin biosynthetic intermediates selected from N-acetyl-nitro-L-tryptophan and N-methyl-nitro-L-tryptophan.

18. The method of claim 13, wherein culturing the genetically engineered *Streptomyces* bacterium comprising the non-native thaxtomin biosynthetic gene cluster comprises culturing in a culture media comprising a halogenated compound, such that the genetically engineered *Streptomyces* bacterium produces halogenated thaxtom in intermediates, and/or halogenated thaxtom in analogs.

19. The method of claim 18, wherein the halogenated thaxtomin analog comprises 5-F-thaxtomin A.

* * * * *